(12) United States Patent
Dilts et al.

(10) Patent No.: US 9,802,987 B2
(45) Date of Patent: Oct. 31, 2017

(54) IMMUNOGENIC FUSION POLYPEPTIDES

(71) Applicant: PFIZER INC., New York, NY (US)

(72) Inventors: Deborah Ann Dilts, Bardonia, NY (US); Annaliesa Sybil Anderson, Upper Saddle River, NJ (US); Kathrin Ute Jansen, New York, NY (US); Justin Keith Moran, West Nyack, NY (US); Mark E Ruppen, Garnerville, NY (US); Eugene Joseph Vidunas, Middletown, NY (US)

(73) Assignee: Pfizer Inc., New York, NY (US)

( * ) Notice: Subject to any disclaimer, the term of this patent is extended or adjusted under 35 U.S.C. 154(b) by 24 days.

(21) Appl. No.: 14/773,324

(22) PCT Filed: Mar. 5, 2014

(86) PCT No.: PCT/IB2014/059462
§ 371 (c)(1),
(2) Date: Sep. 5, 2015

(87) PCT Pub. No.: WO2014/136064
PCT Pub. Date: Sep. 12, 2014

(65) Prior Publication Data
US 2016/0017006 A1    Jan. 21, 2016

Related U.S. Application Data

(60) Provisional application No. 61/775,478, filed on Mar. 8, 2013.

(51) Int. Cl.
*A61K 39/00* (2006.01)
*A61K 39/02* (2006.01)
(Continued)

(52) U.S. Cl.
CPC ............ *C07K 14/22* (2013.01); *A61K 39/092* (2013.01); *A61K 39/095* (2013.01);
(Continued)

(58) Field of Classification Search
CPC .... A61K 39/00; A61K 39/395; A61K 39/095; C07K 14/22
See application file for complete search history.

(56) References Cited

U.S. PATENT DOCUMENTS 4,376,110 A    3/1983    David et al.
4,554,101 A    11/1985   Hopp
(Continued)

FOREIGN PATENT DOCUMENTS

CA    2012311 C    9/1990
EP    0 125 023 B1    11/1984
(Continued)

OTHER PUBLICATIONS

Ausubel et al., Current Protocols in Molecular Biology, Sections 2.10, 6.3 & 6.4 (1995).
(Continued)

*Primary Examiner* — Ja'Na Hines
(74) *Attorney, Agent, or Firm* — Anna C. Chau

(57) ABSTRACT

In one aspect, the invention relates to an isolated polypeptide including the amino acid sequence of a carrier polypeptide and the amino acid sequence of an ORF2086 polypeptide. In another aspect, the invention relates to an immunogenic conjugate including ORF2086 polypeptide and a carrier polypeptide. The invention further includes immunogenic compositions and methods for inducing an immune response against *Neisseria meningitidis* in a mammal.

6 Claims, 4 Drawing Sheets

(51) Int. Cl.
  *A61K 39/38*  (2006.01)
  *A61K 39/385*  (2006.01)
  *C07K 14/22*  (2006.01)
  *A61K 39/095*  (2006.01)
  *C07K 14/315*  (2006.01)
  *A61K 39/09*  (2006.01)

(52) U.S. Cl.
  CPC .. *C07K 14/3156* (2013.01); *A61K 2039/6037* (2013.01); *A61K 2039/6068* (2013.01); *C07K 2319/00* (2013.01); *C07K 2319/55* (2013.01)

(56) References Cited

U.S. PATENT DOCUMENTS

| | | | |
|---|---|---|---|
| 4,650,764 | A | 3/1987 | Temin et al. |
| 4,666,829 | A | 5/1987 | Glenner et al. |
| 4,708,871 | A | 11/1987 | Geysen |
| 4,797,368 | A | 1/1989 | Carter et al. |
| 4,861,719 | A | 8/1989 | Miller |
| 4,912,094 | A | 3/1990 | Myers et al. |
| 4,925,792 | A | 5/1990 | Rappuoli |
| 4,980,289 | A | 12/1990 | Temin et al. |
| 5,057,540 | A | 10/1991 | Kensil et al. |
| 5,078,996 | A | 1/1992 | Conlon, III et al. |
| 5,124,263 | A | 6/1992 | Temin et al. |
| 5,139,941 | A | 8/1992 | Muzyczka et al. |
| 5,254,339 | A | 10/1993 | Morein |
| 5,399,346 | A | 3/1995 | Anderson et al. |
| 5,459,127 | A | 10/1995 | Felgner et al. |
| 5,514,581 | A | 5/1996 | Ferrari et al. |
| 5,550,213 | A | 8/1996 | Anderson et al. |
| 5,565,204 | A | 10/1996 | Kuo et al. |
| 5,580,859 | A | 12/1996 | Felgner et al. |
| 5,583,038 | A | 12/1996 | Stover |
| 5,589,466 | A | 12/1996 | Felgner et al. |
| 5,597,572 | A | 1/1997 | Huergo et al. |
| 5,614,382 | A | 3/1997 | Metcalf |
| 5,668,004 | A | 9/1997 | O'Donnell |
| 5,723,127 | A | 3/1998 | Scott et al. |
| 5,739,118 | A | 4/1998 | Carrano et al. |
| 5,955,580 | A | 9/1999 | Green et al. |
| 6,113,918 | A | 9/2000 | Johnson et al. |
| 6,130,085 | A | 10/2000 | Hamers et al. |
| 6,149,919 | A | 11/2000 | Domenighini et al. |
| 6,165,995 | A | 12/2000 | Hilgers |
| 6,207,646 | B1 | 3/2001 | Krieg et al. |
| 6,245,892 | B1 | 6/2001 | Oaks et al. |
| 6,270,775 | B1 | 8/2001 | Cleary |
| 6,281,337 | B1 | 8/2001 | Cannon-Carlson et al. |
| 6,299,884 | B1 | 10/2001 | Van Nest et al. |
| 6,355,253 | B1 | 3/2002 | Zlotnick |
| 6,355,255 | B1 | 3/2002 | Cleary et al. |
| 6,610,310 | B2 | 8/2003 | Hilgers |
| 6,951,653 | B2 | 10/2005 | Cleary et al. |
| 7,115,730 | B1 | 10/2006 | Pizza et al. |
| 7,118,757 | B1 | 10/2006 | Seid et al. |
| 7,285,281 | B2 | 10/2007 | Green et al. |
| 7,291,588 | B2 | 11/2007 | Pizza et al. |
| 7,332,174 | B2 | 2/2008 | Green et al. |
| 7,361,355 | B2 | 4/2008 | Green et al. |
| 7,384,640 | B1 | 6/2008 | Holmes et al. |
| 7,576,176 | B1 | 8/2009 | Fraser et al. |
| 7,608,278 | B2 | 10/2009 | Hoiseth et al. |
| 7,785,608 | B2 | 8/2010 | Zlotnick et al. |
| 7,803,387 | B2 | 9/2010 | Arico et al. |
| 7,820,789 | B2 | 10/2010 | Kirkham et al. |
| 8,039,007 | B2 | 10/2011 | Rappuoli et al. |
| 8,101,194 | B2 | 1/2012 | Zlotnick et al. |
| 8,273,360 | B2 | 9/2012 | Pizza et al. |
| 8,398,988 | B2 | 3/2013 | Contorni et al. |
| 8,563,006 | B2 | 10/2013 | Zlotnick et al. |
| 8,563,007 | B1 | 10/2013 | Zlotnick et al. |
| 8,574,597 | B2 | 11/2013 | Zlotnick et al. |
| 8,632,995 | B2 | 1/2014 | Sun et al. |
| 8,986,710 | B2 | 3/2015 | Anderson et al. |
| 9,132,182 | B2 | 9/2015 | Zlotnic et al. |
| 2004/0110670 | A1 | 6/2004 | Arico et al. |
| 2004/0167068 | A1 | 8/2004 | Zlotnick et al. |
| 2004/0249125 | A1 | 12/2004 | Pizza et al. |
| 2006/0251670 | A1 | 11/2006 | Comanducci et al. |
| 2007/0020622 | A1 | 1/2007 | Lee et al. |
| 2007/0082007 | A1 | 4/2007 | Zlotnick et al. |
| 2007/0148729 | A1 | 6/2007 | Farley et al. |
| 2007/0253964 | A1 | 11/2007 | Zlotnick et al. |
| 2009/0035328 | A1 | 2/2009 | Granoff |
| 2009/0202593 | A1 | 8/2009 | Zlotnick et al. |
| 2011/0076299 | A1 | 3/2011 | Zlotnick et al. |
| 2011/0189187 | A1 | 8/2011 | Zlotnick |
| 2011/0312510 | A1 | 12/2011 | Mak et al. |
| 2012/0034261 | A1 | 2/2012 | Zlotnick et al. |
| 2012/0070457 | A1 | 3/2012 | Daugherty et al. |
| 2012/0093852 | A1 | 4/2012 | Anderson et al. |
| 2012/0107339 | A1 | 5/2012 | Granoff et al. |
| 2012/0301496 | A1 | 11/2012 | Zlotnick et al. |
| 2013/0171194 | A1 | 7/2013 | Khandke et al. |
| 2014/0113329 | A1 | 4/2014 | Sun et al. |
| 2015/0071959 | A1 | 3/2015 | Anderson et al. |
| 2015/0216960 | A1 | 8/2015 | Zlotnick et al. |

FOREIGN PATENT DOCUMENTS

| | | |
|---|---|---|
| EP | 0 171 496 B1 | 2/1986 |
| EP | 0 173 494 A2 | 3/1986 |
| EP | 0 184 187 A2 | 6/1986 |
| EP | 0 185 573 B1 | 6/1986 |
| EP | 0 467 714 A1 | 7/1991 |
| EP | 0 178 220 B1 | 1/1992 |
| EP | 0 488 528 B1 | 11/1995 |
| EP | 0 453 242 B1 | 8/1996 |
| EP | 1 296 713 B1 | 9/2003 |
| EP | 1 326 634 B1 | 4/2006 |
| EP | 2 351 767 A2 | 8/2011 |
| JP | 1144977 A | 6/1989 |
| WO | 86/01533 A1 | 3/1986 |
| WO | 87/01130 A1 | 2/1987 |
| WO | 87/02671 A1 | 5/1987 |
| WO | 89/07150 A1 | 8/1989 |
| WO | 90/02806 A1 | 3/1990 |
| WO | 90/10458 A1 | 9/1990 |
| WO | 91/18088 A1 | 11/1991 |
| WO | 92/05263 A1 | 4/1992 |
| WO | 92/19265 A1 | 11/1992 |
| WO | 93/09239 A1 | 5/1993 |
| WO | 94/12649 A2 | 6/1994 |
| WO | 94/21807 A2 | 9/1994 |
| WO | 94/26914 A1 | 11/1994 |
| WO | 94/28152 A1 | 12/1994 |
| WO | 94/28938 A1 | 12/1994 |
| WO | 95/02697 A1 | 1/1995 |
| WO | 95/07358 A1 | 3/1995 |
| WO | 95/18863 A1 | 7/1995 |
| WO | 95/21931 A1 | 8/1995 |
| WO | 95/22617 A1 | 8/1995 |
| WO | 95/26411 A2 | 10/1995 |
| WO | 95/28494 A1 | 10/1995 |
| WO | 96/10038 A1 | 4/1996 |
| WO | 96/14086 A1 | 5/1996 |
| WO | 96/17823 A1 | 6/1996 |
| WO | 96/22378 A1 | 7/1996 |
| WO | 96/25508 A1 | 8/1996 |
| WO | 96/29412 A1 | 9/1996 |
| WO | 96/39036 A1 | 12/1996 |
| WO | 96/40718 A1 | 12/1996 |
| WO | 97/19182 A1 | 5/1997 |
| WO | 98/08543 A1 | 3/1998 |
| WO | 98/08874 A1 | 3/1998 |
| WO | 98/17805 A2 | 4/1998 |
| WO | 99/01157 A1 | 1/1999 |
| WO | 99/01158 A1 | 1/1999 |
| WO | 99/01175 A1 | 1/1999 |
| WO | 99/10372 A1 | 3/1999 |
| WO | 99/24578 A2 | 5/1999 |
| WO | 99/27944 A1 | 6/1999 |
| WO | 99/36544 A2 | 7/1999 |

(56) References Cited

FOREIGN PATENT DOCUMENTS

| | | |
|---|---|---|
| WO | 99/40200 A1 | 8/1999 |
| WO | 99/48525 A1 | 9/1999 |
| WO | 99/55730 A2 | 11/1999 |
| WO | 99/55872 A1 | 11/1999 |
| WO | 99/57280 A2 | 11/1999 |
| WO | 99/61053 A1 | 12/1999 |
| WO | 00/18434 A1 | 4/2000 |
| WO | 00/22430 A2 | 4/2000 |
| WO | 00/42192 A1 | 7/2000 |
| WO | 00/43518 A1 | 7/2000 |
| WO | 00/44890 A1 | 8/2000 |
| WO | 00/45841 A2 | 8/2000 |
| WO | 00/50075 A2 | 8/2000 |
| WO | 00/57906 A1 | 10/2000 |
| WO | 00/66741 A2 | 11/2000 |
| WO | 00/66791 A1 | 11/2000 |
| WO | 00/71574 A2 | 11/2000 |
| WO | 00/71725 A2 | 11/2000 |
| WO | 01/04316 A2 | 1/2001 |
| WO | 01/31019 A2 | 5/2001 |
| WO | 01/37863 A2 | 5/2001 |
| WO | 01/38350 A2 | 5/2001 |
| WO | 01/41800 A2 | 6/2001 |
| WO | 01/52885 A1 | 7/2001 |
| WO | 01/64920 A2 | 9/2001 |
| WO | 01/64922 A2 | 9/2001 |
| WO | 02/058737 A2 | 8/2002 |
| WO | 02/079243 A2 | 10/2002 |
| WO | 02/079246 A2 | 10/2002 |
| WO | 02/083710 A2 | 10/2002 |
| WO | 02/083711 A2 | 10/2002 |
| WO | 02/098368 A2 | 12/2002 |
| WO | 02/098369 A2 | 12/2002 |
| WO | 03/007985 A2 | 1/2003 |
| WO | 03/009869 A1 | 2/2003 |
| WO | 03/020756 A2 | 3/2003 |
| WO | 03/047619 A2 | 6/2003 |
| WO | 03/063766 A2 | 8/2003 |
| WO | 03/080678 A1 | 10/2003 |
| WO | 03/094834 A2 | 11/2003 |
| WO | 03/094960 A2 | 11/2003 |
| WO | 2005102384 A2 | 11/2003 |
| WO | 2004/019977 A2 | 3/2004 |
| WO | 2004/019992 A1 | 3/2004 |
| WO | 2004/032958 A1 | 4/2004 |
| WO | 2004/046177 A2 | 6/2004 |
| WO | 2004/048404 A2 | 6/2004 |
| WO | WO 2004/048404 * 6/2004 ........... A61K 39/095 | | |
| WO | 2004/065603 A2 | 8/2004 |
| WO | 2004/067030 A2 | 8/2004 |
| WO | 2004/067033 A1 | 8/2004 |
| WO | 2004/083251 A2 | 9/2004 |
| WO | 2004/094596 A2 | 11/2004 |
| WO | 2005/000345 A2 | 1/2005 |
| WO | 2005/004908 A1 | 1/2005 |
| WO | 2005/020964 A1 | 3/2005 |
| WO | 2005/032583 A2 | 4/2005 |
| WO | 2005/033148 A1 | 4/2005 |
| WO | 2005/090985 A1 | 9/2005 |
| WO | 2005/090986 A2 | 9/2005 |
| WO | 2005/103230 A2 | 11/2005 |
| WO | 2005/105140 A2 | 11/2005 |
| WO | 2005/105141 A2 | 11/2005 |
| WO | 2005/108580 A1 | 11/2005 |
| WO | 2005/113607 A2 | 12/2005 |
| WO | 2006/000920 A2 | 1/2006 |
| WO | 2006/011060 A2 | 2/2006 |
| WO | 2006/024954 A2 | 3/2006 |
| WO | 2006/027685 A2 | 3/2006 |
| WO | 2006/046143 A2 | 5/2006 |
| WO | 2006/067632 A2 | 6/2006 |
| WO | 2006/075170 A1 | 7/2006 |
| WO | 2006/081259 A2 | 8/2006 |
| WO | 2006/096701 A2 | 9/2006 |
| WO | 2006/120576 A2 | 11/2006 |
| WO | 2007/000314 A2 | 1/2007 |
| WO | 2007/000341 A2 | 1/2007 |
| WO | 2007/000342 A2 | 1/2007 |
| WO | 2007/000343 A2 | 1/2007 |
| WO | 2007/026249 A2 | 3/2007 |
| WO | 2007/028408 A1 | 3/2007 |
| WO | 2007/060548 A2 | 5/2007 |
| WO | 2007/071786 A2 | 6/2007 |
| WO | 2007/111940 A2 | 10/2007 |
| WO | 2007/127665 A2 | 11/2007 |
| WO | 2007/127668 A2 | 11/2007 |
| WO | 2007/144316 A2 | 12/2007 |
| WO | 2007/144317 A2 | 12/2007 |
| WO | 2008/001222 A2 | 1/2008 |
| WO | 2008/001224 A2 | 1/2008 |
| WO | 2008/013943 A2 | 1/2008 |
| WO | 2008/079372 A2 | 7/2008 |
| WO | 2008/084411 A2 | 7/2008 |
| WO | WO 2008/079372 * 7/2008 ............. A61K 39/00 | | |
| WO | 2008/149238 A2 | 12/2008 |
| WO | 2009/010877 A2 | 1/2009 |
| WO | 2009/016515 A2 | 2/2009 |
| WO | 2009/050586 A1 | 4/2009 |
| WO | 2009/104097 A2 | 8/2009 |
| WO | 2009/109550 A1 | 9/2009 |
| WO | 2009/114485 A2 | 9/2009 |
| WO | 2009/143168 A2 | 11/2009 |
| WO | 2009/158142 A1 | 12/2009 |
| WO | 2010/027872 A1 | 3/2010 |
| WO | 2010/028096 A2 | 3/2010 |
| WO | 2010/028859 A1 | 3/2010 |
| WO | 2010/067202 A2 | 6/2010 |
| WO | 2010/070453 A2 | 6/2010 |
| WO | 2010/109323 A1 | 9/2010 |
| WO | 2010/109324 A1 | 9/2010 |
| WO | 2010/127172 A2 | 11/2010 |
| WO | 2011/024072 A2 | 3/2011 |
| WO | 2011/039631 A2 | 4/2011 |
| WO | 2011/042516 A2 | 4/2011 |
| WO | 2011/051893 A1 | 5/2011 |
| WO | 2011/080595 A2 | 7/2011 |
| WO | 2011/110531 A2 | 9/2011 |
| WO | 2011/110634 A1 | 9/2011 |
| WO | 2011/110635 A1 | 9/2011 |
| WO | 2011/126863 A1 | 10/2011 |
| WO | 2011/161653 A1 | 12/2011 |
| WO | 2012/020326 A1 | 2/2012 |
| WO | 2012/031271 A1 | 3/2012 |
| WO | 2012/032169 A1 | 3/2012 |
| WO | 2012/032489 A1 | 3/2012 |
| WO | 2012/032498 A2 | 3/2012 |
| WO | 2012/035519 A1 | 3/2012 |
| WO | WO 2012032489 * 3/2012 ........... A61K 39/095 | | |
| WO | 2013/132452 A2 | 9/2013 |
| WO | 2014/136064 A2 | 9/2014 |

OTHER PUBLICATIONS

Martin et al, "Highly Conserved Neisseria meningitidis Surface Protein Confers Protection against Experimental Infection", J. Exp. Med. 185(7):1173-1183 (1997).

Masignani et al, "Vaccination against Neisseria meningitidis Using Three Variants of the Lipoprotein GNA1870", J. Exp. Med. 197(6):789-799 (2003).

Matsuka et al, "Fibrinogen Cleavage by the *Streptococcus pyogenes* Extracellular Cysteine Protease and Generation of Antibodies That Inhibit Enzyme Proteolytic Activity", Infection and Immunity 67(9):4326-4333 (1999).

Mazmanian et al, "*Staphylococcus aureus* Sortase, an Enzyme that Anchors Surface Proteins to the Cell Wall", Science 285:760-763 (1999).

McAtee et al, "Characterization of a Helicobacter pylori vaccine candidate by proteome techniques", Journal of Chromatography B, Biomedical Sciences and Applications 714:325-333 (1998).

McAtee et al, "Identification of Potential Diagnostic and Vaccine Candidates of Helicobacter pylori by "Proteome" Technologies", Helicobacter 3(3):163-169 (1998).

(56) References Cited

OTHER PUBLICATIONS

McAtee et al, "Identification of Potential Diagnostic and Vaccine Candidates of Helicobacter pylori by Two-Dimensional Gel Electrophoresis, Sequence Analysis, and Serum Profiling", Clinical and Diagnostic Laboratory Immunology 5(4):537-542 (1998).
McCormick, "Human Gene Therapy: The First Round", BioTechnology 3(8):689-693 (1985).
McGuiness et al, "Class 1 outer membrane protein of Neisseria meningitidis: epitope analysis of the antigenic diversity between strains, implications for subtype definition and molecular epidemiology", Molecular Microbiology 7 (4):505-514 (1993).
Mejlhede et al, "Ribosomal-1 Frameshifting during Decoding of Bacillus subtilis cdd Occurs at the Sequence CGA AAG", Journal of Bacteriology 181(9):2930-2937 (1999).
Milagres et al., "Specificity of Bactericidal Antibody Response to Serogroup B Miningococcal Strains in Brazilian Children after Immunization with an Outer Membrane Vaccine", Infection and Immunity 66(10):4755-4761 (1998).
Miller et al, "Improved Retroviral Vectors for Gene Transfer and Expression", BioTechniques 7(9):980-990 (1992).
Minutes of Oral Proceedings in Opposition against Novartis EP 1 645 631 dated Mar. 5, 2012.
Mir et al, "Long-term, high level in vivo gene expression after electric pulse-mediated gene transfer into skeletal muscle", Academie des sciences 321:893-899 (1998).
Molinari et al, "The Fibronectin-Binding Protein of Streptococcus pyogenes, Sfbl, Is Involved in the Internalization of Group A Streptococci by Epithelial Cells", Infection and Immunity 65(4):1357-1363 (1997).
Morbidity and Mortality Weekly Report (MMWR), Recommendations and Reports, Case Definitions for Infectious Conditions Under Public Health Surveillance, May 2, 1997, vol. 46, No. RR-10.
Moreno et al, "Immunity and Protection of Mice Against Neisseria meningitidis Group B by Vaccination, Using Polysaccharide Complexed with Outer Membrane Proteins: A Comparison with Purified B Polysaccharide", Infection and Immunity 47(2):527-533 (1985).
Morley et al, "Vaccine prevention of meningococcal disease, coming soon?", Vaccine 20:666-687 (2002).
Morrison et al, "Chimeric human antibody molecules: Mouse antigen-binding domains with human constant region domains", Proc. Natl. Acad. Sci. 81:6851-6855 (1984).
Mountzouros et al, "Detection of Complement-Mediated Antibody-Dependent Bactericidal Activity in a Fluorescence-Based Serum Bactericidal Assay for Group B Neisseria meningitidis", Journal of Clinical Microbiology 38 (8):2878-2884 (2000).
Moxon, "Applications of molecular microbiology to vaccinology," Lancet 350(9086):1240-1244 (1997).
Munkley et al., "Blocking of Bactericidal Killing of Neisseria meningitidis by Antibodies Directed Against Class 4 Outer Membrane Protein", Microbial Pathogenesis 11:447-452 (1991).
Murphy et al, "Sequence Diversity of the Factor H Binding Protein Vaccine Candidate in Epidemiologically Relevant Strains of Serogroup B Neisseria meningitidis" The Journal of Infectious Diseases 200:379-389 (2009).
Nakai et al, "Expert System for Predicting Protein Localization Sites in Gram-Negative Bacteria", Proteins: Structure, Function, and Genetics 11:95-110 (1991).
Naldini et al, "Lentiviruses as gene transfer agents for delivery to non-dividing cells", Current Opinion in Biotechnology 9:457-463 (1998).
Nassif, "A Furtive Pathogen Revealed", Science 287:1767-1768 (2000).
Navarre et al, "Surface Proteins of Gram-Positive Bacteria and Mechanisms of Their Targeting to the Cell Wall Envelope", Microbiology and Molecular Biology Reviews 63(1):174-229 (1999).
NCBI GenBank No. AAF42204.1, Tettelin, H. et al., "Hypothetical protein [Neisseria meningitidis]", Feb. 25, 2000, accessed Jul. 12, 2012.
NCBI GenBank: ACB38141.1, factor H-binding protein [Neisseria meningitidis] (Jun. 4, 2010).
NCBI GenBank No. EF108319.1, O'Leary, M. M. et al., Neisseria meningitidis strain NM452 FHBP/GNA1870 variant (GNA1870) gene, complete cds, Nov. 8, 2006, accessed Sep. 5, 2012.
NCBI GenBank: FJ184233.1, "Neisseria meningitidis factor H binding protein variant B09_004 (fhbp) gene, partial cds" (Aug. 4, 2009).
Neisseria gonorrhoeae FA 1090 chromosome Entire clone gono strain FA1090, complete sequence. GenBank Accession gono AE004969, 2153894 bp, Sep. 26, 2000.
Nielsen et al, "Identification of prokaryotic and eukaryotic signal peptides and prediction of their cleavage sites", Protein Engineering 10(1):1-6 (1997).
Nizet et al, "Genetic Locus for Streptolysin S Production by Group A Streptococcus", Infection and Immunity 68 (7):4245-4254 (2000).
Nordstrand et al, "Allele Substitution of the Streptokinase Gene Reduces the Nephritogenic Capacity of Group A Streptococcal Strain NZ131", Infection and Immunity 68(3):1019-1025 (2000).
Notice of Opposition against Novartis EP 1 645 631 submitted Jul. 23, 2008.
Novartis submits Bexsero®, a multi-component meningococcal B vaccine, for regulatory review in Europe, Novartis Media Release (Dec. 23, 2010).
Olmsted et al, "High-Resolution Visualization by Field Emission Scanning Electron Microscopy of Enterococcus faecalis Surface Proteins Encoded by the Pheromone-Inducible Conjugative Plasmid pCF10", Journal of Bacteriology 175(19):6229-6237 (1993).
Opponent's Further Submission in Preparation of Oral Proceedings in Opposition against Novartis EP 1 645 631 submitted Nov. 3, 2011.
Oudega et al, "A lipoprotein signal peptide plus a cysteine residue at the amino-terminal end of the periplasmic proteins beta-lactamase is sufficient for its lipid modification, processing and membrane localization in Escherichia coli", FEMS Microbiology Letters 108:353-360 (1993).
Oudega et al, "Escherichia coli SecB, SecA, and SecY Proteins Are Required for Expression and Membrane Insertion of the Bacteriocin Release Protein, a Small Lipoprotein", Journal of Bacteriology 175(5):1543-1547 (1993).
Pannekoek et al, "Construction of recombinant neisserial Hsp60 proteins and mapping of antigenic domains", Molecular Microbiology 15(2):277-285 (1995).
Park et al, "DIVCLUS: an automatic method in the GEANFAM-MER package that finds homologous domains in single- and multi-domain proteins", Bioinformatics 14(2):144-150 (1998).
Parkhill, "Campylobacter jejuni genome sequence at the Sanger Centre", (May 8, 1998), available at: http://www.bio.net/bionet/mm/bionews/1997-May/00442.html.
Parkhill et al, "Complete DNA sequence of a serogroup A strain of Neisseria meningitidis Z2491", Nature 404:502-506 (2000).
Patentees' Further Submission Under Rule 116 EPC in Opposition against Novartis EP 1 645 631 submitted Oct. 14, 2011.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
PCT Annex to Form PCT/ISA/206 Communication Relating to the Results of the Partial International Search, PCT/US2007/026238.
PCT International Search Report for PCT/US20071026238 dated Feb. 23, 2009.
Anderson, "Elicitation of Functional Antibodies by a Group B Neisseria meningitidis Bivalent rLP2086 Vaccine in Non-Human Primates", NHP IPNC Poster Presentation 2008.
Bambini et al, "Distribution and genetic variability of three vaccine components in a panel of strains representative of the diversity of serogroup B meningococcus", Vaccine 27:2794-2803 (2009).
Beernink et al, "Prevalence of Factor H-Binding Protein Variants and NadA among Meningococcal Group B Isolates from the United States: Implications for the Development of a Multicomponent Group B Vaccine", The Journal of Infectious Diseases 195:1472-1479 (2007).

(56) References Cited

OTHER PUBLICATIONS

Bergmann et al, "An endogenously synthesized decamer peptide efficiently primes cytotoxic T cells specific for the HIV-1 envelope glycoprotein", Eur. J. Immunol., 23(11):2777-2781 (1993).
Bergmann et al, "Flanking Residues Alter Antigenicity and Immunogenicity of Multi-Unit CTL Epitopes", The Journal of Immunology, 157:3242-3249 (1996).
Borrow et al, "Meningococcal surrogates of protection—serum bactericidal antibody activity", Vaccine 23:2222-2227 (2005).
Coleman et al, "Virus Attenuation by Genome-Scale Changes in Codon Pair Bias", Science, 320:1784-1787 (2008).
Findlow et al, "Multicenter, Open-Label, Randomized Phase II Controlled Trial of an Investigational Recombinant Meningococcal Serogroup B Vaccine With and Without Outer Membrane Vesicles, Administered in Infance", Clinical Infectious Diseases 51(10):1127-1137 (2010).
Geysen et al, "A Priori Delineation of a Peptide Which Mimics a Discontinuous Antigenic Determinant", Molecular Immunology, 23(7):709-715 (1986).
Geysen et al, "Use of peptide synthesis to probe viral antigens for epitopes to a resolution of a single amino acid", Proc. Natl. Acad. Sci. USA, 81(13):3998-4002 (1984).
Harris et al, "Preclinical evidence for the potential of a bivalent fHBP vaccine to prevent Neisseria meningitidis serogroup C disease", Human Vaccines 7(Supplement):68-74 (2011).
Liu et al, "High-throughput imaging of bacterial colonies grown on filter plates with application to serum bactericidal assays", Journal of Immunological Methods 292(1-2):187-193 (2004).
Marshall, H.S., et al., "A phase 2 open-label safety and immunogenicity study of a meningococcal B bivalent rLP2086 vaccine in healthy adults", Vaccine, 31(12):1569-1575 (2013).
Mascioni et al, "Structural Basis for the Immunogenic Properties of the Meningococcal Vaccine Candidate LP2086", Journal of Biological Chemistry 284(13):8738-8746 (2009).
McNeil et al, "Detection of LP2086 on the cell surface of Neisseria meningitidis and its accessibility in the presence of serogroup B capsular polysaccharide", Vaccine 27:3417-3421 (2009).
Murphy, E., "HM807466: Neisseria meningitidis strain M08452 factor H binding protein variant B153 (fhbp) gene, partial cds.", URL:http://getentry.ddbj.nig.ac.jp/getentry/na/HM807466/?filetype=html, Jul. 21, 2010.
NCBI GenBank : ACI46791, "Factor H binding protein variant A04_001, partial [Neisseria meningitidis]". Aug. 4, 2009.
NCBI GenBank: ACI46789.1: "Factor H binding protein variant A62_001, partial [Neisseria meningitidis]", Aug. 4, 2009.
Pajon et al, "Frequency of factor H-binding protein modular groups and susceptibility to cross-reactive bactericidal activity in invasive meningococcal isolates", Vaccine 28:2122-2129 (2010).
Paoletti et al, "Potency of clinical group B streptococcal conjugate vaccines", Vaccine, 19(15-16):2118-2126 (2001).
Patel, M., "Outbreaks of Serogroup B Meningococcal Disease on University Campuses—2013", Medical Officer, Meningitis and Vaccine Preventable Diseases Branch, http://www.cdc.gov/vaccines/acip/meetings/downloads/slides-2014-02/04-Mening-Patel.pdf, 16 Pages, Apr. 3, 2014.
PCT International Search Report for PCT/IB2011/053934 dated Jan. 20, 2012.
PCT International Search Report for PCT/US02/32369 dated Nov. 14, 2003.
Pillai et al, "Outer membrane protein (OMP) based vaccine for Neisseria meningitidis serogroup B", Vaccine 23:2206-2209 (2005).
Pizza et al, "Factor H-binding protein, a unique meningococcal vaccine antigen", Vaccine 26(Supp8):I46-I48 (2008).
Richmond, et al, On Behalf of the 2001 Study Investigators, "Safety, immunogenicity, and tolerability of meningococcal serogroup B bivalent recombinant lipoprotein 2086 vaccine in healthy adolescents: a ranomised, single-blind, placebo-controlled, phase 2 trial", www.thelancet.com/infection, 13 pages, Published online May 7, 2012.

Sastalla et al, "Codon-Optimized Fluorescent Proteins Designed for Expression in Low-GC Gram-Positive Bacteria", Applied and Environmental Microbiology, 75(7):2099-2110 (2009).
Seib et al, "Characterization of Diverse Subvariants of the Meningococcal Factor H (fH) Binding Protein for Their Ability to Bind fH, to Mediate Serum Resistance, and to Induce Bactericidal Antibodies", Infection and Immunity 79 (2):970-981 (2011).
Snape et al, "Immunogenicity of Two Investigational Serogroup B Meningococcal Vaccines in the First Year of Life", The Pediatric Infectious Disease Journal 29(11):e71-e79 (2010).
Suhrbier, "Multi-epitope DNA vaccines", Immunology and Cell Biology, 75(4):402-408 (1997).
Welsch et al, Factor H and Neisserial pathogenesis, Vaccine 26(Supp8):I40-I45 (2008).
Wolf et al, "Conditions Affecting Direct Gene Transfer into Rodent Muscle In Vivo", Biotechniques, 11(4):474-485 (1991).
Wyeth Neisseria Meningitidis Serogroup B Vaccine, Vaccine and Related Biological Products Advisory Committee Pre-Meeting Background Document, URL:http://www.fda.gov/downloads/AdvisoryCommittees/CommitteesMeetingMaterials/BloodVaccinesandOtherBiologics/VaccinesandRelatedBiologicalProductsAdvisoryCommittee/UCM249479.pdf, Mar. 4, 2011.
Zhu et al, "Evaluation of Recombinant Lipidated P2086 Protein as a Vaccine Candidate for Group B Neisseria meningitidis in a Murine Nasal Challenge Model", Infection and Immunity 73(10):6838-6845 (2005).
Graham, "Covalently closed circles of human adenovirus DNA are infectious", The EMBO Journal 3(12):2917-2922 (1984).
Grandi, "Reverse Vaccinology: A Critical Analysis", Encyclopedia of Genetics, Genomics, Proteomics and Bioinformatics, pp. 1320-1330 (2005).
Green et al, "The e (P4) Outer Membrane Protein of Haemophilus influenzae: Biologic Activity of Anti-e Serum and Cloning and Sequencing of the Structural Gene", Infection and Immunity 59(9):3191-3198 (1991).
Greenspan et al, "Defining epitopes: It's not as easy as it seems", Nature Biotechnology 17:936-937 (1999).
Griffin et al, "Computer Analysis of Sequence Data", Methods in Molecular Biology, vol. 24, Part 1, Chapter 1, Humana Press, New Jersey (1994).
Gupta, "Aluminum compounds as vaccine adjuvants", Advanced Drug Delivery Reviews 32(3):155-172 (1998).
Guzman et al, "Tight Regulation, Modulation, and High-Level Expression by Vectors Containing the Arabinose PBAD Promoter", Journal of Bacteriology 177(14):4121-4130 (1995).
Hacker et al, "Pathogenicity islands of virulent bacteria: structure, function and impact on microbial evolution", Molecular Microbiology 23(6):1089-1097 (1997).
Hanski et al, "Expression of protein F, the fibronectin-binding protein of Streptococcus pyogenes JRS4, in heterologous streptococcal and enterococcal strains promotes their adherence to respiratory epithelial cells", Infection and Immunity 60(12):5119-5125 (1992).
Hanski et al, "Protein F, a fibronectin-binding protein, is an adhesin of the group A *Streptococcus Streptococcus pyogenes*", Proc. Natl. Acad. Sci. 89:6172-6176 (1992).
Hansson et al, "Expression of Truncated and Full-Length Forms of the Lyme Disease Borrelia Outer Surface Protein A in *Escherichia coli*", Protein Expression and Purification 6:15-24 (1995).
Hayashi et al, "Lipoproteins in Bacteria", Journal of Bioenergetics and Biomembranes 22(3):451-471 (1990).
Hem et al, "Chapter 9: Structure and Properties of Aluminum-Containing Adjuvants", Vaccine Design: The Subunit and Adjuvant Approach, Plenum Press, New York, pp. 249-276 (1995).
Hernandez-Sanchez et al, "lambda bar minigene-mediated inhibition of protein synthesis involves accumulation of peptidyl-tRNA and starvation for tRNA", The EMBO Journal 17(13):3758-3765 (1998).
Hornyik et al, "Cerebrospinal Fluid Shunt Infection by Neisseria sicca", Pediatr Neurosurg 21:189-191 (1994).
Houghten, "General Method for the rapid solid-phase synthesis of large numbers of peptides: Specificity of antigen-antibody interac-

(56) References Cited

OTHER PUBLICATIONS tion at the level of individual amino acids", Proceedings of the National Academy of Sciences of USA 82:5131-5135 (1985).
Huang et al, "The streptokinase gene of group A streptococci: cloning, expression in *Escherichia coli*, and sequence analysis", Molecular Microbiology 3(2):197-205 (1989).
Hung, "The Neisseria meningitidis Macrophage Infectivity Potentiator Protein Induces Cross-Strain Serum Bactericidal Activity and Is a Potential Serogroup B Vaccine Candidate", Infection and Immunity, 79(9):3784-3791 (2011).
Hynes et al, "Analysis of a Second Bacteriophage Hyaluronidase Gene from Streptococcus pyogenes: Evidence for a Third Hyaluronidase Involved in Extracellular Enzymatic Activity", Infection and Immunity 63(8):3015-3020 (1995).
Hynes et al, "The extracellular hyaluronidase gene (hylA) of *Streptococcus pyogenes*", FEMS Microbiology Letters 184:109-112 (2000).
Interlocutory Decision of the Opposition Division in Opposition against Novartis EP 1 645 631 dated May 21, 2012.
Isberg et al, "Binding and internalization of microorganisms by integrin receptors", Trends in Microbiology 2(1):10-14 (1994).
Jackson et al, U.S. Appl. No. 60/098,685, filed Sep. 1, 1998.
Jiang et al, "Broad vaccine coverage predicted for a bivalent recombinant factor H binding protein based vaccine to prevent serogroup B meningococcal disease", Vaccine 28:6086-6093 (2010).
Johnson et al., "Analysis of the Human Ig Isotype Response to Lactoferrin Binding Protein A from Neisseria meningitidis", FEMS Immunology and Medical Microbiology 25(4):349-354 (1999).
Jones et al, "The Importance of the Location of Antibody Binding on the M6 Protein for Opsonization and Phagocytosis of Group A M6 Streptococci", J. Exp. Med. 167:1114-1123 (1988).
JVCI-CMR website showing Z2491 Sanger sequence (http://cmr.jvci.org/tigr-scripts/CMR/shared/Genomes.cgi and links) printed on Jul. 1, 2010.
Kafri et al, "A Packaging Cell Line for Lentivirus Vectors", Journal of Virology 73(1):576-584 (1999).
Kaplitt et al, "Expression of a Functional Foreign Gene in Adult Mammalian Brain following in Vivo Transfer via a Herpes Simplex Virus Type 1 Defective Viral Vector", Molecular and Cellular Neurosciences 2:320-330 (1991).
Kihlberg et al, "Protein H, an Antiphagocytic Surface Protein in *Streptococcus pyogenes*", Infection and Immunity 67 (4):1708-1714 (1999).
Klein et al, "Distinctive properties of signal sequences from bacterial lipoproteins", Protein Engineering 2(1):15-20 (1988).
Koeberling at el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).
Koebnik, "Proposal for a peptidoglycan-associating alpha-helical motif in the C-terminal regions of some bacterial cell-surface proteins", Molecular Microbiology 16(6):1269-1270 (1995).
Kohler et al, "Continuous cultures of fused cells secreting antibody of predefined specificity", Nature 256:495-497 (1975).
Kuipers et al, "Improved site-directed mutagenesis method using PCR", Nucleic Acids Research 19(16):4558 (1991).
Kuo et al, "Efficient Gene Transfer into Primary Murine Lymphocytes Obviating the Need for Drug Selection", Blood 82(3):845-852 (1993).
Kyte et al, "A Simple Method for Displaying the Hydropathic Character of a Protein", J. Mol. Biol. 157:105-132 (1982).
Landt et al, "A general method for rapid site-directed mutagenesis using the polymerase chain reaction", Gene 96:125-128 (1990).
Lasalle et al, "An Adenovirus Vector for Gene Transfer into Neurons and Glia in the Brain", Science 259:988-990 (1993).

Lebkowski et al, "Adeno-Associated Virus: a Vector System for Efficient Introduction and Integration of DNA into a Variety of Mammalian Cell Types", Molecular and Cellular Biology 8(10):3988-3996 (1988).
Levrero et al, "Defective and nondefective adenovirus vectors for expressing foreign genes in vitro and in vivo", Gene 101:195-202 (1991).
Liu et al, "Chimeric mouse-human IgG1 antibody that can mediate lysis o f cancer cells", Proc. Natl. Acad. Sci. 84:3439-3443 (1987).
Loessner et al, "Evidence for a Holin-Like Protein Gene Fully Embedded Out of Frame in the Endolysin Gene of *Staphylococcus aureus* Bacteriophage 187", Journal of Bacteriology 181(15):4452-4460 (1999).
Lukashin et al, "GeneMark.hmm: new solutions for gene finding", Nucleic Acids Research 26(4):1107-1115 (1998).
Lukomski et al, "Extracellular Cysteine Protease Produced by *Streptococcus pyogenes* Participates in the Pathogenesis of Invasive Skin Infection and Dissemination in Mice", Infection and Immunity 67(4):1779-1788 (1999).
Lunn et al, "Effects of Prolipoprotein Signal Peptide Mutations on Secretion of Hybrid Prolipo-beta-lactamase in *Escherichia coli*", The Journal of Biological Chemistry 262(17):8318-8324 (1987).
Machy et al, "Gene transfer from targeted liposomes to specific lymphoid cells by electroporation", Proc. Natl. Acad. Sci. 85:8027-8031 (1988).
Madore, "Characterization of immune response as an indicator of Haemophilus influenzae type b vaccine efficacy", The Pediatric Infectious Disease Journal 17(9):Supplement:S207-S210 (1998).
Mann, et al, "Construction of a Retrovirus Packaging Mutant and Its Use to Produce Helper-Free Defective Retrovirus", Cell 33:153-159 (1983).
Markowitz et al, "A Safe Packaging Line for Gene Transfer: Separating Viral Genes on Two Different Plasmids", Journal of Virology 62(4):1120-1124 (1988).
Database Geneseq Online, "N. meningitidis NL096 fHBP protein fragment SEQ ID 76", XP002703350, Database accession No. AXQ90374, Nov. 26, 2009.
Database Geneseq Online, "Neisseria meningitidis modified fHBP fusion protein SEQ:140", XP002703351, Database accession No. AZG10689, Apr. 28, 2011.
Database Geneseq Online, "Neisseria meningitidis modified fHBP NL096 Seq:76", XP002703352,Database accession No. AZG10625, Apr. 28, 2011.
Database UniProt Online, "Subname: Full=Factor H binding protein variant A62_001; Subname: Full=Factor H binding protein variant A62_002; Flags: Fragment", XP002703353, Database accession No. COJF81, May 5, 2009.
Frankel et al, "Characterization of diphtheria fusion proteins targeted to the human interleukin-3 receptor", Protein Engineering 13(8):579-591 (2000).
GenBank No. EF108319.1, O'Leary, M.M. et al., Neisseria meningitidis strain NM452 FHBP/GNA1870 variant (GNA1870) gene, complete cds, Nov. 8, 2006, accessed Sep. 5, 2012.
NCBI GenBank: AC146791.12; "Medicago truncatula chromosome 8 clone mth2-123m17, complete sequence"; Sep. 17, 2010; accessed Jun. 3, 2014.
NCBI GenBank: AY330365.1; "Neisseria meningitidis strain CDC1492 factor H binding protein variant A22_001 (fhbp) gene, partial cds"; Mar. 12, 2009; accessed Jun. 3, 2014.
NCBI GenBank: AY330400.1; "Neisseria meningitidis strain M982 factor H binding variant B09_001 (fhbp) gene, partial cds"; Mar. 12, 2009; accessed Jun. 3, 2014.
NCBI GenBank: AY330401.1; "Neisseria meningitidis strain 880049 factor H binding protein variant B03_001 (fhbp) gene, partial cds"; Mar. 12, 2009; accessed Jun. 3, 2014.
NCBI GenBank: FJ184103.1; "Neisseria meningitidis factor H binding protein variant A12_001 (fhbp) gene, partial cds"; Aug. 4, 2009; accessed Jun. 3, 2014.
NCBI GenBank: FJ184126.1; "Neisseria meningitidis factor H binding protein variant B02_001 (fhbp) gene, partial cds"; Aug. 4, 2009; accessed Jun. 3, 2014.

(56) References Cited

OTHER PUBLICATIONS

NCBI GenBank: FJ184157.1; "Neisseria meningitidis factor H binding protein variant B44_001 (fhbp) gene, partial cds"; Aug. 4, 2009; accessed Jun. 3, 2014.

Prome et al. "Structure of the human adult hemoglobin minor fraction A1b by electrospray and secondary ion mass spectrometry. Pyruvic acid as amino-terminal blocking group." J Biol Chem. Jul. 15, 1991;266(20):13050-4.

Prome et al. "Characterization of new amino-terminal blocking groups in the normal human adult hemoglobin Hb A1b," Eur. Mass Spectrom. vol. 1 Issue 2: 195-201 (1995). Received Feb. 5, 1995; Accepted Mar. 28, 1995.

Rose et al., "Pyruvic acid is attached through its central carbon atom to the amino terminus of the recombinant DNA-derived DNA-binding protein Ner of bacteriophage Mu." J Biol Chem. Sep. 25, 1992;267(27):19101-6.

Sankaran, K., et al., "Lipid Modification of Bacterial Prolipoprotein", The Journal of Biological Chemistry, 269 (31):19701-19706 (1994).

University of Oklahoma—Neisseria gonorrhoeae webpage to retrieve genome [online] URL: http://dna1.chem.ou.edu/gono.html, Apr. 5, 2004, accessed Aug. 3, 2012.

Adacel Prescribing information, http://www.fda.gov/downloads/biologicsbloodvaccines/vaccines/approvedproducts/umc142764.pdf, "Revised: [XX/201X]", accessed Feb. 14, 2015.

Budroni, S. et al., "Neisseria Meningitidis is Structured in Clades Associated with Restriction Modification Systems that Modulate Homologous Recombination", PNAS, Mar. 15, 2011,108 (11): 4494-4499 and supporting information pp. 1-17.

Cheetham, et al., "An HPLC Method for the Determination of Acetyl and Pyruvyl Groups in Polysaccharides, Carbohydrade Polymers", School of Chemistry, The University of New South Wales, Dec. 1985, 5 (6): 399-406.

Database Uniprot [Online] Jul. 4, 2004, "SubName: Full=Factor H binding protein variant A05_001";Flags: =Fragment, retrieved from EBI; UNIPROT database accession No. Q6VS29; Database entry from Oct. 28, 2014, entry version 29, sequence version 1See strains Neisseria meningitidis M98-250732 & M98250771.

Database Uniprot [Online] Jul. 5, 2004, "Factor H binding protein variant A22_001"; Flags: Fragment, retrieved from EBI; UNIPROT database accession No. Q6VS35; Database entry from Oct. 28, 2014, entry version 28, sequence version 2 updated on Sep. 23, 2008 See strains Neisseria meningitidis: CDC-1034 and L4-891.

Farley, J., et al. poster entitled "Characterization, Cloning and Expression of Different Subfamlies of the ORF 2086 jene Neisseria Meningitidis", presented at the Thirteenth International Pathogenic Neisseria Conference (the 'IPNC Oslo 2002'), hosted at the Norwegian Institute of Public Health, Oslo, Norway between Sep. 1, 2002 and Sep. 6, 2002, as evidenced by photographs and transcript thereof.

Fredriksen, J.H., et al, "Production, Characterization and Control of MenB-vaccine "Folkehelsa": an Outer Membrane Vesicle Vaccine Against Group B Meningococcal Disease", NIPH Annals, 1991, 14 (2): 67-79.

Gil, J., et al., Proteomic Study via a Non-Gel Based Approach of Meningococcal Outer Membrane Vesicle Vaccine Obtained from Strain CU385 Human Vaccines, 2009, 5 (5): 347-356.

Havrix prescribing information, https://www.gsksource.com/pharma/content/dam/GlaxoSmithKline/US/en/Prescribing_information/Havrix/pdf/Havrix.PDF, revised Jul. 2014, accessed Feb. 18, 2015.

Hedari, et al., Meningococcal Serogroups A, C, W-135, and Y Tetanus Toxoid Conjugate Vaccine: A New Conjugate Vaccine Against Invasive Meningococcal Disease., Infect Drug Resist. Apr. 3, 2014;7:85-99.

Menactra prescribing information, http://www.fda.gov/downloads/BiologicsBloodVaccines/Vaccines/ApprovedProducts/UCM131170.pdf, revised Aug. 26, 2014, accessed Feb. 14, 2015.

Menactra, Australian Public Assessment Report for Groups A, C, Y and W-135 Meningococcal Polysaccharide Diphtheria Toxoid Conjugate Vaccine, https://www.tga.gov.au/file/1277/download , Aug. 31, 2011, accessed Feb. 13, 2015 (part 1 and 2).

Mencevax, New Zealand data sheet, http://www.medsafe.govt.nz/profs/datasheet/m/Mencevaxacwyinj.pdf, date of preparation Mar. 25, 2014, accessed Feb. 14, 2015.

Menveo Package insert, http://www.fda.gov/downloads/BiologicsBloodVaccines/Vaccines/ApprovedProducts/UCM201349.pdf, accessed Feb. 19, 2015, revised Aug. 2013.

Nimenrix product monograph, gsk.com/media/673251/nimenrix.pdf, accessed Feb. 19, 2015, date of revision Jan. 9, 2015.

Nimenrix product monograph, http://webprod5.hc-sc.gc.ca/dpd-bdpp/item-iteme.do?pm-mp=00033642, accessed Mar. 2016. Date of revision Nov. 9, 2015.

Okuda et al, Lipoprotein sortingin bacteria, Annu. Rev. Microbiol., 65:239-259 (2011).

Opposition documents (part 1 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 2) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 3) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 4) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 5) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 6) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 7) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 8) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 9) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Dpposition documents (part 10) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Opposition documents (part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.

Registration document for VA-MENGOC-BC® Vaccine Together with Translation Into English and Translation Certificate.

Resinger, et al., "Safety, Tolerability, and Immunogenicity of Gardasil Given Concomitantly with Menactra and Adacel" Pediatrics, Jun. 2010; 125 (6):1142-1151.

Rodriguez, A.P., et al., "The Epidemiological Impact of Antimeningococcal B Vaccination in Cuba", Mem Inst Oswaldo Cruz, Jul.-Aug. 1999, 94 (4): 433-440.

Rosenqvist, E., et al., "Effect of Aluminium Hydroxide and Meningococcal Serogroup C Capsular Polysaccharide on the Immunogenicity and Reactogenicity of a Group B Neisseria Meningitides Outer Membrane Vesicle Vaccine", Dev Biol Stand, 1998, 92: 323-333.

(56) References Cited

OTHER PUBLICATIONS

Rosenqvist et al, "Human Antibody Responses to Meningococcal Outer Membrane Antigens after Three Doses of the Norwegian Group B Meningococcal Vaccine", Infection and Immunity, 1995, 63(12): 4642-4652.
Sierra, G.V.G., et al.,"Vaccine Against Group B Neisseria Meningitidis: Protection Trial and Mass Vaccination Results in Cuba" NIPH Annals, 1991, 14 (2): 195-210.
Witze et al., Mapping Protein Post-Translational Modifications with Mass Spectrometry, Nat Methods, Oct. 2007; 4(10): 798-806.
*GlaxoSmithKline UK Ltd v Wyeth Holdings LLC* [2016] EWHC 1045 (Ch) (May 12, 2016); Case No. HP-2015-000002; 66 pages; accessed http://www.bailii.org/ew/cases/EWHC/Ch/2016/1045.html on Jul. 11, 2016.
Koeberling, et al., "Bactericidal Antibody Responses Elicited by a Meningococcal Outer Membrane Vesicle Vaccine with Overexpressed Factor H-Binding Protein and Genetically Attenuated Endotoxin", The Journal of Infectious Diseases, Jul. 2008, 198:262-70.
Moe, et al., "Sequential Immunization with Vesicles Prepared from Heterologous Neisseria meningitidis Strains Elicits Broadly Protective Serum Antibodies to Group B Strains", Infection and Immunity, Nov. 2002, 70:11, 6021-6031.
Opposition papers EP2343308 May 2-9, 2016; 274 pages; accessed https://register.epo.org/application?number=EP10183020&Ing=en&tab=doclist on May 16, 2016.
Opposition papers EP2343308 Apr. 6-13, 2016; 30 pages; accessed https://register.epo.org/application?number=EP10183020&Ing=en&tab=doclist on May 16, 2016.
Opposition notice EP2343308_(Nov. 13, 2015); 21 pages; accessed https://register.epo.org/application?number=EP10183020&Ing=en&tab=doclist on Apr. 21, 2016.
Sierra, et al., "Vaccine Against Group B Neisseria Meningitidis: Protection Trial and Mass Vaccination Results in Cuba", NIPH Annals, Dec. 1991, 14:2, 195-210.
Uli, et al., "Outer Membrane Vesicles of VA-MENGOC-BC Vaccine Against Serogroup B of Neisseria Meningitidis: Analysis of Protein Components by Two-Dimensional Gel Electrophoresis and Mass Spectrometry", Proteomics, 2006, 6, 3389-3399.
Sonnenberg et al, "Definition of *Mycobacterium tuberculosis* Culture Filtrate Proteins by Two-Dimensional Polyacrylamide Gel Electrophoresis, N-Terminal Amino Acid Sequencing, and Electrospray Mass Spectrometry", Infection and Immunity 65(11):4515-4524 (1997).
Sonnhammer et al, "Pfam: A Comprehensive Database of Protein Domain Families Based on Seed Alignments", Proteins: Structure, Function, and Genetics 28:405-420 (1997).
Stedman's Medical Dictionary, Illustrated, 24th Edition, Williams & Wilkins, Baltimore, Maryland, p. 707 (1982).
Stevens, "Streptococcal Toxic-Shock Syndrome: Spectrum of Disease, Pathogenesis, and New Concepts in Treatment", Emerging Infectious Diseases 1(3):69-78 (1995).
Stockbauer et al, "A natural variant of the cysteine protease virulence factor of group A *Streptococcus* with an arginine-glycine-aspartic acid (RGD) motif preferentially binds human integrins alphavbeta3 and alphaIIbbeta3", Proc. Natl. Acad. Sci. 96:242-247 (1999).
Stratford-Perricaudet et al, "Widespread Long-term Gene Transfer to Mouse Skeletal Muscles and Heart", J. Clin. Invest. 90:626-630 (1992).
Strauss, "Using DNA Fragments as Probes", Current Protocols in Molecular Biology, Supp. 24, 6.3.1-6.3.6 (1993).
Sun et al, "Chimeric antibody with human constant regions and mouse variable regions directed against carcinoma-associated antigen 17-1A", Proc. Natl. Acad. Sci. 84:214-218 (1987).
Supplementary Declaration by Dr. Julian Parkhill submitted in Opposition Proceedings against Novartis EP1645631 on May 10, 2010.
Supplementary Submission in Opposition Proceedings against Novartis EP 1 645 631 submitted May 25, 2010.
Sutcliff et al, "Lipoproteins of Gram-Positive Bacteria", Journal of Bacteriology 177(5):1123-1128 (1995).
Sworn Statement from Dr. Rino Rappuoli submitted in Opposition Proceedings against Novartis EP1645631 on Oct. 14, 2011.
Sworn Statement from Dr. Giovanna Campanella submitted in Opposition Proceedings against Novartis EP1409013 on Nov. 10, 2011.
Tappero et al, "Immunogenicity of 2 Serogroup B Outer-Membrane Protein Meningococcal Vaccines", JAMA 281 (16):1520-1527 (1999).
Tarkka et al, "Antibody production to a meningococcal outer membrane protein cloned into live *Salmonella typhimurium* aroA vaccine strain", Micrb. Pathogen 6:327-335 (1989).
Telford et al., "Chapter 1: Genomics and Proteomics in Vaccine Design", New Bacterial Vaccines, Kleweur Academic/Plenum Publishers, USA, pp. 1-11 (2003).
Tettelin et al, "Complete Genome Sequence of Neisseria meningitidis Serogroup B Strain MC58", Science 287:1809-1815 (2000).
Ton-That et al, "Purification and characterization of sortase, the transpeptidase that cleaves surface proteins of *Staphylococcus aureus* at the LPXTG motif", Proc Natl Acad Sci 96(22):12424-12429 (1999).
Tondella et al, "Distribution of Neisseria meningitidis Serogroup B Serosubtypes and Serotypes Circulating in the United States", Journal of Clinical Microbiology 38(9):3323-3328 (2000).
Ulmer et al, "Heterologous Protection Against Influenza by Injection of DNA Encoding a Viral Protein", Science 259:1745-1748 (1993).
U.S. Pat. No. 8,398,988 B2 Prosecution History (Feb. 23, 2012-Feb. 27, 2013).
Van Der Ende et al, "Multiple Mechanisms of Phase Variation of PorA in Neisseria meningitidis", Infection and Immunity 68(12):6685-6690 (2000).
Van Der Ende, A., et al., "Deletion of porA by Recombination between Clusters of Repetitive Extragenic Palindromic Sequences in Neisseria meningitidis", Infection and Immunity, 67(6):2928-2934 (1999).
Van Der Ley et al., "Construction of Neisseria meningitidis Strains Carrying Multiple Chromosomal Copies of the porA gene for Use in the production of a Multivalent Outer Membrane Vesicle Vaccine", Vaccine 13(4):401-407 (1995).
Wahl et al, "Improved Radioimaging and Tumor Localization with Monoclonal F(ab')2", J Nucl Med 24:316-325 (1983).
Webster's II New Riverside University Dictionary, The Riverside Publishing Company, p. 933 (1984).
Weldingh et al, "Two-Dimensional Electrophoresis for Analysis of *Mycobacterium tuberculosis* Culture Filtrate and Purification and Characterization of Six Novel Proteins", Infection and Immunity 66(8):3492-3500 (1998).
Welsch et al, "Protective Activity of Monoclonal Antibodies to Genome-Derived Neisserial Antigen 1870, a Neisseria meningitidis Candidate Vaccine", The Journal of Immunology 172:5606-5615 (2004).
Williams et al, "Introduction of foreign genes into tissues of living mice by DNA-coated microprojectiles", Proc. Natl. Acad. Sci. 88:2726-2730 (1991).
Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).
Wolff et al, "Direct Gene Transfer into Mouse Muscle in Vivo", Science 247:1465-1468 (1990).
Woods et al., "Resistance to Meningococcemia Apparently Conferred by Anti-H.8 Monoclonal Antibody Is Due to Contaminating Endotoxin and Not to Specific Immunoprotection", Infection and Immunity 55(8):1927-1928 (1987).
Wu et al, "Receptor-mediated in Vitro Gene Transformation by a Soluble DNA Carrier System", The Journal of Biological Chemistry 262(10):4429-4432 (1987).
Wu et al, "Receptor-mediated Gene Delivery and Expression in Vivo", The Journal of Biological Chemistry 263 (29):14621-14624 (1988).

(56) References Cited

OTHER PUBLICATIONS

Yakushi et al, "Lethality of the Covalent Linkage between Mislocalized Major Outer Membrane Lipoprotein and the Peptidoglycan of *Escherichia coli*", Journal of Bacteriology 179(9):2857-2862 (1997).
Yakushi et al, "A new ABC transporter mediating the detachment of lipid-modified proteins from membranes", Nature Cell Biology 2:212-218 (2000).
York, "Pfizer's Investigational Vaccine, rLP2086, for Invasive Meningococcal Serogroup B Disease", Sabin Vaccine Institute, http://www.sabin.org/sites/sabin.org/files/Laura%20J%20York.pdf, accessed Aug. 1, 2014.
Yutsudo et al, "The Gene Encoding a New Mitogenic Factor in a *Streptococcus pyogenes* Strain Is Distributed Only in Group A Streptococci", Infection and Immunity 62(9):4000-4004 (1994).
Zagursky et al, "Bioinformatics: Use in Bacterial Vaccine Delivery", BioTechniques 31(3):636-659 (2001).
Zavascki et al, "First Case Report of Neisseria lactamica Causing Cavitary Lung Disease in an Adult Organ Transplant Recipient", Journal of Clinical Microbiology 44(7):2666-2668 (2006).
Zollinger, "New and Improved Vaccines Against Meningococcal Disease", New Generation Vaccines, 2nd Ed., Myron M. Levine, et al. eds., Marcel Dekker, Inc., New York, NY pp. 469-488 (1997).
Zufferey et al, "Self-Inactivating Lentivirus Vector for Safe and Efficient In Vivo Gene Delivery", Journal of Virology 72(12):9873-9880 (1998).
Aasel et al., "Most antibodies to PorB and Rmp do not bind to viable meningococci, but bind strongly to ethanol-killed bacteria", Abstract from the 11th International Pathogenic Neisseria Conference (Nice France, Nov. 1-6, 1998), pp. 37-38 (http://neisseria.org/ipnc/history.shtml).
Abdillahi et al, "Whole-cell ELISA for typing Neisseria meningitidis with monoclonal antibodies", FEMS Microbiology Letters 48:367-371 (1987).
Abdillahi et al, "Neisseria meningitidis group B serosubtyping using monoclonal antibodies in whole-cell Elisa", Microbial Pathogenesis 4:27-32 (1988).
Achtman, "Epidemic spread and antigenic variability of Neisseria meningitidis", Trends in Microbiology 3(5):186-192 (1995).
Alm et al, "Genomic-sequence comparison of two unrelated isolates of the human gastric pathogen Helicobacter pylori", Nature 397:176-180 (1999).
Altschul et al, "Basic Local Alignment Search Tool", J. Mol. Biol. 215:403-410 (1990).
Altschul et al, "Protein database searches for multiple alignments", Proc. Natl. Acad. Sci. 87:5509-5513 (1990).
Altschul et al, "Gapped BLAST and PSI-BLAST: a new generation of protein database search programs", Nucleic Acids Research 25(17): 3389-3402 (1997).
Ambrosch et al, "Immunogenicity and side-effects of a new tetravalent meningococcal polysaccharide vaccine", Bulletin of the World Health Organization 61(2):317-323 (1983).
Andersen, et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).
Anderson, "Techniques for the preservation of three-dimensional structure in preparing specimens for the electron microscope", Transactions of the New York Academy of Sciences, 13:130-134 (1951).
Anderson et al; "Potential Impact of the Bivalent rLP2086 Vaccine on Neisseria meningitidis Invasive Disease and Carriage Isolates in Two Adolescent Populations"; poster presented at the 30th Annual Meeting of the European Society for Paediatric Infectious Diseases; May 8-12, 2012; Thessaloniki, Greece; http://epostersonline.s3.amazonaws.com/espid2012/espid2012.02400cf.NORMAL.pdf, May 12, 2012.
Bantam Medical Dictionary, Third Edition, pp. 302-303 (2000).
Barbour et al, "New tricks of tick-borne pathogen", Nature 390:553 & 555 (1997).
Bateman et al, "The Pfam Protein Families Database", Nucleic Acids Research 28(1):263-266 (2000).
Beard et al, "Transcription Mapping of Mouse Adenovirus Type 1 Early Region 3", Virology 175:81-90 (1990).
Beernink, P.T., et al., "The modular architecture of meningococcal factor H-binding protein", Microbiology, 155:2873-2883 (2009).
Bender et al, "Evidence that the Packaging Signal of Moloney Murine Leukemia Virus Extends into the gag Region", Journal of Virology 61(5):1639-1646 (1987).
Benson, "Tandem repeats finder: a program to analyze DNA sequences", Nucleic Acids Research 27(2):573-580 (1999).
Bernfield et al., "Identification of a novel vaccine candidate for group B Neisseria meningitidis", Abstracts of the Thirteenth International Pathogenic Neisseria Conference, (Ed) Caugant et al. Oslo, Norway, p. 116, Sep. 1-6, 2002.
Bernstein et al, "Gene Transfer with Retrovirus Vectors", Genet. Eng. 7:235-261 (1985).
Better et al, *Escherichia coli* Secretion of an Active Chimeric Antibody Fragment, Science 240:1041-1043 (1988).
Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).
Beuvery et al, "Preparation and Physicochemical and Immunological Characterization of Polysaccharide-Outer Membrane Protein Complexes of Neisseria meningitidis", Infection and Immunity 40(1):369-380 (1983).
Biocomputing: Informatics and Genome Projects, Smith D.W., ed., Academic Press, New York (1994).
Bjune, et al., "Effect of Outer Membrane Vesicle Vaccine Against Group B Meningococcal Disease in Norway", The Lancet, 338(8775):1093-1096 (1991).
Boslego et al, "Chapter 17: Gonorrhea Vaccines", Vaccines and Immunotherapy, SJ Cryz Jr. ed., Pergamon Press, pp. 211-223 (1991).
Boulianne et al, "Production of functional chimaeric mouse/human antibody", Nature 312:643-646 (1984).
Brown, "Hybridization Analysis of DNA Blots", Current Protocols in Molecular Biology, Supp. 21, 2.10.1-2.10.16 (1993).
Cabilly et al, "Generation of antibody activity from immunoglobulin polypeptide chains produced in *Escherichia coli*", Proc. Natl. Acad. Sci. 81:3273-3277 (1984).
Callahan, P.M., et al., "The Importance of Surface Charge in the Optimization of Antigen-Adjuvant Interactions", Pharmaceutical Research, 8(7):851-858 (1991).
Cannon, "Conserved Lipoproteins of Pathogenic Neisseria Species Bearing the H.8 Epitope: Lipid-Modified Azurin and H.8 Outer Membrane Protein", Clinical Microbiology Reviews 2(Suppl):S1-S4 (1989).
Cantini et al, "Solution Structure of the Immunodominant Domain of Protective Antigen GNA1870 of Neisseria meningitidis", The Journal of Biological Chemistry 281(11):7220-7227 (2006).
Carillo et al, "The Multiple Sequence Alignment Problem in Biology", SIAM J. Appl. Math. 48(5):1073-1082 (1988).
Chao et al, "Endocarditis due to Neisseria sicca: Report of One Case", Acta Paed Sin 38(3):229-231 (1997).
Chen et al, "Cloning and Expression of the Streptococcal C5a Peptidase Gene in *Escherichia coli*: Linkage to the Type 12 M Protein Gene", Infection and Immunity 57(6):1740-1745 (1989).
Chen et al., "Determination of the Optimal Aligned Spacing Between the Shine—Dalgarno Sequence and the Translation Initiation Codon of *Escherichia coli* mRNAs", Nucleic Acids Research 22(23):4953-4957 (1994).
Chmouryguina et al, "Conservation of the C5a Peptidase Genes in Group A and B Streptococci", Infection and Immunity 64(7):2387-2390 (1996).
Cockerill et al, "Molecular, Serological, and Clinical Features of 16 Consecutive Cases of Invasive Streptococcal Disease", Clinical Infectious Diseases 26:1448-1458 (1998).
Computational Molecular Biology: Sources and Methods for Sequence Analysis, Lesk A.M. et., Oxford University Press, New York, 1988.

(56) References Cited

OTHER PUBLICATIONS

Courtney et al, "Cloning, Sequencing, and Expression of a Fibronectin/Fibrinogen-Binding Protein from Group A Streptococci", Infection and Immunity 62(9):3937-3946 (1994).
Cserzo et al, "Prediction of transmembrane alpha-helices in prokaryotic membrane proteins: the dense alignment surface method", Protein Engineering 10(6):673-676 (1997).
Cunningham et al, "Immunological Crossreactivity Between the Class I Epitope of Streptococcal M Protein and Myosin", Adv Exp Med Biol 418:887-892 (1997).
Curiel et al, "High-Efficiency Gene Transfer Mediated by Adenovirus Coupled to DNA-Polylysine Complexes", Human Gene Therapy 3:147-154 (1992).
Curriculum Vitae of Professor Paul M. Dunman, Ph.D., submitted in Opposition Proceedings against Novartis EP 1 645 631 on Sep. 14, 2011.
Curriculum Vitae of Lakshmi Khandke, Ph.D., submitted in Opposition Proceedings against Novartis EP1409013 on Nov. 18, 2011.
Dale et al, "Passive Protection of Mice Against Group A Streptococcal Pharyngeal Infection by Lipoteichoic Acid", The Journal of Infectious Diseases 169:319-323 (1994).
Dale et al, "Hyaluronate Capsule and Surface M Protein in Resistance to Opsonization of Group A Streptococci", Infection and Immunity 64(5):1495-1501 (1996).
Dale et al, "Recombinant, octavalent group A streptococcal M protein vaccine", Vaccine 14(10):944-948 (1996).
Database EMBL [Online] EBI, Kohara, Y., "Caenorhabditis elegans cDNA clone yk26f2: 5' end, single read," Database accession No. D35881 (Aug. 13, 1994).
Perrett et al, "Towards an improved serogroup B Neisseria meningitidis vaccine", Expert Opin. Biol. Ther. 5 (12):1611-1625 (2005).
Pettersson, et al., "The meningococcal lactoferrin receptor", IPNC Abstract (1998).
Pettersson et al., "Vaccine potential of the Neisseria meningitidis Lactoferrin-binding Proteins LbpA and LbpB", Vaccine, 24(17):3545-3557 (2006).
Phase II clinical results for Novartis vaccine, Novartis Media Release (Oct. 9, 2008).
Phillips, "The challenge of gene therapy and DNA delivery", Journal of Pharmacy and Pharmacology 53:1169-1174 (2001).
Pierschbacher et al, "Influence of Stereochemistry of the Sequence Arg-Gly-Asp-Xaa on Binding Specificity in Cell Adhesion", The Journal of Biological Chemistry 262(36):17294-17298 (1987).
Pizza et al, "Identification of Vaccine Candidates Against Serogroup B Meningococcus by Whole-Genome Sequencing", Science 287:1816-1820 (2000).
Pizza, Preparation of Meningococcal Antigens (2005), available at: http://cordis.europa.eu/search/index.cfm?fuseaction=result.document&RS LANG=EN&RS RCN=7461241&q=.
Podbielski et al, "The Group A Streptococcal virR49 Gene Controls Expression of Four Structural vir Regulon Genes", Infection and Immunity 63(1):9-20 (1995).
Pollitt et al, "Effect of Amino Acid Substitutions at the Signal Peptide Cleavage Site of the Escherichia coli Major Outer Membrane Lipoprotein", The Journal of Biological Chemistry 261(4):1835-1837 (1986).
Poolman et al, "Colony variants of Neisseria meningitidis strain 2996 (B-2b:P1.2): influence of class-5 outer membrane proteins and lipopolysaccharides", J Med Microbiol 19(2):203-209 (1985).
Poolman, "Development of a meningococcal vaccine," Infectious Agents and Disease 4(1):13-28 (1995).
Poolman, "Bacterial Outer Membrane Protein Vaccines: The Meningococcal Example", Advances in Experimental Medicine & Biology 397:73-77 (1996).
Preliminary Opinion of the Opposition Division in Opposition against Novartis EP 1 645 631 dated Jun. 24, 2011.
Proft et al, "Identification and Characterization of Novel Superantigens from Streptococcus pyogenes", J. Exp. Med. 189(1):89-101 (1999).
Progress through the Sanger Institute FTP Server, submitted in Opposition Proceedings against Novartis EP1645631 on May 8, 2009.
Prosecution history of U.S. Appl. No. 13/455,326, dated Apr. 26, 2013.
PSORT analysis of 200 of the sequences disclosed in PCT/US99/09346, submitted in Opposition Proceedings against Novartis EP1645631 on May 25, 2010.
PSORT analysis of SEQ ID Nos. 4 and 6, and of 'Contig295' 300mer, submitted in Opposition Proceedings against Novartis EP1645631 on May 8, 2009.
PSORT prediction result for SEQ ID No. 2, submitted in Opposition Proceedings against Novartis EP1645631 on May 25, 2010.
Pugsley, "The Complete General Secretory Pathway in Gram-Negative Bacteria", Microbiological Reviews 57 (1):50-108 (1993).
Quinn et al, "Immunological Relationship between the Class I Epitope of Streptococcal M Protein and Myosin", Infection and Immunity 66(9):4418-4424 (1998).
Random House Dictionary, Random House, New York, p. 546 (1984).
Reda et al, "Phylogenetic Distribution of Streptococcal Superantigen SSA Allelic Variants Provides Evidence for Horizontal Transfer of ssa within Streptococcus pyogenes", Infection and Immunity 64(4):1161-1165 (1996).
Rinaudo et al, "Vaccinology in the genome era", The Journal of Clinical Investigation, 119(9):2515-2525 (2009).
Romero et al, "Current Status of Meningococcal Group B Vaccine Candidates: Capsular or Noncapsular?" Clinical Microbiology Reviews 7(4):559-575 (1994).
Rosenqvist et al, "Human Antibody Responses to Meningococcal Outer Membrane Antigens after Three Doses of the Norwegian Group B Meningococcal Vaccine", Infection and Immunity 63(12):4642-4652 (1995).
Rosenstein et al, "Meningococcal Vaccines", Infectious Disease Clinics of North America 15(1):155-169 (2001).
Ross, et al., "Identification of Vaccine Candidate Antigens from a Genomic Analysis of Porphyromonas gingivalis", Vaccine 19:4135-4142 (2001).
Sahagan et al, "A Genetically Engineered Murine/Human Chimeric Antibody Retains Specificity for Human Tumor-Associated Antigen", The Journal of Immunology 137(3):1066-1074 (1986).
Salzberg et al, "Microbial gene identification using interpolated Markov models", Nucleic Acids Research 26 (2):544-548 (1998).
Sambrook et al, "Analysis and Cloning of Eukaryotic Genomic DNA", Molecular Cloning: A Laboratory Manual, Second Edition, Cold Spring Harbor Laboratory Press, Cold Spring Harbor, New York, Chapter 9, pp. 9.1-9.62 (1989).
Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).
Sambrook et al, Molecular Cloning: A Laboratory Manual, Third Edition, Cold Spring Harbor Laboratory Press, Cold Spring Harbor, New York (2001).
Samulski et al, "A Recombinant Plasmid from Which an Infectious Adeno-Associated Virus Genome Can Be Excised In Vitro and Its Use to Study Viral Replication", Journal of Virology 61(10):3096-3101 (1987).
Samulski et al, "Helper-Free Stocks of Recombinant Adeno-Associated Viruses: Normal Integration Does Not Require Viral Gene Expression", Journal of Virology 63(9):3822-3828 (1989).
Sanger Centre FTP files [online] URL: ftp://ftp.sanger.ac.uk/pub/pathogens/nm/, dated Jul. 23, 2008.
Sanger Centre's "Projects" website as of Dec. 10, 1997 as retrievable via http://web.archive.org, accessed Mar. 15, 2010.
Sankaran et al, "Modification of Bacterial Lipoproteins", Methods in Enzymology 250:683-697 (1995).
Saukkonen et al, "Protective efficacy of monoclonal antibodies to class 1 and class 3 outer membrane proteins of Neisseria meningitidis B:15:P1.16 in infant rat infection model: new prospects for vaccine development", Microbial Pathogenesis 3:261-267 (1987).

(56) References Cited

OTHER PUBLICATIONS

Sedegah et al, "Protection against malaria by immunization with plasmid DNA encoding circumsporozoite protein", Proc. Natl. Acad. Sci. 91:9866-9870 (1994).
Sedegah et al, "Improving Protective Immunity Induced by DNA-Based Immunization: Priming with Antigen and GM-CSF-Encoding Plasmid DNA and Boosting witih Antigen-Expressing Recombinant Poxvirus", The Journal of Immunology 164:5905-5912 (2000).
Sepelyak et al, "Adsorption of Pepsin by Aluminum Hydroxide I: Adsorption Mechanism", Journal of Pharmaceutical Sciences 73(11):1514-1517 (1984).
Sequence Analysis Primer, Gribskov and Devereux, eds., M Stockton Press, New York 1991.
Sequence Analysis in Molecular Biology. Treasure Trove or Trivial Pursuit, Gunnar von Heijne, Academic Press (1987).
Sequence for "Putative Lipoprotein [Neisseria Meningitidis Z2491]", NCBI Reference Sequence:YP_002342062.1, dated May 6, 2009, accessed Aug. 4, 2009.
Serruto et al, "Genome-based approaches to develop vaccines against bacterial pathogens", Vaccine 27:3245-3250 (2009).
Smith et al., "Nucleotide sequence determination and genetic analysis of the bacteroides plasmid, pBl143," Plasmid 34(3):211-222 (1995).
Snapper et al, "Bacterial Lipoproteins May Substitute for Cytokines in the Humoral Immune Response to T Cell-Independent Type II Antigens", The Journal of Immunology 155:5582-5589 (1995).
Snapper et al, "IL-3 and Granulocyte-Macrophage Colony-Stimulating Factor Strongly Induce Ig secretion by Sort-Purified Murine B Cells Activated Through the Membrane Ig, but Not the CD40, Signaling Pathway", The Journal of Immunology 154:5842-5850 (1995).
Database Geneseq 'Online', "Neisseria meningitidis ORF 741 protein sequence SEQ ID No. 2536", XP002320506, Mar. 21, 2000.
Database Geneseq 'Online', "N. gonorrhoeae amino acid sequence SEQ ID 1586", XP002320505, Mar. 7, 2003.
Database Geneseq Online, "Neisseria meningitides ORF2086 protein-encoding gene SedID61" AAY75530, Jan. 29, 2004.
Database Geneseq Online, "Neisseria meningitides ORF2086 protein-encoding gene SedID61" AAZ54292-NT, Jan. 29, 2004.
Database UniPro 'Online', "Hypothetical Protein NMB1870", XP002308111, Oct. 1, 2000.
Database UniProt 'Online', "Putative lipoprotein N meningitidis (Serotype A)", XP002320503, Oct. 1, 2000.
Datasheet for MENCEVAX™, International Data Sheet version 2.1 (May 15, 2000).
Datasheet for MENOMUNE™, product information as of Feb. 2001.
Datasheet for MeNZB® vaccine product prepared Jun. 23, 2009.
De et al, "Purification and characterization of *Streptococcus pneumoniae* palmitoylated pneumococcal surface adhesin A expressed in *Escherichia coli*", Vaccine 18:1811-1821 (2000).
Declaration by Dr. Julian Parkhill, submitted in Opposition Proceedings against Novartis EP1645631 on Jul. 23, 2008.
Declaration of Dr. Ellen Murphy, submitted in Opposition Proceedings against Novartis EP 1 645 631 on Sep. 14, 2011.
Declaration by Professor Paul Dunman, submitted in Opposition Proceedings against Novartis EP1645631 on Sep. 14, 2011.
Declaration of Emilio A. Emini, Ph.D., submitted in Opposition Proceedings against Novartis EP1645631 on Nov. 3, 2011.
Declaration of Lakshmi Khandke, Ph.D., submitted in Opposition Proceedings against Novartis EP1409013 on Dec. 21, 2011.
Definition of "epitope" from Henderson's Dictionary of Biological Terms, 11th edition, Eleanor Lawrence ed., pp. 37, 184 and cover pages (1997).
Delgado et al., "Lipoprotein NMB0928 from Neisseria meningitidis Serogroup B as a Novel Vaccine Candidate", Vaccine 25:8420-8431 (2007).
Dempsey et al., "The physical map of the chromosome of a serogroup A strain of Neisseria meningitidis shows complex rearrangements relative to the chromosomes of the two mapped strains of the closely related species N. gonorrhoeae," Journal of Bacteriology 177(22):6390-6400 (1995).
Devereux et al, "A comprehensive set of sequence analysis programs for the VAX", Nucleic Acids Research 12 (1):387-395 (1984).
Duby et al, "Using Synthetic Oligonucleotides as Probes", Current Protocols in Molecular Biology, Supp. 2, 6.4.1-6.4.10 (1993).
Eddy, "Hidden Markov models", Current Opinion in Structural Biology 6:361-365 (1996).
Ellen et al, "M Protein-Associated Adherence of *Streptococcus pyogenes* to Epithelial Surfaces: Prerequisite for Virulence", Infection and Immunity 5(5):826-830 (1972).
Ellis, "New Technologies for Making Vaccines", Vaccines, Plotkin et al. editors, W.B. Saunders Company, Philadelphia, Chapter 29, pp. 568-575 (1988).
Eng et al, "An Approach to Correlate Tandem Mass Spectral Data of Peptides with Amino Acid Sequences in a Protein Database", J Am Soc Mass Spectrom 5:976-989 (1994).
EP Application No. 07075161.5 Response to Communication submitted Oct. 28, 2009.
Erdile et al, "Role of Attached Lipid in Immunogenicity of Borrelia burgdorferi OspA", Infection and Immunity 61 (1):81-90 (1993).
Farley et al., "Characterization, cloning and expression of different subfamilies of the ORF2086 gene from Neisseria meningitidis", Abstracts of the Thirteenth International Pathogenic Neisseria Conference, (Ed) Caugant et al., Oslo, Norway, p. 124, Sep. 1-6, 2002.
Feavers et al, "Meningococcal protein antigens and vaccines", Vaccine 275:B42-B50 (2009).
Felgner et al, "Lipofection: A highly efficient, lipid-mediated DNA-transfection procedure", Proc. Natl. Acad. Sci. 84:7413-7417 (1987).
Felgner et al, "Cationic liposome-mediated transfection", Nature 337:387-388 (1989).
Final Written Submission in Preparation of Oral Proceedings in Opposition against Novartis EP 1 645 631 submitted Sep. 14, 2011.
Fischetti et al, "Conservation of a hexapeptide sequence in the anchor region of surface proteins from Gram-positive cocci", Molecular Microbiology 4(9):1603-1605 (1990).
Fleischmann et al, "Whole-Genome Random Sequencing and Assembly of Haemophilus influenzae Rd", Science 269:496-501 (1995).
Fletcher et al, "Vaccine Potential of the Neisseria meningitidis 2086 Lipoprotein", Infection and Immunity 72 (4):2088-2100 (2004).
Fogg et al, "Constitutive Expression of Fibronectin Binding in *Streptococcus pyogenes* as a Result of Anaerobic Activation of rofA", Journal of Bacteriology 179(19):6172-6180 (1997).
Fontana et al, "A genomic approach to identify vaccine candidates against gonococcus", Abstract from the 13th International Pathogenic Neisseria Conference, Oslo Norway, Sep. 1-6 2002, p. 248 (http://neisseria.org/ipnc/history.shtml).
Foster et al, "Surface protein adhesins of *Staphylococcus aureus*", Trends in Microbiology 6(12):484-488 (1998).
Fraser et al, "Genomic sequence of a Lyme disease spirochaete, Borrelia burgdorferi", Nature 390:580-591 (1997).
Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).
Fukasawa et al, "Neisseria meningitidis serogroup C polysaccharide and serogroup B outer membrane vesicle conjugate as a bivalent meningococcus vaccine candidate", Vaccine 17:2951-2958 (1999).
Gentz et al, "Bioassay for trans-activation using purified human immunodeficiency virus tat-encoded protein: Trans-activation requires mRNA synthesis", Proc. Natl. Acad. Sci. 86:821-824 (1989).
Giuliani et al, "The Region Comprising Amino Acids 100 to 255 of Neisseria meningitidis Lipoprotein GNA 1870 Elicits Bactericidal Antibodies", Infection and Immunity 73(2):1151-1160 (2005).
Giuliani et al, "A universal vaccine for serogroup B meningococcus" Proc Natl Acad Sci 103(29):10834-10839 (2006).

(56) References Cited

OTHER PUBLICATIONS

Gold et al., "Chapter 78. Translational Initiation", *Escherichia coli* and *Salmonella typhimurium*: Cellular and Molecular Biology, Ed. Neidhardt FC, vol. 2, pp. 1302-1307 (1987).

Goldschneider et al, "Human Immunity to the Meningococcus I. The Role of Humoral Antibodies", Journal of Experimental Medicine 129(6):1307-1326 (1969).

Goldschneider et al, "Human Immunity to the Meningococcus II. Development of Natural Immunity", Journal of Experimental Medicine 129(6):1327-1348 (1969).

Gomez et al, "The Bacillus subtilis lipoprotein LplA causes cell lysis when expressed in *Escherichia coli*", Microbiology 140:1839-1845 (1994).

Gotschlich et al, "Human Immunity to the Meningococcus. IV. Immunogenicity of Group A and Group C Meningococcal Polysaccharides in Human Volunteers", Journal of Experimental Medicine 129(6):1367-1384 (1969).

Gotschlich et al, "Human Immunity to the Meningococcus. V. The Effect of Immunization with Meningococcal Group C Polysaccharide on the Carrier State", Journal of Experimental Medicine 129(6):1385-1395 (1969).

Graham et al, "Characteristics of a Human Cell Line Transformed by DNA from Human Adenovirus Type 5", J. Gen. Virology 36:59-72 (1977).

\* cited by examiner

SEQUENCE LISTING

```
<160> NUMBER OF SEQ ID NOS: 158

<210> SEQ ID NO 1
<211> LENGTH: 468
<212> TYPE: PRT
<213> ORGANISM: Artificial Sequence
<220> FEATURE:
<223> OTHER INFORMATION: Synthetic sequence

<400> SEQUENCE: 1

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30
```

-continued

```
Lys Glu Gly Asn Gln Leu Pro Asp Glu Phe Val Val Ile Glu Arg Lys
             35                  40                  45

Lys Arg Ser Leu Ser Thr Asn Thr Ser Asp Ile Ser Val Thr Ala Thr
 50                  55                  60

Asn Asp Ser Arg Leu Tyr Pro Gly Ala Leu Leu Val Val Asp Glu Thr
 65                  70                  75                  80

Leu Leu Glu Asn Asn Pro Thr Leu Leu Ala Val Asp Arg Ala Pro Met
                 85                  90                  95

Thr Tyr Ser Ile Asp Leu Pro Gly Leu Ala Ser Ser Asp Ser Phe Leu
                100                 105                 110

Gln Val Glu Asp Pro Ser Asn Ser Ser Val Arg Gly Ala Val Asn Asp
            115                 120                 125

Leu Leu Ala Lys Trp His Gln Asp Tyr Gly Gln Val Asn Asn Val Pro
130                 135                 140

Met Gln Tyr Glu Lys Ile Thr Ala His Ser Met Glu Gln Leu Lys Val
145                 150                 155                 160

Lys Phe Gly Ser Asp Phe Glu Lys Thr Gly Asn Ser Leu Asp Ile Asp
                165                 170                 175

Phe Asn Ser Val His Ser Gly Glu Lys Gln Ile Gln Ile Val Asn Phe
            180                 185                 190

Lys Gln Ile Tyr Tyr Thr Val Ser Val Asp Ala Val Lys Asn Pro Gly
        195                 200                 205

Asp Val Phe Gln Asp Thr Val Thr Val Glu Asp Leu Lys Gln Arg Gly
    210                 215                 220

Ile Ser Ala Glu Arg Pro Leu Val Tyr Ile Ser Ser Val Ala Tyr Gly
225                 230                 235                 240

Arg Gln Val Tyr Leu Lys Leu Glu Thr Thr Ser Lys Ser Asp Glu Val
                245                 250                 255

Glu Ala Ala Phe Glu Ala Leu Ile Lys Gly Val Lys Val Ala Pro Gln
            260                 265                 270

Thr Glu Trp Lys Gln Ile Leu Asp Asn Thr Glu Val Lys Ala Val Ile
        275                 280                 285

Leu Gly Gly Asp Pro Ser Ser Gly Ala Arg Val Val Thr Gly Lys Val
    290                 295                 300

Asp Met Val Glu Asp Leu Ile Gln Glu Gly Ser Arg Phe Thr Ala Asp
305                 310                 315                 320

His Pro Gly Leu Pro Ile Ser Tyr Thr Thr Ser Phe Leu Arg Asp Asn
                325                 330                 335

Val Val Ala Thr Phe Gln Asn Ser Thr Asp Tyr Val Glu Thr Lys Val
            340                 345                 350

Thr Ala Tyr Arg Asn Gly Asp Leu Leu Leu Asp His Ser Gly Ala Tyr
        355                 360                 365

Val Ala Gln Tyr Tyr Ile Thr Trp Asp Glu Leu Ser Tyr Asp His Gln
    370                 375                 380

Gly Lys Glu Val Leu Thr Pro Lys Ala Trp Asp Arg Asn Gly Gln Asp
385                 390                 395                 400

Leu Thr Ala His Phe Thr Thr Ser Ile Pro Leu Lys Gly Asn Val Arg
                405                 410                 415

Asn Leu Ser Val Lys Ile Arg Glu Cys Thr Gly Leu Ala Trp Glu Trp
            420                 425                 430

Trp Arg Thr Val Tyr Glu Lys Thr Asp Leu Pro Leu Val Arg Lys Arg
        435                 440                 445

Thr Ile Ser Ile Trp Gly Thr Thr Leu Tyr Pro Gln Val Glu Asp Lys
```

```
             450                 455                 460

Val Glu Asn Asp
465

<210> SEQ ID NO 2
<211> LENGTH: 728
<212> TYPE: PRT
<213> ORGANISM: Artificial Sequence
<220> FEATURE:
<223> OTHER INFORMATION: Synthetic sequence

<400> SEQUENCE: 2

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
    50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Asp Ser Phe Leu
            100                 105                 110

Gln Val Glu Asp Pro Ser Asn Ser Ser Val Arg Gly Ala Val Asn Asp
        115                 120                 125

Leu Leu Ala Lys Trp His Gln Asp Tyr Gly Gln Val Asn Asn Val Pro
    130                 135                 140

Met Gln Tyr Glu Lys Ile Thr Ala His Ser Met Glu Gln Leu Lys Val
145                 150                 155                 160

Lys Phe Gly Ser Asp Phe Glu Lys Thr Gly Asn Ser Leu Asp Ile Asp
                165                 170                 175

Phe Asn Ser Val His Ser Gly Glu Lys Gln Ile Gln Ile Val Asn Phe
            180                 185                 190

Lys Gln Ile Tyr Tyr Thr Val Ser Val Asp Ala Val Lys Asn Pro Gly
        195                 200                 205

Asp Val Phe Gln Asp Thr Val Thr Val Glu Asp Leu Lys Gln Arg Gly
    210                 215                 220

Ile Ser Ala Glu Arg Pro Leu Val Tyr Ile Ser Ser Val Ala Tyr Gly
225                 230                 235                 240

Arg Gln Val Tyr Leu Lys Leu Glu Thr Thr Ser Lys Ser Asp Glu Val
                245                 250                 255

Glu Ala Ala Phe Glu Ala Leu Ile Lys Gly Val Lys Val Ala Pro Gln
            260                 265                 270

Thr Glu Trp Lys Gln Ile Leu Asp Asn Thr Glu Val Lys Ala Val Ile
        275                 280                 285

Leu Gly Gly Asp Pro Ser Ser Gly Ala Arg Val Val Thr Gly Lys Val
    290                 295                 300

Asp Met Val Glu Asp Leu Ile Gln Glu Gly Ser Arg Phe Thr Ala Asp
305                 310                 315                 320

His Pro Gly Leu Pro Ile Ser Tyr Thr Thr Ser Phe Leu Arg Asp Asn
                325                 330                 335

Val Val Ala Thr Phe Gln Asn Ser Thr Asp Tyr Val Glu Thr Lys Val
```

```
              340             345             350
Thr Ala Tyr Arg Asn Gly Asp Leu Leu Asp His Ser Gly Ala Tyr
        355             360             365

Val Ala Gln Tyr Tyr Ile Thr Trp Asp Glu Leu Ser Tyr Asp His Gln
    370             375             380

Gly Lys Glu Val Leu Thr Pro Lys Ala Trp Asp Arg Asn Gly Gln Asp
385             390             395             400

Leu Thr Ala His Phe Thr Thr Ser Ile Pro Leu Lys Gly Asn Val Arg
                405             410             415

Asn Leu Ser Val Lys Ile Arg Glu Cys Thr Gly Leu Ala Trp Glu Trp
            420             425             430

Trp Arg Thr Val Tyr Glu Lys Thr Asp Leu Pro Leu Val Arg Lys Arg
                435             440             445

Thr Ile Ser Ile Trp Gly Thr Thr Leu Tyr Pro Gln Val Glu Asp Lys
            450             455             460

Val Glu Asn Asp Ser Ser Gly Ser Gly Gly Gly Gly Val Ala
465             470             475             480

Ala Asp Ile Gly Thr Gly Leu Ala Asp Ala Leu Thr Ala Pro Leu Asp
                485             490             495

His Lys Asp Lys Gly Leu Lys Ser Leu Thr Leu Glu Asp Ser Ile Ser
                500             505             510

Gln Asn Gly Thr Leu Thr Leu Ser Ala Gln Gly Ala Glu Lys Thr Phe
            515             520             525

Lys Val Gly Asp Lys Asp Asn Ser Leu Asn Thr Gly Lys Leu Lys Asn
            530             535             540

Asp Lys Ile Ser Arg Phe Asp Phe Val Gln Lys Ile Glu Val Asp Gly
545             550             555             560

Gln Thr Ile Thr Leu Ala Ser Gly Glu Phe Gln Ile Tyr Lys Gln Asp
                565             570             575

His Ser Ala Val Val Ala Leu Gln Ile Glu Lys Ile Asn Asn Pro Asp
            580             585             590

Lys Ile Asp Ser Leu Ile Asn Gln Arg Ser Phe Leu Val Ser Gly Leu
            595             600             605

Gly Gly Glu His Thr Ala Phe Asn Gln Leu Pro Ser Gly Lys Ala Glu
    610             615             620

Tyr His Gly Lys Ala Phe Ser Ser Asp Asp Ala Gly Gly Lys Leu Thr
625             630             635             640

Tyr Thr Ile Asp Phe Ala Ala Lys Gln Gly His Gly Lys Ile Glu His
                645             650             655

Leu Lys Thr Pro Glu Gln Asn Val Glu Leu Ala Ser Ala Glu Leu Lys
            660             665             670

Ala Asp Glu Lys Ser His Ala Val Ile Leu Gly Asp Thr Arg Tyr Gly
            675             680             685

Ser Glu Glu Lys Gly Thr Tyr His Leu Ala Leu Phe Gly Asp Arg Ala
    690             695             700

Gln Glu Ile Ala Gly Ser Ala Thr Val Lys Ile Arg Glu Lys Val His
705             710             715             720

Glu Ile Gly Ile Ala Gly Lys Gln
                725
```

<210> SEQ ID NO 3
<211> LENGTH: 1410
<212> TYPE: DNA
<213> ORGANISM: Artificial Sequence

```
<220> FEATURE:
<223> OTHER INFORMATION: Synthetic sequence

<400> SEQUENCE: 3
atggcaaata aagcagtaaa tgactttata ctagctatga attacgataa aaagaaactc      60
ttgacccatc agggagaaag tattgaaaat cgtttcatca agagggtaa tcagctaccc      120 gatgagtttg ttgttatcga agaaagaag cggagcttgt cgacaaatac aagtgatatt     180
tctgtaacag ctaccaacga cagtcgcctc tatcctggag cacttctcgt agtggatgag     240
accttgttag agaataatcc cactcttctt gcggttgatc gtgctccgat gacttatagt     300
attgatttgc ctggtttggc aagtagcgat agctttctcc aagtggaaga ccccagcaat    360
tcaagtgttc gcggagcggt aaacgatttg ttggctaagt ggcatcaaga ttatggtcag    420
gtcaataatg tcccaatgca gtatgaaaaa ataacggctc acagcatgga acaactcaag    480
gtcaagtttg gttctgactt tgaaaagaca gggaattctc ttgatattga ttttaactct    540
gtccattcag gtgaaaagca gattcagatt gttaatttta gcagattta ttatacagtc     600 agcgtagacg ctgttaaaaa tccaggagat gtgtttcaag atactgtaac ggtagaggat    660
ttaaaacaga gaggaatttc tgcagagcgt cctttggtct atatttcgag tgttgcttat    720
gggcgccaag tctatctcaa gttggaaacc acgagtaaga gtgatgaagt agaggctgct    780
tttgaggctt tgataaaagg agtcaaggta gctcctcaga cagagtggaa gcagattttg    840
gacaatacag aagtgaaggc ggttatttta gggggcgacc caagttcggg tgcccgagtt    900
gtaacaggca aggtggatat ggtagaggac ttgattcaag aaggcagtcg ctttacagca    960
gatcatccag gcttgccgat ttcctataca acttctttt tacgtgacaa tgtagttgcg    1020
acctttcaaa acagtacaga ctatgttgag actaaggtta cagcttacag aaacggagat    1080
ttactgctgg atcatagtgg tgcctatgtt gcccaatatt atattacttg ggatgaatta    1140
tcctatgatc atcaaggtaa ggaagtcttg actcctaagg cttgggacag aaatgggcag    1200
gatttgacgg ctcactttac cactagtatt cctttaaaag ggaatgttcg taatctctct    1260
gtcaaaatta gagagtgtac cgggcttgcc tgggaatggt ggcgtacggt ttatgaaaaa    1320
accgatttgc cactagtgcg taagcggacg atttctattt ggggaacaac tctctatcct    1380
caggtagagg ataaggtaga aaatgactag                                    1410

<210> SEQ ID NO 4
<211> LENGTH: 1280
<212> TYPE: DNA
<213> ORGANISM: Artificial Sequence
<220> FEATURE:
<223> OTHER INFORMATION: Synthetic sequence

<400> SEQUENCE: 4
atggcaaata aagcagtaaa tgactttata ctagctatga attacgataa aaagaaactc      60
ttgacccatc agggagaaag tattgaaaat cgtttcatca agagggtaa tcagctaccc      120 gatgagtttg ttgttatcga agaaagaag cggagcttgt cgacaaatac aagtgatatt     180
tctgtaacag ctaccaacga cagtcgcctc tatcctggag cacttctcgt agtggatgag     240
accttgttag agaataatcc cactcttctt gcggttgatc gtgctccgat gacttatagt     300
attgatttgc ctggtttggc aagtagcgat agctttctcc aagtggaaga ccccagcaat    360
tcaagtgttc gcggagcggt aaacgatttg ttggctaagt ggcatcaaga ttatggtcag    420
gtcaataatg tcccaatgca gtatgaaaaa ataacggctc acagcatgga acaactcaag    480
```

```
gtcaagtttg gttctgactt tgaaaagaca gggaattctc ttgatattga ttttaactct      540
gtccattcag gtgaaaagca gattcagatt gttaatttta agcagattta ttatacagtc      600
agcgtagacg ctgttaaaaa tccaggagat gtgtttcaag atactgtaac ggtagaggat      660
ttaaaacaga gaggaaattt ctgcagagcgt cctttggtct atatttcgag tgttgcttat      720
gggcgccaag tctatctcaa gttggaaacc acgagtaaga gtgatgaagt agaggctgct      780
tttgaggctt tgataaaagg agtcaaggta gctcctcaga cagagtggaa gcagattttg      840
gacaatacag aagtgaaggc ggttatttta gggggcgacc caagttcggg tgcccgagtt      900
gtaacaggca aggtggatat ggtagaggac ttgattcaag aaggcagtcg ctttacagca      960
gatcatccag gcttgccgat tcctataca acttctttt tacgtgacaa tgtagttgcg      1020
acctttcaaa acagtacaga ctatgttgag actaaggtta cagcttacag aaacggagat     1080
ttactgctgg atcatagtgg tgcctatgtt gcccaatatt atattacttg ggatgaatta     1140
tcctatgatc atcaaggtaa ggaagtcttg actcctaagg cttgggacag aaatgggcag     1200
gatttgacgg ctcactttac cactagtatt cctttaaaag ggaatgttcg taatctctct     1260
gtcaaaatta gagagtgtac                                                 1280
```

<210> SEQ ID NO 5
<211> LENGTH: 260
<212> TYPE: PRT
<213> ORGANISM: Artificial Sequence
<220> FEATURE:
<223> OTHER INFORMATION: Synthetic sequence

<400> SEQUENCE: 5

```
Ser Ser Gly Ser Gly Ser Gly Gly Gly Val Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Ser Gln Asn Gly Thr
        35                  40                  45

Leu Thr Leu Ser Ala Gln Gly Ala Glu Lys Thr Phe Lys Val Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Gly Gly Glu His
    130                 135                 140

Thr Ala Phe Asn Gln Leu Pro Ser Gly Lys Ala Glu Tyr His Gly Lys
145                 150                 155                 160

Ala Phe Ser Ser Asp Asp Ala Gly Gly Lys Leu Thr Tyr Thr Ile Asp
                165                 170                 175

Phe Ala Ala Lys Gln Gly His Gly Lys Ile Glu His Leu Lys Thr Pro
            180                 185                 190

Glu Gln Asn Val Glu Leu Ala Ser Ala Glu Leu Lys Ala Asp Glu Lys
        195                 200                 205

Ser His Ala Val Ile Leu Gly Asp Thr Arg Tyr Gly Ser Glu Glu Lys
    210                 215                 220
```

-continued

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
            245                 250                 255

Ala Gly Lys Gln
            260

<210> SEQ ID NO 6
<211> LENGTH: 786
<212> TYPE: DNA
<213> ORGANISM: Artificial Sequence
<220> FEATURE:
<223> OTHER INFORMATION: Synthetic sequence

<400> SEQUENCE: 6
atgagctctg gaagcggaag cgggggcggt ggagttgcag cagacattgg aacaggatta      60
gcagatgcac tgacggcacc gttggatcat aaagacaaag gcttgaaatc gcttacctta     120
gaagattcta tttcacaaaa tggcacccct accttgtccg cgcaaggcgc tgaaaaaact     180
tttaaagtcg gtgacaaaga taatagctta aatacaggta aactcaaaaa tgataaaatc     240
tcgcgttttg atttcgtgca aaaaatcgaa gtagatggcc aaaccattac attagcaagc     300
ggtgaattcc aaatatataa acaagaccat tcagcagtcg ttgcattgca aattgaaaaa     360
atcaacaacc ccgacaaaat cgacagcctg ataaaccaac gttccttcct tgtcagcggt     420
ttgggcggtg aacatacagc cttcaaccaa ttaccaagcg gcaaagcgga gtatcacggt     480
aaagcattta gctcagatga tgcaggcggt aaattaactt atacaattga ctttgcagca     540
aaacaaggac atggcaaaat tgaacattta aaaacacccg aacagaacgt agagctcgca     600
tccgcagaac tcaaagcaga tgaaaaatca cacgcagtca ttttgggtga cacgcgctac     660
ggcagcgaag aaaaaggtac ttaccactta gctcttttg gcgaccgagc tcaagaaatc      720
gcaggtagcg caaccgtaaa gataagggaa aaggttcacg aaattgggat cgcgggcaaa     780
caataa                                                                786

<210> SEQ ID NO 7
<211> LENGTH: 2199
<212> TYPE: DNA
<213> ORGANISM: Artificial Sequence
<220> FEATURE:
<223> OTHER INFORMATION: Synthetic sequence

<400> SEQUENCE: 7
atgagctctg gaagcggaag cgggggcggt ggagttgcag cagacattgg aacaggatta      60
gcagatgcac tgacggcacc gttggatcat aaagacaaag gcttgaaatc gcttacctta     120
gaagattcta tttcacaaaa tggcacccct accttgtccg cgcaaggcgc tgaaaaaact     180
tttaaagtcg gtgacaaaga taatagctta aatacaggta aactcaaaaa tgataaaatc     240
tcgcgttttg atttcgtgca aaaaatcgaa gtagatggcc aaaccattac attagcaagc     300
ggtgaattcc aaatatataa acaagaccat tcagcagtcg ttgcattgca aattgaaaaa     360
atcaacaacc ccgacaaaat cgacagcctg ataaaccaac gttccttcct tgtcagcggt     420
ttgggcggtg aacatacagc cttcaaccaa ttaccaagcg gcaaagcgga gtatcacggt     480
aaagcattta gctcagatga tgcaggcggt aaattaactt atacaattga ctttgcagca     540
aaacaaggac atggcaaaat tgaacattta aaaacacccg aacagaacgt agagctcgca     600
tccgcagaac tcaaagcaga tgaaaaatca cacgcagtca ttttgggtga cacgcgctac     660

```
ggcagcgaag aaaaaggtac ttaccactta gctcttttg gcgaccgagc tcaagaaatc    720
gcaggtagcg caaccgtaaa gataagggaa aaggttcacg aaattgggat cgcgggcaaa    780
caaggaagcg gtgcaaataa agcagtaaat gactttatac tagctatgaa ttacgataaa    840
aagaaactct tgacccatca gggagaaagt attgaaaatc gtttcatcaa agagggtaat    900
cagctacccg atgagtttgt tgttatcgaa agaaagaagc ggagcttgtc gacaaataca    960
agtgatattt ctgtaacagc taccaacgac agtcgcctct atcctggagc acttctcgta   1020
gtggatgaga ccttgttaga gaataatccc actcttcttg cggttgatcg tgctccgatg   1080
acttatagta ttgatttgcc tggtttggca gtagcgata gctttctcca agtggaagac   1140
cccagcaatt caagtgttcg cggagcggta acgatttgt tggctaagtg catcaagat    1200
tatggtcagg tcaataatgt cccaatgcag tatgaaaaaa taacggctca cagcatggaa   1260
caactcaagg tcaagtttgg ttctgacttt gaaaagacag ggaattctct tgatattgat   1320
tttaactctg tccattcagg tgaaaagcag attcagattg ttaattttaa gcagatttat   1380
tatacagtca gcgtagacgc tgttaaaaat ccaggagatg tgtttcaaga tactgtaacg   1440
gtagaggatt taaaacagag aggaatttct gcagagcgtc ctttggtcta tatttcgagt   1500
gttgcttatg ggcgccaagt ctatctcaag ttggaaacca cgagtaagag tgatgaagta   1560
gaggctgctt tgaggcttt gataaaagga gtcaaggtag ctcctcagac agagtggaag   1620
cagattttgg acaatacaga agtgaaggcg gttatttag ggggcgaccc aagttcgggt    1680
gcccgagttg taacaggcaa ggtggatatg gtagaggact tgattcaaga aggcagtcgc   1740
tttacagcag atcatccagg cttgccgatt tcctatacaa cttctttttt acgtgacaat   1800
gtagttgcga ccttcaaaa cagtacagac tatgttgaga ctaaggttac agcttacaga    1860
aacggagatt tactgctgga tcatagtggt gcctatgttg cccaatatta tattacttgg   1920
gatgaattat cctatgatca tcaaggtaag gaagtcttga ctcctaaggc ttgggacaga   1980
aatgggcagg atttgacggc tcactttacc actagtattc cttaaaaagg gaatgttcgt   2040
aatctctctg tcaaaattag agagtgtacc gggcttgcct gggaatggtg gcgtacggtt   2100
tatgaaaaaa ccgatttgcc actagtgcgt aagcggacga tttctatttg gggaacaact   2160
ctctatcctc aggtagagga taaggtagaa atgactaa                            2199

<210> SEQ ID NO 8
<211> LENGTH: 731
<212> TYPE: PRT
<213> ORGANISM: Artificial Sequence
<220> FEATURE:
<223> OTHER INFORMATION: Synthetic sequence

<400> SEQUENCE: 8

Ser Ser Gly Ser Gly Ser Gly Gly Gly Gly Val Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Ser Gln Asn Gly Thr
        35                  40                  45

Leu Thr Leu Ser Ala Gln Gly Ala Glu Lys Thr Phe Lys Val Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
```

```
                         85                  90                  95
Leu Ala Ser Gly Glu Phe Gln Ile Tyr Lys Gln Asp His Ser Ala Val
                100                 105                 110

Val Ala Leu Gln Ile Glu Lys Ile Asn Asn Pro Asp Lys Ile Asp Ser
                115                 120                 125

Leu Ile Asn Gln Arg Ser Phe Leu Val Ser Gly Leu Gly Gly Glu His
            130                 135                 140

Thr Ala Phe Asn Gln Leu Pro Ser Gly Lys Ala Glu Tyr His Gly Lys
145                 150                 155                 160

Ala Phe Ser Ser Asp Ala Gly Gly Lys Leu Thr Tyr Thr Ile Asp
                165                 170                 175

Phe Ala Ala Lys Gln Gly His Gly Lys Ile Glu His Leu Lys Thr Pro
                180                 185                 190

Glu Gln Asn Val Glu Leu Ala Ser Ala Glu Leu Lys Ala Asp Glu Lys
                195                 200                 205

Ser His Ala Val Ile Leu Gly Asp Thr Arg Tyr Gly Ser Glu Glu Lys
            210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
                245                 250                 255

Ala Gly Lys Gln Gly Ser Gly Ala Asn Lys Ala Val Asn Asp Phe Ile
                260                 265                 270

Leu Ala Met Asn Tyr Asp Lys Lys Leu Leu Thr His Gln Gly Glu
            275                 280                 285

Ser Ile Glu Asn Arg Phe Ile Lys Glu Gly Asn Gln Leu Pro Asp Glu
            290                 295                 300

Phe Val Val Ile Glu Arg Lys Lys Arg Ser Leu Ser Thr Asn Thr Ser
305                 310                 315                 320

Asp Ile Ser Val Thr Ala Thr Asn Asp Ser Arg Leu Tyr Pro Gly Ala
                325                 330                 335

Leu Leu Val Val Asp Glu Thr Leu Leu Glu Asn Asn Pro Thr Leu Leu
            340                 345                 350

Ala Val Asp Arg Ala Pro Met Thr Tyr Ser Ile Asp Leu Pro Gly Leu
            355                 360                 365

Ala Ser Ser Asp Ser Phe Leu Gln Val Glu Asp Pro Ser Asn Ser Ser
            370                 375                 380

Val Arg Gly Ala Val Asn Asp Leu Leu Ala Lys Trp His Gln Asp Tyr
385                 390                 395                 400

Gly Gln Val Asn Asn Val Pro Met Gln Tyr Glu Lys Ile Thr Ala His
                405                 410                 415

Ser Met Glu Gln Leu Lys Val Lys Phe Gly Ser Asp Phe Glu Lys Thr
            420                 425                 430

Gly Asn Ser Leu Asp Ile Asp Phe Asn Ser Val His Ser Gly Glu Lys
            435                 440                 445

Gln Ile Gln Ile Val Asn Phe Lys Gln Ile Tyr Tyr Thr Val Ser Val
            450                 455                 460

Asp Ala Val Lys Asn Pro Gly Asp Val Phe Gln Asp Thr Val Thr Val
465                 470                 475                 480

Glu Asp Leu Lys Gln Arg Gly Ile Ser Ala Glu Arg Pro Leu Val Tyr
                485                 490                 495

Ile Ser Ser Val Ala Tyr Gly Arg Gln Val Tyr Leu Lys Leu Glu Thr
                500                 505                 510
```

Thr Ser Lys Ser Asp Glu Val Glu Ala Ala Phe Glu Ala Leu Ile Lys
        515                 520                 525

Gly Val Lys Val Ala Pro Gln Thr Glu Trp Lys Gln Ile Leu Asp Asn
        530                 535                 540

Thr Glu Val Lys Ala Val Ile Leu Gly Gly Asp Pro Ser Ser Gly Ala
545                 550                 555                 560

Arg Val Val Thr Gly Lys Val Asp Met Val Glu Asp Leu Ile Gln Glu
                565                 570                 575

Gly Ser Arg Phe Thr Ala Asp His Pro Gly Leu Pro Ile Ser Tyr Thr
            580                 585                 590

Thr Ser Phe Leu Arg Asp Asn Val Val Ala Thr Phe Gln Asn Ser Thr
        595                 600                 605

Asp Tyr Val Glu Thr Lys Val Thr Ala Tyr Arg Asn Gly Asp Leu Leu
        610                 615                 620

Leu Asp His Ser Gly Ala Tyr Val Ala Gln Tyr Tyr Ile Thr Trp Asp
625                 630                 635                 640

Glu Leu Ser Tyr Asp His Gln Gly Lys Glu Val Leu Thr Pro Lys Ala
                645                 650                 655

Trp Asp Arg Asn Gly Gln Asp Leu Thr Ala His Phe Thr Ser Ile
            660                 665                 670

Pro Leu Lys Gly Asn Val Arg Asn Leu Ser Val Lys Ile Arg Glu Cys
        675                 680                 685

Thr Gly Leu Ala Trp Glu Trp Trp Arg Thr Val Tyr Glu Lys Thr Asp
        690                 695                 700

Leu Pro Leu Val Arg Lys Arg Thr Ile Ser Ile Trp Gly Thr Thr Leu
705                 710                 715                 720

Tyr Pro Gln Val Glu Asp Lys Val Glu Asn Asp
                725                 730

<210> SEQ ID NO 9
<211> LENGTH: 1608
<212> TYPE: DNA
<213> ORGANISM: Artificial Sequence
<220> FEATURE:
<223> OTHER INFORMATION: Synthetic sequence

<400> SEQUENCE: 9
ggcgctgatg atgttgttga ttcttctaaa tcttttgtga tggaaaactt ttcttcgtac      60
cacgggacta aacctggtta tgtagattcc attcaaaaag gtatacaaaa gccaaaatct     120
ggtacacaag gaaattatga cgatgattgg aaagagtttt atagtaccga caataaatac     180
gacgctgcgg atactctgt agataatgaa aacccgctct ctggaaaagc tggaggcgtg     240
gtcaaagtga cgtatccagg actgacgaag gttctcgcac taaaagtgga taatgccgaa     300
actattaaga aagagttagg tttaagtctc actgaaccgt tgatggagca agtcggaacg     360
gaagagttta tcaaaaggtt cggtgatggt gcttcgcgtg tagtgctcag ccttcccttc     420
gctgagggga gttctagcgt tgaatatatt aataactggg aacaggcgaa agcgttaagc     480
gtagaacttg agattaattt tgaaacccgt ggaaaacgtg gccaagatgc gatgtatgag     540
tatatggctc aagcctgtgc aggaaatcgt gtcaggcgat cagtaggtag ctcattgtca     600
tgcataaatc ttgattggga tgtcataagg ataaaacta agacaaagat agagtctttg     660
aaagagcatg gccctatcaa aaataaaatg agcgaaagtc ccaataaaac agtatctgag     720
gaaaaagcta acaataccct agaagaattt catcaaacgg cattagagca tcctgaattg     780

```
tcagaactta aaaccgttac tgggaccaat cctgtattcg ctggggctaa ctatgcggcg    840
tgggcagtaa acgttgcgca agttatcgat agcgaaacag ctgataattt ggaaaagaca    900
actgctgctc tttcgatact tcctggtatc ggtagcgtaa tgggcattgc agacggtgcc    960
gttcaccaca atacagaaga gatagtggca caatcaatag cttatcatc tttaatggtt   1020 gctcaagcta ttccattggt aggagagcta gttgatattg gtttcgctgc atataatttt   1080
gtagagagta ttatcaattt atttcaagta gttcataatt cgtataatcg tcccgcgtat   1140
tctccggggc ataaaacgca accatttctt catgacgggt atgctgtcag ttggaacact   1200
gttgaagatt cgataatccg aactggtttt caaggggaga gtgggcacga cataaaaatt   1260
actgctgaaa ataccccgct tccaatcgcg ggtgtcctac taccgactat tcctggaaag   1320
ctggacgtta ataagtccaa gactcatatt tccgtaaatg gtcggaaaat aaggatgcgt   1380
tgcagagcta tagacggtga tgtaactttt tgtcgcccta atctcctgt ttatgttggt    1440 aatggtgtgc atgcgaatct tcacgtggca tttcacagaa gcagctcgga gaaaattcat   1500
tctaatgaaa tttcatcgga ttccataggc gttcttgggt accagaaaac agtagatcac   1560
accaaggtta attctaagct atcgctattt tttgaaatca aagctga                 1608

<210> SEQ ID NO 10
<211> LENGTH: 535
<212> TYPE: PRT
<213> ORGANISM: Artificial Sequence
<220> FEATURE:
<223> OTHER INFORMATION: Synthetic sequence

<400> SEQUENCE: 10

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220
```

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
        290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
530                 535

<210> SEQ ID NO 11
<211> LENGTH: 579
<212> TYPE: DNA
<213> ORGANISM: Artificial Sequence
<220> FEATURE:
<223> OTHER INFORMATION: Synthetic sequence

<400> SEQUENCE: 11
ggcgctgatg atgttgttga ttcttctaaa tcttttgtga tggaaaactt ttcttcgtac      60
cacgggacta aacctggtta tgtagattcc attcaaaaag gtatacaaaa gccaaaatct     120
ggtacacaag gaaattatga cgatgattgg aaagagtttt atagtaccga caataaatac     180
gacgctgcgg gatactctgt agataatgaa aacccgctct ctggaaaagc tggaggcgtg     240

```
gtcaaagtga cgtatccagg actgacgaag gttctcgcac taaaagtgga taatgccgaa    300
actattaaga aagagttagg tttaagtctc actgaaccgt tgatggagca agtcggaacg    360
gaagagttta tcaaaaggtt cggtgatggt gcttcgcgtg tagtgctcag ccttcccttc    420
gctgagggga gttctagcgt tgaatatatt aataactggg aacaggcgaa agcgttaagc    480
gtagaacttg agattaattt tgaaacccgt ggaaaacgtg gccaagatgc gatgtatgag    540
tatatggctc aagcctgtgc aggaaatcgt gtcaggcga                           579
```

```
<210> SEQ ID NO 12
<211> LENGTH: 193
<212> TYPE: PRT
<213> ORGANISM: Artificial Sequence
<220> FEATURE:
<223> OTHER INFORMATION: Synthetic sequence

<400> SEQUENCE: 12
```

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg

```
<210> SEQ ID NO 13
<211> LENGTH: 2391
<212> TYPE: DNA
<213> ORGANISM: Artificial Sequence
<220> FEATURE:
<223> OTHER INFORMATION: Synthetic sequence

<400> SEQUENCE: 13
```

```
atgggcgctg atgatgttgt tgattcttct aaatcttttg tgatggaaaa ctttcctcg     60 taccacggga ctaaacctgg ttatgtagat tccattcaaa aaggtataca aaagccaaaa   120
tctggtacac aaggaaatta tgacgatgat tggaaagagt tttatagtac cgacaataaa   180
tacgacgctg cgggatactc tgtagataat gaaaacccgc tctctggaaa agctggaggc   240
gtggtcaaag tgacgtatcc aggactgacg aaggttctcg cactaaaagt ggataatgcc   300
```

```
gaaactatta agaaagagtt aggtttaagt ctcactgaac cgttgatgga gcaagtcgga      360
acggaagagt ttatcaaaag gttcggtgat ggtgcttcgc gtgtagtgct cagccttccc      420
ttcgctgagg ggagttctag cgttaatat attaataact gggaacaggc gaaagcgtta       480
agcgtagaac ttgagattaa ttttgaaacc cgtggaaaac gtggccaaga tgcgatgtat      540
gagtatatgg ctcaagcctg tgcaggaaat cgtgtcaggc gatcagtagg tagctcattg      600
tcatgcataa atcttgattg ggatgtcata agggataaaa ctaagacaaa gatagagtct      660
ttgaaagagc atggccctat caaaaataaa atgagcgaaa gtcccaataa aacagtatct      720
gaggaaaaag ctaaacaata cctagaagaa tttcatcaaa cggcattaga gcatcctgaa      780
ttgtcagaac ttaaaaccgt tactgggacc aatcctgtat tcgctggggc taactatgcg      840
gcgtgggcag taaacgttgc gcaagttatc gatagcgaaa cagctgataa tttggaaaag      900
acagctgctg ctctttcgat acttcctggt atcggtagcg taatgggcat tgcagacggt      960
gccgttcacc acaatacaga agagatagtg gcacaatcaa tagctttatc gtctttaatg     1020
gttgctcaag ctattccatt ggtaggagag ctagttgata ttggtttcgc tgcatataat     1080
tttgtagaga gtattatcaa tttatttcaa gtagttcata attcgtataa tcgtcccgcg     1140
tattctccgg ggcataaaac gcaaccattt cttcatgacg ggtatgctgt cagttggaac     1200
actgttgaag attcgataat ccgaactggt tttcaagggg agagtgggca cgacataaaa     1260
attactgctg aaaataccc gcttccaatc gcgggtgtcc tactaccgac tattcctgga      1320
aagctggacg ttaataagtc caagactcat atttccgtaa atggtcggaa ataaggatg      1380 cgttgcagag ctatagacgg tgatgtaact ttttgtcgcc ttaaatctcc tgtttatgtt     1440
ggtaatggtg tgcatgcgaa tcttcacgtg gcatttcaca gaagcagctc ggagaaaatt     1500
cattctaatg aaatttcgtc ggattccata ggcgttcttg ggtaccagaa acagtagat      1560 cacaccaagg ttaattctaa gctatcgcta ttttttgaaa tcaaaagcag ctctggaagc     1620
ggaagcgggg gcggtggagt tgcagcagac attggaacag gattagcaga tgcactgacg     1680
gcaccgttgg atcataaaga caaaggcttg aaatcgctta ccttagaaga ttctatttca     1740
caaaatggca cccttacctt gtccgcgcaa ggcgctgaaa aaacttttaa agtcggtgac     1800
aaagataata gcttaaatac aggtaaactc aaaaatgata aaatctcgcg ttttgatttc     1860
gtgcaaaaaa tcgaagtaga tggccaaacc attacattag caagcggtga attccaaata     1920
tataaacaag accattcagc agtcgttgca ttgcaaattg aaaaaatcaa caaccccgac     1980
aaaatcgaca gcctgataaa ccaacgttcc ttccttgtca gcggtttggg cggtgaacat     2040
acagccttca accaattacc aagcggcaaa gcggagtatc acggtaaagc atttagctca     2100
gatgatgcag gcggtaaatt aacttataca attgactttg cagcaaaaca aggacatggc     2160
aaaattgaac atttaaaaac acccgaacag aacgtagagc tcgcatccgc agaactaaaa     2220
gcagatgaaa atcacacgc agtcattttg ggtgacacgc gctacggcag cgaagaaaaa      2280
ggtacttacc acttagctct ttttggcgac cgagctcaag aaatcgcagg tagcgcaacc     2340
gtaaagataa gggaaaaggt tcacgaaatt gggatcgcgg gcaaacaata a              2391
```

<210> SEQ ID NO 14
<211> LENGTH: 795
<212> TYPE: PRT
<213> ORGANISM: Artificial Sequence
<220> FEATURE:
<223> OTHER INFORMATION: Synthetic sequence -continued

<400> SEQUENCE: 14

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Ala Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415
```

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Leu Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser Ser Gly Ser Gly Ser Gly Gly Gly Gly
    530                 535                 540

Gly Val Ala Ala Asp Ile Gly Thr Gly Leu Ala Asp Ala Leu Thr Ala
545                 550                 555                 560

Pro Leu Asp His Lys Asp Lys Gly Leu Lys Ser Leu Thr Leu Glu Asp
                565                 570                 575

Ser Ile Ser Gln Asn Gly Thr Leu Thr Leu Ser Ala Gln Gly Ala Glu
            580                 585                 590

Lys Thr Phe Lys Val Gly Asp Lys Asp Asn Ser Leu Asn Thr Gly Lys
        595                 600                 605

Leu Lys Asn Asp Lys Ile Ser Arg Phe Asp Phe Val Gln Lys Ile Glu
    610                 615                 620

Val Asp Gly Gln Thr Ile Thr Leu Ala Ser Gly Glu Phe Gln Ile Tyr
625                 630                 635                 640

Lys Gln Asp His Ser Ala Val Val Ala Leu Gln Ile Glu Lys Ile Asn
                645                 650                 655

Asn Pro Asp Lys Ile Asp Ser Leu Ile Asn Gln Arg Ser Phe Leu Val
            660                 665                 670

Ser Gly Leu Gly Gly Glu His Thr Ala Phe Asn Gln Leu Pro Ser Gly
        675                 680                 685

Lys Ala Glu Tyr His Gly Lys Ala Phe Ser Ser Asp Asp Ala Gly Gly
    690                 695                 700

Lys Leu Thr Tyr Thr Ile Asp Phe Ala Ala Lys Gln Gly His Gly Lys
705                 710                 715                 720

Ile Glu His Leu Lys Thr Pro Glu Gln Asn Val Glu Leu Ala Ser Ala
                725                 730                 735

Glu Leu Lys Ala Asp Lys Ser His Ala Val Ile Leu Gly Asp Thr
            740                 745                 750

Arg Tyr Gly Ser Glu Glu Lys Gly Thr Tyr His Leu Ala Leu Phe Gly
        755                 760                 765

Asp Arg Ala Gln Glu Ile Ala Gly Ser Ala Thr Val Lys Ile Arg Glu
    770                 775                 780

Lys Val His Glu Ile Gly Ile Ala Gly Lys Gln
785                 790                 795

<210> SEQ ID NO 15
<211> LENGTH: 2400
<212> TYPE: DNA
<213> ORGANISM: Artificial Sequence
<220> FEATURE:

<223> OTHER INFORMATION: Synthetic sequence

<400> SEQUENCE: 15

```
atgagctctg gaagcggaag cggggcggt ggagttgcag cagacattgg aacaggatta      60
gcagatgcac tgacggcacc gttggatcat aaagacaaag gcttgaaatc gcttaccttaa   120
gaagattcta tttcacaaaa tggcaccctt accttgtccg cgcaaggcgc tgaaaaaact   180
tttaaagtcg gtgacaaaga taatagctta aatacaggta aactcaaaaa tgataaaatc   240
tcgcgttttg atttcgtgca aaaaatcgaa gtagatggcc aaaccattac attagcaagc   300
ggtgaattcc aaatatataa acaagaccat tcagcagtcg ttgcattgca aattgaaaaa   360
atcaacaacc ccgacaaaat cgacagcctg ataaaccaac gttccttcct tgtcagcggt   420
ttgggcggtg aacatacagc cttcaaccaa ttaccaagcg gcaaagcgga gtatcacgtt   480
aaagcattta gctcagatga tgcaggcggt aaattaactt atacaattga ctttgcagca   540
aaacaaggac atggcaaaat tgaacattta aaaacacccg aacagaacgt agagctcgca   600
tccgcagaac tcaaagcaga tgaaaaatca cacgcagtca ttttgggtga cacgcgctac   660
ggcagcgaag aaaaaggtac ttaccactta gctcttttg cgaccgagc tcaagaaatc   720
gcaggtagcg caaccgtaaa gataagggaa aaggttcacg aaattgggat cgcgggcaaa   780
caaggaagcg gtggcgctga tgatgttgtt gattcttcta aatcttttgt gatggaaaac   840
ttttcttcgt accacgggac taaacctggt tatgtagatt ccattcaaaa aggtatacaa   900
aagccaaaat ctggtacaca aggaaattat gacgatgatt ggaaagagtt ttatagtacc   960
gacaataaat acgacgctgc gggatactct gtagataatg aaaacccgct ctctggaaaa  1020
gctggaggcg tggtcaaagt gacgtatcca ggactgacga aggttctcgc actaaaagtg  1080
gataatgccg aaactattaa gaaagagtta ggtttaagtc tcactgaacc gttgatggag  1140
caagtcggaa cggaagagtt tatcaaaagg ttcggtgatg gtgcttcgcg tgtagtgctc  1200
agccttccct tcgctgaggg gagttctagc gttaatata ttaataactg gaacaggcg    1260
aaagcgttaa gcgtagaact tgagattaat tttgaaaccc gtggaaaacg tggccaagat  1320
gcgatgtatg agtatatggc tcaagcctgt gcaggaaatc gtgtcaggcg atcagtaggt  1380
agctcattgt catgcataaa tcttgattgg gatgtcataa gggataaaac taagacaaag  1440
atagagtctt tgaaagagca tggccctatc aaaaataaaa tgagcgaaag tcccaataaa  1500
acagtatctg aggaaaaagc taaacaatac ctagaagaat tcatcaaac ggcattagag   1560
catcctgaat tgtcagaact taaaaccgtt actgggacca atcctgtatt cgctggggct  1620
aactatgcgg cgtgggcagt aaacgttgcg caagttatcg atagcgaaac agctgataat  1680
ttggaaaaga caactgctgc tctttcgata cttcctggta tcggtagcgt aatgggcatt  1740
gcagacggtg ccgttcacca caatacagaa gagatagtgg cacaatcaat agctttatcg  1800
tctttaatgg ttgctcaagc tattccattg gtaggagagc tagttgatat tggtttcgct  1860
gcatataatt ttgtagagag tattatcaat ttatttcaag tagttcataa ttcgtataat  1920
cgtcccgcgt attctccggg gcataaaacg caaccatttc ttcatgacgg gtatgctgtc  1980
agttggaaca ctgttgaaga ttcgataatc cgaactggtt tcaagggga gagtgggcac  2040
gacataaaaa ttactgctga aaatacccccg cttccaatcg cgggtgtcct actaccgact  2100
attcctggaa agctggacgt taataagtcc aagactcata tttccgtaaa tggtcggaaa  2160
ataaggatgc gttgcagagc tatagacggt gatgtaactt tttgtcgccc taaatctcct  2220
gtttatgttg gtaatggtgt gcatgcgaat cttcacgtgg catttcacag aagcagctcg  2280
```

```
gagaaaattc attctaatga aatttcgtcg gattccatag gcgttcttgg gtaccagaaa    2340
acagtagatc acaccaaggt taattctaag ctatcgctat ttttgaaat caaaagctaa     2400
```

<210> SEQ ID NO 16
<211> LENGTH: 798
<212> TYPE: PRT
<213> ORGANISM: Artificial Sequence
<220> FEATURE:
<223> OTHER INFORMATION: Synthetic sequence

<400> SEQUENCE: 16

```
Ser Ser Gly Ser Gly Ser Gly Gly Gly Val Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Ser Gln Asn Gly Thr
        35                  40                  45

Leu Thr Leu Ser Ala Gln Gly Ala Glu Lys Thr Phe Lys Val Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Ser Gly Lys Ala Glu Tyr His Gly Lys
145                 150                 155                 160

Ala Phe Ser Ser Asp Asp Ala Gly Gly Lys Leu Thr Tyr Thr Ile Asp
                165                 170                 175

Phe Ala Ala Lys Gln Gly His Gly Lys Ile Glu His Leu Lys Thr Pro
            180                 185                 190

Glu Gln Asn Val Glu Leu Ala Ser Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
                245                 250                 255

Ala Gly Lys Gln Gly Ser Gly Ala Asp Asp Val Val Asp Ser Ser
            260                 265                 270

Lys Ser Phe Val Met Glu Asn Phe Ser Ser Tyr His Gly Thr Lys Pro
        275                 280                 285

Gly Tyr Val Asp Ser Ile Gln Lys Gly Ile Gln Lys Pro Lys Ser Gly
    290                 295                 300

Thr Gln Gly Asn Tyr Asp Asp Asp Trp Lys Glu Phe Tyr Ser Thr Asp
305                 310                 315                 320

Asn Lys Tyr Asp Ala Ala Gly Tyr Ser Val Asp Asn Glu Asn Pro Leu
                325                 330                 335

Ser Gly Lys Ala Gly Gly Val Val Lys Val Thr Tyr Pro Gly Leu Thr
```

```
                340             345             350
Lys Val Leu Ala Leu Lys Val Asp Asn Ala Glu Thr Ile Lys Lys Glu
            355                 360                 365

Leu Gly Leu Ser Leu Thr Glu Pro Leu Met Glu Gln Val Gly Thr Glu
            370                 375                 380

Glu Phe Ile Lys Arg Phe Gly Asp Gly Ala Ser Arg Val Val Leu Ser
385                 390                 395                 400

Leu Pro Phe Ala Glu Gly Ser Ser Val Glu Tyr Ile Asn Asn Trp
                405                 410                 415

Glu Gln Ala Lys Ala Leu Ser Val Glu Leu Glu Ile Asn Phe Glu Thr
            420                 425                 430

Arg Gly Lys Arg Gly Gln Asp Ala Met Tyr Glu Tyr Met Ala Gln Ala
            435                 440                 445

Cys Ala Gly Asn Arg Val Arg Ser Val Gly Ser Ser Leu Ser Cys
            450                 455                 460

Ile Asn Leu Asp Trp Asp Val Ile Arg Asp Lys Thr Lys Thr Lys Ile
465                 470                 475                 480

Glu Ser Leu Lys Glu His Gly Pro Ile Lys Asn Lys Met Ser Glu Ser
                485                 490                 495

Pro Asn Lys Thr Val Ser Glu Glu Lys Ala Lys Gln Tyr Leu Glu Glu
                500                 505                 510

Phe His Gln Thr Ala Leu Glu His Pro Glu Leu Ser Glu Leu Lys Thr
            515                 520                 525

Val Thr Gly Thr Asn Pro Val Phe Ala Gly Ala Asn Tyr Ala Ala Trp
            530                 535                 540

Ala Val Asn Val Ala Gln Val Ile Asp Ser Glu Thr Ala Asp Asn Leu
545                 550                 555                 560

Glu Lys Thr Thr Ala Ala Leu Ser Ile Leu Pro Gly Ile Gly Ser Val
                565                 570                 575

Met Gly Ile Ala Asp Gly Ala Val His His Asn Thr Glu Glu Ile Val
            580                 585                 590

Ala Gln Ser Ile Ala Leu Ser Ser Leu Met Val Ala Gln Ala Ile Pro
            595                 600                 605

Leu Val Gly Glu Leu Val Asp Ile Gly Phe Ala Ala Tyr Asn Phe Val
            610                 615                 620

Glu Ser Ile Ile Asn Leu Phe Gln Val Val His Asn Ser Tyr Asn Arg
625                 630                 635                 640

Pro Ala Tyr Ser Pro Gly His Lys Thr Gln Pro Phe Leu His Asp Gly
                645                 650                 655

Tyr Ala Val Ser Trp Asn Thr Val Glu Asp Ser Ile Ile Arg Thr Gly
                660                 665                 670

Phe Gln Gly Glu Ser Gly His Asp Ile Lys Ile Thr Ala Glu Asn Thr
            675                 680                 685

Pro Leu Pro Ile Ala Gly Val Leu Leu Pro Thr Ile Pro Gly Lys Leu
            690                 695                 700

Asp Val Asn Lys Ser Lys Thr His Ile Ser Val Asn Gly Arg Lys Ile
705                 710                 715                 720

Arg Met Arg Cys Arg Ala Ile Asp Gly Asp Val Thr Phe Cys Arg Pro
                725                 730                 735

Lys Ser Pro Val Tyr Val Gly Asn Gly Val His Ala Asn Leu His Val
                740                 745                 750

Ala Phe His Arg Ser Ser Ser Glu Lys Ile His Ser Asn Glu Ile Ser
            755                 760                 765
```

Ser Asp Ser Ile Gly Val Leu Gly Tyr Gln Lys Thr Val Asp His Thr
       770                 775                 780

Lys Val Asn Ser Lys Leu Ser Leu Phe Phe Glu Ile Lys Ser
785                 790                 795

<210> SEQ ID NO 17
<211> LENGTH: 1365
<212> TYPE: DNA
<213> ORGANISM: Artificial Sequence
<220> FEATURE:
<223> OTHER INFORMATION: Synthetic sequence

<400> SEQUENCE: 17

```
atgggcgctg atgatgttgt tgattcttct aaatcttttg tgatggaaaa ctttcttcg      60
taccacggga ctaaacctgg ttatgtagat tccattcaaa aaggtataca aaagccaaaa    120
tctggtacac aaggaaatta tgacgatgat tggaagagt tttatagtac cgacaataaa    180
tacgacgctc cggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gaagctctgg aagcggaagc    600
gggggcggtg gagttgcagc agacattgga acaggattag cagatgcact gacggcaccg    660
ttggatcata aagacaaagg cttgaaatcg cttaccttag aagattctat ttcacaaaat    720
ggcacccta ccttgtccgc gcaaggcgct gaaaaaactt taaagtcgg tgacagagat    780
aatagcttaa atacaggtaa actcaaaaat gataaaatct cgcgttttga tttcgtgcaa    840
aaaatcgaag tagatggcca aaccattaca ttagcaagcg gtgaattcca aatatataaa    900
caagaccatt cagcagtcgt tgcattgcaa attgaaaaaa tcaacaaccc cgacaaaatc    960
gacagcctga taaccaacg ttccttcctt gtcagcggtt gggcggtga acatacagcc   1020
ttcaaccaat taccaagcgg caaagcggag tatcacggta agcatttag ctcagatgat   1080
gcaggcggta aattaactta tacaattgac tttgcagcaa acaaggaca tggcaaaatt   1140
gaacatttaa aaacacccga acagaacgta gagctcgcaa ccgcagaact caaagcagat   1200
gaaaaatcac acgcagtcat tttgggtgac acgcgctacg gcagcgaaga aaaaggtact   1260
taccacttag ctctttttgg cgaccgagct caagaaatcg caggtagcgc aaccgtaaag   1320
ataagggaaa aggttcacga aattgggatc gcgggcaaac aataa              1365
```

<210> SEQ ID NO 18
<211> LENGTH: 453
<212> TYPE: PRT
<213> ORGANISM: Artificial Sequence
<220> FEATURE:
<223> OTHER INFORMATION: Synthetic sequence

<400> SEQUENCE: 18

Gly Ala Asp Asp Val Val Asp Ser Ser Lys Ser Phe Val Met Glu Asn
1                5                  10                  15

Phe Ser Tyr His Gly Thr Lys Pro Gly Tyr Val Asp Ser Ile Gln
            20                  25                  30

-continued

```
Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Phe Ile Lys Arg Phe Gly
            115                 120                 125

Asp Gly Ala Ser Arg Val Val Leu Ser Leu Pro Phe Ala Glu Gly Ser
            130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Ser Gly Ser Gly Ser Gly Gly Gly Val Ala Ala Asp Ile
            195                 200                 205

Gly Thr Gly Leu Ala Asp Ala Leu Thr Ala Pro Leu Asp His Lys Asp
            210                 215                 220

Lys Gly Leu Lys Ser Leu Thr Leu Glu Asp Ser Ile Ser Gln Asn Gly
225                 230                 235                 240

Thr Leu Thr Leu Ser Ala Gln Gly Ala Glu Lys Thr Phe Lys Val Gly
            245                 250                 255

Asp Arg Asp Asn Ser Leu Asn Thr Gly Lys Leu Lys Asn Asp Lys Ile
            260                 265                 270

Ser Arg Phe Asp Phe Val Gln Lys Ile Glu Val Asp Gly Gln Thr Ile
            275                 280                 285

Thr Leu Ala Ser Gly Glu Phe Gln Ile Tyr Lys Gln Asp His Ser Ala
            290                 295                 300

Val Val Ala Leu Gln Ile Glu Lys Ile Asn Asn Pro Asp Lys Ile Asp
305                 310                 315                 320

Ser Leu Ile Asn Gln Arg Ser Phe Leu Val Ser Gly Leu Gly Gly Glu
            325                 330                 335

His Thr Ala Phe Asn Gln Leu Pro Ser Gly Lys Ala Glu Tyr His Gly
            340                 345                 350

Lys Ala Phe Ser Ser Asp Asp Ala Gly Gly Lys Leu Thr Tyr Thr Ile
            355                 360                 365

Asp Phe Ala Ala Lys Gln Gly His Gly Lys Ile Glu His Leu Lys Thr
            370                 375                 380

Pro Glu Gln Asn Val Glu Leu Ala Thr Glu Leu Lys Ala Asp Glu
385                 390                 395                 400

Lys Ser His Ala Val Ile Leu Gly Asp Thr Arg Tyr Gly Ser Glu Glu
            405                 410                 415

Lys Gly Thr Tyr His Leu Ala Leu Phe Gly Asp Arg Ala Gln Glu Ile
            420                 425                 430

Ala Gly Ser Ala Thr Val Lys Ile Arg Glu Lys Val His Glu Ile Gly
            435                 440                 445

Ile Ala Gly Lys Gln
```

<210> SEQ ID NO 19
<211> LENGTH: 258
<212> TYPE: PRT
<213> ORGANISM: Artificial Sequence
<220> FEATURE:
<223> OTHER INFORMATION: Synthetic sequence

<400> SEQUENCE: 19

Cys Gly Ser Ser Gly Gly Gly Val Ala Ala Asp Ile Gly Thr Gly
1               5                   10                  15

Leu Ala Asp Ala Leu Thr Ala Pro Leu Asp His Lys Asp Lys Gly Leu
                20                  25                  30

Lys Ser Leu Thr Leu Glu Asp Ser Ile Ser Gln Asn Gly Thr Leu Thr
            35                  40                  45

Leu Ser Ala Gln Gly Ala Glu Lys Thr Phe Lys Val Gly Asp Lys Asp
        50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
130                 135                 140

Phe Asn Gln Leu Pro Ser Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Ser Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 20
<211> LENGTH: 260
<212> TYPE: PRT
<213> ORGANISM: Neisseria meningitidis (group B)

<400> SEQUENCE: 20

Cys Ser Ser Gly Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

```
Gly Thr Leu Thr Leu Ser Ala Gln Gly Ala Glu Lys Thr Tyr Gly Asn
 50                  55                  60

Gly Asp Ser Leu Asn Thr Gly Lys Leu Lys Asn Asp Lys Val Ser Arg
 65                  70                  75                  80

Phe Asp Phe Ile Arg Gln Ile Glu Val Asp Gly Gln Leu Ile Thr Leu
                 85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260

<210> SEQ ID NO 21
<211> LENGTH: 471
<212> TYPE: PRT
<213> ORGANISM: Streptococcus pneumoniae

<400> SEQUENCE: 21

Met Ala Asn Lys Ala Val Asn Asp Phe Ile Leu Ala Met Asn Tyr Asp
 1               5                  10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
 50                  55                  60

Thr Asn Asp Ser Arg Leu Tyr Pro Gly Ala Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160
```

```
Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 22
<211> LENGTH: 254
<212> TYPE: PRT
<213> ORGANISM: Neisseria meningitidis (group B)

<400> SEQUENCE: 22

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
```

```
            50                  55                  60
Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
        130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 23
<211> LENGTH: 261
<212> TYPE: PRT
<213> ORGANISM: Neisseria meningitidis (group B)

<400> SEQUENCE: 23

Cys Ser Ser Gly Ser Gly Ser Gly Gly Gly Val Ala Ala Asp Ile
 1               5                  10                  15

Gly Thr Gly Leu Ala Asp Ala Leu Thr Ala Pro Leu Asp His Lys Asp
                20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
        50                  55                  60

Asp Lys Asp Asn Ser Leu Asn Thr Gly Lys Leu Lys Asn Asp Lys Ile
 65                  70                  75                  80

Ser Arg Phe Asp Phe Val Gln Lys Ile Glu Val Asp Gly Gln Thr Ile
                 85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175
```

```
Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 24
<211> LENGTH: 259
<212> TYPE: PRT
<213> ORGANISM: Neisseria meningitidis (group B)

<400> SEQUENCE: 24

Cys Ser Ser Gly Gly Gly Gly Gly Val Ala Ala Asp Ile Gly Thr
1               5                   10                  15

Gly Leu Ala Asp Ala Leu Thr Ala Pro Leu Asp His Lys Asp Lys Gly
            20                  25                  30

Leu Lys Ser Leu Thr Leu Glu Asp Ser Ile Pro Gln Asn Gly Thr Leu
        35                  40                  45

Thr Leu Ser Ala Gln Gly Ala Glu Lys Thr Phe Lys Ala Gly Asp Lys
    50                  55                  60

Asp Asn Ser Leu Asn Thr Gly Lys Leu Lys Asn Asp Lys Ile Ser Arg
65                  70                  75                  80

Phe Asp Phe Val Gln Lys Ile Glu Val Asp Gly Gln Thr Ile Thr Leu
                85                  90                  95

Ala Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
130                 135                 140

Ala Phe Asn Gln Leu Pro Gly Asp Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln

<210> SEQ ID NO 25
<211> LENGTH: 260
```

```
<212> TYPE: PRT
<213> ORGANISM: Neisseria meningitidis (group B)

<400> SEQUENCE: 25

Cys Ser Ser Gly Gly Gly Ser Gly Gly Ile Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Pro Gln Asn Gly Thr
            35                  40                  45

Leu Thr Leu Ser Ala Gln Gly Ala Glu Lys Thr Phe Lys Ala Gly Asp
50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
            115                 120                 125

Leu Ile Asn Gln Arg Ser Phe Leu Val Ser Gly Leu Gly Gly Glu His
130                 135                 140

Thr Ala Phe Asn Gln Leu Pro Gly Gly Lys Ala Glu Tyr His Gly Lys
145                 150                 155                 160

Ala Phe Ser Ser Asp Asp Pro Asn Gly Arg Leu His Tyr Ser Ile Asp
                165                 170                 175

Phe Thr Lys Lys Gln Gly Tyr Gly Arg Ile Glu His Leu Lys Thr Pro
            180                 185                 190

Glu Gln Asn Val Glu Leu Ala Ser Ala Glu Leu Lys Ala Asp Glu Lys
            195                 200                 205

Ser His Ala Val Ile Leu Gly Asp Thr Arg Tyr Gly Ser Glu Glu Lys
            210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
                245                 250                 255

Ala Gly Lys Gln
            260

<210> SEQ ID NO 26
<211> LENGTH: 257
<212> TYPE: PRT
<213> ORGANISM: Neisseria meningitidis (group B)

<400> SEQUENCE: 26

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Lys
            20                  25                  30

Ser Leu Thr Leu Glu Asp Ser Ile Ser Gln Asn Gly Thr Leu Thr Leu
            35                  40                  45

Ser Ala Gln Gly Ala Glu Lys Thr Phe Lys Val Gly Asp Lys Asp Asn
50                  55                  60

Ser Leu Asn Thr Gly Lys Leu Lys Asn Asp Lys Ile Ser Arg Phe Asp
65                  70                  75                  80
```

-continued

```
Phe Val Gln Lys Ile Glu Val Asp Gly Gln Thr Ile Thr Leu Ala Ser
                85                  90                  95

Gly Glu Phe Gln Ile Tyr Lys Gln Asn His Ser Ala Val Val Ala Leu
            100                 105                 110

Gln Ile Glu Lys Ile Asn Asn Pro Asp Lys Ile Asp Ser Leu Ile Asn
        115                 120                 125

Gln Arg Ser Phe Leu Val Ser Gly Leu Gly Gly Glu His Thr Ala Phe
    130                 135                 140

Asn Gln Leu Pro Gly Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ala Ala Glu Leu Lys Ala Asp Glu Lys Ser His Ala
        195                 200                 205

Val Ile Leu Gly Asp Thr Arg Tyr Gly Ser Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Ser Ile Ala Gly Lys
                245                 250                 255

Gln
```

<210> SEQ ID NO 27
<211> LENGTH: 254
<212> TYPE: PRT
<213> ORGANISM: Neisseria meningitidis (group B)

<400> SEQUENCE: 27

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190
```

Ala Ser Ala Glu Leu Lys Ala Asp Glu Lys Ser His Ala Val Ile Leu
            195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 28
<211> LENGTH: 254
<212> TYPE: PRT
<213> ORGANISM: Neisseria meningitidis (group B)

<400> SEQUENCE: 28

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 29
<211> LENGTH: 254
<212> TYPE: PRT
<213> ORGANISM: Neisseria meningitidis (group B)

<400> SEQUENCE: 29

Cys Ser Ser Gly Gly Gly Gly Val Ala Ala Asp Ile Gly Ala Gly Leu
1               5                   10                  15

Ala Asp Ala Leu Thr Thr Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 30
<211> LENGTH: 254
<212> TYPE: PRT
<213> ORGANISM: Neisseria meningitidis (group B)

<400> SEQUENCE: 30

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

```
Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 31
<211> LENGTH: 254
<212> TYPE: PRT
<213> ORGANISM: Neisseria meningitidis (group B)

<400> SEQUENCE: 31

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
                100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
        130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Ser Ile Ala Gly Lys Gln
                245                 250
```

<210> SEQ ID NO 32
<211> LENGTH: 262
<212> TYPE: PRT
<213> ORGANISM: Neisseria meningitidis (group B)

<400> SEQUENCE: 32

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Ser Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 33
<211> LENGTH: 255
<212> TYPE: PRT
<213> ORGANISM: Neisseria meningitidis (group B)

<400> SEQUENCE: 33

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg

-continued

```
            65                  70                  75                  80
Gln Ile Glu Val Asp Gly Gln Leu Ile Thr Leu Glu Ser Gly Glu Phe
                85                  90                  95
Gln Val Tyr Lys Gln Ser His Ser Ala Leu Thr Ala Leu Gln Thr Glu
            100                 105                 110
Gln Glu Gln Asp Pro Glu His Ser Gly Lys Met Val Ala Lys Arg Arg
            115                 120                 125
Phe Lys Ile Gly Asp Ile Ala Gly Glu His Thr Ser Phe Asp Lys Leu
130                 135                 140
Pro Lys Asp Val Met Ala Thr Tyr Arg Gly Thr Ala Phe Gly Ser Asp
145                 150                 155                 160
Asp Ala Gly Gly Lys Leu Thr Tyr Thr Ile Asp Phe Ala Ala Lys Gln
                165                 170                 175
Gly His Gly Lys Ile Glu His Leu Lys Ser Pro Glu Leu Asn Val Glu
            180                 185                 190
Leu Ala Thr Ala Tyr Ile Lys Pro Asp Glu Lys His His Ala Val Ile
            195                 200                 205
Ser Gly Ser Val Leu Tyr Asn Gln Asp Glu Lys Gly Ser Tyr Ser Leu
        210                 215                 220
Gly Ile Phe Gly Gly Gln Ala Gln Glu Val Ala Gly Ser Ala Glu Val
225                 230                 235                 240
Glu Thr Ala Asn Gly Ile His His Ile Gly Leu Ala Ala Lys Gln
                245                 250                 255

<210> SEQ ID NO 34
<211> LENGTH: 263
<212> TYPE: PRT
<213> ORGANISM: Neisseria meningitidis (group B)

<400> SEQUENCE: 34

Cys Ser Ser Gly Gly Gly Gly Ser Gly Gly Gly Gly Val Ala Ala Asp
1               5                   10                  15
Ile Gly Ala Gly Leu Ala Asp Ala Leu Thr Ala Pro Leu Asp His Lys
                20                  25                  30
Asp Lys Gly Leu Lys Ser Leu Thr Leu Glu Asp Ser Ile Ser Gln Asn
            35                  40                  45
Gly Thr Leu Thr Leu Ser Ala Gln Gly Ala Glu Arg Thr Phe Lys Ala
        50                  55                  60
Gly Asp Lys Asp Asn Ser Leu Asn Thr Gly Lys Leu Lys Asn Asp Lys
65                  70                  75                  80
Ile Ser Arg Phe Asp Phe Ile Arg Gln Ile Glu Val Asp Gly Gln Leu
                85                  90                  95
Ile Thr Leu Glu Ser Gly Glu Phe Gln Val Tyr Lys Gln Ser His Ser
            100                 105                 110
Ala Leu Thr Ala Leu Gln Thr Glu Gln Val Gln Asp Ser Glu His Ser
        115                 120                 125
Gly Lys Met Val Ala Lys Arg Gln Phe Arg Ile Gly Asp Ile Val Gly
    130                 135                 140
Glu His Thr Ser Phe Asp Lys Leu Pro Lys Asp Val Met Ala Thr Tyr
145                 150                 155                 160
Arg Gly Thr Ala Phe Gly Ser Asp Asp Ala Gly Gly Lys Leu Thr Tyr
                165                 170                 175
Thr Ile Asp Phe Ala Ala Lys Gln Gly His Gly Lys Ile Glu His Leu
            180                 185                 190
```

```
Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Thr Ala Asn Gly Ile Arg His
            245                 250                 255

Ile Gly Leu Ala Ala Lys Gln
            260

<210> SEQ ID NO 35
<211> LENGTH: 255
<212> TYPE: PRT
<213> ORGANISM: Neisseria meningitidis (group B)

<400> SEQUENCE: 35

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 36
<211> LENGTH: 255
<212> TYPE: PRT
<213> ORGANISM: Neisseria meningitidis (group B)

<400> SEQUENCE: 36
```

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Ile Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
            195                 200                 205

Ser Gly Ser Val Leu Tyr Asn Gln Ala Glu Lys Gly Ser Tyr Ser Leu
210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 37
<211> LENGTH: 255
<212> TYPE: PRT
<213> ORGANISM: Neisseria meningitidis (group B)

<400> SEQUENCE: 37

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

```
Phe Arg Ile Gly Asp Ile Ala Gly Glu His Thr Ser Phe Asp Lys Leu
            130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 38
<211> LENGTH: 255
<212> TYPE: PRT
<213> ORGANISM: Neisseria meningitidis (group B)

<400> SEQUENCE: 38

Cys Ser Ser Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
            130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
```

<210> SEQ ID NO 39
<211> LENGTH: 255
<212> TYPE: PRT
<213> ORGANISM: Neisseria meningitidis (group B)

<400> SEQUENCE: 39

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 40
<211> LENGTH: 263
<212> TYPE: PRT
<213> ORGANISM: Neisseria meningitidis (group B)

<400> SEQUENCE: 40

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys

```
                65                  70                  75                  80
Ile Ser Arg Phe Asp Phe Ile Arg Gln Ile Glu Val Asp Gly Gln Leu
                    85                  90                  95

Ile Thr Leu Glu Ser Gly Glu Phe Gln Val Tyr Lys Gln Ser His Ser
                100                 105                 110

Ala Leu Thr Ala Leu Gln Thr Glu Gln Val Gln Asp Ser Glu His Ser
                115                 120                 125

Gly Lys Met Val Ala Lys Arg Gln Phe Arg Ile Gly Asp Ile Val Gly
            130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
                180                 185                 190

Lys Ser Pro Glu Leu Asn Val Asp Leu Ala Ala Ala Asp Ile Lys Pro
            195                 200                 205

Asp Glu Lys His His Ala Val Ile Ser Gly Ser Val Leu Tyr Asn Gln
            210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 41
<211> LENGTH: 255
<212> TYPE: PRT
<213> ORGANISM: Neisseria meningitidis (group B)

<400> SEQUENCE: 41

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175
```

-continued

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255

<210> SEQ ID NO 42
<211> LENGTH: 259
<212> TYPE: PRT
<213> ORGANISM: Artificial Sequence
<220> FEATURE:
<223> OTHER INFORMATION: Synthetic sequence

<400> SEQUENCE: 42

Ser Ser Gly Gly Gly Ser Gly Gly Ile Ala Ala Asp Ile Gly Thr
1               5                   10                  15

Gly Leu Ala Asp Ala Leu Thr Ala Pro Leu Asp His Lys Asp Lys Gly
            20                  25                  30

Leu Lys Ser Leu Thr Leu Glu Asp Ser Ile Pro Gln Asn Gly Thr Leu
        35                  40                  45

Thr Leu Ser Ala Gln Gly Ala Glu Lys Thr Phe Lys Ala Gly Asp Lys
    50                  55                  60

Asp Asn Ser Leu Asn Thr Gly Lys Leu Lys Asn Asp Lys Ile Ser Arg
65                  70                  75                  80

Phe Asp Phe Val Gln Lys Ile Glu Val Asp Gly Gln Thr Ile Thr Leu
                85                  90                  95

Ala Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Gly Gly Lys Ala Glu Tyr His Gly Lys Ala
145                 150                 155                 160

Phe Ser Ser Asp Asp Pro Asn Gly Arg Leu His Tyr Ser Ile Asp Phe
                165                 170                 175

Thr Lys Lys Gln Gly Tyr Gly Arg Ile Glu His Leu Lys Thr Pro Glu
            180                 185                 190

Gln Asn Val Glu Leu Ala Ser Ala Glu Leu Lys Ala Asp Glu Lys Ser
        195                 200                 205

His Ala Val Ile Leu Gly Asp Thr Arg Tyr Gly Ser Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Arg Glu Lys Val His Glu Ile Gly Ile Ala
                245                 250                 255

Gly Lys Gln

<210> SEQ ID NO 43
<211> LENGTH: 258
<212> TYPE: PRT

<213> ORGANISM: Artificial Sequence
<220> FEATURE:
<223> OTHER INFORMATION: Synthetic sequence

<400> SEQUENCE: 43

```
Ser Ser Gly Gly Gly Gly Gly Val Ala Ala Asp Ile Thr Gly
1               5                   10                  15

Leu Ala Asp Ala Leu Thr Ala Pro Leu Asp His Lys Asp Lys Gly Leu
                20                  25                  30

Lys Ser Leu Thr Leu Glu Asp Ser Ile Pro Gln Asn Gly Thr Leu Thr
            35                  40                  45

Leu Ser Ala Gln Gly Ala Glu Lys Thr Phe Lys Ala Gly Asp Lys Asp
50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
130                 135                 140

Phe Asn Gln Leu Pro Gly Asp Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ala Ala Glu Leu Lys Ala Asp Glu Lys Ser His
        195                 200                 205

Ala Val Ile Leu Gly Asp Thr Arg Tyr Gly Ser Glu Glu Lys Gly Thr
210                 215                 220

Tyr His Leu Ala Leu Phe Gly Asp Arg Ala Gln Glu Ile Ala Gly Ser
225                 230                 235                 240

Ala Thr Val Lys Ile Gly Glu Lys Val His Glu Ile Gly Ile Ala Gly
                245                 250                 255

Lys Gln
```

<210> SEQ ID NO 44
<211> LENGTH: 260
<212> TYPE: PRT
<213> ORGANISM: Artificial Sequence
<220> FEATURE:
<223> OTHER INFORMATION: Synthetic sequence

<400> SEQUENCE: 44

```
Ser Ser Gly Ser Gly Ser Gly Gly Gly Val Ala Ala Asp Ile Gly
1               5                   10                  15

Thr Gly Leu Ala Asp Ala Leu Thr Ala Pro Leu Asp His Lys Asp Lys
                20                  25                  30

Gly Leu Lys Ser Leu Thr Leu Glu Asp Ser Ile Ser Gln Asn Gly Thr
            35                  40                  45

Leu Thr Leu Ser Ala Gln Gly Ala Glu Lys Thr Phe Lys Val Gly Asp
        50                  55                  60

Lys Asp Asn Ser Leu Asn Thr Gly Lys Leu Lys Asn Asp Lys Ile Ser
```

```
                65                  70                  75                  80
Arg Phe Asp Phe Val Gln Lys Ile Glu Val Asp Gly Gln Thr Ile Thr
                    85                  90                  95
Leu Ala Ser Gly Glu Phe Gln Ile Tyr Lys Gln Asp His Ser Ala Val
                100                 105                 110
Val Ala Leu Gln Ile Glu Lys Ile Asn Asn Pro Asp Lys Ile Asp Ser
                115                 120                 125
Leu Ile Asn Gln Arg Ser Phe Leu Val Ser Gly Leu Gly Gly Glu His
            130                 135                 140
Thr Ala Phe Asn Gln Leu Pro Ser Gly Lys Ala Glu Tyr His Gly Lys
145                 150                 155                 160
Ala Phe Ser Ser Asp Asp Ala Gly Gly Lys Leu Thr Tyr Thr Ile Asp
                165                 170                 175
Phe Ala Ala Lys Gln Gly His Gly Lys Ile Glu His Leu Lys Thr Pro
                180                 185                 190
Glu Gln Asn Val Glu Leu Ala Ser Ala Glu Leu Lys Ala Asp Glu Lys
                195                 200                 205
Ser His Ala Val Ile Leu Gly Asp Thr Arg Tyr Gly Ser Glu Glu Lys
            210                 215                 220
Gly Thr Tyr His Leu Ala Leu Phe Gly Asp Arg Ala Gln Glu Ile Ala
225                 230                 235                 240
Gly Ser Ala Thr Val Lys Ile Arg Glu Lys Val His Glu Ile Gly Ile
                245                 250                 255
Ala Gly Lys Gln
            260

<210> SEQ ID NO 45
<211> LENGTH: 256
<212> TYPE: PRT
<213> ORGANISM: Artificial Sequence
<220> FEATURE:
<223> OTHER INFORMATION: Synthetic sequence

<400> SEQUENCE: 45

Ser Ser Gly Gly Gly Gly Val Ala Ala Asp Ile Gly Ala Gly Leu Ala
1               5                   10                  15
Asp Ala Leu Thr Ala Pro Leu Asp His Lys Asp Lys Gly Leu Lys Ser
                20                  25                  30
Leu Thr Leu Glu Asp Ser Ile Ser Gln Asn Gly Thr Leu Thr Leu Ser
            35                  40                  45
Ala Gln Gly Ala Glu Lys Thr Phe Lys Val Gly Asp Lys Asp Asn Ser
        50                  55                  60
Leu Asn Thr Gly Lys Leu Lys Asn Asp Lys Ile Ser Arg Phe Asp Phe
65                  70                  75                  80
Val Gln Lys Ile Glu Val Asp Gly Gln Thr Ile Thr Leu Ala Ser Gly
                85                  90                  95
Glu Phe Gln Ile Tyr Lys Gln Asn His Ser Ala Val Val Ala Leu Gln
                100                 105                 110
Ile Glu Lys Ile Asn Asn Pro Asp Lys Ile Asp Ser Leu Ile Asn Gln
            115                 120                 125
Arg Ser Phe Leu Val Ser Gly Leu Gly Gly Glu His Thr Ala Phe Asn
        130                 135                 140
Gln Leu Pro Gly Gly Lys Ala Glu Tyr His Gly Lys Ala Phe Ser Ser
145                 150                 155                 160
Asp Asp Ala Gly Gly Lys Leu Thr Tyr Thr Ile Asp Phe Ala Ala Lys
```

```
                    165                 170                 175
Gln Gly His Gly Lys Ile Glu His Leu Lys Thr Pro Glu Gln Asn Val
                180                 185                 190
Glu Leu Ala Ala Ala Glu Leu Lys Ala Asp Glu Lys Ser His Ala Val
            195                 200                 205
Ile Leu Gly Asp Thr Arg Tyr Gly Ser Glu Glu Lys Gly Thr Tyr His
    210                 215                 220
Leu Ala Leu Phe Gly Asp Arg Ala Gln Glu Ile Ala Gly Ser Ala Thr
225                 230                 235                 240
Val Lys Ile Gly Glu Lys Val His Glu Ile Ser Ile Ala Gly Lys Gln
                245                 250                 255

<210> SEQ ID NO 46
<211> LENGTH: 253
<212> TYPE: PRT
<213> ORGANISM: Artificial Sequence
<220> FEATURE:
<223> OTHER INFORMATION: Synthetic sequence

<400> SEQUENCE: 46

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Gly Gly Lys Ala Glu Tyr His Gly Lys Ala Phe Ser Ser Asp Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
                180                 185                 190

Ser Ala Glu Leu Lys Ala Asp Glu Lys Ser His Ala Val Ile Leu Gly
            195                 200                 205

Asp Thr Arg Tyr Gly Ser Glu Lys Gly Thr Tyr His Leu Ala Leu
        210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250

<210> SEQ ID NO 47
<211> LENGTH: 258
<212> TYPE: PRT
```

<213> ORGANISM: Artificial Sequence
<220> FEATURE:
<223> OTHER INFORMATION: Synthetic sequence

<400> SEQUENCE: 47

```
Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Ser Leu Gln Ser Leu Thr Leu Asp Gln Ser Val Arg Lys Asn Glu
        35                  40                  45

Lys Leu Lys Leu Ala Ala Gln Gly Ala Glu Lys Thr Tyr Gly Asn Gly
50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Thr Ile Thr Leu Ala
                85                  90                  95

Ser Gly Glu Phe Gln Ile Tyr Lys Gln Asn His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
130                 135                 140

Phe Asn Gln Leu Pro Asp Gly Lys Ala Glu Tyr His Gly Lys Ala Phe
145                 150                 155                 160

Ser Ser Asp Asp Pro Asn Gly Arg Leu His Tyr Ser Ile Asp Phe Thr
                165                 170                 175

Lys Lys Gln Gly Tyr Gly Arg Ile Glu His Leu Lys Thr Pro Glu Gln
            180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Glu Glu Lys Gly Thr
210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln
```

<210> SEQ ID NO 48
<211> LENGTH: 253
<212> TYPE: PRT
<213> ORGANISM: Artificial Sequence
<220> FEATURE:
<223> OTHER INFORMATION: Synthetic sequence

<400> SEQUENCE: 48

```
Ser Ser Gly Gly Gly Val Ala Ala Asp Ile Gly Ala Gly Leu Ala
1               5                   10                  15

Asp Ala Leu Thr Thr Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
50                  55                  60

Gly Lys Leu Lys Asn Asp Lys Val Ser Arg Phe Asp Phe Ile Arg Gln
```

```
              65                  70                  75                  80
Ile Glu Val Asp Gly Gln Thr Ile Thr Leu Ala Ser Gly Glu Phe Gln
                    85                  90                  95

Ile Tyr Lys Gln Asn His Ser Ala Val Val Ala Leu Gln Ile Glu Lys
                100                 105                 110

Ile Asn Asn Pro Asp Lys Ile Asp Ser Leu Ile Asn Gln Arg Ser Phe
                115                 120                 125

Leu Val Ser Gly Leu Gly Gly Glu His Thr Ala Phe Asn Gln Leu Pro
            130                 135                 140

Asp Gly Lys Ala Glu Tyr His Gly Lys Ala Phe Ser Ser Asp Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
                180                 185                 190

Ser Ala Glu Leu Lys Ala Asp Glu Lys Ser His Ala Val Ile Leu Gly
                195                 200                 205

Asp Thr Arg Tyr Gly Gly Glu Glu Lys Gly Thr Tyr His Leu Ala Leu
            210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250

<210> SEQ ID NO 49
<211> LENGTH: 253
<212> TYPE: PRT
<213> ORGANISM: Artificial Sequence
<220> FEATURE:
<223> OTHER INFORMATION: Synthetic sequence

<400> SEQUENCE: 49

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
                115                 120                 125

Leu Val Ser Gly Leu Gly Gly Glu His Thr Ala Phe Asn Gln Leu Pro
            130                 135                 140

Asp Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
```

```
                180              185                  190
Ala Ala Glu Leu Lys Ala Asp Glu Lys Ser His Ala Val Ile Leu Gly
            195                 200                 205

Asp Thr Arg Tyr Gly Ser Glu Glu Lys Gly Thr Tyr His Leu Ala Leu
            210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250

<210> SEQ ID NO 50
<211> LENGTH: 253
<212> TYPE: PRT
<213> ORGANISM: Artificial Sequence
<220> FEATURE:
<223> OTHER INFORMATION: Synthetic sequence

<400> SEQUENCE: 50

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
    130                 135                 140

Asp Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ala Ala Glu Leu Lys Ala Asp Glu Lys Ser His Ala Val Ile Leu Gly
        195                 200                 205

Asp Thr Arg Tyr Gly Ser Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Gly Glu Lys Val His Glu Ile Ser Ile Ala Gly Lys Gln
                245                 250

<210> SEQ ID NO 51
<211> LENGTH: 253
<212> TYPE: PRT
<213> ORGANISM: Artificial Sequence
<220> FEATURE:
<223> OTHER INFORMATION: Synthetic sequence
```

<400> SEQUENCE: 51

```
Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Ser Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ser Ala Glu Leu Lys Ala Asp Glu Lys Ser His Ala Val Ile Leu Gly
        195                 200                 205

Asp Thr Arg Tyr Gly Gly Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250
```

<210> SEQ ID NO 52
<211> LENGTH: 261
<212> TYPE: PRT
<213> ORGANISM: Artificial Sequence
<220> FEATURE:
<223> OTHER INFORMATION: Synthetic sequence

<400> SEQUENCE: 52

```
Ser Ser Gly Gly Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Pro Gln Asn Gly
        35                  40                  45

Thr Leu Thr Leu Ser Ala Gln Gly Ala Glu Lys Thr Phe Lys Ala Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95
```

Thr Leu Ala Ser Gly Glu Phe Gln Ile Tyr Lys Gln Asn His Ser Ala
                100                 105                 110

Val Val Ala Leu Gln Ile Glu Lys Ile Asn Asn Pro Asp Lys Ile Asp
            115                 120                 125

Ser Leu Ile Asn Gln Arg Ser Phe Leu Val Ser Gly Leu Gly Gly Glu
        130                 135                 140

His Thr Ala Phe Asn Gln Leu Pro Gly Asp Lys Ala Glu Tyr His Gly
145                 150                 155                 160

Lys Ala Phe Ser Ser Asp Pro Asn Gly Arg Leu His Tyr Thr Ile
                165                 170                 175

Asp Phe Thr Asn Lys Gln Gly Tyr Gly Arg Ile Glu His Leu Lys Thr
            180                 185                 190

Pro Glu Leu Asn Val Asp Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Gly Glu Lys Val His Glu Ile Gly
                245                 250                 255

Ile Ala Gly Lys Gln
            260

<210> SEQ ID NO 53
<211> LENGTH: 259
<212> TYPE: PRT
<213> ORGANISM: Artificial Sequence
<220> FEATURE:
<223> OTHER INFORMATION: Synthetic sequence

<400> SEQUENCE: 53

Ser Ser Gly Gly Gly Gly Ser Gly Gly Gly Gly Val Thr Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Tyr Gly Asn Gly
    50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Leu Ile Thr Leu Glu
                85                  90                  95

Ser Gly Glu Phe Gln Val Tyr Lys Gln Ser His Ser Ala Leu Thr Ala
            100                 105                 110

Leu Gln Thr Glu Gln Glu Gln Asp Pro Glu His Ser Glu Lys Met Val
        115                 120                 125

Ala Lys Arg Arg Phe Arg Ile Gly Asp Ile Ala Gly Glu His Thr Ser
    130                 135                 140

Phe Asp Lys Leu Pro Lys Asp Val Met Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Asp Leu Ala Val Ala Tyr Ile Lys Pro Asp Glu Lys His
            195                 200                 205

His Ala Val Ile Ser Gly Ser Val Leu Tyr Asn Gln Asp Glu Lys Gly
    210                 215                 220

Ser Tyr Ser Leu Gly Ile Phe Gly Lys Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 54
<211> LENGTH: 262
<212> TYPE: PRT
<213> ORGANISM: Artificial Sequence
<220> FEATURE:
<223> OTHER INFORMATION: Synthetic sequence

<400> SEQUENCE: 54

Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Arg Thr Phe Lys Ala Gly
    50                  55                  60

Asp Lys Asp Asn Ser Leu Asn Thr Gly Lys Leu Lys Asn Asp Lys Ile
65                  70                  75                  80

Ser Arg Phe Asp Phe Ile Arg Gln Ile Glu Val Asp Gly Gln Leu Ile
                85                  90                  95

Thr Leu Glu Ser Gly Glu Phe Gln Val Tyr Lys Gln Ser His Ser Ala
            100                 105                 110

Leu Thr Ala Leu Gln Thr Glu Gln Val Gln Asp Ser Glu His Ser Gly
        115                 120                 125

Lys Met Val Ala Lys Arg Gln Phe Arg Ile Gly Asp Ile Val Gly Glu
    130                 135                 140

His Thr Ser Phe Asp Lys Leu Pro Lys Asp Val Met Ala Thr Tyr Arg
145                 150                 155                 160

Gly Thr Ala Phe Gly Ser Asp Ala Gly Lys Leu Thr Tyr Thr
                165                 170                 175

Ile Asp Phe Ala Ala Lys Gln Gly His Gly Lys Ile Glu His Leu Lys
            180                 185                 190

Ser Pro Glu Leu Asn Val Asp Leu Ala Ala Asp Ile Lys Pro Asp
        195                 200                 205

Glu Lys His His Ala Val Ile Ser Gly Ser Val Leu Tyr Asn Gln Ala
    210                 215                 220

Glu Lys Gly Ser Tyr Ser Leu Gly Ile Phe Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
            260

<210> SEQ ID NO 55
<211> LENGTH: 254
<212> TYPE: PRT

<213> ORGANISM: Artificial Sequence
<220> FEATURE:
<223> OTHER INFORMATION: Synthetic sequence

<400> SEQUENCE: 55

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Val Gln Asp Ser Glu Asp Ser Gly Lys Met Val Ala Lys Arg Gln Phe
            115                 120                 125

Arg Ile Gly Asp Ile Ala Gly Glu His Thr Ser Phe Asp Lys Leu Pro
130                 135                 140

Lys Gly Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Glu Leu
            180                 185                 190

Ala Thr Ala Tyr Ile Lys Pro Asp Glu Lys Arg His Ala Val Ile Ser
        195                 200                 205

Gly Ser Val Leu Tyr Asn Gln Asp Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile His His Ile Gly Leu Ala Ala Lys Gln
                245                 250

<210> SEQ ID NO 56
<211> LENGTH: 254
<212> TYPE: PRT
<213> ORGANISM: Artificial Sequence
<220> FEATURE:
<223> OTHER INFORMATION: Synthetic sequence

<400> SEQUENCE: 56

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Ile Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

-continued

```
Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Ser Asp Asp
145                 150                 155                 160

Ala Gly Gly Lys Leu Ile Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ala Asp Ile Lys Pro Asp Glu Lys His His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250

<210> SEQ ID NO 57
<211> LENGTH: 254
<212> TYPE: PRT
<213> ORGANISM: Artificial Sequence
<220> FEATURE:
<223> OTHER INFORMATION: Synthetic sequence

<400> SEQUENCE: 57

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190
```

Ala Ala Ser Asp Ile Lys Pro Asp Lys Lys Arg His Ala Val Ile Ser
            195                 200                 205

Gly Ser Val Leu Tyr Asn Gln Ala Glu Lys Gly Ser Tyr Ser Leu Gly
        210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250

<210> SEQ ID NO 58
<211> LENGTH: 254
<212> TYPE: PRT
<213> ORGANISM: Artificial Sequence
<220> FEATURE:
<223> OTHER INFORMATION: Synthetic sequence

<400> SEQUENCE: 58

Ser Ser Gly Gly Gly Val Ala Ala Asp Ile Gly Ala Val Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250

<210> SEQ ID NO 59
<211> LENGTH: 254
<212> TYPE: PRT
<213> ORGANISM: Artificial Sequence
<220> FEATURE:
<223> OTHER INFORMATION: Synthetic sequence

<400> SEQUENCE: 59

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65              70                  75                  80

Ile Glu Val Asp Gly Gln Leu Ile Thr Leu Ser Gly Glu Phe Gln
                85                  90                  95

Val Tyr Lys Gln Ser His Ser Ala Leu Thr Ala Phe Gln Thr Glu Gln
            100                 105                 110

Ile Gln Asp Ser Glu His Ser Gly Lys Met Val Ala Lys Arg Gln Phe
            115                 120                 125

Arg Ile Gly Asp Ile Ala Gly Glu His Thr Ser Phe Asp Lys Leu Pro
130                 135                 140

Glu Gly Gly Arg Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

Asn Gly Lys Ile Glu His Leu Lys Ser Pro Glu Leu Asn Val Asp Leu
            180                 185                 190

Ala Ala Ala Asp Ile Lys Pro Asp Gly Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250

<210> SEQ ID NO 60
<211> LENGTH: 262
<212> TYPE: PRT
<213> ORGANISM: Artificial Sequence
<220> FEATURE:
<223> OTHER INFORMATION: Synthetic sequence

<400> SEQUENCE: 60

Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Arg Thr Phe Lys Ala Gly
    50                  55                  60

Asp Lys Asp Asn Ser Leu Asn Thr Gly Lys Leu Lys Asn Asp Lys Ile
65              70                  75                  80

Ser Arg Phe Asp Phe Ile Arg Gln Ile Glu Val Asp Gly Gln Leu Ile
                85                  90                  95

Thr Leu Glu Ser Gly Glu Phe Gln Val Tyr Lys Gln Ser His Ser Ala
            100                 105                 110

```
Leu Thr Ala Leu Gln Thr Glu Gln Val Gln Asp Ser Glu His Ser Gly
        115                 120                 125

Lys Met Val Ala Lys Arg Gln Phe Arg Ile Gly Asp Ile Val Gly Glu
    130                 135                 140

His Thr Ser Phe Gly Lys Leu Pro Lys Asp Val Met Ala Thr Tyr Arg
145                 150                 155                 160

Gly Thr Ala Phe Gly Ser Asp Asp Ala Gly Gly Lys Leu Thr Tyr Thr
                165                 170                 175

Ile Asp Phe Ala Ala Lys Gln Gly His Gly Lys Ile Glu His Leu Lys
                180                 185                 190

Ser Pro Glu Leu Asn Val Asp Leu Ala Ala Asp Ile Lys Pro Asp
        195                 200                 205

Glu Lys His His Ala Val Ile Ser Gly Ser Val Leu Tyr Asn Gln Ala
        210                 215                 220

Glu Lys Gly Ser Tyr Ser Leu Gly Ile Phe Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
            260

<210> SEQ ID NO 61
<211> LENGTH: 254
<212> TYPE: PRT
<213> ORGANISM: Artificial Sequence
<220> FEATURE:
<223> OTHER INFORMATION: Synthetic sequence

<400> SEQUENCE: 61

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Val Gln Asp Ser Glu Asp Ser Gly Lys Met Val Ala Lys Arg Gln Phe
            115                 120                 125

Arg Ile Gly Asp Ile Ala Gly Glu His Thr Ser Phe Asp Lys Leu Pro
    130                 135                 140

Lys Gly Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
            195                 200                 205
```

```
Gly Asp Thr Arg Tyr Gly Gly Glu Glu Lys Gly Thr Tyr His Leu Ala
        210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 62
<211> LENGTH: 259
<212> TYPE: PRT
<213> ORGANISM: Artificial Sequence
<220> FEATURE:
<223> OTHER INFORMATION: Synthetic sequence

<400> SEQUENCE: 62

Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
                20                  25                  30

Lys Gly Leu Gln Ser Leu Thr Leu Asp Gln Ser Val Arg Lys Asn Glu
            35                  40                  45

Lys Leu Lys Leu Ala Ala Gln Gly Ala Glu Lys Thr Tyr Gly Asn Gly
        50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Lys Leu Ile Thr Leu Glu
                85                  90                  95

Ser Gly Glu Phe Gln Val Tyr Lys Gln Ser His Ser Ala Leu Thr Ala
            100                 105                 110

Leu Gln Thr Glu Gln Val Gln Asp Ser Glu Asp Ser Gly Lys Met Val
        115                 120                 125

Ala Lys Arg Gln Phe Arg Ile Gly Asp Ile Ala Gly Glu His Thr Ser
    130                 135                 140

Phe Asp Lys Leu Pro Lys Gly Gly Ser Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Glu Leu Ala Thr Ala Tyr Ile Lys Pro Asp Glu Lys Arg
        195                 200                 205

His Ala Val Ile Ser Gly Ser Val Leu Tyr Asn Gln Asp Glu Lys Gly
    210                 215                 220

Ser Tyr Ser Leu Gly Ile Phe Gly Gly Gln Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 63
<211> LENGTH: 255
<212> TYPE: PRT
<213> ORGANISM: Artificial Sequence
<220> FEATURE:
<223> OTHER INFORMATION: Synthetic sequence

<400> SEQUENCE: 63
```

```
Gly Ser Ser Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
            165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
            245                 250                 255

<210> SEQ ID NO 64
<211> LENGTH: 254
<212> TYPE: PRT
<213> ORGANISM: Artificial Sequence
<220> FEATURE:
<223> OTHER INFORMATION: Synthetic sequence

<400> SEQUENCE: 64

Gly Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110
```

```
Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
        130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 65
<211> LENGTH: 768
<212> TYPE: DNA
<213> ORGANISM: Artificial Sequence
<220> FEATURE:
<223> OTHER INFORMATION: Synthetic sequence

<400> SEQUENCE: 65
ggcagcagcg gaggcggcgg tgtcgccgcc gacatcggcg cggtgcttgc cgatgcacta      60
accgcaccgc tcgaccataa agacaaaagt ttgcagtctt tgacgctgga tcagtccgtc     120
aggaaaaacg agaaactgaa gctggcggca caaggtgcgg aaaaaactta tggaaacggc     180
gacagcctca atacgggcaa attgaagaac gacaaggtca gccgcttcga ctttatccgt     240
caaatcgaag tggacgggca gctcattacc ttggagagcg agagttcca agtgtacaaa      300
caaagccatt ccgccttaac cgcccttcag accgagcaag tacaagattc ggagcattca     360
gggaagatgg ttgcgaaacg ccagttcaga atcggcgata tagcgggtga acatacatct     420
tttgacaagc ttcccgaagg cggcagggcg acatatcgcg ggacggcatt cggttcagac     480
gatgccagtg aaaactgac ctacaccata gatttcgccg ccaagcaggg acacggcaaa      540
atcgaacatt tgaaatcgcc agaactcaat gttgacctgg ccgcctccga tatcaagccg     600
gataaaaaac gccatgccgt catcagcggt tccgtccttt acaaccaagc cgagaaaggc     660
agttactctc taggcatctt tggcgggcaa gcccaggaag ttgccggcag cgcagaagtg     720
gaaaccgcaa acggcatacg ccatatcggt cttgccgcca agcagtaa                  768

<210> SEQ ID NO 66
<211> LENGTH: 783
<212> TYPE: DNA
<213> ORGANISM: Neisseria meningitidis (group B)

<400> SEQUENCE: 66
tgcagcagcg gaggcggcgg aagcggcggt atcgccgccg acatcggcac ggggcttgcc      60
gatgcactaa ctgcgccgct cgaccataaa gacaaaggtt tgaaatccct gacattggaa     120
gactccattc cccaaaacgg aacactgacc ctgtcggcac aaggtgcgga aaaaactttc     180
aaagccggcg acaaagacaa cagcctcaac acgggcaaac tgaagaacga caaaatcagc     240
```

```
cgcttcgact tcgtgcaaaa aatcgaagtg gacggacaaa ccatcacact ggcaagcggc      300
gaatttcaaa tatacaaaca ggaccactcc gccgtcgttg ccctacagat tgaaaaaatc      360
aacaaccccg acaaaatcga cagcctgata accaacgct ccttccttgt cagcggtttg      420
ggcggagaac ataccgcctt caaccaactg cccggcggca aagccgagta tcacggcaaa      480
gcattcagct ccgacgaccc gaacggcagg ctgcactact ccattgattt taccaaaaaa      540
cagggttacg gcagaatcga cacctgaaa acgcccgagc agaatgtcga gcttgcctcc      600
gccgaactca aagcagatga aaatcacac gccgtcattt tgggcgacac gcgctacggc      660
agcgaagaaa aaggcactta ccacctcgct cttttcggcg accgagccca agaaatcgcc      720
ggctcggcaa ccgtgaagat aagggaaaag gttcacgaaa tcggcatcgc cggcaaacag      780
tag                                                                   783

<210> SEQ ID NO 67
<211> LENGTH: 789
<212> TYPE: DNA
<213> ORGANISM: Neisseria meningitidis (group B)

<400> SEQUENCE: 67
tgcagcagcg gaggaggcgg aagcggaggc ggcggtgtcg ccgccgacat cggcacgggg       60
cttgccgatg cactaaccgc accgctcgac cataaagaca aaggtttgaa atccctgaca      120
ttggaagact ccattcccca aaacggaaca ctgaccctgt cggcacaagg tgcggaaaaa      180
actttcaaag ccggcgacaa agacaacagc ctcaacacgg gcaaactgaa gaacgacaaa      240
atcagccgct tcgacttcgt gcaaaaaatc gaagtggacg gacaaaccat cacgctggca      300
agcggcgaat tcaaatata caaacagaac cactccgccg tcgttgccct acagattgaa      360
aaaatcaaca ccccgacaa aatcgacagc ctgataaacc aacgctcctt ccttgtcagc      420
ggtttgggcg gagaacatac cgccttcaac caactgcccg cgacaaagc cgagtatcac      480 ggcaaagcat tcagctccga cgacccgaac ggcaggctgc actacaccat cgatttacc      540 aacaaacagg gttacggcag aatcgaacac ctgaaaacgc ccgaactcaa tgtcgatctg      600
gcctccgccg aactcaaagc agatgaaaaa tcacacgccg tcattttggg cgacacgcgc      660
tacggcagcg aagaaaaagg cacttaccac ctcgcccttt cggcgaccg cgcccaagaa      720 atcgccggct cggcaaccgt gaagataggg aaaaggttc acgaaatcgg catcgccggc      780
aaacagtag                                                             789

<210> SEQ ID NO 68
<211> LENGTH: 780
<212> TYPE: DNA
<213> ORGANISM: Neisseria meningitidis (group B)

<400> SEQUENCE: 68
tgcagcagcg gaggcggagg cggcggtgtc gccgccgaca tcggcacggg gcttgccgat       60
gcactaactg cgccgctcga ccataaagac aaaggtttga atccctgac attggaagac      120 tccattcccc aaaacggaac actgaccctg tcggcacaag gtgcggaaaa aactttcaaa      180
gccgcgcaca aagacaacag cctcaacacg ggcaaactga gaacgacaa atcagccgc      240 ttcgacttcg tgcaaaaaat cgaagtggac ggacaaacca tcacactggc aagcggcgaa      300
tttcaaatat acaaacagga ccactccgcc gtcgttgccc tacagattga aaaaatcaac      360
aaccccgaca aaatcgacag cctgataaac caacgctcct ccttgtcag cggtttgggc      420
```

| | |
|---|---:|
| ggagaacata ccgccttcaa ccaactgccc ggcgacaaag ccgagtatca cggcaaagca | 480 |
| ttcagctccg acgatgccgg cggaaaactg acctatacca tagattttgc cgccaaacag | 540 |
| ggacacggca aaatcgaaca cctgaaaaca cccgagcaaa atgtcgagct tgccgccgcc | 600 |
| gaactcaaag cagatgaaaa atcacacgcc gtcattttgg gcgacacgcg ctacggcagc | 660 |
| gaagaaaaag gcacttacca cctcgccctt ttcggcgacc gcgcccaaga aatcgccggc | 720 |
| tcggcaaccg tgaagatagg ggaaaaggtt cacgaaatcg gcatcgccgg caaacagtag | 780 |

<210> SEQ ID NO 69
<211> LENGTH: 786
<212> TYPE: DNA
<213> ORGANISM: Neisseria meningitidis (group B)

<400> SEQUENCE: 69

| | |
|---|---:|
| tgcagcagcg aagcggaag cggaggcggc ggtgtcgccg ccgacatcgg cacagggctt | 60 |
| gccgatgcac taactgcgcc gctcgaccat aaagacaaag gtttgaaatc cctgacattg | 120 |
| gaagactcca tttcccaaaa cggaacactg accctgtcgg cacaaggtgc ggaaaaaact | 180 |
| ttcaaagtcg gcgacaaaga caacagtctc aatacaggca aattgaagaa cgacaaaatc | 240 |
| agccgcttcg actttgtgca aaaaatcgaa gtggacggac aaaccatcac gctggcaagc | 300 |
| ggcgaatttc aaatatacaa acaggaccac tccgccgtcg ttgccctaca gattgaaaaa | 360 |
| atcaacaacc ccgacaaaat cgacagcctg ataaaccaac gctccttcct tgtcagcggt | 420 |
| ttgggcggag aacataccgc cttcaaccaa ctgcccagcg caaagccga gtatcacggc | 480 |
| aaagcattca gctccgacga tgccggcgga aaactgacct ataccataga ttttgccgcc | 540 |
| aaacagggac acggcaaaat cgaacacctg aaaacacccg agcagaatgt cgagcttgcc | 600 |
| tccgccgaac tcaaagcaga tgaaaaatca cacgccgtca ttttgggcga cacgcgctac | 660 |
| ggcagcgaag aaaaaggcac ttaccacctc gctcttttcg gcgaccgagc ccaagaaatc | 720 |
| gccggctcgg caaccgtgaa gataagggaa aaggttcacg aaatcggcat cgccggcaaa | 780 |
| cagtag | 786 |

<210> SEQ ID NO 70
<211> LENGTH: 774
<212> TYPE: DNA
<213> ORGANISM: Neisseria meningitidis (group B)

<400> SEQUENCE: 70

| | |
|---|---:|
| tgcagcagcg gaggcggcgg tgtcgccgcc gacatcggcg cggggcttgc cgatgcacta | 60 |
| accgcaccgc tcgaccataa agacaaaggt ttgaaatccc tgacattgga agactccatt | 120 |
| tcccaaaacg gaacactgac cctgtcggca caaggtgcgg aaaaactttt caaagtcggc | 180 |
| gacaaagaca acagtctcaa tacaggcaaa ttgaagaacg acaaaatcag ccgcttcgac | 240 |
| tttgtgcaaa aaatcgaagt ggacggacaa accatcacgc tggcaagcgg cgaatttcaa | 300 |
| atatacaaac agaaccactc cgccgtcgtt gccctacaga ttgaaaaaat caacaacccc | 360 |
| gacaaaatcg acagcctgat aaaccaacgc tccttccttg tcagcggttt gggcggagaa | 420 |
| cataccgcct tcaaccaact gcccggcggc aaagccgagt atcacggcaa agcattcagc | 480 |
| tccgacgatg ccggcggaaa actgacctat accatagatt ttgccgccaa acagggacac | 540 |
| ggcaaaatcg aacacctgaa aacacccgag caaaatgtcg agcttgccgc cgccgaactc | 600 |
| aaagcagatg aaaaatcaca cgccgtcatt ttgggcgaca cgcgctacgg cagcgaagaa | 660 |
| aaaggcactt accacctcgc cctttttcggc gaccgcgctc aagaaatcgc cggctcggca | 720 |

```
accgtgaaga taggagaaaa ggttcacgaa atcagcatcg ccggcaaaca gtag        774
```

<210> SEQ ID NO 71
<211> LENGTH: 765
<212> TYPE: DNA
<213> ORGANISM: Neisseria meningitidis (group B)

<400> SEQUENCE: 71

```
tgcagcagcg gaggcggcgg tgtcgccgcc gacatcggcg cggggcttgc cgatgcacta   60
accgcaccgc tcgaccataa agacaaaagt ttgcagtctt tgacgctgga tcagtccgtc  120
aggaaaaacg agaaactgaa gctggcggca caaggtgcgg aaaaaactta tggaaacggc  180
gacagcctca atacgggcaa attgaagaac gacaaggtca gccgcttcga ctttatccgt  240
caaatcgaag tggacgggca gctcattacc ttggagagcg gagagttcca aatatacaaa  300
caggaccact ccgccgtcgt tgccctacag attgaaaaaa tcaacaaccc gacaaaatc   360
gacagcctga taaccaacg ctccttcctt gtcagcggtt tgggtggaga acataccgcc  420
ttcaaccaac tgcccggcgg caaagccgag tatcacggca agcattcag ctccgacgac   480
ccgaacggca ggctgcacta ctccattgat tttaccaaaa acagggtta cggcagaatc   540
gaacacctga aaacgcccga gcagaatgtc gagcttgcct ccgccgaact caaagcagat  600
gaaaaatcac acgccgtcat tttgggcgac acgcgctacg gcagcgaaga aaaaggcact  660
taccacctcg ctcttttcgg cgaccgagcc caagaaatcg ccggctcggc aaccgtgaag  720
ataagggaaa aggttcacga atcggcatc gccggcaaac agtag                   765
```

<210> SEQ ID NO 72
<211> LENGTH: 765
<212> TYPE: DNA
<213> ORGANISM: Neisseria meningitidis (group B)

<400> SEQUENCE: 72

```
tgcagcagcg gaggcggcgg tgtcgccgcc gacatcggcg cggggcttgc cgatgcacta   60
accgcaccgc tcgaccataa agacaaaagt ttgcagtctt tgacgctgga tcagtccgtc  120
aggaaaaacg agaaactgaa gctggcggca caaggtgcgg aaaaaactta tggaaacggc  180
gacagcctca atacgggcaa attgaagaac gacaaggtca gccgcttcga ctttatccgt  240
caaatcgaag tggacggaca aaccatcacg ctggcaagcg gcgaatttca aatatacaaa  300
cagaaccact ccgccgtcgt tgccctacag attgaaaaaa tcaacaaccc gacaaaatc   360
gacagcctga taaccaacg ctccttcctt gtcagcggtt tgggcggaga acataccgcc   420
ttcaaccaac tgcctgacgg caaagccgag tatcacggca agcattcag ctccgacgac   480
ccgaacggca ggctgcacta ctccattgat tttaccaaaa acagggtta cggcagaatc   540
gaacacctga aaacgcccga gcagaatgtc gagcttgcct ccgccgaact caaagcagat  600
gaaaaatcac acgccgtcat tttgggcgac acgcgctacg gcggcgaaga aaaaggcact  660
taccacctcg cccttttcgg cgaccgcgcc caagaaatcg ccggctcggc aaccgtgaag  720
ataagggaaa aggttcacga atcggcatc gccggcaaac agtag                   765
```

<210> SEQ ID NO 73
<211> LENGTH: 765
<212> TYPE: DNA
<213> ORGANISM: Neisseria meningitidis (group B)

<400> SEQUENCE: 73

```
tgcagcagcg gaggcggcgg tgtcgccgcc gacatcggcg cggggcttgc cgatgcacta    60
accacaccgc tcgaccataa agacaaaagt ttgcagtctt tgacgctgga tcagtccgtc   120
aggaaaaacg agaaactgaa gctggcggca caaggtgcgg aaaaaactta tggaaacggc   180
gacagcctca atacgggcaa attgaagaac gacaaggtca gccgcttcga ctttatccgt   240
caaatcgaag tggacggaca aaccatcacg ctggcaagcg gcgaatttca aatatacaaa   300
cagaaccact ccgccgtcgt tgccctacag attgaaaaaa tcaacaaccc cgacaaaatc   360
gacagcctga taaaccaacg ctccttcctt gtcagcggtt tgggcggaga acataccgcc   420
ttcaaccaac tgcctgacgg caaagccgag tatcacggca aagcattcag ctccgacgac   480
ccgaacggca ggctgcacta ctccattgat tttaccaaaa acagggtta cggcagaatc   540 gaacacctga aaacgcccga gcagaatgtc gagcttgcct ccgccgaact caaagcagat   600
gaaaaatcac acgccgtcat tttgggcgac acgcgctacg gcggcgaaga aaaaggcact   660
taccacctcg ccctttttcgg cgaccgcgcc aagaaaatcg ccggctcggc aaccgtgaag   720
ataagggaaa aggttcacga atcggcatc gccggcaaac agtag             765

<210> SEQ ID NO 74
<211> LENGTH: 765
<212> TYPE: DNA
<213> ORGANISM: Neisseria meningitidis (group B)

<400> SEQUENCE: 74
tgcagcagcg gaggcggcgg tgtcgccgcc gacatcggcg cggggcttgc cgatgcacta    60
accgcaccgc tcgaccataa agacaaaagt ttgcagtctt tgacgctgga tcagtccgtc   120
aggaaaaacg agaaactgaa gctggcggca caaggtgcgg aaaaaactta tggaaacggc   180
gacagcctca atacgggcaa attgaagaac gacaaggtca gccgcttcga ctttatccgt   240
caaatcgaag tggacgggca gctcattacc ttggagagcg gagagttcca aatatacaaa   300
caggaccact ccgccgtcgt tgccctacag attgaaaaaa tcaacaaccc cgacaaaatc   360
gacagcctga taaaccaacg ctccttcctt gtcagcggtt tgggcggaga acataccgcc   420
ttcaaccaac tgcctgacgg caaagccgag tatcacggca aagcattcag ctccgacgat   480
gctggcggaa aactgaccta ccatagatt tcgccgcca acagggaca cggcaaaatc   540 gaacacctga aaacacccga gcaaaatgtc gagcttgccg ccgccgaact caaagcagat   600
gaaaaatcac acgccgtcat tttgggcgac acgcgctacg gcagcgaaga aaaaggcact   660
taccacctcg ccctttttcgg cgaccgcgcc aagaaaatcg ccggctcggc aaccgtgaag   720
ataggggaaa aggttcacga atcggcatc gccggcaaac agtag             765

<210> SEQ ID NO 75
<211> LENGTH: 765
<212> TYPE: DNA
<213> ORGANISM: Neisseria meningitidis (group B)

<400> SEQUENCE: 75
tgcagcagcg gaggcggcgg tgtcgccgcc gacatcggcg cggggcttgc cgatgcacta    60
accgcaccgc tcgaccataa agacaaaagt ttgcagtctt tgacgctgga tcagtccgtc   120
aggaaaaacg agaaactgaa gctggcggca caaggtgcgg aaaaaactta tggaaacggc   180
gacagcctca atacgggcaa attgaagaac gacaaggtca gccgcttcga ctttatccgt   240
caaatcgaag tggacgggca gctcattacc ttggagagcg gagagttcca aatatacaaa   300
caggaccact ccgccgtcgt tgccctacag attgaaaaaa tcaacaaccc cgacaaaatc   360
```

```
gacagcctga taaaccaacg ctccttcctt gtcagcggtt tgggcggaga acataccgcc    420
ttcaaccaac tgcctgacgg caaagccgag tatcacggca aagcattcag ctccgacgat    480
gctggcggaa aactgaccta taccatagat ttcgccgcca acagggaca  cggcaaaatc    540 gaacacctga aaacacccga gcaaaatgtc gagcttgccg ccgccgaact caaagcagat    600
gaaaaatcac acgccgtcat tttgggcgac acgcgctacg gcagcgaaga aaaaggcact    660
taccacctcg ccctttttcgg cgaccgcgcc caagaaatcg ccggctcggc aaccgtgaag    720
ataggagaaa aggttcacga aatcagcatc gccggcaaac agtag                    765
```

<210> SEQ ID NO 76
<211> LENGTH: 765
<212> TYPE: DNA
<213> ORGANISM: Neisseria meningitidis (group B)

<400> SEQUENCE: 76

```
tgcagcagcg gaggcggcgg tgtcgccgcc gacatcggcg cggggcttgc cgatgcacta     60
accgcaccgc tcgaccataa agacaaaagt ttgcagtctt tgacgctgga tcagtccgtc    120
aggaaaaacg agaaactgaa gctggcggca caaggtgcgg aaaaaactta tggaaacggc    180
gacagcctca atacgggcaa attgaagaac gacaaggtca gccgcttcga ctttatccgt    240
caaatcgaag tggacgggca gctcattacc ttggagagcg gagagttcca aatatacaaa    300
caggaccact ccgccgtcgt tgccctacag attgaaaaaa tcaacaaccc cgacaaaatc    360
gacagcctga taaaccaacg ctccttcctt gtcagcggtt tgggtggaga acataccgcc    420
ttcaaccaac tgcccagcgg caaagccgag tatcacggca aagcattcag ctccgacgat    480
gctggcggaa aactgaccta taccatagat ttcgccgcca acagggaca  cggcaaaatc    540 gaacacttga aaacacccga gcaaaatgtc gagcttgcct ccgccgaact caaagcagat    600
gaaaaatcac acgccgtcat tttgggcgac acgcgctacg gcggcgaaga aaaaggcact    660
taccacctcg ccctttttcgg cgaccgcgcc caagaaatcg ccggctcggc aaccgtgaag    720
ataagggaaa aggttcacga aatcggcatc gccggcaaac agtag                    765
```

<210> SEQ ID NO 77
<211> LENGTH: 783
<212> TYPE: DNA
<213> ORGANISM: Neisseria meningitidis (group B)

<400> SEQUENCE: 77

```
tgcagcagcg gaggcggcgg aagcggaggc ggcggtgtca ccgccgacat cggcacgggg     60
cttgccgatg cactaactgc gccgctcgac cataaagaca aaggtttgaa atccctgaca    120
ttggaagact ccatttccca aaacggaaca ctgaccctgt cggcacaagg tgcggaaaaa    180
acttatggaa acggcgacag ccttaatacg ggcaaattga agaacgacaa ggtcagccgt    240
ttcgacttta tccgtcaaat cgaagtggac gggcagctca ttaccttgga gagcggagag    300
ttccaagtgt acaaacaaag ccattccgcc ttaaccgccc ttcagaccga gcaagaacaa    360
gatccagagc attccgagaa gatggttgcg aaacgccggt tcagaatcgg cgacatagcg    420
ggcgaacata catcttttga caagcttccc aaagacgtca tggcgacata tcgcgggacg    480
gcgttcggtt cagacgatgc cggcggaaaa ctgacctata ctatagattt tgctgccaaa    540
cagggacacg gcaaaatcga acatttgaaa tcgccggaac tcaatgtcga tctgccgtc    600 gcctatatca agccggatga aaaacaccat gccgtcatca gcggttccgt tctttacaac    660
```

| | |
|---|---|
| caagacgaga aaggcagtta ctccctcggt atctttggcg aaaaagccca ggaagttgcc | 720 |
| ggcagcgcgg aagtggaaac cgcaaacggc atacaccata tcggtcttgc cgccaagcag | 780 |
| taa | 783 |

<210> SEQ ID NO 78
<211> LENGTH: 792
<212> TYPE: DNA
<213> ORGANISM: Neisseria meningitidis (group B)

<400> SEQUENCE: 78

| | |
|---|---|
| tgcagcagcg gaggcggcgg aagcggaggc ggcggtgtcg ccgccgacat cggcgcgggg | 60 |
| cttgccgatg cactaaccgc accgctcgac cataaagaca aaggtttgaa atccctgaca | 120 |
| ttggaagact ccatttccca aaacggaaca ctgaccctgt cggcacaagg tgcggaaaga | 180 |
| actttcaaag ccggcgacaa agacaacagt ctcaacacag gcaaactgaa gaacgacaaa | 240 |
| atcagccgct tcgactttat ccgtcaaatc gaagtggacg ggcagctcat taccttggag | 300 |
| agcggagagt tccaagtgta caaacaaagc cattccgcct taaccgccct tcagaccgag | 360 |
| caagtacaag actcggagca ttccgggaag atggttgcga aacgccagtt cagaatcggc | 420 |
| gacatagtgg gcgaacatac atcttttgac aagcttccca aagacgtcat ggcgacatat | 480 |
| cgcgggacgg cgttcggttc agacgatgcc ggcggaaaac tgacctacac catagatttc | 540 |
| gccgccaagc agggacacgg caaaatcgaa catttgaaat cgcctgaact caatgttgac | 600 |
| ctggccgccg ccgatatcaa gccggatgaa aaacaccatg ccgtcatcag cggttccgtc | 660 |
| ctttacaacc aagccgagaa aggcagttac tctctaggca tctttggcgg gcaagcccag | 720 |
| gaagttgccg gcagcgcgga agtggaaacc gcaaacggca tacgccatat cggtcttgcc | 780 |
| gccaagcaat aa | 792 |

<210> SEQ ID NO 79
<211> LENGTH: 792
<212> TYPE: DNA
<213> ORGANISM: Neisseria meningitidis (group B)

<400> SEQUENCE: 79

| | |
|---|---|
| tgcagcagcg gaggcggcgg aagcggaggc ggcggtgtcg ccgccgacat cggcgcgggg | 60 |
| cttgccgatg cactaaccgc accgctcgac cataaagaca aaggtttgaa atccctgaca | 120 |
| ttggaagact ccatttccca aaacggaaca ctgaccctgt cggcacaagg tgcggaaaga | 180 |
| actttcaaag ccggcgacaa agacaacagt ctcaacacag gcaaactgaa gaacgacaaa | 240 |
| atcagccgct tcgactttat ccgtcaaatc gaagtggacg ggcagctcat taccttggag | 300 |
| agcggagagt tccaagtgta caaacaaagc cattccgcct taaccgccct tcagaccgag | 360 |
| caagtacaag actcggagca ttccgggaag atggttgcga aacgccagtt cagaatcggc | 420 |
| gacatagtgg gcgaacatac atcttttggc aagcttccca aagacgtcat ggcgacatat | 480 |
| cgcgggacgg cgttcggttc agacgatgcc ggcggaaaac tgacctacac catagatttc | 540 |
| gccgccaagc agggacacgg caaaatcgaa catttgaaat cgccagaact caatgttgac | 600 |
| ctggccgccg ccgatatcaa gccggatgaa aaacaccatg ccgtcatcag cggttccgtc | 660 |
| ctttacaacc aagccgagaa aggcagttac tctctaggca tctttggcgg gcaagcccag | 720 |
| gaagttgccg gcagcgcgga agtggaaacc gcaaacggca tacgccatat cggtcttgcc | 780 |
| gccaagcaat aa | 792 |

<210> SEQ ID NO 80
<211> LENGTH: 768
<212> TYPE: DNA
<213> ORGANISM: Neisseria meningitidis (group B)

<400> SEQUENCE: 80

| | | | | | |
|---|---|---|---|---|---|
| tgcagcagcg | gaggcggcgg | tgtcgccgcc | gacatcggcg | cggggcttgc | cgatgcacta | 60 |
| accgcaccgc | tcgaccataa | agacaaaagt | ttgcagtctt | tgacgctgga | tcagtccgtc | 120 |
| aggaaaaacg | agaaactgaa | gctggcggca | caaggtgcgg | aaaaaactta | tggaaacggc | 180 |
| gacagcctta | atacgggcaa | attgaagaac | gacaaggtca | gccgtttcga | ctttatccgt | 240 |
| caaatcgaag | tggacgggca | gctcattacc | ttggagagcg | gagagttcca | agtgtacaaa | 300 |
| caaagccatt | ccgccttaac | cgcccttcag | accgagcaag | aacaagatcc | agagcattcc | 360 |
| gggaagatgg | ttgcgaaacg | ccggttcaaa | atcggcgaca | tagcgggcga | acatacatct | 420 |
| tttgacaagc | ttcccaaaga | cgtcatggcg | acatatcgcg | ggacggcgtt | cggttcagac | 480 |
| gatgccggcg | aaaactgac | ctatactata | gattttgctg | ccaaacaggg | acacggcaaa | 540 |
| atcgaacatt | tgaaatcgcc | cgaactcaat | gtcgagcttg | ccaccgccta | tatcaagccg | 600 |
| gatgaaaaac | accatgccgt | catcagcggt | tccgtccttt | acaatcaaga | cgagaaaggc | 660 |
| agttactccc | tcggtatctt | tggcgggcaa | gcccaggaag | ttgccggcag | cgcggaagtg | 720 |
| gaaaccgcaa | acggcataca | ccatatcggt | cttgccgcca | agcaataa | | 768 |

<210> SEQ ID NO 81
<211> LENGTH: 768
<212> TYPE: DNA
<213> ORGANISM: Neisseria meningitidis (group B)

<400> SEQUENCE: 81

| | | | | | |
|---|---|---|---|---|---|
| tgcagcagcg | gagggggcgg | tgtcgccgcc | gacatcggtg | cggggcttgc | cgatgcacta | 60 |
| accgcaccgc | tcgaccataa | agacaaaggt | ttgcagtctt | taacgctgga | tcagtccgtc | 120 |
| aggaaaaacg | agaaactgaa | gctggcggca | caaggtgcgg | aaaaaactta | tggaaacggc | 180 |
| gacagcctta | atacgggcaa | attgaagaac | gacaaggtca | gccgcttcga | ctttatccgt | 240 |
| caaatcgaag | tggacgggaa | gctcattacc | ttggagagcg | gagagttcca | agtgtacaaa | 300 |
| caaagccatt | ccgccttaac | cgcccttcag | accgagcaag | tacaagactc | ggaggattcc | 360 |
| gggaagatgg | ttgcgaaacg | ccagttcaga | atcggcgaca | tagcgggcga | acatacatct | 420 |
| tttgacaagc | ttcccaaagg | cggcagtgcg | acatatcgcg | ggacggcgtt | cggttcagac | 480 |
| gatgctggcg | aaaactgac | ctatactata | gatttcgccg | ccaagcaggg | acacggcaaa | 540 |
| atcgaacatt | tgaaatcgcc | cgaactcaat | gtcgagcttg | ccaccgccta | tatcaagccg | 600 |
| gatgaaaaac | gccatgccgt | tatcagcggt | tccgtccttt | acaaccaaga | cgagaaaggc | 660 |
| agttactccc | tcggtatctt | tggcgggcaa | gcccaggaag | ttgccggcag | cgcggaagtg | 720 |
| gaaaccgcaa | acggcataca | ccatatcggt | cttgccgcca | agcagtaa | | 768 |

<210> SEQ ID NO 82
<211> LENGTH: 768
<212> TYPE: DNA
<213> ORGANISM: Neisseria meningitidis (group B)

<400> SEQUENCE: 82

| | | | | | |
|---|---|---|---|---|---|
| tgcagcagcg | gagggggcgg | tgtcgccgcc | gacatcggtg | cggggcttgc | cgatgcacta | 60 |
| accgcaccgc | tcgaccataa | agacaaaggt | ttgcagtctt | tgatactgga | tcagtccgtc | 120 |

| | |
|---|---|
| aggaaaaacg aaaaactgaa gctggcggca caaggtgcgg aaaaaactta tggaaacggc | 180 |
| gacagcctca atacgggcaa attgaagaac gacaaggtca gccgcttcga ctttatccgt | 240 |
| caaatcgaag tggacgggca gctcattacc ttggagagcg gagagttcca agtgtacaaa | 300 |
| caaagccatt ccgccttaac cgcccttcag accgagcaag tacaagactc ggagcattcc | 360 |
| gggaagatgg ttgcgaaacg ccagttcaga atcggcgaca tagcgggcga acatacatct | 420 |
| tttgacaagc ttcccgaagg cggcagggcg acatatcgcg ggacggcgtt cagttcagac | 480 |
| gatgccggtg aaaactgat ttacaccata gatttcgccg ccaagcaggg acacggcaaa | 540 |
| atcgaacatt tgaaatcgcc agaactcaat gtcgacctag ccgccgccga tatcaagccg | 600 |
| gatgaaaaac accatgccgt catcagcggt tccgtccttt acaaccaagc cgagaaaggc | 660 |
| agttactccc tcggtatctt tggcggaaaa gcccaggaag ttgccggcag cgcggaagtg | 720 |
| aaaaccgtaa acggcatacg ccatatcggc cttgccgcca agcaataa | 768 |

<210> SEQ ID NO 83
<211> LENGTH: 768
<212> TYPE: DNA
<213> ORGANISM: Neisseria meningitidis (group B)

<400> SEQUENCE: 83

| | |
|---|---|
| tgcagcagcg gaggcggcgg tgtcgccgcc gacatcggcg cggggcttgc cgatgcacta | 60 |
| accgcaccgc tcgaccataa agacaaaagt ttgcagtctt tgacgctgga tcagtccgtc | 120 |
| aggaaaaacg agaaactgaa gctggcggca caaggtgcgg aaaaaactta tggaaacggc | 180 |
| gacagcctca atacgggcaa attgaagaac gacaaggtca gccgcttcga ctttatccgt | 240 |
| caaatcgaag tggacgggca gctcattacc ttggagagcg gagagttcca agtgtacaaa | 300 |
| caaagccatt ccgccttaac cgcccttcag accgagcaag tacaagattc ggagcattca | 360 |
| gggaagatgg ttgcgaaacg ccagttcaga atcggcgata tagcgggtga acatacatct | 420 |
| tttgacaaac ttcccgaagg cggcagggcg acatatcgcg ggacggcatt cggttcagac | 480 |
| gatgccagtg aaaactgac ctacaccata gatttcgccg ccaagcaggg acacggcaaa | 540 |
| atcgaacatt tgaaatcgcc agaactcaat gttgacctgg ccgcctccga tatcaagccg | 600 |
| gataaaaaac gccatgccgt catcagcggt tccgtccttt acaaccaagc cgagaaaggc | 660 |
| agttactctc taggcatctt tggcgggcaa gcccaggaag ttgccggcag cgcagaagtg | 720 |
| gaaaccgcaa acggcatacg ccatatcggt cttgccgcca agcagtaa | 768 |

<210> SEQ ID NO 84
<211> LENGTH: 768
<212> TYPE: DNA
<213> ORGANISM: Neisseria meningitidis (group B)

<400> SEQUENCE: 84

| | |
|---|---|
| tgcagcagcg gaggcggcgg tgtcgccgcc gacatcggcg cggtgcttgc cgatgcacta | 60 |
| accgcaccgc tcgaccataa agacaaaagt ttgcagtctt tgacgctgga tcagtccgtc | 120 |
| aggaaaaacg agaaactgaa gctggcggca caaggtgcgg aaaaaactta tggaaacggc | 180 |
| gacagcctca atacgggcaa attgaagaac gacaaggtca gccgcttcga ctttatccgt | 240 |
| caaatcgaag tggacgggca gctcattacc ttggagagcg gagagttcca agtgtacaaa | 300 |
| caaagccatt ccgccttaac cgcccttcag accgagcaag tacaagattc ggagcattca | 360 |
| gggaagatgg ttgcgaaacg ccagttcaga atcggcgata tagcgggtga acatacatct | 420 |
| tttgacaagc ttcccgaagg cggcagggcg acatatcgcg ggacggcatt cggttcagac | 480 |

```
gatgccagtg gaaaactgac ctacaccata gatttcgccg ccaagcaggg acacggcaaa    540
atcgaacatt tgaaatcgcc agaactcaat gttgacctgg ccgcctccga tatcaagccg    600
gataaaaaac gccatgccgt catcagcggt tccgtccttt acaaccaagc cgagaaaggc    660
agttactctc taggcatctt tggcgggcaa gcccaggaag ttgccggcag cgcagaagtg    720
gaaaccgcaa acggcatacg ccatatcggt cttgccgcca agcagtaa                 768

<210> SEQ ID NO 85
<211> LENGTH: 768
<212> TYPE: DNA
<213> ORGANISM: Neisseria meningitidis (group B)

<400> SEQUENCE: 85
tgcagcagcg agggggtgg tgtcgccgcc gacatcggtg cggggcttgc cgatgcacta      60
accgcaccgc tcgaccataa agacaaaggt ttgcagtctt tgacgctgga tcagtccgtc    120
aggaaaaacg agaaactgaa gctggcggca caaggtgcgg aaaaaactta tggaaacggt    180
gacagcctca atacgggcaa attgaagaac gacaaggtca gccgtttcga cttatccgc     240 caaatcgaag tggacgggca gctcattacc ttggagagtg gagagttcca agtatacaaa    300
caaagccatt ccgccttaac cgcctttcag accgagcaaa tacaagattc ggagcattcc    360
gggaagatgg ttgcgaaacg ccagttcaga atcggcgaca tagcgggcga acatacatct    420
tttgacaagc ttcccgaagg cggcagggcg acatatcgcg ggacggcgtt cggttcagac    480
gatgccggcg gaaaactgac ctacaccata gatttcgccg ccaagcaggg aaacggcaaa    540
atcgaacatt tgaaatcgcc agaactcaat gtcgacctgg ccgccgccga tatcaagccg    600
gatggaaaac gccatgccgt catcagcggt tccgtccttt acaaccaagc cgagaaaggc    660
agttactccc tcggtatctt tggcggaaaa gcccaggaag ttgccggcag cgcggaagtg    720
aaaaccgtaa acggcatacg ccatatcggc cttgccgcca agcaataa                 768

<210> SEQ ID NO 86
<211> LENGTH: 783
<212> TYPE: DNA
<213> ORGANISM: Artificial Sequence
<220> FEATURE:
<223> OTHER INFORMATION: Synthetic sequence

<400> SEQUENCE: 86
agcagcggaa gcggaagcgg aggcggcggt gtcgccgccg acatcggcac agggcttgcc     60
gatgcactaa ctgcgccgct cgaccataaa gacaaaggtt tgaaatccct gacattggaa    120
gactccattt cccaaaacgg aacactgacc ctgtcggcac aaggtgcgga aaaactttc     180 aaagtcggcg acaaagacaa cagtctcaat acaggcaaat tgaagaacga caaatcagc     240 cgcttcgact ttgtgcaaaa aatcgaagtg gacggacaaa ccatcacgct ggcaagcggc    300
gaatttcaaa tatacaaaca ggaccactcc gccgtcgttg ccctacagat tgaaaaaatc    360
aacaaccccg acaaaatcga cagcctgata aaccaacgct ccttccttgt cagcggtttg    420
ggcggagaac ataccgcctt caaccaactg cccagcggca agccgagta tcacggcaaa     480 gcattcagct ccgacgatgc cggcggaaaa ctgacctata ccatagattt tgccgccaaa    540
cagggacacg gcaaaatcga cacctgaaa cacccgagc agaatgtcga gcttgcctcc     600
gccgaactca agcagatga aaatcacac gccgtcattt tggcgacac gcgctacggc       660 agcgaagaaa aaggcactta ccacctcgct cttttcggcg accgagccca agaaatcgcc    720
```

```
ggctcggcaa ccgtgaagat aagggaaaag gttcacgaaa tcggcatcgc cggcaaacag    780
tag                                                                  783
```

<210> SEQ ID NO 87
<211> LENGTH: 765
<212> TYPE: DNA
<213> ORGANISM: Neisseria meningitidis (group B)

<400> SEQUENCE: 87

```
tgcagcagcg gagggggcgg tgtcgccgcc gacattggtg cggggcttgc cgatgcacta     60
accgcaccgc tcgaccataa agacaaaagt ttgcagtctt tgacgctgga tcagtccgtc    120
aggaaaaacg agaaactgaa gctggcggca caaggtgcgg aaaaaactta tggaaacggc    180
gacagcctca atacgggcaa attgaagaac gacaaggtca gccgcttcga ctttatccgt    240
caaatcgaag tggacggaca aaccatcacg ctggcaagcg gcgaatttca aatatacaaa    300
cagaaccact ccgccgtcgt tgccctacag attgaaaaaa tcaacaaccc gacaaaatc    360 gacagcctga taaccaacg ctccttcctt gtcagcggtt tgggcggaga acataccgcc    420
ttcaaccaac tgcctgacgg caaagccgag tatcacggca agcattcag ctccgacgac    480 ccgaacggca ggctgcacta ctccattgat tttaccaaaa acagggtta cggcagaatc    540 gaacacctga aaacgcccga gcagaatgtc gagcttgcct ccgccgaact caaagcagat    600
gaaaaatcac acgccgtcat tttgggcgac acgcgctacg gcggcaagaa aaaaggcact    660
taccacctcg ccctttttcgg cgaccgcgcc caagaaatcg ccggctcggc aaccgtgaag    720
ataagggaaa aggttcacga atcggcatc gccggcaaac agtag                    765
```

<210> SEQ ID NO 88
<211> LENGTH: 471
<212> TYPE: PRT
<213> ORGANISM: Streptococcus pneumoniae

<400> SEQUENCE: 88

```
Met Ala Asn Lys Ala Val Asn Asp Phe Ile Leu Ala Met Asn Tyr Asp
  1               5                  10                  15

Lys Lys Lys Leu Leu Thr His Gln Gly Glu Ser Ile Glu Asn Arg Phe
             20                  25                  30

Ile Lys Glu Gly Asn Gln Leu Pro Asp Glu Phe Val Val Ile Glu Arg
         35                  40                  45

Lys Lys Arg Ser Leu Ser Thr Asn Thr Ser Asp Ile Ser Val Thr Ala
     50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175
```

Asp Ile Asp Phe Asn Ser Val His Ser Gly Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 89
<211> LENGTH: 499
<212> TYPE: PRT
<213> ORGANISM: Clostridium perfringens

<400> SEQUENCE: 89

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Ala Gly Asn Lys Phe Ile Val Val Glu Arg
65                  70                  75                  80

```
Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Glu Ala Ile
        115                 120                 125

Asn Ile Asn Ile Asp Leu Pro Gly Leu Lys Gly Glu Asn Ser Ile Lys
    130                 135                 140

Val Asp Asp Pro Thr Tyr Gly Lys Val Ser Gly Ala Ile Asp Glu Leu
145                 150                 155                 160

Val Ser Lys Trp Asn Glu Lys Tyr Ser Ser Thr His Thr Leu Pro Ala
                165                 170                 175

Arg Thr Gln Tyr Ser Glu Ser Met Val Tyr Ser Lys Ser Gln Ile Ser
            180                 185                 190

Ser Ala Leu Asn Val Asn Ala Lys Val Leu Glu Asn Ser Leu Gly Val
        195                 200                 205

Asp Phe Asn Ala Val Ala Asn Asn Glu Lys Lys Val Met Ile Leu Ala
    210                 215                 220

Tyr Lys Gln Ile Phe Tyr Thr Val Ser Ala Asp Leu Pro Lys Asn Pro
225                 230                 235                 240

Ser Asp Leu Phe Asp Asp Ser Val Thr Phe Asn Asp Leu Lys Gln Lys
                245                 250                 255

Gly Val Ser Asn Glu Ala Pro Pro Leu Met Val Ser Asn Val Ala Tyr
            260                 265                 270

Gly Arg Thr Ile Tyr Val Lys Leu Glu Thr Thr Ser Ser Lys Asp
    275                 280                 285

Val Gln Ala Ala Phe Lys Ala Leu Ile Lys Asn Thr Asp Ile Lys Asn
290                 295                 300

Ser Gln Gln Tyr Lys Asp Ile Tyr Glu Asn Ser Ser Phe Thr Ala Val
305                 310                 315                 320

Val Leu Gly Gly Asp Ala Gln Glu His Asn Lys Val Val Thr Lys Asp
            325                 330                 335

Phe Asp Glu Ile Arg Lys Val Ile Lys Asp Asn Ala Thr Phe Ser Thr
        340                 345                 350

Lys Asn Pro Ala Tyr Pro Ile Ser Tyr Thr Ser Val Phe Leu Lys Asp
    355                 360                 365

Asn Ser Val Ala Ala Val His Asn Lys Thr Asp Tyr Ile Glu Thr Thr
    370                 375                 380

Ser Thr Glu Tyr Ser Lys Gly Lys Ile Asn Leu Asp His Ser Gly Ala
385                 390                 395                 400

Tyr Val Ala Gln Phe Glu Val Ala Trp Asp Glu Val Ser Tyr Asp Lys
                405                 410                 415

Glu Gly Asn Glu Val Leu Thr His Lys Thr Trp Asp Gly Asn Tyr Gln
            420                 425                 430

Asp Lys Thr Ala His Tyr Ser Thr Val Ile Pro Leu Glu Ala Asn Ala
    435                 440                 445

Arg Asn Ile Arg Ile Lys Ala Arg Glu Cys Thr Gly Leu Ala Trp Glu
    450                 455                 460

Trp Trp Arg Asp Val Ile Ser Glu Tyr Asp Val Pro Leu Thr Asn Asn
465                 470                 475                 480

Ile Asn Val Ser Ile Trp Gly Thr Thr Leu Tyr Pro Gly Ser Ser Ile
                485                 490                 495
```

Thr Tyr Asn

<210> SEQ ID NO 90
<211> LENGTH: 532
<212> TYPE: PRT
<213> ORGANISM: Streptococcus intermedius

<400> SEQUENCE: 90

| | | | | | | | | | | | | | | |
|---|---|---|---|---|---|---|---|---|---|---|---|---|---|---|
| Met<br>1 | Lys | Thr | Lys | Gln<br>5 | Asn | Ile | Ala | Arg | Lys<br>10 | Leu | Ser | Arg | Val | Val<br>15 | Leu |
| Leu | Ser | Thr | Leu<br>20 | Val | Leu | Ser | Ser | Ala<br>25 | Ala | Pro | Ile | Ser | Ala<br>30 | Ala | Phe |
| Ala | Glu | Thr<br>35 | Pro | Thr | Lys | Pro | Lys<br>40 | Ala | Ala | Gln | Thr | Glu<br>45 | Lys | Lys | Thr |
| Glu | Lys<br>50 | Lys | Pro | Glu | Asn | Ser<br>55 | Asn | Ser | Glu | Ala | Ala<br>60 | Lys | Lys | Ala | Leu |
| Asn<br>65 | Asp | Tyr | Ile | Trp | Gly<br>70 | Leu | Gln | Tyr | Asp | Lys<br>75 | Leu | Asn | Ile | Leu | Thr<br>80 |
| His | Gln | Gly | Glu | Lys<br>85 | Leu | Lys | Asn | His | Ser<br>90 | Ser | Arg | Glu | Ala | Phe<br>95 | His |
| Arg | Pro | Gly | Glu<br>100 | Tyr | Val | Val | Ile | Glu<br>105 | Lys | Lys | Gln | Ser | Ile<br>110 | Ser |
| Asn | Ala | Thr<br>115 | Ser | Lys | Leu | Ser | Val<br>120 | Ser | Ser | Ala | Asn | Asp<br>125 | Asp | Arg | Ile |
| Phe | Pro<br>130 | Gly | Ala | Leu | Leu | Lys<br>135 | Ala | Asp | Gln | Ser | Leu<br>140 | Leu | Glu | Asn | Leu |
| Pro<br>145 | Thr | Leu | Ile | Pro | Val<br>150 | Asn | Arg | Gly | Lys | Thr<br>155 | Thr | Ile | Ser | Val | Asn<br>160 |
| Leu | Pro | Gly | Leu | Lys<br>165 | Asn | Gly | Glu | Ser | Asn<br>170 | Leu | Thr | Val | Glu | Asn<br>175 | Pro |
| Ser | Asn | Ser | Thr<br>180 | Val | Arg | Thr | Ala | Val<br>185 | Asn | Asn | Leu | Val | Glu<br>190 | Lys | Trp |
| Ile | Gln | Asn<br>195 | Tyr | Ser | Lys | Thr | His<br>200 | Ala | Val | Pro | Ala | Arg<br>205 | Met | Gln | Tyr |
| Glu | Ser<br>210 | Ile | Ser | Ala | Gln | Ser<br>215 | Met | Ser | Gln | Leu | Gln<br>220 | Ala | Lys | Phe | Gly |
| Ala<br>225 | Asp | Phe | Ser | Lys | Val<br>230 | Gly | Ala | Pro | Leu | Asn<br>235 | Val | Asp | Phe | Ser | Ser<br>240 |
| Val | His | Lys | Gly | Glu<br>245 | Lys | Gln | Val | Phe | Ile<br>250 | Ala | Asn | Phe | Arg | Gln<br>255 | Val |
| Tyr | Tyr | Thr | Ala<br>260 | Ser | Val | Asp | Ser | Pro<br>265 | Asn | Ser | Pro | Ser | Ala<br>270 | Leu | Phe |
| Gly | Ser | Gly<br>275 | Ile | Thr | Pro | Thr | Asp<br>280 | Leu | Ile | Asn | Arg | Gly<br>285 | Val | Asn | Ser |
| Lys | Thr<br>290 | Pro | Pro | Val | Tyr | Val<br>295 | Ser | Asn | Val | Ser | Tyr<br>300 | Gly | Arg | Ala | Met |
| Tyr<br>305 | Val | Lys | Phe | Glu | Thr<br>310 | Thr | Ser | Lys | Ser | Thr<br>315 | Lys | Val | Gln | Ala | Ala<br>320 |
| Ile | Asp | Ala | Val | Val<br>325 | Lys | Gly | Ala | Lys | Leu<br>330 | Lys | Ala | Gly | Thr | Glu<br>335 | Tyr |
| Glu | Asn | Ile | Leu<br>340 | Lys | Asn | Thr | Lys | Ile<br>345 | Thr | Ala | Val | Val | Leu<br>350 | Gly | Gly |
| Asn | Pro | Gly<br>355 | Glu | Ala | Ser | Lys | Val<br>360 | Ile | Thr | Gly | Asn | Ile<br>365 | Asp | Thr | Leu |

```
Lys Asp Leu Ile Gln Lys Gly Ser Asn Phe Ser Ala Gln Ser Pro Ala
    370                 375                 380

Val Pro Ile Ser Tyr Thr Thr Ser Phe Val Lys Asp Asn Ser Ile Ala
385                 390                 395                 400

Thr Ile Gln Asn Asn Thr Asp Tyr Ile Glu Thr Lys Val Thr Ser Tyr
                405                 410                 415

Lys Asp Gly Ala Leu Thr Leu Asn His Asp Gly Ala Phe Val Ala Arg
            420                 425                 430

Phe Tyr Val Tyr Trp Glu Glu Leu Gly His Asp Ala Asp Gly Tyr Glu
        435                 440                 445

Thr Ile Arg Ser Arg Ser Trp Ser Gly Asn Gly Tyr Asn Arg Gly Ala
    450                 455                 460

His Tyr Ser Thr Thr Leu Arg Phe Lys Gly Asn Val Arg Asn Ile Arg
465                 470                 475                 480

Val Lys Val Leu Gly Ala Thr Gly Leu Ala Trp Glu Pro Trp Arg Leu
                485                 490                 495

Ile Tyr Ser Lys Asn Asp Leu Pro Leu Val Pro Gln Arg Asn Ile Ser
            500                 505                 510

Thr Trp Gly Thr Thr Leu His Pro Gln Phe Glu Asp Lys Val Val Lys
        515                 520                 525

Asp Asn Thr Asp
        530

<210> SEQ ID NO 91
<211> LENGTH: 501
<212> TYPE: PRT
<213> ORGANISM: Paenibacillus alvei

<400> SEQUENCE: 91

Met Lys Lys Lys Ser Asn His Leu Lys Gly Arg Lys Val Leu Val Ser
1               5                   10                  15

Leu Leu Val Ser Leu Gln Val Phe Ala Phe Ala Ser Ile Ser Ser Ala
                20                  25                  30

Ala Pro Thr Glu Pro Asn Asp Ile Asp Met Gly Ile Ala Gly Leu Asn
            35                  40                  45

Tyr Asn Arg Asn Glu Val Leu Ala Ile Gln Gly Asp Gln Ile Ser Ser
    50                  55                  60

Phe Val Pro Lys Glu Gly Ile Gln Ser Asn Gly Lys Phe Ile Val Val
65                  70                  75                  80

Glu Arg Asp Lys Lys Ser Leu Thr Thr Ser Pro Val Asp Ile Ser Ile
                85                  90                  95

Val Asp Ser Ile Thr Asn Arg Thr Tyr Pro Gly Ala Ile Gln Leu Ala
            100                 105                 110

Asn Lys Asp Phe Ala Asp Asn Gln Pro Ser Leu Val Met Ala Ala Arg
        115                 120                 125

Lys Pro Leu Asp Ile Ser Ile Asp Leu Pro Gly Leu Lys Asn Glu Asn
    130                 135                 140

Thr Ile Ser Val Gln Asn Pro Asn Tyr Gly Thr Val Ser Ser Ala Ile
145                 150                 155                 160

Asp Gln Leu Val Ser Thr Trp Gly Glu Lys Tyr Ser Ser Thr His Thr
                165                 170                 175

Leu Pro Ala Arg Leu Gln Tyr Ala Glu Ser Met Val Tyr Ser Gln Asn
            180                 185                 190

Gln Ile Ser Ser Ala Leu Asn Val Asn Ala Lys Val Leu Asn Gly Thr
        195                 200                 205
```

```
Leu Gly Ile Asp Phe Asn Ala Val Ala Asn Gly Glu Lys Lys Val Met
        210                 215                 220

Val Ala Ala Tyr Lys Gln Ile Phe Tyr Thr Val Ser Ala Gly Leu Pro
225                 230                 235                 240

Asn Asn Pro Ser Asp Leu Phe Asp Asp Ser Val Thr Phe Ala Glu Leu
                245                 250                 255

Ala Arg Lys Gly Val Ser Asn Glu Ala Pro Pro Leu Met Val Ser Asn
            260                 265                 270

Val Ala Tyr Gly Arg Thr Ile Tyr Val Lys Leu Glu Thr Thr Ser Lys
        275                 280                 285

Ser Asn Asp Val Gln Thr Ala Phe Lys Leu Leu Asn Asn Pro Ser
290                 295                 300

Ile Gln Ala Ser Gly Gln Tyr Lys Asp Ile Tyr Glu Asn Ser Ser Phe
305                 310                 315                 320

Thr Ala Val Val Leu Gly Gly Asp Ala Gln Thr His Asn Gln Val Val
                325                 330                 335

Thr Lys Asp Phe Asn Val Ile Gln Ser Val Ile Lys Asp Asn Ala Gln
                340                 345                 350

Phe Ser Ser Lys Asn Pro Ala Tyr Pro Ile Ser Tyr Thr Ser Val Phe
            355                 360                 365

Leu Lys Asp Asn Ser Ile Ala Ala Val His Asn Asn Thr Glu Tyr Ile
        370                 375                 380

Glu Thr Lys Thr Thr Glu Tyr Ser Lys Gly Lys Ile Lys Leu Asp His
385                 390                 395                 400

Ser Gly Ala Tyr Val Ala Gln Phe Glu Val Tyr Trp Asp Glu Phe Ser
                405                 410                 415

Tyr Asp Ala Asp Gly Gln Glu Ile Val Thr Arg Lys Ser Trp Asp Gly
            420                 425                 430

Asn Trp Arg Asp Arg Ser Ala His Phe Ser Thr Glu Ile Pro Leu Pro
        435                 440                 445

Pro Asn Ala Lys Asn Ile Arg Ile Phe Ala Arg Glu Cys Thr Gly Leu
450                 455                 460

Ala Trp Glu Trp Trp Arg Thr Val Val Asp Glu Tyr Asn Val Pro Leu
465                 470                 475                 480

Ala Ser Asp Ile Asn Val Ser Ile Trp Gly Thr Thr Leu Tyr Pro Lys
                485                 490                 495

Ser Ser Ile Thr His
            500

<210> SEQ ID NO 92
<211> LENGTH: 512
<212> TYPE: PRT
<213> ORGANISM: Bacillus anthracis

<400> SEQUENCE: 92

Met Ile Phe Leu Asn Ile Lys Lys Asn Thr Lys Arg Arg Lys Phe Leu
1               5                   10                  15

Ala Cys Leu Leu Val Ser Leu Cys Thr Ile His Tyr Ser Ser Ile Ser
            20                  25                  30

Phe Ala Glu Thr Gln Ala Gly Asn Ala Thr Gly Ala Ile Lys Asn Ala
        35                  40                  45

Ser Asp Ile Asn Thr Gly Ile Ala Asn Leu Lys Tyr Asp Ser Arg Asp
    50                  55                  60

Ile Leu Ala Val Asn Gly Asp Lys Val Glu Ser Phe Ile Pro Lys Glu
```

```
            65                  70                  75                  80
Ser Ile Asn Ser Asn Gly Lys Phe Val Val Glu Arg Glu Lys Lys
                    85                  90                  95

Ser Leu Thr Thr Ser Pro Val Asp Ile Leu Ile Asp Ser Val Val
                100                 105                 110

Asn Arg Thr Tyr Pro Gly Ala Val Gln Leu Ala Asn Lys Ala Phe Ala
                115                 120                 125

Asp Asn Gln Pro Ser Leu Leu Val Ala Lys Arg Lys Pro Leu Asn Ile
130                 135                 140

Ser Ile Asp Leu Pro Gly Met Arg Lys Glu Asn Thr Ile Thr Val Gln
145                 150                 155                 160

Asn Pro Thr Tyr Gly Asn Val Ala Gly Ala Val Asp Asp Leu Val Ser
                165                 170                 175

Thr Trp Asn Glu Lys Tyr Ser Thr Thr His Thr Leu Pro Ala Arg Met
                180                 185                 190

Gln Tyr Thr Glu Ser Met Val Tyr Ser Lys Ser Gln Ile Ala Ser Ala
                195                 200                 205

Leu Asn Val Asn Ala Lys Tyr Leu Asp Asn Ser Leu Asn Ile Asp Phe
            210                 215                 220

Asn Ala Val Ala Asn Gly Glu Lys Lys Val Met Val Ala Ala Tyr Lys
225                 230                 235                 240

Gln Ile Phe Tyr Thr Val Ser Ala Glu Leu Pro Asn Asn Pro Ser Asp
                245                 250                 255

Leu Phe Asp Asn Ser Val Thr Phe Asp Glu Leu Thr Arg Lys Gly Val
                260                 265                 270

Ser Asn Ser Ala Pro Pro Val Met Val Ser Asn Val Ala Tyr Gly Arg
            275                 280                 285

Thr Val Tyr Val Lys Leu Glu Thr Thr Ser Lys Ser Lys Asp Val Gln
                290                 295                 300

Ala Ala Phe Lys Ala Leu Leu Lys Asn Asn Ser Val Glu Thr Ser Gly
305                 310                 315                 320

Gln Tyr Lys Asp Ile Phe Glu Glu Ser Thr Phe Thr Ala Val Val Leu
                325                 330                 335

Gly Gly Asp Ala Lys Glu His Asn Lys Val Val Thr Lys Asp Phe Asn
                340                 345                 350

Glu Ile Arg Asn Ile Ile Lys Asp Asn Ala Glu Leu Ser Phe Lys Asn
                355                 360                 365

Pro Ala Tyr Pro Ile Ser Tyr Thr Ser Thr Phe Leu Lys Asp Asn Ala
                370                 375                 380

Thr Ala Ala Val His Asn Asn Thr Asp Tyr Ile Glu Thr Thr Thr Thr
385                 390                 395                 400

Glu Tyr Ser Ser Ala Lys Met Thr Leu Asp His Tyr Gly Ala Tyr Val
                405                 410                 415

Ala Gln Phe Asp Val Phe Trp Asp Glu Phe Thr Phe Asp Gln Asn Gly
                420                 425                 430

Lys Glu Val Leu Thr His Lys Thr Trp Glu Gly Ser Gly Lys Asp Lys
                435                 440                 445

Thr Ala His Tyr Ser Thr Val Ile Pro Leu Pro Asn Ser Lys Asn
                450                 455                 460

Ile Lys Ile Val Ala Arg Glu Cys Thr Gly Leu Ala Trp Glu Trp Trp
465                 470                 475                 480

Arg Thr Ile Ile Asn Glu Gln Asn Val Pro Leu Thr Asn Glu Ile Lys
                485                 490                 495
```

Val Ser Ile Gly Gly Thr Thr Leu Tyr Pro Thr Ala Thr Ile Ser His
500 505 510

<210> SEQ ID NO 93
<211> LENGTH: 485
<212> TYPE: PRT
<213> ORGANISM: Bacillus cereus

<400> SEQUENCE: 93

Met Lys Asn Phe Lys Gly Arg Lys Phe Leu Thr Cys Val Leu Val Ser
1 5 10 15

Leu Cys Thr Leu Asn Tyr Ser Ser Ile Ser Phe Ala Glu Thr Gln Ala
20 25 30

Gly His Ala Asn Asp Ile Thr Lys Asn Ala Ser Ser Ile Asp Thr Gly
35 40 45

Ile Gly Asn Leu Thr Tyr Asn Asn Gln Glu Val Leu Ala Val Asn Gly
50 55 60

Asp Lys Val Glu Ser Phe Val Pro Lys Glu Ser Ile Asn Ser Asn Gly
65 70 75 80

Lys Phe Val Val Val Asp Val Arg Lys Asn His Leu Gln Arg His Gln
85 90 95

Ser Ile Phe Arg Leu Leu Asp Ser Val Ala Asn Arg Thr Tyr Pro Gly
100 105 110

Ala Val Gln Leu Ala Asn Lys Ala Phe Ala Asp Asn Gln Pro Ser Leu
115 120 125

Leu Val Ala Lys Arg Lys Pro Leu Asn Ile Ser Ile Asp Leu Pro Gly
130 135 140

Met Arg Lys Glu Asn Thr Ile Thr Val Gln Asn Pro Thr Tyr Gly Asn
145 150 155 160

Val Ala Gly Ala Val Asp Asp Leu Val Ser Thr Trp Asn Glu Lys Tyr
165 170 175

Ser Ala Thr His Thr Leu Pro Ala Arg Met Gln Tyr Thr Glu Ser Met
180 185 190

Val Tyr Ser Lys Ala Gln Ile Ala Ser Ala Leu Asn Val Asn Ala Lys
195 200 205

Tyr Leu Asp Asn Ser Leu Asn Ile Asp Phe Asn Ala Val Ala Asn Gly
210 215 220

Glu Lys Lys Val Met Val Ala Ala Tyr Lys Gln Ile Phe Tyr Thr Val
225 230 235 240

Ser Ala Glu Leu Pro Asn Asn Pro Ser Asp Leu Phe Asp Asn Ser Val
245 250 255

Thr Phe Gly Glu Leu Thr Arg Lys Gly Val Ser Asn Ser Ala Pro Pro
260 265 270

Val Met Val Ser Asn Val Ala Tyr Gly Arg Thr Val Tyr Val Lys Leu
275 280 285

Glu Thr Thr Ser Lys Ser Lys Asp Val Gln Ala Ala Phe Lys Ala Leu
290 295 300

Leu Lys Asn Asn Ser Val Glu Thr Ser Gly Gln Tyr Lys Asp Ile Phe
305 310 315 320

Glu Glu Ser Thr Phe Thr Ala Val Val Leu Gly Gly Asp Ala Lys Glu
325 330 335

His Asn Lys Val Val Thr Lys Asp Phe Asn Glu Ile Arg Asn Ile Ile
340 345 350

Lys Asp Asn Ala Glu Leu Ser Phe Lys Asn Pro Ala Tyr Pro Ile Ser

```
            355                 360                 365
Tyr Thr Ser Thr Phe Leu Lys Asp Asn Ala Thr Ala Ala Val His Asn
        370                 375                 380

Asn Thr Asp Tyr Ile Glu Thr Thr Thr Glu Tyr Ser Ser Ala Lys
385                 390                 395                 400

Met Thr Leu Asp His Tyr Gly Ala Tyr Val Ala Gln Phe Asp Val Ser
                405                 410                 415

Trp Asp Gly Phe Thr Phe Asp Gln Asn Gly Lys Glu Ile Leu Thr His
                420                 425                 430

Lys Thr Trp Glu Gly Ser Gly Lys Asp Lys Thr Ala His Tyr Ser Thr
            435                 440                 445

Val Ile Pro Leu Pro Asn Ser Lys Asn Ile Lys Ile Val Ala Arg
    450                 455                 460

Glu Cys Thr Gly Leu Ala Trp Glu Trp Trp Arg Thr Ile Ile Lys Met
465                 470                 475                 480

Asn Lys Met Phe His
                485

<210> SEQ ID NO 94
<211> LENGTH: 528
<212> TYPE: PRT
<213> ORGANISM: Listeria ivanovii

<400> SEQUENCE: 94

Met Lys Lys Ile Met Leu Leu Met Thr Leu Leu Leu Val Ser Leu
1               5                   10                  15

Pro Leu Ala Gln Glu Ala Gln Ala Asp Ala Ser Val Tyr Ser Tyr Gln
                20                  25                  30

Gly Ile Ile Ser His Met Ala Pro Pro Ala Ser Pro Pro Ala Lys Pro
            35                  40                  45

Lys Thr Pro Val Glu Lys Lys Asn Ala Ala Gln Ile Asp Gln Tyr Ile
    50                  55                  60

Gln Gly Leu Asp Tyr Asp Lys Asn Asn Ile Leu Val Tyr Asp Gly Glu
65                  70                  75                  80

Ala Val Lys Asn Val Pro Pro Lys Ala Gly Tyr Lys Glu Gly Asn Gln
                85                  90                  95

Tyr Ile Val Val Glu Lys Lys Lys Ser Ile Asn Gln Asn Asn Ala
            100                 105                 110

Asp Ile Gln Val Ile Asn Ser Leu Ala Ser Leu Thr Tyr Pro Gly Ala
        115                 120                 125

Leu Val Lys Ala Asn Ser Glu Leu Val Glu Asn Gln Pro Asp Val Leu
    130                 135                 140

Pro Val Lys Arg Asp Ser Val Thr Leu Ser Ile Asp Leu Pro Gly Met
145                 150                 155                 160

Val Asn His Asp Asn Glu Ile Val Val Gln Asn Ala Thr Lys Ser Asn
                165                 170                 175

Ile Asn Asp Gly Val Asn Thr Leu Val Asp Arg Trp Asn Asn Lys Tyr
            180                 185                 190

Ser Glu Glu Tyr Pro Asn Ile Ser Ala Lys Ile Asp Tyr Asp Gln Glu
        195                 200                 205

Met Ala Tyr Ser Glu Ser Gln Leu Val Ala Lys Phe Gly Ala Ala Phe
    210                 215                 220

Lys Ala Val Asn Asn Ser Leu Asn Val Asn Phe Gly Ala Ile Ser Glu
225                 230                 235                 240
```

Gly Lys Val Gln Glu Val Ile Asn Phe Lys Gln Ile Tyr Tyr Thr
                245                 250                 255

Val Asn Val Asn Glu Pro Thr Ser Pro Ser Arg Phe Phe Gly Lys Ser
            260                 265                 270

Val Thr Lys Glu Asn Leu Gln Ala Leu Gly Val Asn Ala Glu Asn Pro
        275                 280                 285

Pro Ala Tyr Ile Ser Ser Val Ala Tyr Gly Arg Asp Ile Phe Val Lys
    290                 295                 300

Leu Ser Thr Ser Ser His Ser Thr Arg Val Lys Ala Ala Phe Asp Thr
305                 310                 315                 320

Ala Phe Lys Gly Lys Ser Val Lys Gly Asp Thr Glu Leu Glu Asn Ile
            325                 330                 335

Ile Gln Asn Ala Ser Phe Lys Ala Val Ile Tyr Gly Gly Ser Ala Lys
            340                 345                 350

Asp Glu Val Glu Ile Ile Asp Gly Asp Leu Ser Lys Leu Arg Asp Ile
            355                 360                 365

Leu Lys Gln Gly Ala Asn Phe Asp Lys Lys Asn Pro Gly Val Pro Ile
    370                 375                 380

Ala Tyr Thr Thr Asn Phe Leu Lys Asp Asn Gln Leu Ala Val Val Lys
385                 390                 395                 400

Asn Asn Ser Glu Tyr Ile Glu Thr Thr Ser Lys Ala Tyr Ser Asp Gly
            405                 410                 415

Lys Ile Asn Leu Asp His Ser Gly Ala Tyr Val Ala Arg Phe Asn Val
            420                 425                 430

Thr Trp Asp Glu Val Ser Tyr Asp Ala Asn Gly Asn Glu Val Val Glu
    435                 440                 445

His Lys Lys Trp Ser Glu Asn Asp Lys Asp Lys Leu Ala His Phe Thr
    450                 455                 460

Thr Ser Ile Tyr Leu Pro Gly Asn Ala Arg Asn Ile Asn Ile His Ala
465                 470                 475                 480

Lys Glu Cys Thr Gly Leu Ala Trp Glu Trp Arg Thr Val Val Asp
            485                 490                 495

Asp Arg Asn Leu Pro Leu Val Lys Asn Arg Asn Val Cys Ile Trp Gly
            500                 505                 510

Thr Thr Leu Tyr Pro Ala Tyr Ser Asp Thr Val Asp Asn Pro Ile Lys
        515                 520                 525

<210> SEQ ID NO 95
<211> LENGTH: 534
<212> TYPE: PRT
<213> ORGANISM: Arcanobacterium pyogenes

<400> SEQUENCE: 95

Met Lys Arg Lys Ala Phe Ala Ser Leu Val Ala Ser Val Val Ala Ala
1               5                   10                  15

Ala Thr Val Thr Met Pro Thr Ala Ser Phe Ala Ala Gly Leu Gly Asn
            20                  25                  30

Ser Ser Gly Leu Thr Asp Gly Leu Ser Ala Pro Arg Ala Ser Ile Ser
        35                  40                  45

Pro Thr Asp Lys Val Asp Leu Lys Ser Ala Gln Glu Thr Asp Glu Thr
    50                  55                  60

Gly Val Asp Lys Tyr Ile Arg Gly Leu Lys Tyr Asp Pro Ser Gly Val
65                  70                  75                  80

Leu Ala Val Lys Gly Glu Ser Ile Glu Asn Val Pro Val Thr Lys Asp
            85                  90                  95

```
Gln Leu Lys Asp Gly Thr Tyr Thr Val Phe Lys His Glu Arg Lys Ser
            100                 105                 110
Phe Asn Asn Leu Arg Ser Asp Ile Ser Ala Phe Asp Ala Asn Asn Ala
        115                 120                 125
His Val Tyr Pro Gly Ala Leu Val Leu Ala Asn Lys Asp Leu Ala Lys
    130                 135                 140
Gly Ser Pro Thr Ser Ile Gly Ile Ala Arg Ala Pro Gln Thr Val Ser
145                 150                 155                 160
Val Asp Leu Pro Gly Leu Val Asp Gly Lys Asn Lys Val Val Ile Asn
                165                 170                 175
Asn Pro Thr Lys Ser Ser Val Thr Gln Gly Leu Asn Gly Leu Leu Asp
            180                 185                 190
Gly Trp Ile Gln Arg Asn Ser Lys Tyr Pro Asp His Ala Ala Lys Ile
        195                 200                 205
Ser Tyr Asp Glu Thr Met Val Thr Ser Lys Arg Gln Leu Glu Ala Lys
    210                 215                 220
Leu Gly Leu Gly Phe Glu Lys Val Ser Ala Lys Leu Asn Val Asp Phe
225                 230                 235                 240
Asp Ala Ile His Lys Arg Glu Arg Gln Val Ala Ile Ala Ser Phe Lys
                245                 250                 255
Gln Ile Tyr Tyr Thr Ala Ser Val Asp Thr Pro Thr Ser Pro His Ser
            260                 265                 270
Val Phe Gly Pro Asn Val Thr Ala Gln Asp Leu Lys Asp Arg Gly Val
        275                 280                 285
Asn Asn Lys Asn Pro Leu Gly Tyr Ile Ser Ser Val Ser Tyr Gly Arg
    290                 295                 300
Gln Ile Phe Val Lys Leu Glu Thr Thr Ser Thr Ser Asn Asp Val Gln
305                 310                 315                 320
Ala Ala Phe Ser Gly Leu Phe Lys Ala Lys Phe Gly Asn Leu Ser Thr
                325                 330                 335
Glu Phe Lys Ala Lys Tyr Ala Asp Ile Leu Asn Lys Thr Arg Ala Thr
            340                 345                 350
Val Tyr Ala Val Gly Gly Ser Ala Arg Gly Gly Val Glu Val Ala Thr
        355                 360                 365
Gly Asn Ile Asp Ala Leu Lys Lys Ile Lys Glu Glu Ser Thr Tyr
    370                 375                 380
Ser Thr Lys Val Pro Ala Val Pro Val Ser Tyr Ala Val Asn Phe Leu
385                 390                 395                 400
Lys Asp Asn Gln Leu Ala Ala Val Arg Ser Ser Gly Asp Tyr Ile Glu
                405                 410                 415
Thr Thr Ala Thr Thr Tyr Lys Ser Gly Glu Ile Thr Phe Arg His Gly
            420                 425                 430
Gly Gly Tyr Val Ala Lys Phe Arg Leu Lys Trp Asp Glu Ile Ser Tyr
        435                 440                 445
Asp Pro Gln Gly Lys Glu Ile Arg Thr Pro Lys Thr Trp Ser Gly Asn
    450                 455                 460
Trp Ala Ala Arg Thr Leu Gly Phe Arg Glu Thr Ile Gln Leu Pro Ala
465                 470                 475                 480
Asn Ala Arg Asn Ile His Val Glu Ala Gly Glu Ala Thr Gly Leu Ala
                485                 490                 495
Trp Asp Pro Trp Trp Thr Val Ile Asn Lys Lys Asn Leu Pro Leu Val
            500                 505                 510
```

Pro His Arg Glu Ile Val Leu Lys Gly Thr Thr Leu Asn Pro Trp Val
            515                 520                 525

Glu Asp Asn Val Lys Ser
        530

<210> SEQ ID NO 96
<211> LENGTH: 530
<212> TYPE: PRT
<213> ORGANISM: Listeria seeligeri

<400> SEQUENCE: 96

Met Lys Ile Phe Gly Leu Val Ile Met Ser Leu Leu Phe Val Ser Leu
1               5                   10                  15

Pro Ile Thr Gln Gln Pro Glu Ala Arg Asp Val Pro Ala Tyr Asp Arg
            20                  25                  30

Ser Glu Val Thr Ile Ser Pro Ala Glu Thr Pro Glu Ser Pro Pro Ala
        35                  40                  45

Thr Pro Lys Thr Pro Val Glu Lys Lys His Ala Glu Glu Ile Asn Lys
    50                  55                  60

Tyr Ile Trp Gly Leu Asn Tyr Asp Lys Asn Ser Ile Leu Val Tyr Gln
65                  70                  75                  80

Gly Glu Ala Val Thr Asn Val Pro Pro Lys Gly Tyr Lys Asp Gly
                85                  90                  95

Ser Glu Tyr Ile Val Val Glu Lys Lys Lys Gly Ile Asn Gln Asn
            100                 105                 110

Asn Ala Asp Ile Ser Val Ile Asn Ala Ile Ser Ser Leu Thr Tyr Pro
            115                 120                 125

Gly Ala Leu Val Lys Ala Asn Arg Glu Leu Val Glu Asn Gln Pro Asn
    130                 135                 140

Val Leu Pro Val Lys Arg Asp Ser Leu Thr Leu Ser Val Asp Leu Pro
145                 150                 155                 160

Gly Met Thr Lys Lys Asp Asn Lys Ile Phe Val Lys Asn Pro Thr Lys
                165                 170                 175

Ser Asn Val Asn Asn Ala Val Asn Thr Leu Val Glu Arg Trp Asn Asp
            180                 185                 190

Lys Tyr Ser Lys Ala Tyr Pro Asn Ile Asn Ala Lys Ile Asp Tyr Ser
        195                 200                 205

Asp Glu Met Ala Tyr Ser Glu Ser Gln Leu Ile Ala Lys Phe Gly Thr
    210                 215                 220

Ala Phe Lys Ala Val Asn Asn Ser Leu Asn Val Asn Phe Glu Ala Ile
225                 230                 235                 240

Ser Asp Gly Lys Val Gln Glu Glu Val Ile Ser Phe Lys Gln Ile Tyr
                245                 250                 255

Tyr Asn Ile Asn Val Asn Glu Pro Thr Ser Pro Ser Lys Phe Phe Gly
            260                 265                 270

Gly Ser Val Thr Lys Glu Gln Leu Asp Ala Leu Gly Val Asn Ala Glu
        275                 280                 285

Asn Pro Pro Ala Tyr Ile Ser Ser Val Ala Tyr Gly Arg Gln Val Tyr
    290                 295                 300

Val Lys Leu Ser Ser Ser Ser His Ser Asn Lys Val Lys Thr Ala Phe
305                 310                 315                 320

Glu Ala Ala Met Ser Gly Lys Ser Val Lys Gly Asp Val Glu Leu Thr
                325                 330                 335

Asn Ile Ile Lys Asn Ser Ser Phe Lys Ala Val Ile Tyr Gly Gly Ser
            340                 345                 350

```
Ala Lys Glu Glu Val Glu Ile Ile Asp Gly Asn Leu Gly Glu Leu Arg
            355                 360                 365

Asp Ile Leu Lys Lys Gly Ser Thr Tyr Asp Arg Glu Asn Pro Gly Val
        370                 375                 380

Pro Ile Ser Tyr Thr Thr Asn Phe Leu Lys Asp Asn Asp Leu Ala Val
385                 390                 395                 400

Val Lys Asn Asn Ser Glu Tyr Ile Glu Thr Thr Ser Lys Ser Tyr Thr
                405                 410                 415

Asp Gly Lys Ile Asn Ile Asp His Ser Gly Gly Tyr Val Ala Gln Phe
            420                 425                 430

Asn Ile Ser Trp Asp Glu Val Ser Tyr Asp Glu Asn Gly Asn Glu Ile
        435                 440                 445

Lys Val His Lys Lys Trp Gly Glu Asn Tyr Lys Ser Lys Leu Ala His
    450                 455                 460

Phe Thr Ser Ser Ile Tyr Leu Pro Gly Asn Ala Arg Asn Ile Asn Ile
465                 470                 475                 480

Tyr Ala Arg Glu Cys Thr Gly Leu Phe Trp Glu Trp Trp Arg Thr Val
                485                 490                 495

Ile Asp Asp Arg Asn Leu Pro Leu Val Lys Asn Arg Asn Val Ser Ile
            500                 505                 510

Trp Gly Thr Thr Leu Tyr Pro Arg His Ser Asn Asn Val Asp Asn Pro
        515                 520                 525

Ile Gln
    530

<210> SEQ ID NO 97
<211> LENGTH: 574
<212> TYPE: PRT
<213> ORGANISM: Streptococcus pyogenes

<400> SEQUENCE: 97

Met Lys Asp Met Ser Asn Lys Lys Thr Phe Lys Lys Tyr Ser Arg Val
1               5                   10                  15

Ala Gly Leu Leu Thr Ala Ala Leu Ile Ile Gly Asn Leu Val Thr Ala
            20                  25                  30

Asn Ala Glu Ser Asn Lys Gln Asn Thr Ala Ser Thr Glu Thr Thr Thr
        35                  40                  45

Thr Asn Glu Gln Pro Lys Pro Glu Ser Ser Glu Leu Thr Thr Glu Lys
    50                  55                  60

Ala Gly Gln Lys Thr Asp Asp Met Leu Asn Ser Asn Asp Met Ile Lys
65                  70                  75                  80

Leu Ala Pro Lys Glu Met Pro Leu Glu Ser Ala Glu Lys Glu Lys
                85                  90                  95

Lys Ser Glu Asp Lys Lys Ser Glu Glu Asp His Thr Glu Glu Ile
            100                 105                 110

Asn Asp Lys Ile Tyr Ser Leu Asn Tyr Asn Glu Leu Glu Val Leu Ala
        115                 120                 125

Lys Asn Gly Glu Thr Ile Glu Asn Phe Val Pro Lys Glu Gly Val Lys
    130                 135                 140

Lys Ala Asp Lys Phe Ile Val Ile Glu Arg Lys Lys Asn Ile Asn
145                 150                 155                 160

Thr Thr Pro Val Asp Ile Ser Ile Ile Asp Ser Val Thr Asp Arg Thr
                165                 170                 175

Tyr Pro Ala Ala Leu Gln Leu Ala Asn Lys Gly Phe Thr Glu Asn Lys
```

```
            180                 185                 190
Pro Asp Ala Val Val Thr Lys Arg Asn Pro Gln Lys Ile His Ile Asp
            195                 200                 205

Leu Pro Gly Met Gly Asp Lys Ala Thr Val Glu Val Asn Asp Pro Thr
            210                 215                 220

Tyr Ala Asn Val Ser Thr Ala Ile Asp Asn Leu Val Asn Gln Trp His
225                 230                 235                 240

Asp Asn Tyr Ser Gly Gly Asn Thr Leu Pro Ala Arg Thr Gln Tyr Thr
                245                 250                 255

Glu Ser Met Val Tyr Ser Lys Ser Gln Ile Glu Ala Ala Leu Asn Val
            260                 265                 270

Asn Ser Lys Ile Leu Asp Gly Thr Leu Gly Ile Asp Phe Lys Ser Ile
            275                 280                 285

Ser Lys Gly Glu Lys Lys Val Met Ile Ala Ala Tyr Lys Gln Ile Phe
            290                 295                 300

Tyr Thr Val Ser Ala Asn Leu Pro Asn Pro Ala Asp Val Phe Asp
305                 310                 315                 320

Lys Ser Val Thr Phe Lys Glu Leu Gln Arg Lys Gly Val Ser Asn Glu
                325                 330                 335

Ala Pro Pro Leu Phe Val Ser Asn Val Ala Tyr Gly Arg Thr Val Phe
            340                 345                 350

Val Lys Leu Glu Thr Ser Ser Lys Ser Asn Asp Val Glu Ala Ala Phe
            355                 360                 365

Ser Ala Ala Leu Lys Gly Thr Asp Val Lys Thr Asn Gly Lys Tyr Ser
            370                 375                 380

Asp Ile Leu Glu Asn Ser Ser Phe Thr Ala Val Val Leu Gly Gly Asp
385                 390                 395                 400

Ala Ala Glu His Asn Lys Val Val Thr Lys Asp Phe Asp Val Ile Arg
                405                 410                 415

Asn Val Ile Lys Asp Asn Ala Thr Phe Ser Arg Lys Asn Pro Ala Tyr
            420                 425                 430

Pro Ile Ser Tyr Thr Ser Val Phe Leu Lys Asn Asn Lys Ile Ala Gly
            435                 440                 445

Val Asn Asn Arg Thr Glu Tyr Val Glu Thr Thr Ser Thr Glu Tyr Thr
            450                 455                 460

Ser Gly Lys Ile Asn Leu Ser His Arg Gly Ala Tyr Val Ala Gln Tyr
465                 470                 475                 480

Glu Ile Leu Trp Asp Glu Ile Asn Tyr Asp Asp Lys Gly Lys Glu Val
                485                 490                 495

Ile Thr Lys Arg Arg Trp Asp Asn Asn Trp Tyr Ser Lys Thr Ser Pro
            500                 505                 510

Phe Ser Thr Val Ile Pro Leu Gly Ala Asn Ser Arg Asn Ile Arg Ile
            515                 520                 525

Met Ala Arg Glu Cys Thr Gly Leu Ala Trp Gly Trp Arg Lys Val
            530                 535                 540

Ile Asp Glu Arg Asp Val Lys Leu Ser Lys Glu Ile Asn Val Asn Ile
545                 550                 555                 560

Ser Gly Ser Thr Leu Ser Pro Tyr Gly Ser Ile Thr Tyr Lys
                565                 570

<210> SEQ ID NO 98
<211> LENGTH: 497
<212> TYPE: PRT
<213> ORGANISM: Streptococcus suis
```

<400> SEQUENCE: 98

```
Met Arg Lys Ser Ser His Leu Ile Leu Ser Ile Val Ser Leu Ala
1               5                   10                  15

Leu Val Gly Val Thr Pro Leu Ser Val Leu Ala Asp Ser Lys Gln Asp
            20                  25                  30

Ile Asn Gln Tyr Phe Gln Ser Leu Thr Tyr Glu Pro Gln Glu Ile Leu
        35                  40                  45

Thr Asn Glu Gly Glu Tyr Ile Asp Asn Pro Pro Ala Thr Thr Gly Met
    50                  55                  60

Leu Glu Asn Gly Arg Phe Val Val Leu Arg Arg Glu Lys Lys Asn Ile
65                  70                  75                  80

Thr Asn Asn Ser Ala Asp Ile Ala Val Ile Asp Ala Lys Ala Ala Asn
                85                  90                  95

Ile Tyr Pro Gly Ala Leu Leu Arg Ala Asp Gln Asn Leu Leu Asp Asn
            100                 105                 110

Asn Pro Thr Leu Ile Ser Ile Ala Arg Gly Asp Leu Thr Leu Ser Leu
        115                 120                 125

Asn Leu Pro Gly Leu Ala Asn Gly Asp Ser His Thr Val Val Asn Ser
    130                 135                 140

Pro Thr Arg Ser Thr Val Arg Thr Gly Val Asn Asn Leu Leu Ser Lys
145                 150                 155                 160

Trp Asn Asn Thr Tyr Ala Gly Glu Tyr Gly Asn Thr Gln Ala Glu Leu
                165                 170                 175

Gln Tyr Asp Glu Thr Met Ala Tyr Ser Met Ser Gln Leu Lys Thr Lys
            180                 185                 190

Phe Gly Thr Ser Phe Glu Lys Ile Ala Val Pro Leu Asp Ile Asn Phe
        195                 200                 205

Asp Ala Val Asn Ser Gly Glu Lys Gln Val Gln Ile Val Asn Phe Lys
    210                 215                 220

Gln Ile Tyr Tyr Thr Val Ser Val Asp Glu Pro Glu Ser Pro Ser Lys
225                 230                 235                 240

Leu Phe Ala Glu Gly Thr Thr Val Lys Asn Leu Lys Arg Asn Gly Ile
                245                 250                 255

Thr Asp Glu Val Pro Pro Val Tyr Val Ser Ser Val Ser Tyr Gly Arg
            260                 265                 270

Ser Met Phe Ile Lys Leu Glu Thr Ser Ser Arg Ser Thr Gln Val Gln
        275                 280                 285

Ala Ala Phe Lys Ala Ala Ile Lys Gly Val Asp Ile Ser Gly Asn Ala
    290                 295                 300

Glu Tyr Gln Asp Ile Leu Lys Asn Thr Ser Phe Ser Ala Tyr Ile Phe
305                 310                 315                 320

Gly Gly Asp Ala Gly Ser Ala Ala Thr Val Val Ser Gly Asn Ile Glu
                325                 330                 335

Thr Leu Lys Lys Ile Ile Glu Glu Gly Ala Arg Tyr Gly Lys Leu Asn
            340                 345                 350

Pro Gly Val Pro Ile Ser Tyr Ser Thr Asn Phe Val Lys Asp Asn Arg
        355                 360                 365

Pro Ala Gln Ile Leu Ser Asn Ser Glu Tyr Ile Glu Thr Thr Ser Thr
    370                 375                 380

Val His Asn Ser Ser Ala Leu Thr Leu Asp His Ser Gly Ala Tyr Val
385                 390                 395                 400

Ala Lys Tyr Asn Ile Thr Trp Glu Glu Val Ser Tyr Asn Glu Ala Gly
```

```
                   405                 410                 415
Glu Glu Val Trp Glu Pro Lys Ala Trp Asp Lys Asn Gly Val Asn Leu
                420                 425                 430

Thr Ser His Trp Ser Glu Thr Ile Gln Ile Pro Gly Asn Ala Arg Asn
            435                 440                 445

Leu His Val Asn Ile Gln Glu Cys Thr Gly Leu Ala Trp Glu Trp Trp
        450                 455                 460

Arg Thr Val Tyr Asp Lys Asp Leu Pro Leu Val Gly Gln Arg Lys Ile
465                 470                 475                 480

Thr Ile Trp Gly Thr Thr Leu Tyr Pro Gln Tyr Ala Asp Glu Val Ile
                485                 490                 495

Glu

<210> SEQ ID NO 99
<211> LENGTH: 527
<212> TYPE: PRT
<213> ORGANISM: Clostridium tetani

<400> SEQUENCE: 99

Met Asn Lys Asn Val Leu Lys Phe Val Ser Arg Ser Leu Leu Ile Phe
1               5                  10                  15

Ser Met Thr Gly Leu Ile Ser Asn Tyr Asn Ser Ser Asn Val Leu Ala
                20                  25                  30

Lys Gly Asn Val Glu Glu His Ser Leu Ile Asn Asn Gly Gln Val Val
            35                  40                  45

Thr Ser Asn Thr Lys Cys Asn Leu Ala Lys Asp Asn Ser Ser Asp Ile
50                  55                  60

Asp Lys Asn Ile Tyr Gly Leu Ser Tyr Asp Pro Arg Lys Ile Leu Ser
65                  70                  75                  80

Tyr Asn Gly Glu Gln Val Glu Asn Phe Val Pro Ala Glu Gly Phe Glu
                85                  90                  95

Asn Pro Asp Lys Phe Ile Val Lys Arg Glu Lys Lys Ser Ile Ser
                100                 105                 110

Asp Ser Thr Ala Asp Ile Ser Ile Ile Asp Ser Ile Asn Asp Arg Thr
            115                 120                 125

Tyr Pro Gly Ala Ile Gln Leu Ala Asn Arg Asn Leu Met Glu Asn Lys
130                 135                 140

Pro Asp Ile Ile Ser Cys Glu Arg Lys Pro Ile Thr Ile Ser Val Asp
145                 150                 155                 160

Leu Pro Gly Met Ala Glu Asp Gly Lys Lys Val Val Asn Ser Pro Thr
                165                 170                 175

Tyr Ser Ser Val Asn Ser Ala Ile Asn Ser Ile Leu Asp Thr Trp Asn
            180                 185                 190

Ser Lys Tyr Ser Ser Lys Tyr Thr Ile Pro Thr Arg Met Ser Tyr Ser
        195                 200                 205

Asp Thr Met Val Tyr Ser Gln Ser Gln Leu Ser Ala Ala Val Gly Cys
210                 215                 220

Asn Phe Lys Ala Leu Asn Lys Ala Leu Asn Ile Asp Phe Asp Ser Ile
225                 230                 235                 240

Phe Lys Gly Glu Lys Lys Val Met Leu Leu Ala Tyr Lys Gln Ile Phe
                245                 250                 255

Tyr Thr Val Ser Val Asp Pro Pro Asn Arg Pro Ser Asp Leu Phe Gly
            260                 265                 270

Asp Ser Val Thr Phe Asp Glu Leu Ala Leu Lys Gly Ile Asn Asn Asn
```

```
                275                 280                 285
Asn Pro Pro Ala Tyr Val Ser Asn Val Ala Tyr Gly Arg Thr Ile Tyr
290                 295                 300

Val Lys Leu Glu Thr Thr Ser Lys Ser Ser His Val Lys Ala Ala Phe
305                 310                 315                 320

Lys Ala Leu Ile Asn Asn Gln Asp Ile Ser Ser Asn Ala Glu Tyr Lys
                325                 330                 335

Asp Ile Leu Asn Gln Ser Ser Phe Thr Ala Thr Val Leu Gly Gly Gly
                340                 345                 350

Ala Gln Glu His Asn Lys Ile Ile Thr Lys Asp Phe Asp Glu Ile Arg
                355                 360                 365

Asn Ile Ile Lys Asn Asn Ser Val Tyr Ser Pro Gln Asn Pro Gly Tyr
370                 375                 380

Pro Ile Ser Tyr Thr Thr Thr Phe Leu Lys Asp Asn Ser Ile Ala Ser
385                 390                 395                 400

Val Asn Asn Lys Thr Glu Tyr Ile Glu Thr Thr Ala Thr Glu Tyr Thr
                405                 410                 415

Asn Gly Lys Ile Val Leu Asp His Ser Gly Ala Tyr Val Ala Gln Phe
                420                 425                 430

Gln Val Thr Trp Asp Glu Val Ser Tyr Asp Glu Lys Gly Asn Glu Ile
                435                 440                 445

Val Glu His Lys Ala Trp Glu Gly Asn Asn Arg Asp Arg Thr Ala His
                450                 455                 460

Phe Asn Thr Glu Ile Tyr Leu Lys Gly Asn Ala Arg Asn Ile Ser Val
465                 470                 475                 480

Lys Ile Arg Glu Cys Thr Gly Leu Ala Trp Glu Trp Trp Arg Thr Ile
                485                 490                 495

Val Asp Val Lys Asn Ile Pro Leu Ala Lys Glu Arg Thr Phe Tyr Ile
                500                 505                 510

Trp Gly Thr Thr Leu Tyr Pro Lys Thr Ser Ile Glu Thr Lys Met
                515                 520                 525

<210> SEQ ID NO 100
<211> LENGTH: 529
<212> TYPE: PRT
<213> ORGANISM: Listeria monocytogenes

<400> SEQUENCE: 100

Met Lys Lys Ile Met Leu Val Phe Ile Thr Leu Ile Leu Ile Ser Leu
1               5                   10                  15

Pro Ile Ala Gln Gln Thr Glu Ala Lys Asp Ala Ser Ala Phe His Lys
                20                  25                  30

Glu Asp Leu Ile Ser Ser Met Ala Pro Pro Thr Ser Pro Pro Ala Ser
                35                  40                  45

Pro Lys Thr Pro Ile Glu Lys Lys His Ala Asp Glu Ile Asp Lys Tyr
                50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
                115                 120                 125
```

```
Ala Leu Val Lys Ala Asn Ser Glu Leu Val Glu Asn Gln Pro Asp Val
130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Lys Asn Ala Thr Lys Ser
                165                 170                 175

Asn Val Asn Asn Ala Val Asn Thr Leu Val Glu Arg Trp Asn Glu Lys
                180                 185                 190

Tyr Ala Gln Ala Tyr Pro Asn Val Ser Ala Lys Ile Asp Tyr Asp Asp
                195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
                275                 280                 285

Pro Pro Ala Tyr Ile Ser Ser Val Ala Tyr Gly Arg Gln Val Tyr Leu
290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Ile Asn Tyr Asp Pro Glu Gly Asn Glu Ile Val
                435                 440                 445

Gln His Lys Asn Trp Ser Glu Asn Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
                500                 505                 510

Gly Thr Thr Leu Tyr Pro Lys Tyr Ser Asn Ser Val Asp Asn Pro Ile
                515                 520                 525

Glu

<210> SEQ ID NO 101
```

<211> LENGTH: 512
<212> TYPE: PRT
<213> ORGANISM: Bacillus thuringiensis

<400> SEQUENCE: 101

Met Ile Phe Leu Asn Ile Lys Lys Asn Gly Lys Arg Arg Lys Phe Leu
1               5                   10                  15

Thr Cys Val Leu Val Ser Leu Cys Thr Leu Asn Tyr Ser Ser Thr Ser
            20                  25                  30

Phe Ala Glu Thr Gln Ala Gly His Ala Thr Asp Ile Thr Lys Asn Ala
        35                  40                  45

Ser Ser Ile Asp Thr Gly Ile Gly Asn Leu Thr Tyr Asn Asn Gln Glu
    50                  55                  60

Val Leu Ala Val Asn Gly Asp Lys Val Glu Ser Phe Val Pro Lys Glu
65                  70                  75                  80

Ser Ile Asn Ser Asn Gly Lys Phe Val Val Glu Arg Glu Lys Lys
                85                  90                  95

Ser Leu Thr Thr Ser Pro Val Asp Ile Ser Ile Asp Ser Val Ala
                100                 105                 110

Asn Arg Thr Tyr Pro Gly Ala Val Gln Leu Ala Asn Lys Ala Phe Ala
            115                 120                 125

Asp Asn Gln Pro Ser Leu Leu Val Ala Lys Arg Lys Pro Leu Asn Ile
    130                 135                 140

Ser Ile Asp Leu Pro Gly Met Arg Lys Glu Asn Thr Ile Thr Val Gln
145                 150                 155                 160

Asn Pro Thr Tyr Gly Asn Val Ala Gly Ala Val Asp Asp Leu Val Ser
                165                 170                 175

Thr Trp Asn Glu Lys Tyr Ser Glu Thr His Thr Leu Pro Ala Arg Met
            180                 185                 190

Gln Tyr Thr Glu Ser Met Val Tyr Ser Lys Ser Gln Ile Ala Ser Ala
        195                 200                 205

Leu Asn Val Asn Ala Lys Tyr Leu Asp Asn Ser Leu Asn Ile Asp Phe
    210                 215                 220

Asn Ala Val Ala Asn Gly Glu Lys Lys Val Met Val Ala Ala Tyr Lys
225                 230                 235                 240

Gln Ile Phe Tyr Thr Val Ser Ala Glu Leu Pro Asn Asn Pro Ser Asp
                245                 250                 255

Leu Phe Asp Asn Ser Val Thr Phe Asp Glu Leu Thr Arg Lys Gly Val
            260                 265                 270

Ser Asn Ser Ala Pro Pro Val Met Val Ser Asn Val Ala Tyr Gly Arg
        275                 280                 285

Thr Val Tyr Val Lys Leu Glu Thr Thr Ser Lys Ser Lys Asp Val Gln
    290                 295                 300

Ala Ala Phe Lys Ala Leu Leu Lys Asn Asn Ser Val Glu Thr Ser Gly
305                 310                 315                 320

Gln Tyr Lys Asp Ile Phe Glu Glu Ser Thr Phe Thr Ala Val Val Leu
                325                 330                 335

Gly Gly Asp Ala Lys Glu His Asn Lys Val Val Thr Lys Asp Phe Asn
            340                 345                 350

Glu Ile Arg Asn Ile Ile Lys Asp Asn Ala Glu Leu Ser Phe Lys Asn
        355                 360                 365

Pro Ala Tyr Pro Ile Ser Tyr Thr Ser Thr Phe Leu Lys Asp Asn Ala
    370                 375                 380

Thr Ala Ala Val His Asn Asn Thr Asp Tyr Ile Glu Thr Thr Thr Thr

```
                385                 390                 395                 400
Glu Tyr Ser Ser Ala Lys Met Thr Leu Asp His Tyr Gly Ala Tyr Val
                    405                 410                 415

Ala Gln Phe Asp Val Ser Trp Asp Glu Phe Thr Phe Asp Gln Asn Gly
                420                 425                 430

Lys Glu Val Leu Thr His Lys Thr Trp Glu Gly Ser Gly Lys Asp Lys
            435                 440                 445

Thr Ala His Tyr Ser Thr Val Ile Pro Leu Pro Pro Asn Ser Lys Asn
        450                 455                 460

Ile Lys Ile Val Ala Arg Glu Cys Thr Gly Leu Ala Trp Glu Trp Trp
465                 470                 475                 480

Arg Thr Ile Ile Asn Glu Gln Asn Val Pro Leu Thr Asn Glu Ile Lys
                485                 490                 495

Val Ser Ile Gly Gly Thr Thr Leu Tyr Pro Thr Ala Ser Ile Ser His
            500                 505                 510
```

<210> SEQ ID NO 102
<211> LENGTH: 18
<212> TYPE: PRT
<213> ORGANISM: Streptococcus pneumoniae

<400> SEQUENCE: 102

```
Val Pro Ala Arg Met Gln Tyr Glu Lys Ile Thr Ala His Ser Met Glu
1               5                   10                  15

Gln Leu
```

<210> SEQ ID NO 103
<211> LENGTH: 18
<212> TYPE: PRT
<213> ORGANISM: Clostridium perfringens

<400> SEQUENCE: 103

```
Leu Pro Ala Arg Thr Gln Tyr Ser Glu Ser Met Val Tyr Ser Lys Ser
1               5                   10                  15

Gln Ile
```

<210> SEQ ID NO 104
<211> LENGTH: 18
<212> TYPE: PRT
<213> ORGANISM: Streptococcus intermedius

<400> SEQUENCE: 104

```
Val Pro Ala Arg Met Gln Tyr Glu Ser Ile Ser Ala Gln Ser Met Ser
1               5                   10                  15

Gln Leu
```

<210> SEQ ID NO 105
<211> LENGTH: 18
<212> TYPE: PRT
<213> ORGANISM: Paenibacillus alvei

<400> SEQUENCE: 105

```
Leu Pro Ala Arg Leu Gln Tyr Ala Glu Ser Met Val Tyr Ser Gln Asn
1               5                   10                  15

Gln Ile
```

<210> SEQ ID NO 106
<211> LENGTH: 18
<212> TYPE: PRT

<213> ORGANISM: Bacillus anthracis

<400> SEQUENCE: 106

Leu Pro Ala Arg Thr Gln Tyr Ser Glu Ser Met Val Tyr Ser Lys Ser
1               5                   10                  15

Gln Leu

<210> SEQ ID NO 107
<211> LENGTH: 18
<212> TYPE: PRT
<213> ORGANISM: Bacillus cereus

<400> SEQUENCE: 107

Leu Pro Ala Arg Thr Gln Tyr Ser Glu Ser Met Val Tyr Ser Lys Ser
1               5                   10                  15

Gln Ile

<210> SEQ ID NO 108
<211> LENGTH: 18
<212> TYPE: PRT
<213> ORGANISM: Listeria ivanovii

<400> SEQUENCE: 108

Ile Ser Ala Lys Ile Asp Tyr Asp Gln Glu Met Ala Tyr Ser Glu Ser
1               5                   10                  15

Gln Leu

<210> SEQ ID NO 109
<211> LENGTH: 18
<212> TYPE: PRT
<213> ORGANISM: Clostridium perfringens

<400> SEQUENCE: 109

Leu Pro Ala Arg Thr Gln Tyr Ser Glu Ser Met Val Tyr Ser Lys Ser
1               5                   10                  15

Gln Ile

<210> SEQ ID NO 110
<211> LENGTH: 18
<212> TYPE: PRT
<213> ORGANISM: Listeria seeligeri

<400> SEQUENCE: 110

Ile Asn Ala Lys Ile Asp Tyr Ser Asp Glu Met Ala Tyr Ser Glu Ser
1               5                   10                  15

Gln Leu

<210> SEQ ID NO 111
<211> LENGTH: 18
<212> TYPE: PRT
<213> ORGANISM: Streptococcus pyogenes

<400> SEQUENCE: 111

Leu Pro Ala Arg Thr Gln Tyr Thr Glu Ser Met Val Tyr Ser Lys Ser
1               5                   10                  15

Gln Ile

<210> SEQ ID NO 112
<211> LENGTH: 18
<212> TYPE: PRT
<213> ORGANISM: Streptococcus suis -continued

<400> SEQUENCE: 112

Thr Gln Ala Glu Leu Gln Tyr Asp Glu Thr Met Ala Tyr Ser Met Ser
1               5                   10                  15

Gln Leu

<210> SEQ ID NO 113
<211> LENGTH: 18
<212> TYPE: PRT
<213> ORGANISM: Clostridium tetani

<400> SEQUENCE: 113

Ile Pro Thr Arg Met Ser Tyr Ser Asp Thr Met Val Tyr Ser Gln Ser
1               5                   10                  15

Gln Leu

<210> SEQ ID NO 114
<211> LENGTH: 18
<212> TYPE: PRT
<213> ORGANISM: Listeria monocytogenes

<400> SEQUENCE: 114

Val Ser Ala Lys Ile Asp Tyr Asp Asp Glu Met Ala Tyr Ser Glu Ser
1               5                   10                  15

Gln Leu

<210> SEQ ID NO 115
<211> LENGTH: 18
<212> TYPE: PRT
<213> ORGANISM: Bacillus thuringiensis

<400> SEQUENCE: 115

Leu Pro Ala Arg Met Gln Tyr Thr Glu Ser Met Val Tyr Ser Lys Ser
1               5                   10                  15

Gln Ile

<210> SEQ ID NO 116
<211> LENGTH: 499
<212> TYPE: PRT
<213> ORGANISM: Clostridium perfringens

<400> SEQUENCE: 116

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
                20                  25                  30

Asp Lys Asn Gln Ser Ile Asp Ser Gly Ile Ser Ser Leu Ser Tyr Asn
            35                  40                  45

Arg Asn Glu Val Leu Ala Ser Asn Gly Asp Lys Ile Glu Ser Phe Val
        50                  55                  60

Pro Lys Glu Gly Lys Lys Ala Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Glu Ala Ile
        115                 120                 125

```
Asn Ile Asn Ile Asp Leu Pro Gly Leu Lys Gly Glu Asn Ser Ile Lys
    130                 135                 140

Val Asp Asp Pro Thr Tyr Gly Lys Val Ser Gly Ala Ile Asp Glu Leu
145                 150                 155                 160

Val Ser Lys Trp Asn Glu Lys Tyr Ser Ser Thr His Thr Leu Pro Ala
                165                 170                 175

Arg Thr Gln Tyr Ser Glu Ser Met Val Tyr Ser Lys Ser Gln Ile Ser
            180                 185                 190

Ser Ala Leu Asn Val Asn Ala Lys Val Leu Glu Asn Ser Leu Gly Val
        195                 200                 205

Asp Phe Asn Ala Val Ala Asn Asn Glu Lys Lys Val Met Ile Leu Ala
    210                 215                 220

Tyr Lys Gln Ile Phe Tyr Thr Val Ser Ala Asp Leu Pro Lys Asn Pro
225                 230                 235                 240

Ser Asp Leu Phe Asp Asp Ser Val Thr Phe Asn Asp Leu Lys Gln Lys
                245                 250                 255

Gly Val Ser Asn Glu Ala Pro Pro Leu Met Val Ser Asn Val Ala Tyr
            260                 265                 270

Gly Arg Thr Ile Tyr Val Lys Leu Glu Thr Thr Ser Ser Ser Lys Asp
        275                 280                 285

Val Gln Ala Ala Phe Lys Ala Leu Ile Lys Asn Thr Asp Ile Lys Asn
    290                 295                 300

Ser Gln Gln Tyr Lys Asp Ile Tyr Glu Asn Ser Ser Phe Thr Ala Val
305                 310                 315                 320

Val Leu Gly Gly Asp Ala Gln Glu His Asn Lys Val Val Thr Lys Asp
                325                 330                 335

Phe Asp Glu Ile Arg Lys Val Ile Lys Asp Asn Ala Thr Phe Ser Thr
            340                 345                 350

Lys Asn Pro Ala Tyr Pro Ile Ser Tyr Thr Ser Val Phe Leu Lys Asp
        355                 360                 365

Asn Ser Val Ala Ala Val His Asn Lys Thr Asp Tyr Ile Glu Thr Thr
    370                 375                 380

Ser Thr Glu Tyr Ser Lys Gly Lys Ile Asn Leu Asp His Ser Gly Ala
385                 390                 395                 400

Tyr Val Ala Gln Phe Glu Val Ala Trp Asp Glu Val Ser Tyr Asp Lys
                405                 410                 415

Glu Gly Asn Glu Val Leu Thr His Lys Thr Trp Asp Gly Asn Tyr Gln
            420                 425                 430

Asp Lys Thr Ala His Tyr Ser Thr Val Ile Pro Leu Glu Ala Asn Ala
        435                 440                 445

Arg Asn Ile Arg Ile Lys Ala Arg Glu Cys Thr Gly Leu Ala Trp Glu
    450                 455                 460

Trp Trp Arg Asp Val Ile Ser Glu Tyr Asp Val Pro Leu Thr Asn Asn
465                 470                 475                 480

Ile Asn Val Ser Ile Trp Gly Thr Thr Leu Tyr Pro Gly Ser Ser Ile
                485                 490                 495

Thr Tyr Asn
```

<210> SEQ ID NO 117
<211> LENGTH: 470
<212> TYPE: PRT
<213> ORGANISM: Artificial Sequence
<220> FEATURE:
<223> OTHER INFORMATION: Synthetic sequence

```
<400> SEQUENCE: 117

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Ser Phe Leu
                100                 105                 110

Gln Val Glu Asp Pro Ser Asn Ser Ser Val Arg Gly Ala Val Asn Asp
            115                 120                 125

Leu Leu Ala Lys Trp His Gln Asp Tyr Gly Gln Val Asn Asn Val Pro
130                 135                 140

Ala Arg Met Gln Tyr Glu Lys Ile Thr Ala His Ser Met Glu Gln Leu
145                 150                 155                 160

Lys Val Lys Phe Gly Ser Asp Phe Glu Lys Thr Gly Asn Ser Leu Asp
                165                 170                 175

Ile Asp Phe Asn Ser Val His Ser Gly Glu Lys Gln Ile Gln Ile Val
                180                 185                 190

Asn Phe Lys Gln Ile Tyr Tyr Thr Val Ser Val Asp Ala Val Lys Asn
            195                 200                 205

Pro Gly Asp Val Phe Gln Asp Thr Val Thr Val Glu Asp Leu Lys Gln
210                 215                 220

Arg Gly Ile Ser Ala Glu Arg Pro Leu Val Tyr Ile Ser Ser Val Ala
225                 230                 235                 240

Tyr Gly Arg Gln Val Tyr Leu Lys Leu Glu Thr Thr Ser Lys Ser Asp
                245                 250                 255

Glu Val Glu Ala Ala Phe Glu Ala Leu Ile Lys Gly Val Lys Val Ala
                260                 265                 270

Pro Gln Thr Glu Trp Lys Gln Ile Leu Asp Asn Thr Glu Val Lys Ala
            275                 280                 285

Val Ile Leu Gly Gly Asp Pro Ser Ser Gly Ala Arg Val Val Thr Gly
290                 295                 300

Lys Val Asp Met Val Glu Asp Leu Ile Gln Glu Gly Ser Arg Phe Thr
305                 310                 315                 320

Ala Asp His Pro Gly Leu Pro Ile Ser Tyr Thr Thr Ser Phe Leu Arg
                325                 330                 335

Asp Asn Val Val Ala Thr Phe Gln Asn Ser Thr Asp Tyr Val Glu Thr
                340                 345                 350

Lys Val Thr Ala Tyr Arg Asn Gly Asp Leu Leu Asp His Ser Gly
            355                 360                 365

Ala Tyr Val Ala Gln Tyr Ile Thr Trp Asp Glu Leu Ser Tyr Asp
370                 375                 380

His Gln Gly Lys Glu Val Leu Thr Pro Lys Ala Trp Asp Arg Asn Gly
385                 390                 395                 400

Gln Asp Leu Thr Ala His Phe Thr Thr Ser Ile Pro Leu Lys Gly Asn
                405                 410                 415
```

-continued

```
Val Arg Asn Leu Ser Val Lys Ile Arg Glu Cys Thr Gly Leu Ala Trp
            420                 425                 430

Glu Trp Trp Arg Thr Val Tyr Glu Lys Thr Asp Leu Pro Leu Val Arg
        435                 440                 445

Lys Arg Thr Ile Ser Ile Trp Gly Thr Thr Asp Tyr Pro Gln Val Glu
450                 455                 460

Asp Lys Val Glu Asn Asp
465                 470

<210> SEQ ID NO 118
<211> LENGTH: 470
<212> TYPE: PRT
<213> ORGANISM: Artificial Sequence
<220> FEATURE:
<223> OTHER INFORMATION: Synthetic sequence

<400> SEQUENCE: 118

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
    50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Asp Ser Phe Leu
            100                 105                 110

Gln Val Glu Asp Pro Ser Asn Ser Ser Val Arg Gly Ala Val Asn Asp
        115                 120                 125

Leu Leu Ala Lys Trp His Gln Asp Tyr Gly Gln Val Asn Asn Val Pro
    130                 135                 140

Ala Arg Met Gln Tyr Glu Lys Ile Thr Ala His Ser Met Glu Gln Leu
145                 150                 155                 160

Lys Val Lys Phe Gly Ser Asp Phe Glu Lys Thr Gly Asn Ser Leu Asp
                165                 170                 175

Ile Asp Phe Asn Ser Val His Ser Gly Glu Lys Gln Ile Gln Ile Val
            180                 185                 190

Asn Phe Lys Gln Ile Tyr Tyr Thr Val Ser Val Asp Ala Val Arg Asn
        195                 200                 205

Pro Gly Asp Val Phe Gln Asp Thr Val Thr Val Glu Asp Leu Lys Gln
    210                 215                 220

Arg Gly Ile Ser Ala Glu Arg Pro Leu Val Tyr Ile Ser Ser Val Ala
225                 230                 235                 240

Tyr Gly Arg Gln Val Tyr Leu Lys Leu Glu Thr Thr Ser Lys Ser Asp
                245                 250                 255

Glu Val Glu Ala Ala Phe Glu Ala Leu Ile Lys Gly Val Lys Val Ala
            260                 265                 270

Pro Gln Thr Glu Trp Lys Gln Ile Leu Asp Asn Thr Glu Val Lys Ala
        275                 280                 285

Val Ile Leu Gly Gly Asp Pro Ser Ser Gly Ala Arg Val Val Thr Gly
    290                 295                 300
```

```
Lys Val Asp Met Val Glu Asp Leu Ile Gln Glu Gly Ser Arg Phe Thr
305                 310                 315                 320

Ala Asp His Pro Gly Leu Pro Ile Ser Tyr Thr Thr Ser Phe Leu Arg
                325                 330                 335

Asp Asn Val Val Ala Thr Phe Gln Asn Ser Thr Asp Tyr Val Glu Thr
            340                 345                 350

Lys Val Thr Ala Tyr Arg Asn Gly Asp Leu Leu Asp His Ser Gly
        355                 360                 365

Ala Tyr Val Ala Gln Tyr Tyr Ile Thr Trp Asp Glu Leu Ser Tyr Asp
    370                 375                 380

His Gln Gly Lys Glu Val Leu Thr Pro Lys Ala Trp Asp Arg Asn Gly
385                 390                 395                 400

Gln Asp Leu Thr Ala His Phe Thr Thr Ser Ile Pro Leu Lys Gly Asn
                405                 410                 415

Val Arg Asn Leu Ser Val Lys Ile Arg Glu Cys Thr Gly Leu Ala Trp
            420                 425                 430

Glu Trp Trp Arg Thr Val Tyr Glu Lys Thr Asp Leu Pro Leu Val Arg
        435                 440                 445

Lys Arg Thr Ile Ser Ile Trp Gly Thr Thr Asp Tyr Pro Gln Val Glu
    450                 455                 460

Asp Lys Val Glu Asn Asp
465                 470

<210> SEQ ID NO 119
<211> LENGTH: 468
<212> TYPE: PRT
<213> ORGANISM: Artificial Sequence
<220> FEATURE:
<223> OTHER INFORMATION: Synthetic sequence

<400> SEQUENCE: 119

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
    50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
            85                  90                  95

Thr Tyr Ser Ile Asp Leu Pro Gly Leu Ala Ser Ser Asp Ser Phe Leu
                100                 105                 110

Gln Val Glu Asp Pro Ser Asn Ser Ser Val Arg Gly Ala Val Asn Asp
            115                 120                 125

Leu Leu Ala Lys Trp His Gln Asp Tyr Gly Gln Val Asn Asn Val Pro
130                 135                 140

Met Gln Tyr Glu Lys Ile Thr Ala His Ser Met Glu Gln Leu Lys Val
145                 150                 155                 160

Lys Phe Gly Ser Asp Phe Glu Lys Thr Gly Asn Ser Leu Asp Ile Asp
                165                 170                 175

Phe Asn Ser Val His Ser Gly Glu Lys Gln Ile Gln Ile Val Asn Phe
            180                 185                 190
```

```
Lys Gln Ile Tyr Tyr Thr Val Ser Val Asp Ala Val Lys Asn Pro Gly
            195                 200                 205

Asp Val Phe Gln Asp Thr Val Thr Val Glu Asp Leu Lys Gln Arg Gly
        210                 215                 220

Ile Ser Ala Glu Arg Pro Leu Val Tyr Ile Ser Ser Val Ala Tyr Gly
225                 230                 235                 240

Arg Gln Val Tyr Leu Lys Leu Glu Thr Thr Ser Lys Ser Asp Glu Val
                245                 250                 255

Glu Ala Ala Phe Glu Ala Leu Ile Lys Gly Val Lys Val Ala Pro Gln
            260                 265                 270

Thr Glu Trp Lys Gln Ile Leu Asp Asn Thr Glu Val Lys Ala Val Ile
        275                 280                 285

Leu Gly Gly Asp Pro Ser Ser Gly Ala Arg Val Val Thr Gly Lys Val
    290                 295                 300

Asp Met Val Glu Asp Leu Ile Gln Glu Gly Ser Arg Phe Thr Ala Asp
305                 310                 315                 320

His Pro Gly Leu Pro Ile Ser Tyr Thr Thr Ser Phe Leu Arg Asp Asn
                325                 330                 335

Val Val Ala Thr Phe Gln Asn Ser Thr Asp Tyr Val Glu Thr Lys Val
            340                 345                 350

Thr Ala Tyr Arg Asn Gly Asp Leu Leu Leu Asp His Ser Gly Ala Tyr
        355                 360                 365

Val Ala Gln Tyr Tyr Ile Thr Trp Asp Glu Leu Ser Tyr Asn His Gln
    370                 375                 380

Gly Lys Glu Val Leu Thr Pro Lys Ala Trp Asp Arg Asn Gly Gln Asp
385                 390                 395                 400

Leu Thr Ala His Phe Thr Thr Ser Ile Pro Leu Lys Gly Asn Val Arg
                405                 410                 415

Asn Leu Ser Val Lys Ile Arg Glu Cys Thr Gly Leu Ala Trp Glu Trp
            420                 425                 430

Trp Arg Thr Val Tyr Glu Lys Thr Asp Leu Pro Leu Val Arg Lys Arg
        435                 440                 445

Thr Ile Ser Ile Trp Gly Thr Thr Leu Tyr Pro Gln Val Glu Asp Lys
    450                 455                 460

Val Glu Asn Asp
465

<210> SEQ ID NO 120
<211> LENGTH: 470
<212> TYPE: PRT
<213> ORGANISM: Artificial Sequence
<220> FEATURE:
<223> OTHER INFORMATION: Synthetic sequence

<400> SEQUENCE: 120

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Ile Glu Arg Lys
        35                  40                  45

Lys Arg Ser Leu Ser Thr Asn Thr Ser Asp Ile Ser Val Thr Ala Thr
    50                  55                  60

Asn Asp Ser Arg Leu Tyr Pro Gly Ala Leu Leu Val Val Asp Glu Thr
65                  70                  75                  80
```

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Asp Ser Phe Leu
            100                 105                 110

Gln Val Glu Asp Pro Ser Asn Ser Ser Val Arg Gly Ala Val Asn Asp
        115                 120                 125

Leu Leu Ala Lys Trp His Gln Asp Tyr Gly Gln Val Asn Asn Val Pro
130                 135                 140

Ala Arg Met Gln Tyr Glu Lys Ile Thr Ala His Ser Met Glu Gln Leu
145                 150                 155                 160

Lys Val Lys Phe Gly Ser Asp Phe Glu Lys Thr Gly Asn Ser Leu Asp
                165                 170                 175

Ile Asp Phe Asn Ser Val His Ser Gly Glu Lys Gln Ile Gln Ile Val
            180                 185                 190

Asn Phe Lys Gln Ile Tyr Tyr Thr Val Ser Val Asp Ala Val Lys Asn
        195                 200                 205

Pro Gly Asp Val Phe Gln Asp Thr Val Thr Val Glu Asp Leu Lys Gln
210                 215                 220

Arg Gly Ile Ser Ala Glu Arg Pro Leu Val Tyr Ile Ser Ser Val Ala
225                 230                 235                 240

Tyr Gly Arg Gln Val Tyr Leu Lys Leu Glu Thr Thr Ser Lys Ser Asp
                245                 250                 255

Glu Val Glu Ala Ala Phe Glu Ala Leu Ile Lys Gly Val Lys Val Ala
            260                 265                 270

Pro Gln Thr Glu Trp Lys Gln Ile Leu Asp Asn Thr Glu Val Lys Ala
        275                 280                 285

Val Ile Leu Gly Gly Asp Pro Ser Ser Gly Ala Arg Val Val Thr Gly
290                 295                 300

Lys Val Asp Met Val Glu Asp Leu Ile Gln Glu Gly Ser Arg Phe Thr
305                 310                 315                 320

Ala Asp His Pro Gly Leu Pro Ile Ser Tyr Thr Thr Ser Phe Leu Arg
                325                 330                 335

Asp Asn Val Ala Thr Phe Gln Asn Ser Thr Asp Tyr Val Glu Thr
            340                 345                 350

Lys Val Thr Ala Tyr Arg Asn Gly Asp Leu Leu Leu Asp His Ser Gly
        355                 360                 365

Ala Tyr Val Ala Gln Tyr Tyr Ile Thr Trp Asp Glu Leu Ser Tyr Asp
370                 375                 380

His Gln Gly Lys Glu Val Leu Thr Pro Lys Ala Trp Asp Arg Asn Gly
385                 390                 395                 400

Gln Asp Leu Thr Ala His Phe Thr Thr Ser Ile Pro Leu Lys Gly Asn
                405                 410                 415

Val Arg Asn Leu Ser Val Lys Ile Arg Glu Cys Thr Gly Leu Ala Phe
            420                 425                 430

Glu Trp Trp Arg Thr Val Tyr Glu Lys Thr Asp Leu Pro Leu Val Arg
        435                 440                 445

Lys Arg Thr Ile Ser Ile Trp Gly Thr Thr Leu Tyr Pro Gln Val Glu
450                 455                 460

Asp Lys Val Glu Asn Asp
465                 470

<210> SEQ ID NO 121
<211> LENGTH: 789

```
<212> TYPE: DNA
<213> ORGANISM: Artificial Sequence
<220> FEATURE:
<223> OTHER INFORMATION: Synthetic sequence

<400> SEQUENCE: 121
agctctggag gtggaggaag cgggggcggt ggagttgcag cagacattgg agcaggatta      60
gcagatgcac tgacggcacc gttggatcat aaagacaaag gcttgaaatc gcttaccttta   120
gaagattcta tttcacaaaa tggcacccta accttgtccg cgcaaggcgc tgaacgtact    180
tttaaagccg gtgacaaaga taatagctta aatacaggta aactcaaaaa tgataaaatc    240
tcgcgttttg atttcattcg tcaaatcgaa gtagatggcc aacttattac attagaaagc    300
ggtgaattcc aagtatataa acaatcccat tcagcactta cagcattgca aaccgaacag    360
gtccaagact cagaacattc cggcaaaatg gtagctaaac gtcaattccg catcggtgac    420
attgtcggtg aacatacaag cttcggaaaa ttaccaaaag atgtgatggc gacctatcgc    480
ggtacggcat ttggatcaga tgatgcaggc ggtaaattaa cttatacaat tgactttgca    540
gcaaaacaag gacatggcaa aattgaacat ttaaaatctc ccgaacttaa cgtagatctc    600
gcagcagcag atattaaacc agatgaaaaa caccacgcag tcatttcagg ttcagtttta    660
tacaatcagg cagaaaaagg ttcgtactct ttaggtattt ttggcgggca agctcaagaa    720
gttgcaggta gcgcagaagt agaaacggca aatggcattc gtcacattgg gttagcggcg    780
aaacaataa                                                            789

<210> SEQ ID NO 122
<211> LENGTH: 780
<212> TYPE: DNA
<213> ORGANISM: Artificial Sequence
<220> FEATURE:
<223> OTHER INFORMATION: Synthetic sequence

<400> SEQUENCE: 122
agctctggag gtggaggaag cgggggcggt ggagttgcag cagacattgg agcaggatta      60
gcagatgcac tgacggcacc gttggatcat aaagacaaag gcttgcagtc gcttaccttta   120
gatcagtctg tcaggaaaaa tgagaaactt aagttggcgg cgcaaggcgc tgaaaaaact    180
tatggaaacg gtgacagctt aaatacaggt aaactcaaaa atgataaagt ctcgcgtttt    240
gatttcattc gtcaaatcga agtagatggc aagcttatta cattagaaag cggtgaattc    300
caagtatata aacaatccca ttcagcactt acagcattgc aaaccgaaca ggtccaagac    360
tcagaagatt ccggcaaaat ggtagctaaa cgtcaattcc gcatcggtga cattgcgggt    420
gaacatacaa gcttcgacaa attaccaaaa ggcggcagtg cgacctatcg cggtacggca    480
tttggatcag atgatgcagg cggtaaatta acttatacaa ttgactttgc agcaaaacaa    540
ggacatggca aaattgaaca tttaaaatct cccgaactta acgtagagct cgcaaccgca    600
tatattaaac cagatgaaaa acgccacgca gtcatttcag gttcagtttt atacaatcag    660
gacgaaaaag gttcgtactc tttaggtatt tttggcgggc aagctcaaga agttgcaggt    720
agcgcagaag tagaaacggc aaatggcatt caccacattg ggttagcggc gaaacaataa    780

<210> SEQ ID NO 123
<211> LENGTH: 765
<212> TYPE: DNA
<213> ORGANISM: Artificial Sequence
<220> FEATURE:
<223> OTHER INFORMATION: Synthetic sequence
```

<400> SEQUENCE: 123

```
agctctggag gtggaggagt tgcagcagac attggagcag gattagcaga tgcactgacg    60
gcaccgttgg atcataaaga caaaggcttg cagtcgctta ccttagatca gtctgtcagg   120
aaaaatgaga aacttaagtt ggcggcgcaa ggcgctgaaa aaacttatgg aaacggtgac   180
agcttaaata caggtaaact caaaaatgat aaagtctcgc gttttgattt cattcgtcaa   240
atcgaagtag atggcaagct tattacatta gaaagcggtg aattccaagt atataaacaa   300
tcccattcag cacttacagc attgcaaacc gaacaggtcc aagactcaga agattccggc   360
aaaatggtag ctaaacgtca attccgcatc ggtgacattg cgggtgaaca tacaagcttc   420
gacaaattac caaaaggcgg cagtgcgacc tatcgcggta cggcatttgg atcagatgat   480
gcaggcggta aattaactta tacaattgac tttgcagcaa acaaggaca tggcaaaatt    540
gaacatttaa aatctcccga acttaacgta gagctcgcaa ccgcatatat taaaccagat   600
gaaaaacgcc acgcagtcat ttcaggttca gttttataca atcaggacga aaaaggttcg   660
tactctttag gtattttttgg cgggcaagct caagaagttg caggtagcgc agaagtagaa   720
acggcaaatg gcattcacca cattgggtta gcggcgaaac aataa                   765
```

<210> SEQ ID NO 124
<211> LENGTH: 765
<212> TYPE: DNA
<213> ORGANISM: Artificial Sequence
<220> FEATURE:
<223> OTHER INFORMATION: Synthetic sequence

<400> SEQUENCE: 124

```
agcagcgggg gcggtggagt tgcagcagac attggagcag gattagcaga tgcactgacg    60
gcaccgttgg atcataaaga caaaggcttg cagtcgctta ccttagatca gtctgtcagg   120
aaaaatgaga aacttaagtt ggcggcgcaa ggcgctgaaa aaacttatgg aaacggtgac   180
agcttaaata caggtaaact caaaaatgat aaagtctcgc gttttgattt cattcgtcaa   240
atcgaagtag atggcaagct tattacatta gaaagcggtg aattccaagt atataaacaa   300
tcccattcag cacttacagc attgcaaacc gaacaggtcc aagactcaga agattccggc   360
aaaatggtag ctaaacgtca attccgcatc ggtgacattg cgggtgaaca tacaagcttc   420
gacaaattac caaaaggcgg cagtgcgacc tatcgcggta cggcatttgg atcagatgat   480
gcaggcggta aattaactta tacaattgac tttgcagcaa acaaggaca tggcaaaatt    540
gaacatttaa aatctcccga acttaacgta gagctcgcaa ccgcatatat taaaccagat   600
gaaaaacgcc acgcagtcat ttcaggttca gttttataca atcaggacga aaaaggttcg   660
tactctttag gtattttttgg cgggcaagct caagaagttg caggtagcgc agaagtagaa   720
acggcaaatg gcattcacca cattgggtta gcggcgaaac aataa                   765
```

<210> SEQ ID NO 125
<211> LENGTH: 786
<212> TYPE: DNA
<213> ORGANISM: Artificial Sequence
<220> FEATURE:
<223> OTHER INFORMATION: Synthetic sequence

<400> SEQUENCE: 125

```
atgagctctg gaagcggaag cgggggcggt ggagttgcag cagacattgg aacaggatta    60
gcagatgcac tgacggcacc gttggatcat aaagacaaag gcttgaaatc gcttaccttta  120
gaagattcta tttcacaaaa tggcacccct accttgtccg cgcaaggcgc tgaaaaaact   180
```

-continued

```
tttaaagtcg gtgacaaaga taatagctta aatacaggta aactcaaaaa tgataaaatc    240
tcgcgttttg atttcgtgca aaaatcgaa gtagatggcc aaaccattac attagcaagc    300
ggtgaattcc aaatatataa acaagaccat tcagcagtcg ttgcattgca aattgaaaaa    360
atcaacaacc ccgacaaaat cgacagcctg ataaaccaac gttccttcct tgtcagcggt    420
ttgggcggtg aacatacagc cttcaaccaa ttaccaagcg gcaaagcgga gtatcacggt    480
aaagcattta gctcagatga tgcaggcggt aaattaactt atacaattga ctttgcagca    540
aaacaaggac atggcaaaat tgaacattta aaaacacccg aacagaacgt agagctcgca    600
tccgcagaac tcaaagcaga tgaaaaatca cacgcagtca ttttgggtga cacgcgctac    660
ggcagcgaag aaaaaggtac ttaccactta gctcttttg gcgaccgagc tcaagaaatc    720
gcaggtagcg caaccgtaaa gataagggaa aaggttcacg aaattgggat cgcgggcaaa    780
caataa                                                               786
```

<210> SEQ ID NO 126
<211> LENGTH: 786
<212> TYPE: DNA
<213> ORGANISM: Artificial Sequence
<220> FEATURE:
<223> OTHER INFORMATION: Synthetic sequence

<400> SEQUENCE: 126

```
atgtccagcg gttcaggcag cggcggtgga ggcgtggcag cagatatcgg aacaggttta     60
gcagatgctc tgacagcacc cttagatcac aaagacaaag gacttaaatc actgacattg    120
gaagattcta tctcgcaaaa tggtactctc actctttcag cccaaggcgc agaaaaaaca    180
tttaaagtag gcgataaaga taactcctta aatacaggta aattaaaaaa tgacaaaatc    240
tcacggtttg atttcgttca gaaaattgaa gtagatggac aaacgattac attagcaagc    300
ggcgaattcc aaatttataa acaagaccat tcagcagtag tagcattaca aatcgaaaaa    360
attaacaacc cggacaaaat tgattctctt attaaccaac gctcttttct cgtatcagga    420
cttggtggtg aacatacagc gtttaatcaa ctgccgtcag gaaaagcaga atatcatggt    480
aaagcatttt catcagacga cgcaggtggc aaactgacct atactattga ctttgcagca    540
aaacagggac atggaaaaat tgaacattta aaaacacccg aacagaacgt agaactggcc    600
tcagcagaat tgaaagctga tgaaaaatcc catgcagtaa ttttaggcga tacacgttac    660
ggtagcgaag aaaaaggtac atatcactta gctctttttg gcgatcgtgc tcaagaaatt    720
gctggttccg caacagttaa aatccgtgaa aagtacatg aaatcggcat tgcaggtaaa    780
caataa                                                               786
```

<210> SEQ ID NO 127
<211> LENGTH: 765
<212> TYPE: DNA
<213> ORGANISM: Artificial Sequence
<220> FEATURE:
<223> OTHER INFORMATION: Synthetic sequence

<400> SEQUENCE: 127

```
atgagctctg gaggtggagg agttgcagca gacattggag caggattagc agatgcactg     60
acggcaccgt tggatcataa agacaaaagt ttgcagtcgc ttaccttaga tcagtctgtc    120
aggaaaaatg agaaacttaa gttggcggcg caaggcgctg aaaaaactta tggaaacggt    180
gacagcttaa atacaggtaa actcaaaaat gataaagtct cgcgttttga tttcattcgt    240
```

| | |
|---|---|
| caaatcgaag tagatggcca acttattaca ttagaaagcg gtgaattcca aatatataaa | 300 |
| caagaccatt cagcagtcgt tgcattgcaa attgaaaaaa tcaacaaccc cgacaaaatc | 360 |
| gacagcctga taaaccaacg ttccttcctt gtcagcggtt tgggcggtga acatacagcc | 420 |
| ttcaaccaat taccaagcgg caaagcggag tatcacggta aagcatttag ctcagatgat | 480 |
| gcaggcggta aattaactta tacaattgac tttgcagcaa acaaggaca tggcaaaatt | 540 |
| gaacatttaa aaacacccga acagaacgta gagctcgcat ccgcagaact caaagcagat | 600 |
| gaaaaatcac acgcagtcat tttgggtgac acgcgctacg gcggcgaaga aaaaggtact | 660 |
| taccacttag ctcttttgg cgaccgagct caagaaatcg caggtagcgc aaccgtaaag | 720 |
| ataagggaaa aggttcacga aattgggatc gcgggcaaac aataa | 765 |

<210> SEQ ID NO 128
<211> LENGTH: 768
<212> TYPE: DNA
<213> ORGANISM: Artificial Sequence
<220> FEATURE:
<223> OTHER INFORMATION: Synthetic sequence

<400> SEQUENCE: 128

| | |
|---|---|
| atgagcagcg gagggggcgg tgtcgccgcc gacatcggtg cggggcttgc cgatgcacta | 60 |
| accgcaccgc tcgaccataa agacaaaggt ttgcagtctt taacgctgga tcagtccgtc | 120 |
| aggaaaaacg agaaactgaa gctggcggca caaggtgcgg aaaaaactta tggaaacggc | 180 |
| gacagcctta atacgggcaa attgaagaac gacaaggtca gccgcttcga ctttatccgt | 240 |
| caaatcgaag tggacgggaa gctcattacc ttggagagcg gagagttcca agtgtacaaa | 300 |
| caaagccatt ccgccttaac cgcccttcag accgagcaag tacaagactc ggaggattcc | 360 |
| gggaagatgg ttgcgaaacg ccagttcaga atcggcgaca tagcgggcga acatacatct | 420 |
| tttgacaagc ttcccaaagg cggcagtgcg acatatcgcg ggacggcgtt cggttcagac | 480 |
| gatgctggcg aaaactgac ctatactata gatttcgccg ccaaacaggg acacggcaaa | 540 |
| atcgaacact tgaaaacacc cgagcaaaat gtcgagcttg cctccgccga actcaaagca | 600 |
| gatgaaaaat cacacgccgt cattttgggc gacacgcgct acggcggcga agaaaaaggc | 660 |
| acttaccacc tcgccctttt cggcgaccgc gcccaagaaa tcgccggctc ggcaaccgtg | 720 |
| aagataaggg aaaaggttca cgaaatcggc atcgccggca acagtaa | 768 |

<210> SEQ ID NO 129
<211> LENGTH: 780
<212> TYPE: DNA
<213> ORGANISM: Artificial Sequence
<220> FEATURE:
<223> OTHER INFORMATION: Synthetic sequence

<400> SEQUENCE: 129

| | |
|---|---|
| atgagctctg gaggtggagg aagcgggggc ggtggagttg cagcagacat tggagcagga | 60 |
| ttagcagatg cactgacggc accgttggat cataaagaca aagtttgca gtcgcttacc | 120 |
| ttagatcagt ctgtcaggaa aaatgagaaa cttaagttgg cggcgcaagg cgctgaaaaa | 180 |
| acttatggaa acggtgacag cttaaataca ggtaaactca aaaatgataa agtctcgcgt | 240 |
| tttgatttca ttcgtcaaat cgaagtagat ggccaaacca ttacattagc aagcggtgaa | 300 |
| ttccaaatat ataaacaaaa ccattcagca gtcgttgcat tgcaaattga aaaaatcaac | 360 |
| aaccccgaca aatcgacag cctgataaac caacgttcct tccttgtcag cggtttgggc | 420 |
| ggtgaacata cagccttcaa ccaattacca gacggcaaag cggagtatca cggtaaagca | 480 |

```
tttagctcag atgatccgaa cggtaggtta cactattcca ttgactttac caaaaaacaa      540
ggatacggca gaattgaaca tttaaaaacg cccgaacaga acgtagagct cgcatccgca      600
gaactcaaag cagatgaaaa atcacacgca gtcattttgg gtgacacgcg ctacggcggc      660
gaagaaaaag gtacttacca cttagccctt tttggcgacc gcgctcaaga aatcgcaggt      720
agcgcaaccg taaagataag ggaaaaggtt cacgaaattg ggatcgcggg caaacaataa      780
```

<210> SEQ ID NO 130
<211> LENGTH: 252
<212> TYPE: PRT
<213> ORGANISM: Artificial Sequence
<220> FEATURE:
<223> OTHER INFORMATION: Synthetic sequence

<400> SEQUENCE: 130

```
Gly Gly Gly Gly Val Ala Ala Asp Ile Gly Ala Gly Leu Ala Asp Ala
1               5                   10                  15

Leu Thr Ala Pro Leu Asp His Lys Asp Lys Gly Leu Gln Ser Leu Thr
            20                  25                  30

Leu Asp Gln Ser Val Arg Lys Asn Glu Lys Leu Lys Leu Ala Ala Gln
        35                  40                  45

Gly Ala Glu Lys Thr Tyr Gly Asn Gly Asp Ser Leu Asn Thr Gly Lys
    50                  55                  60

Leu Lys Asn Asp Lys Val Ser Arg Phe Asp Phe Ile Arg Gln Ile Glu
65                  70                  75                  80

Val Asp Gly Gln Leu Ile Thr Leu Glu Ser Gly Glu Phe Gln Val Tyr
                85                  90                  95

Lys Gln Ser His Ser Ala Leu Thr Ala Phe Gln Thr Glu Gln Ile Gln
            100                 105                 110

Asp Ser Glu His Ser Gly Lys Met Val Ala Lys Arg Gln Phe Arg Ile
        115                 120                 125

Gly Asp Ile Ala Gly Glu His Thr Ser Phe Asp Lys Leu Pro Glu Gly
    130                 135                 140

Gly Arg Ala Thr Tyr Arg Gly Thr Ala Phe Gly Ser Asp Asp Ala Gly
145                 150                 155                 160

Gly Lys Leu Thr Tyr Thr Ile Asp Phe Ala Ala Lys Gln Gly Asn Gly
                165                 170                 175

Lys Ile Glu His Leu Lys Ser Pro Glu Leu Asn Val Asp Leu Ala Ala
            180                 185                 190

Ala Asp Ile Lys Pro Asp Gly Lys Arg His Ala Val Ile Ser Gly Ser
        195                 200                 205

Val Leu Tyr Asn Gln Ala Glu Lys Gly Ser Tyr Ser Leu Gly Ile Phe
    210                 215                 220

Gly Gly Lys Ala Gln Glu Val Ala Gly Ser Ala Glu Val Lys Thr Val
225                 230                 235                 240

Asn Gly Ile Arg His Ile Gly Leu Ala Ala Lys Gln
                245                 250
```

<210> SEQ ID NO 131
<211> LENGTH: 765
<212> TYPE: DNA
<213> ORGANISM: Artificial Sequence
<220> FEATURE:
<223> OTHER INFORMATION: Synthetic sequence

<400> SEQUENCE: 131

```
ggcagcagcg gaggcggcgg tgtcgccgcc gacatcggcg cggggcttgc cgatgcacta    60
accgcaccgc tcgaccataa agacaaaagt ttgcagtctt tgacgctgga tcagtccgtc   120
aggaaaaacg agaaactgaa gctggcggca caaggtgcgg aaaaaactta tggaaacggc   180
gacagcctca atacgggcaa attgaagaac gacaaggtca gccgcttcga ctttatccgt   240
caaatcgaag tggacgggca gctcattacc ttggagagcg agagttcca aatatacaaa    300 caggaccact ccgccgtcgt tgccctacag attgaaaaaa tcaacaaccc cgacaaaatc   360
gacagcctga taaccaacg ctccttcctt gtcagcggtt tgggtggaga acataccgcc    420
ttcaaccaac tgcccagcgg caaagccgag tatcacggca agcattcag ctccgacgat    480 gctggcggaa aactgaccta taccatagat ttcgccgcca acagggaca cggcaaaatc    540 gaacacttga aaacacccga gcaaaatgtc gagcttgcct ccgccgaact caaagcagat   600
gaaaaatcac acgccgtcat tttgggcgac acgcgctacg gcggcgaaga aaaaggcact   660
taccacctcg ccctttttcgg cgaccgcgcc caagaaatcg ccggctcggc aaccgtgaag   720
ataagggaaa aggttcacga aatcggcatc gccggcaaac agtaa                   765
```

<210> SEQ ID NO 132
<211> LENGTH: 254
<212> TYPE: PRT
<213> ORGANISM: Artificial Sequence
<220> FEATURE:
<223> OTHER INFORMATION: Synthetic sequence

<400> SEQUENCE: 132

```
Gly Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
```

```
                225                 230                 235                 240

Ile Arg Glu Lys Val His Glu Ile Gly Ile Ala Gly Lys Gln
                245                 250
```

<210> SEQ ID NO 133
<211> LENGTH: 765
<212> TYPE: DNA
<213> ORGANISM: Artificial Sequence
<220> FEATURE:
<223> OTHER INFORMATION: Synthetic sequence

<400> SEQUENCE: 133

```
agcagcggag ggggcggtgt cgccgccgac atcggtgcgg ggcttgccga tgcactaacc    60
gcaccgctcg accataaaga caaaggtttg cagtctttaa cactggatca gtccgtcagg   120
aaaaacgaga aactgaagct ggcggcacaa ggtgcggaaa aaacttatgg aaacggcgac   180
agccttaata cgggcaaatt gaagaacgac aaggtcagcc gcttcgactt tatccgtcaa   240
atcgaagtgg acgggaagct cattaccttg gagagcggag agttccaagt gtacaaacaa   300
agccattccg ccttaaccgc ccttcagacc gagcaagtac aagactcgga ggattccggg   360
aagatggttg cgaaacgcca gttcagaatc ggcgacatag cgggcgaaca tacatctttt   420
gacaagcttc ccaaaggcgg cagtgcgaca tatcgcggga cggcgttcgg ttcagacgat   480
gctggcggaa aactgaccta tactatagat tcgccgccaa gcagggaca cggcaaaatc    540 gaacatttga atcgcccga actcaatgtc gagcttgcca ccgcctatat caagccggat   600
gaaaaacgcc atgccgttat cagcggttcc gtcctttaca accaagacga aaaggcagt    660 tactccctcg gtatctttgg cgggcaagcc caggaagttg ccggcagcgc ggaagtggaa   720
accgcaaacg gcatacacca tatcggtctt gccgccaagc agtaa                    765
```

<210> SEQ ID NO 134
<211> LENGTH: 789
<212> TYPE: DNA
<213> ORGANISM: Artificial Sequence
<220> FEATURE:
<223> OTHER INFORMATION: Synthetic sequence

<400> SEQUENCE: 134

```
agcagcggag gcggcggaag cggaggcggc ggtgtcgccg ccgacatcgg cgcggggctt    60
gccgatgcac taaccgcacc gctcgaccat aaagacaaag gtttgaaatc cctgacattg   120
gaagactcca tttcccaaaa cggaacactg accctgtcgg cacaaggtgc ggaaagaact   180
ttcaaagccg cgacaaaga caacagtctc aacacaggca aactgaagaa cgacaaaatc   240
agccgcttcg actttatccg tcaaatcgaa gtggacgggc agctcattac cttggagagc   300
ggagagttcc aagtgtacaa acaaagccat tccgccttaa ccgccttca gaccgagcaa    360 gtacaagact cggagcattc cggaagatg gttgcgaaac gccagttcag aatcggcgac   420
atagtgggcg aacatacatc ttttggcaag cttcccaaag acgtcatggc gacatatcgc   480
gggacggcgt tcggttcaga cgatgccggc ggaaaactga cctacaccat agatttcgcc   540
gccaagcagg gacacggcaa aatcgaacat ttgaatcgc cagaactcaa tgttgacctg   600
gccgccgccg atatcaagcc ggatgaaaaa caccatgccg tcatcagcgg ttccgtcctt   660
tacaaccaag ccgagaaagg cagttactct ctaggcatct ttggcgggca agcccaggaa   720
gttgccggca gcgcggaagt ggaaaccgca acggcatac gccatatcgg tcttgccgcc   780
aagcaataa                                                            789
```

<210> SEQ ID NO 135
<211> LENGTH: 257
<212> TYPE: PRT
<213> ORGANISM: Artificial Sequence
<220> FEATURE:
<223> OTHER INFORMATION: Synthetic sequence

<400> SEQUENCE: 135

```
Gly Ser Ser Gly Gly Gly Val Ala Ala Asp Ile Gly Thr Gly Leu
1               5                   10                  15

Ala Asp Ala Leu Thr Ala Pro Leu Asp His Lys Asp Lys Gly Leu Lys
            20                  25                  30

Ser Leu Thr Leu Glu Asp Ser Ile Ser Gln Asn Gly Leu Thr Leu
        35                  40                  45

Ser Ala Gln Gly Ala Glu Lys Thr Phe Lys Val Gly Asp Lys Asp Asn
    50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asp His Ser Ala Val Val Ala Leu
            100                 105                 110

Gln Ile Glu Lys Ile Asn Asn Pro Asp Lys Ile Asp Ser Leu Ile Asn
        115                 120                 125

Gln Arg Ser Phe Leu Val Ser Gly Leu Gly Gly Glu His Thr Ala Phe
    130                 135                 140

Asn Gln Leu Pro Ser Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ser Ala Glu Leu Lys Ala Asp Glu Lys Ser His Ala
        195                 200                 205

Val Ile Leu Gly Asp Thr Arg Tyr Gly Ser Glu Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Arg Glu Lys Val His Glu Ile Gly Ile Ala Gly Lys
                245                 250                 255

Gln
```

<210> SEQ ID NO 136
<211> LENGTH: 727
<212> TYPE: PRT
<213> ORGANISM: Artificial Sequence
<220> FEATURE:
<223> OTHER INFORMATION: Synthetic sequence

<400> SEQUENCE: 136

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45
```

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140

Pro Met Gln Tyr Glu Lys Ile Thr Ala His Ser Met Glu Gln Leu Lys
145                 150                 155                 160

Val Lys Phe Gly Ser Asp Phe Glu Lys Thr Gly Asn Ser Leu Asp Ile
                165                 170                 175

Asp Phe Asn Ser Val His Ser Gly Glu Lys Gln Ile Gln Ile Val Asn
                180                 185                 190

Phe Lys Gln Ile Tyr Tyr Thr Val Ser Val Asp Ala Val Lys Asn Pro
            195                 200                 205

Gly Asp Val Phe Gln Asp Thr Val Thr Val Glu Asp Leu Lys Gln Arg
        210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
                245                 250                 255

Val Glu Ala Ala Phe Glu Ala Leu Ile Lys Gly Val Lys Val Ala Pro
                260                 265                 270

Gln Thr Glu Trp Lys Gln Ile Leu Asp Asn Thr Glu Val Lys Ala Val
            275                 280                 285

Ile Leu Gly Gly Asp Pro Ser Ser Gly Ala Arg Val Val Thr Gly Lys
        290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
                340                 345                 350

Val Thr Ala Tyr Arg Asn Gly Asp Leu Leu Asp His Ser Gly Ala
            355                 360                 365

Tyr Val Ala Gln Tyr Tyr Ile Thr Trp Asp Glu Leu Ser Tyr Asp His
        370                 375                 380

Gln Gly Lys Glu Val Leu Thr Pro Lys Ala Trp Asp Arg Asn Gly Gln
385                 390                 395                 400

Asp Leu Thr Ala His Phe Thr Ser Ile Pro Leu Lys Gly Asn Val
                405                 410                 415

Arg Asn Leu Ser Val Lys Ile Arg Glu Cys Thr Gly Leu Ala Trp Glu
                420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
        450                 455                 460

Lys Val Glu Asn Asp Ser Ser Gly Gly Gly Gly Ser Gly Gly Gly Gly

```
            465                 470                 475                 480
Val Ala Ala Asp Ile Gly Ala Gly Leu Ala Asp Ala Leu Thr Ala Pro
                485                 490                 495
Leu Asp His Lys Asp Lys Ser Leu Gln Ser Leu Thr Leu Asp Gln Ser
            500                 505                 510
Val Arg Lys Asn Glu Lys Leu Lys Leu Ala Ala Gln Gly Ala Glu Lys
        515                 520                 525
Thr Tyr Gly Asn Gly Asp Ser Leu Asn Thr Gly Lys Leu Lys Asn Asp
    530                 535                 540
Lys Val Ser Arg Phe Asp Phe Ile Arg Gln Ile Glu Val Asp Gly Gln
545                 550                 555                 560
Thr Ile Thr Leu Ala Ser Gly Glu Phe Gln Ile Tyr Lys Gln Asn His
                565                 570                 575
Ser Ala Val Val Ala Leu Gln Ile Glu Lys Ile Asn Asn Pro Asp Lys
            580                 585                 590
Ile Asp Ser Leu Ile Asn Gln Arg Ser Phe Leu Val Ser Gly Leu Gly
        595                 600                 605
Gly Glu His Thr Ala Phe Asn Gln Leu Pro Asp Gly Lys Ala Glu Tyr
    610                 615                 620
His Gly Lys Ala Phe Ser Ser Asp Asp Pro Asn Gly Arg Leu His Tyr
625                 630                 635                 640
Ser Ile Asp Phe Thr Lys Lys Gln Gly Tyr Gly Arg Ile Glu His Leu
                645                 650                 655
Lys Thr Pro Glu Gln Asn Val Glu Leu Ala Ser Ala Glu Leu Lys Ala
            660                 665                 670
Asp Glu Lys Ser His Ala Val Ile Leu Gly Asp Thr Arg Tyr Gly Gly
        675                 680                 685
Glu Glu Lys Gly Thr Tyr His Leu Ala Leu Phe Gly Asp Arg Ala Gln
    690                 695                 700
Glu Ile Ala Gly Ser Ala Thr Val Lys Ile Arg Glu Lys Val His Glu
705                 710                 715                 720
Ile Gly Ile Ala Gly Lys Gln
                725

<210> SEQ ID NO 137
<211> LENGTH: 726
<212> TYPE: PRT
<213> ORGANISM: Artificial Sequence
<220> FEATURE:
<223> OTHER INFORMATION: Synthetic sequence

<400> SEQUENCE: 137

Ala Asn Lys Ala Val Asn Asp Phe Ile Leu Ala Met Asn Tyr Asp Lys
1               5                   10                  15
Lys Lys Leu Leu Thr His Gln Gly Glu Ser Ile Glu Asn Arg Phe Ile
            20                  25                  30
Lys Glu Gly Asn Gln Leu Pro Asp Glu Phe Val Val Ile Glu Arg Lys
        35                  40                  45
Lys Arg Ser Leu Ser Thr Asn Thr Ser Asp Ile Ser Val Thr Ala Thr
    50                  55                  60
Asn Asp Ser Arg Leu Tyr Pro Gly Ala Leu Leu Val Val Asp Glu Thr
65                  70                  75                  80
Leu Leu Glu Asn Asn Pro Thr Leu Leu Ala Val Asp Arg Ala Pro Met
                85                  90                  95
Thr Tyr Ser Ile Asp Leu Pro Gly Leu Ala Ser Ser Asp Ser Phe Leu
```

```
              100                 105                 110
    Gln Val Glu Asp Pro Ser Asn Ser Val Arg Gly Ala Val Asn Asp
        115                 120                 125
    Leu Leu Ala Lys Trp His Gln Asp Tyr Gly Gln Val Asn Asn Val Pro
        130                 135                 140
    Met Gln Tyr Glu Lys Ile Thr Ala His Ser Met Gln Leu Lys Val
145                 150                 155                 160
    Lys Phe Gly Ser Asp Phe Glu Lys Thr Gly Asn Ser Leu Asp Ile Asp
                    165                 170                 175
    Phe Asn Ser Val His Ser Gly Glu Lys Gln Ile Gln Ile Val Asn Phe
                    180                 185                 190
    Lys Gln Ile Tyr Tyr Thr Val Ser Val Asp Ala Val Lys Asn Pro Gly
                    195                 200                 205
    Asp Val Phe Gln Asp Thr Val Thr Val Glu Asp Leu Lys Gln Arg Gly
                    210                 215                 220
    Ile Ser Ala Glu Arg Pro Leu Val Tyr Ile Ser Ser Val Ala Tyr Gly
225                 230                 235                 240
    Arg Gln Val Tyr Leu Lys Leu Glu Thr Thr Ser Lys Ser Asp Glu Val
                    245                 250                 255
    Glu Ala Ala Phe Glu Ala Leu Ile Lys Gly Val Lys Val Ala Pro Gln
                    260                 265                 270
    Thr Glu Trp Lys Gln Ile Leu Asp Asn Thr Glu Val Lys Ala Val Ile
                    275                 280                 285
    Leu Gly Gly Asp Pro Ser Ser Gly Ala Arg Val Val Thr Gly Lys Val
        290                 295                 300
    Asp Met Val Glu Asp Leu Ile Gln Glu Gly Ser Arg Phe Thr Ala Asp
305                 310                 315                 320
    His Pro Gly Leu Pro Ile Ser Tyr Thr Thr Ser Phe Leu Arg Asp Asn
                    325                 330                 335
    Val Val Ala Thr Phe Gln Asn Ser Thr Asp Tyr Val Glu Thr Lys Val
                    340                 345                 350
    Thr Ala Tyr Arg Asn Gly Asp Leu Leu Leu Asp His Ser Gly Ala Tyr
                    355                 360                 365
    Val Ala Gln Tyr Tyr Ile Thr Trp Asp Glu Leu Ser Tyr Asp His Gln
                    370                 375                 380
    Gly Lys Glu Val Leu Thr Pro Lys Ala Trp Asp Arg Asn Gly Gln Asp
385                 390                 395                 400
    Leu Thr Ala His Phe Thr Thr Ser Ile Pro Leu Lys Gly Asn Val Arg
                    405                 410                 415
    Asn Leu Ser Val Lys Ile Arg Glu Cys Thr Gly Leu Ala Trp Glu Trp
                    420                 425                 430
    Trp Arg Thr Val Tyr Glu Lys Thr Asp Leu Pro Leu Val Arg Lys Arg
                    435                 440                 445
    Thr Ile Ser Ile Trp Gly Thr Thr Leu Tyr Pro Gln Val Glu Asp Lys
                    450                 455                 460
    Val Glu Asn Asp Ser Ser Gly Gly Gly Ser Gly Gly Gly Val
465                 470                 475                 480
    Ala Ala Asp Ile Gly Ala Gly Leu Ala Asp Ala Leu Thr Ala Pro Leu
                    485                 490                 495
    Asp His Lys Asp Lys Ser Leu Gln Ser Leu Thr Leu Asp Gln Ser Val
                    500                 505                 510
    Arg Lys Asn Glu Lys Leu Lys Leu Ala Ala Gln Gly Ala Glu Lys Thr
                    515                 520                 525
```

Tyr Gly Asn Gly Asp Ser Leu Asn Thr Gly Lys Leu Lys Asn Asp Lys
            530                 535                 540

Val Ser Arg Phe Asp Phe Ile Arg Gln Ile Glu Val Asp Gly Gln Thr
545                 550                 555                 560

Ile Thr Leu Ala Ser Gly Glu Phe Gln Ile Tyr Lys Gln Asn His Ser
            565                 570                 575

Ala Val Val Ala Leu Gln Ile Glu Lys Ile Asn Asn Pro Asp Lys Ile
            580                 585                 590

Asp Ser Leu Ile Asn Gln Arg Ser Phe Leu Val Ser Gly Leu Gly Gly
            595                 600                 605

Glu His Thr Ala Phe Asn Gln Leu Pro Asp Gly Lys Ala Glu Tyr His
            610                 615                 620

Gly Lys Ala Phe Ser Ser Asp Asp Pro Asn Gly Arg Leu His Tyr Ser
625                 630                 635                 640

Ile Asp Phe Thr Lys Lys Gln Gly Tyr Gly Arg Ile Glu His Leu Lys
            645                 650                 655

Thr Pro Glu Gln Asn Val Glu Leu Ala Ser Ala Glu Leu Lys Ala Asp
            660                 665                 670

Glu Lys Ser His Ala Val Ile Leu Gly Asp Thr Arg Tyr Gly Gly Glu
            675                 680                 685

Glu Lys Gly Thr Tyr His Leu Ala Leu Phe Gly Asp Arg Ala Gln Glu
            690                 695                 700

Ile Ala Gly Ser Ala Thr Val Lys Ile Arg Glu Lys Val His Glu Ile
705                 710                 715                 720

Gly Ile Ala Gly Lys Gln
            725

<210> SEQ ID NO 138
<211> LENGTH: 728
<212> TYPE: PRT
<213> ORGANISM: Artificial Sequence
<220> FEATURE:
<223> OTHER INFORMATION: Synthetic sequence

<400> SEQUENCE: 138

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
            85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
130                 135                 140

Pro Met Gln Tyr Glu Lys Ile Thr Ala His Ser Met Glu Gln Leu Lys
145                 150                 155                 160

```
Val Lys Phe Gly Ser Asp Phe Glu Lys Thr Gly Asn Ser Leu Asp Ile
            165                 170                 175

Asp Phe Asn Ser Val His Ser Gly Glu Lys Gln Ile Gln Ile Val Asn
            180                 185                 190

Phe Lys Gln Ile Tyr Tyr Thr Val Ser Val Asp Ala Val Lys Asn Pro
            195                 200                 205

Gly Asp Val Phe Gln Asp Thr Val Thr Val Glu Asp Leu Lys Gln Arg
210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
            245                 250                 255

Val Glu Ala Ala Phe Glu Ala Leu Ile Lys Gly Val Lys Val Ala Pro
            260                 265                 270

Gln Thr Glu Trp Lys Gln Ile Leu Asp Asn Thr Glu Val Lys Ala Val
            275                 280                 285

Ile Leu Gly Gly Asp Pro Ser Ser Gly Ala Arg Val Val Thr Gly Lys
            290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Asp His Ser Gly Ala
            355                 360                 365

Tyr Val Ala Gln Tyr Tyr Ile Thr Trp Asp Glu Leu Ser Tyr Asp His
370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
450                 455                 460

Lys Val Glu Asn Asp Ser Gly Gly Gly Ser Gly Gly Gly Gly
465                 470                 475                 480

Val Thr Ala Asp Ile Gly Thr Gly Leu Ala Asp Ala Leu Thr Ala Pro
                485                 490                 495

Leu Asp His Lys Asp Lys Gly Leu Lys Ser Leu Thr Leu Glu Asp Ser
                500                 505                 510

Ile Ser Gln Asn Gly Thr Leu Thr Leu Ser Ala Gln Gly Ala Glu Lys
            515                 520                 525

Thr Tyr Gly Asn Gly Asp Ser Leu Asn Thr Gly Lys Leu Lys Asn Asp
530                 535                 540

Lys Val Ser Arg Phe Asp Phe Ile Arg Gln Ile Glu Val Asp Gly Gln
545                 550                 555                 560

Leu Ile Thr Leu Glu Ser Gly Glu Phe Gln Val Tyr Lys Gln Ser His
                565                 570                 575
```

```
Ser Ala Leu Thr Ala Leu Gln Thr Glu Gln Glu Gln Asp Pro Glu His
            580                 585                 590

Ser Glu Lys Met Val Ala Lys Arg Arg Phe Arg Ile Gly Asp Ile Ala
    595                 600                 605

Gly Glu His Thr Ser Phe Asp Lys Leu Pro Lys Asp Val Met Ala Thr
610                 615                 620

Tyr Arg Gly Thr Ala Phe Gly Ser Asp Ala Gly Gly Lys Leu Thr
625                 630                 635                 640

Tyr Thr Ile Asp Phe Ala Ala Lys Gln Gly His Gly Lys Ile Glu His
                645                 650                 655

Leu Lys Ser Pro Glu Leu Asn Val Asp Leu Ala Val Ala Tyr Ile Lys
            660                 665                 670

Pro Asp Glu Lys His His Ala Val Ile Ser Gly Ser Val Leu Tyr Asn
            675                 680                 685

Gln Asp Glu Lys Gly Ser Tyr Ser Leu Gly Ile Phe Gly Glu Lys Ala
            690                 695                 700

Gln Glu Val Ala Gly Ser Ala Glu Val Glu Thr Ala Asn Gly Ile His
705                 710                 715                 720

His Ile Gly Leu Ala Ala Lys Gln
                725

<210> SEQ ID NO 139
<211> LENGTH: 727
<212> TYPE: PRT
<213> ORGANISM: Artificial Sequence
<220> FEATURE:
<223> OTHER INFORMATION: Synthetic sequence

<400> SEQUENCE: 139

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
    50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Asp Ser Phe Leu
            100                 105                 110

Gln Val Glu Asp Pro Ser Asn Ser Ser Val Arg Gly Ala Val Asn Asp
        115                 120                 125

Leu Leu Ala Lys Trp His Gln Asp Tyr Gly Gln Val Asn Asn Val Pro
    130                 135                 140

Met Gln Tyr Glu Lys Ile Thr Ala His Ser Met Glu Gln Leu Lys Val
145                 150                 155                 160

Lys Phe Gly Ser Asp Phe Glu Lys Thr Gly Asn Ser Leu Asp Ile Asp
                165                 170                 175

Phe Asn Ser Val His Ser Gly Glu Lys Gln Ile Gln Ile Val Asn Phe
            180                 185                 190

Lys Gln Ile Tyr Tyr Thr Val Ser Val Asp Ala Val Lys Asn Pro Gly
        195                 200                 205
```

```
Asp Val Phe Gln Asp Thr Val Thr Val Glu Asp Leu Lys Gln Arg Gly
    210                 215                 220

Ile Ser Ala Glu Arg Pro Leu Val Tyr Ile Ser Ser Val Ala Tyr Gly
225                 230                 235                 240

Arg Gln Val Tyr Leu Lys Leu Glu Thr Thr Ser Lys Ser Asp Glu Val
                245                 250                 255

Glu Ala Ala Phe Glu Ala Leu Ile Lys Gly Val Lys Val Ala Pro Gln
            260                 265                 270

Thr Glu Trp Lys Gln Ile Leu Asp Asn Thr Val Lys Ala Val Ile
        275                 280                 285

Leu Gly Gly Asp Pro Ser Ser Gly Ala Arg Val Thr Gly Lys Val
    290                 295                 300

Asp Met Val Glu Asp Leu Ile Gln Glu Gly Ser Arg Phe Thr Ala Asp
305                 310                 315                 320

His Pro Gly Leu Pro Ile Ser Tyr Thr Thr Ser Phe Leu Arg Asp Asn
                325                 330                 335

Val Val Ala Thr Phe Gln Asn Ser Thr Asp Tyr Val Glu Thr Lys Val
            340                 345                 350

Thr Ala Tyr Arg Asn Gly Asp Leu Leu Leu Asp His Ser Gly Ala Tyr
        355                 360                 365

Val Ala Gln Tyr Tyr Ile Thr Trp Asp Glu Leu Ser Tyr Asp His Gln
    370                 375                 380

Gly Lys Glu Val Leu Thr Pro Lys Ala Trp Asp Arg Asn Gly Gln Asp
385                 390                 395                 400

Leu Thr Ala His Phe Thr Thr Ser Ile Pro Leu Lys Gly Asn Val Arg
                405                 410                 415

Asn Leu Ser Val Lys Ile Arg Glu Cys Thr Gly Leu Ala Trp Glu Trp
            420                 425                 430

Trp Arg Thr Val Tyr Glu Lys Thr Asp Leu Pro Leu Val Arg Lys Arg
        435                 440                 445

Thr Ile Ser Ile Trp Gly Thr Thr Leu Tyr Pro Gln Val Glu Asp Lys
    450                 455                 460

Val Glu Asn Asp Ser Ser Gly Gly Gly Ser Gly Gly Gly Val
465                 470                 475                 480

Thr Ala Asp Ile Gly Thr Gly Leu Ala Asp Ala Leu Thr Ala Pro Leu
                485                 490                 495

Asp His Lys Asp Lys Gly Leu Lys Ser Leu Thr Leu Glu Asp Ser Ile
            500                 505                 510

Ser Gln Asn Gly Thr Leu Thr Leu Ser Ala Gln Gly Ala Glu Lys Thr
        515                 520                 525

Tyr Gly Asn Gly Asp Ser Leu Asn Thr Gly Lys Leu Lys Asn Asp Lys
    530                 535                 540

Val Ser Arg Phe Asp Phe Ile Arg Gln Ile Glu Val Asp Gly Gln Leu
545                 550                 555                 560

Ile Thr Leu Glu Ser Gly Glu Phe Gln Val Tyr Lys Gln Ser His Ser
                565                 570                 575

Ala Leu Thr Ala Leu Gln Thr Glu Gln Glu Gln Asp Pro Glu His Ser
            580                 585                 590

Glu Lys Met Val Ala Lys Arg Arg Phe Arg Ile Gly Asp Ile Ala Gly
        595                 600                 605

Glu His Thr Ser Phe Asp Lys Leu Pro Lys Asp Val Met Ala Thr Tyr
    610                 615                 620

Arg Gly Thr Ala Phe Gly Ser Asp Asp Ala Gly Gly Lys Leu Thr Tyr
```

```
            625                 630                 635                 640
Thr Ile Asp Phe Ala Ala Lys Gln Gly His Gly Lys Ile Glu His Leu
                    645                 650                 655

Lys Ser Pro Glu Leu Asn Val Asp Leu Ala Val Ala Tyr Ile Lys Pro
                660                 665                 670

Asp Glu Lys His His Ala Val Ile Ser Gly Ser Val Leu Tyr Asn Gln
            675                 680                 685

Asp Glu Lys Gly Ser Tyr Ser Leu Gly Ile Phe Gly Glu Lys Ala Gln
        690                 695                 700

Glu Val Ala Gly Ser Ala Glu Val Thr Ala Asn Gly Ile His His
705                 710                 715                 720

Ile Gly Leu Ala Ala Lys Gln
                725

<210> SEQ ID NO 140
<211> LENGTH: 723
<212> TYPE: PRT
<213> ORGANISM: Artificial Sequence
<220> FEATURE:
<223> OTHER INFORMATION: Synthetic sequence

<400> SEQUENCE: 140

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Met Gln Tyr Glu Lys Ile Thr Ala His Ser Met Glu Gln Leu Lys
145                 150                 155                 160

Val Lys Phe Gly Ser Asp Phe Glu Lys Thr Gly Asn Ser Leu Asp Ile
                165                 170                 175

Asp Phe Asn Ser Val His Ser Gly Glu Lys Gln Ile Gln Ile Val Asn
            180                 185                 190

Phe Lys Gln Ile Tyr Tyr Thr Val Ser Val Asp Ala Val Lys Asn Pro
        195                 200                 205

Gly Asp Val Phe Gln Asp Thr Val Thr Val Glu Asp Leu Lys Gln Arg
    210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
                245                 250                 255

Val Glu Ala Ala Phe Glu Ala Leu Ile Lys Gly Val Lys Val Ala Pro
```

```
            260                 265                 270
Gln Thr Glu Trp Lys Gln Ile Leu Asp Asn Thr Glu Val Lys Ala Val
            275                 280                 285

Ile Leu Gly Gly Asp Pro Ser Ser Gly Ala Arg Val Val Thr Gly Lys
            290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
                340                 345                 350

Val Thr Ala Tyr Arg Asn Gly Asp Leu Leu Leu Asp His Ser Gly Ala
                355                 360                 365

Tyr Val Ala Gln Tyr Tyr Ile Thr Trp Asp Glu Leu Ser Tyr Asp His
            370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
                420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
            450                 455                 460

Lys Val Glu Asn Asp Ser Ser Gly Gly Gly Val Ala Ala Asp Ile
465                 470                 475                 480

Gly Ala Gly Leu Ala Asp Ala Leu Thr Ala Pro Leu Asp His Lys Asp
                485                 490                 495

Lys Gly Leu Gln Ser Leu Thr Leu Asp Gln Ser Val Arg Lys Asn Glu
                500                 505                 510

Lys Leu Lys Leu Ala Ala Gln Gly Ala Glu Lys Thr Tyr Gly Asn Gly
                515                 520                 525

Asp Ser Leu Asn Thr Gly Lys Leu Lys Asn Asp Lys Val Ser Arg Phe
                530                 535                 540

Asp Phe Ile Arg Gln Ile Glu Val Asp Gly Lys Leu Ile Thr Leu Glu
545                 550                 555                 560

Ser Gly Glu Phe Gln Val Tyr Lys Gln Ser His Ser Ala Leu Thr Ala
                565                 570                 575

Leu Gln Thr Glu Gln Val Gln Asp Ser Glu Asp Ser Gly Lys Met Val
                580                 585                 590

Ala Lys Arg Gln Phe Arg Ile Gly Asp Ile Ala Gly Glu His Thr Ser
            595                 600                 605

Phe Asp Lys Leu Pro Lys Gly Gly Ser Ala Thr Tyr Arg Gly Thr Ala
            610                 615                 620

Phe Gly Ser Asp Asp Ala Gly Gly Lys Leu Thr Tyr Thr Ile Asp Phe
625                 630                 635                 640

Ala Ala Lys Gln Gly His Gly Lys Ile Glu His Leu Lys Ser Pro Glu
                645                 650                 655

Leu Asn Val Glu Leu Ala Thr Ala Tyr Ile Lys Pro Asp Glu Lys Arg
                660                 665                 670

His Ala Val Ile Ser Gly Ser Val Leu Tyr Asn Gln Asp Glu Lys Gly
                675                 680                 685
```

```
Ser Tyr Ser Leu Gly Ile Phe Gly Gly Gln Ala Gln Glu Val Ala Gly
    690                 695                 700
Ser Ala Glu Val Glu Thr Ala Asn Gly Ile His His Ile Gly Leu Ala
705                 710                 715                 720
Ala Lys Gln

<210> SEQ ID NO 141
<211> LENGTH: 722
<212> TYPE: PRT
<213> ORGANISM: Artificial Sequence
<220> FEATURE:
<223> OTHER INFORMATION: Synthetic sequence

<400> SEQUENCE: 141

Ala Asn Lys Ala Val Asn Asp Phe Ile Leu Ala Met Asn Tyr Asp Lys
1               5                   10                  15
Lys Lys Leu Leu Thr His Gln Gly Glu Ser Ile Glu Asn Arg Phe Ile
                20                  25                  30
Lys Glu Gly Asn Gln Leu Pro Asp Glu Phe Val Val Ile Glu Arg Lys
            35                  40                  45
Lys Arg Ser Leu Ser Thr Asn Thr Ser Asp Ile Ser Val Thr Ala Thr
50                  55                  60
Asn Asp Ser Arg Leu Tyr Pro Gly Ala Leu Leu Val Val Asp Glu Thr
65                  70                  75                  80
Leu Leu Glu Asn Asn Pro Thr Leu Leu Ala Val Asp Arg Ala Pro Met
                85                  90                  95
Thr Tyr Ser Ile Asp Leu Pro Gly Leu Ala Ser Ser Asp Ser Phe Leu
            100                 105                 110
Gln Val Glu Asp Pro Ser Asn Ser Ser Val Arg Gly Ala Val Asn Asp
        115                 120                 125
Leu Leu Ala Lys Trp His Gln Asp Tyr Gly Gln Val Asn Asn Val Pro
130                 135                 140
Met Gln Tyr Glu Lys Ile Thr Ala His Ser Met Glu Gln Leu Lys Val
145                 150                 155                 160
Lys Phe Gly Ser Asp Phe Glu Lys Thr Gly Asn Ser Leu Asp Ile Asp
                165                 170                 175
Phe Asn Ser Val His Ser Gly Glu Lys Gln Ile Gln Ile Val Asn Phe
            180                 185                 190
Lys Gln Ile Tyr Tyr Thr Val Ser Val Asp Ala Val Lys Asn Pro Gly
        195                 200                 205
Asp Val Phe Gln Asp Thr Val Thr Val Glu Asp Leu Lys Gln Arg Gly
210                 215                 220
Ile Ser Ala Glu Arg Pro Leu Val Tyr Ile Ser Ser Val Ala Tyr Gly
225                 230                 235                 240
Arg Gln Val Tyr Leu Lys Leu Glu Thr Ser Lys Ser Asp Glu Val
                245                 250                 255
Glu Ala Ala Phe Glu Ala Leu Ile Lys Gly Val Lys Val Ala Pro Gln
            260                 265                 270
Thr Glu Trp Lys Gln Ile Leu Asp Asn Thr Glu Val Lys Ala Val Ile
        275                 280                 285
Leu Gly Gly Asp Pro Ser Ser Gly Ala Arg Val Val Thr Gly Lys Val
        290                 295                 300
Asp Met Val Glu Asp Leu Ile Gln Glu Gly Ser Arg Phe Thr Ala Asp
305                 310                 315                 320
```

His Pro Gly Leu Pro Ile Ser Tyr Thr Thr Ser Phe Leu Arg Asp Asn
                325                 330                 335

Val Val Ala Thr Phe Gln Asn Ser Thr Asp Tyr Val Glu Thr Lys Val
            340                 345                 350

Thr Ala Tyr Arg Asn Gly Asp Leu Leu Leu Asp His Ser Gly Ala Tyr
        355                 360                 365

Val Ala Gln Tyr Tyr Ile Thr Trp Asp Glu Leu Ser Tyr Asp His Gln
    370                 375                 380

Gly Lys Glu Val Leu Thr Pro Lys Ala Trp Asp Arg Asn Gly Gln Asp
385                 390                 395                 400

Leu Thr Ala His Phe Thr Thr Ser Ile Pro Leu Lys Gly Asn Val Arg
                405                 410                 415

Asn Leu Ser Val Lys Ile Arg Glu Cys Thr Gly Leu Ala Trp Glu Trp
            420                 425                 430

Trp Arg Thr Val Tyr Glu Lys Thr Asp Leu Pro Leu Val Arg Lys Arg
        435                 440                 445

Thr Ile Ser Ile Trp Gly Thr Thr Leu Tyr Pro Gln Val Glu Asp Lys
    450                 455                 460

Val Glu Asn Asp Ser Ser Gly Gly Gly Val Ala Ala Asp Ile Gly
465                 470                 475                 480

Ala Gly Leu Ala Asp Ala Leu Thr Ala Pro Leu Asp His Lys Asp Lys
                485                 490                 495

Gly Leu Gln Ser Leu Thr Leu Asp Gln Ser Val Arg Lys Asn Glu Lys
            500                 505                 510

Leu Lys Leu Ala Ala Gln Gly Ala Glu Lys Thr Tyr Gly Asn Gly Asp
        515                 520                 525

Ser Leu Asn Thr Gly Lys Leu Lys Asn Asp Lys Val Ser Arg Phe Asp
    530                 535                 540

Phe Ile Arg Gln Ile Glu Val Asp Gly Lys Leu Ile Thr Leu Glu Ser
545                 550                 555                 560

Gly Glu Phe Gln Val Tyr Lys Gln Ser His Ser Ala Leu Thr Ala Leu
                565                 570                 575

Gln Thr Glu Gln Val Gln Asp Ser Glu Asp Ser Gly Lys Met Val Ala
            580                 585                 590

Lys Arg Gln Phe Arg Ile Gly Asp Ile Ala Gly Glu His Thr Ser Phe
        595                 600                 605

Asp Lys Leu Pro Lys Gly Gly Ser Ala Thr Tyr Arg Gly Thr Ala Phe
    610                 615                 620

Gly Ser Asp Asp Ala Gly Gly Lys Leu Thr Tyr Thr Ile Asp Phe Ala
625                 630                 635                 640

Ala Lys Gln Gly His Gly Lys Ile Glu His Leu Lys Ser Pro Glu Leu
                645                 650                 655

Asn Val Glu Leu Ala Thr Ala Tyr Ile Lys Pro Asp Glu Lys Arg His
            660                 665                 670

Ala Val Ile Ser Gly Ser Val Leu Tyr Asn Gln Asp Glu Lys Gly Ser
        675                 680                 685

Tyr Ser Leu Gly Ile Phe Gly Gly Gln Ala Gln Glu Val Ala Gly Ser
    690                 695                 700

Ala Glu Val Glu Thr Ala Asn Gly Ile His His Ile Gly Leu Ala Ala
705                 710                 715                 720

Lys Gln

<210> SEQ ID NO 142

-continued

```
<211> LENGTH: 723
<212> TYPE: PRT
<213> ORGANISM: Artificial Sequence
<220> FEATURE:
<223> OTHER INFORMATION: Synthetic sequence

<400> SEQUENCE: 142
```

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Met Gln Tyr Glu Lys Ile Thr Ala His Ser Met Glu Gln Leu Lys
145                 150                 155                 160

Val Lys Phe Gly Ser Asp Phe Glu Lys Thr Gly Asn Ser Leu Asp Ile
                165                 170                 175

Asp Phe Asn Ser Val His Ser Gly Glu Lys Gln Ile Gln Ile Val Asn
            180                 185                 190

Phe Lys Gln Ile Tyr Tyr Thr Val Ser Val Asp Ala Val Lys Asn Pro
        195                 200                 205

Gly Asp Val Phe Gln Asp Thr Val Thr Val Glu Asp Leu Lys Gln Arg
    210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
                245                 250                 255

Val Glu Ala Ala Phe Glu Ala Leu Ile Lys Gly Val Lys Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Leu Asp His Ser Gly Ala
        355                 360                 365

Tyr Val Ala Gln Tyr Tyr Ile Thr Trp Asp Glu Leu Ser Tyr Asp His
    370                 375                 380

```
Gln Gly Lys Glu Val Leu Thr Pro Lys Ala Trp Asp Arg Asn Gly Gln
385                 390                 395                 400

Asp Leu Thr Ala His Phe Thr Ser Ile Pro Leu Lys Gly Asn Val
            405                 410                 415

Arg Asn Leu Ser Val Lys Ile Arg Glu Cys Thr Gly Leu Ala Trp Glu
        420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
        450                 455                 460

Lys Val Glu Asn Asp Ser Ser Gly Gly Gly Val Ala Ala Asp Ile
465                 470                 475                 480

Gly Ala Gly Leu Ala Asp Ala Leu Thr Ala Pro Leu Asp His Lys Asp
            485                 490                 495

Lys Gly Leu Gln Ser Leu Thr Leu Asp Gln Ser Val Arg Lys Asn Glu
        500                 505                 510

Lys Leu Lys Leu Ala Ala Gln Gly Ala Glu Lys Thr Tyr Gly Asn Gly
            515                 520                 525

Asp Ser Leu Asn Thr Gly Lys Leu Lys Asn Asp Lys Val Ser Arg Phe
530                 535                 540

Asp Phe Ile Arg Gln Ile Glu Val Asp Gly Gln Leu Ile Thr Leu Glu
545                 550                 555                 560

Ser Gly Glu Phe Gln Val Tyr Lys Gln Ser His Ser Ala Leu Thr Ala
            565                 570                 575

Phe Gln Thr Glu Gln Ile Gln Asp Ser Glu His Ser Gly Lys Met Val
        580                 585                 590

Ala Lys Arg Gln Phe Arg Ile Gly Asp Ile Ala Gly Glu His Thr Ser
            595                 600                 605

Phe Asp Lys Leu Pro Glu Gly Gly Arg Ala Thr Tyr Arg Gly Thr Ala
610                 615                 620

Phe Gly Ser Asp Asp Ala Gly Gly Lys Leu Thr Tyr Thr Ile Asp Phe
625                 630                 635                 640

Ala Ala Lys Gln Gly Asn Gly Lys Ile Glu His Leu Lys Ser Pro Glu
            645                 650                 655

Leu Asn Val Asp Leu Ala Ala Ala Asp Ile Lys Pro Asp Gly Lys Arg
        660                 665                 670

His Ala Val Ile Ser Gly Ser Val Leu Tyr Asn Gln Ala Glu Lys Gly
            675                 680                 685

Ser Tyr Ser Leu Gly Ile Phe Gly Gly Lys Ala Gln Glu Val Ala Gly
        690                 695                 700

Ser Ala Glu Val Lys Thr Val Asn Gly Ile Arg His Ile Gly Leu Ala
705                 710                 715                 720

Ala Lys Gln

<210> SEQ ID NO 143
<211> LENGTH: 722
<212> TYPE: PRT
<213> ORGANISM: Artificial Sequence
<220> FEATURE:
<223> OTHER INFORMATION: Synthetic sequence

<400> SEQUENCE: 143

Ala Asn Lys Ala Val Asn Asp Phe Ile Leu Ala Met Asn Tyr Asp Lys
1               5                   10                  15
```

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Asp Ser Phe Leu
            100                 105                 110

Gln Val Glu Asp Pro Ser Asn Ser Ser Val Arg Gly Ala Val Asn Asp
        115                 120                 125

Leu Leu Ala Lys Trp His Gln Asp Tyr Gly Gln Val Asn Asn Val Pro
130                 135                 140

Met Gln Tyr Glu Lys Ile Thr Ala His Ser Met Glu Gln Leu Lys Val
145                 150                 155                 160

Lys Phe Gly Ser Asp Phe Glu Lys Thr Gly Asn Ser Leu Asp Ile Asp
            165                 170                 175

Phe Asn Ser Val His Ser Gly Glu Lys Gln Ile Gln Ile Val Asn Phe
        180                 185                 190

Lys Gln Ile Tyr Tyr Thr Val Ser Val Asp Ala Val Lys Asn Pro Gly
195                 200                 205

Asp Val Phe Gln Asp Thr Val Thr Val Glu Asp Leu Lys Gln Arg Gly
210                 215                 220

Ile Ser Ala Glu Arg Pro Leu Val Tyr Ile Ser Ser Val Ala Tyr Gly
225                 230                 235                 240

Arg Gln Val Tyr Leu Lys Leu Glu Thr Thr Ser Lys Ser Asp Glu Val
            245                 250                 255

Glu Ala Ala Phe Glu Ala Leu Ile Lys Gly Val Lys Val Ala Pro Gln
        260                 265                 270

Thr Glu Trp Lys Gln Ile Leu Asp Asn Thr Glu Val Lys Ala Val Ile
275                 280                 285

Leu Gly Gly Asp Pro Ser Ser Gly Ala Arg Val Val Thr Gly Lys Val
290                 295                 300

Asp Met Val Glu Asp Leu Ile Gln Glu Gly Ser Arg Phe Thr Ala Asp
305                 310                 315                 320

His Pro Gly Leu Pro Ile Ser Tyr Thr Thr Ser Phe Leu Arg Asp Asn
            325                 330                 335

Val Val Ala Thr Phe Gln Asn Ser Thr Asp Tyr Val Glu Thr Lys Val
        340                 345                 350

Thr Ala Tyr Arg Asn Gly Asp Leu Leu Leu Asp His Ser Gly Ala Tyr
355                 360                 365

Val Ala Gln Tyr Tyr Ile Thr Trp Asp Glu Leu Ser Tyr Asp His Gln
370                 375                 380

Gly Lys Glu Val Leu Thr Pro Lys Ala Trp Asp Arg Asn Gly Gln Asp
385                 390                 395                 400

Leu Thr Ala His Phe Thr Thr Ser Ile Pro Leu Lys Gly Asn Val Arg
            405                 410                 415

Asn Leu Ser Val Lys Ile Arg Glu Cys Thr Gly Leu Ala Trp Glu Trp
        420                 425                 430

Trp Arg Thr Val Tyr Glu Lys Thr Asp Leu Pro Leu Val Arg Lys Arg

```
                    435                 440                 445
Thr Ile Ser Ile Trp Gly Thr Thr Leu Tyr Pro Gln Val Glu Asp Lys
    450                 455                 460

Val Glu Asn Asp Ser Ser Gly Gly Gly Val Ala Ala Asp Ile Gly
465                 470                 475                 480

Ala Gly Leu Ala Asp Ala Leu Thr Ala Pro Leu Asp His Lys Asp Lys
                    485                 490                 495

Gly Leu Gln Ser Leu Thr Leu Asp Gln Ser Val Arg Lys Asn Glu Lys
                500                 505                 510

Leu Lys Leu Ala Ala Gln Gly Ala Glu Lys Thr Tyr Gly Asn Gly Asp
            515                 520                 525

Ser Leu Asn Thr Gly Lys Leu Lys Asn Asp Lys Val Ser Arg Phe Asp
530                 535                 540

Phe Ile Arg Gln Ile Glu Val Asp Gly Gln Leu Ile Thr Leu Glu Ser
545                 550                 555                 560

Gly Glu Phe Gln Val Tyr Lys Gln Ser His Ser Ala Leu Thr Ala Phe
                565                 570                 575

Gln Thr Glu Gln Ile Gln Asp Ser Glu His Ser Gly Lys Met Val Ala
                580                 585                 590

Lys Arg Gln Phe Arg Ile Gly Asp Ile Ala Gly Glu His Thr Ser Phe
            595                 600                 605

Asp Lys Leu Pro Glu Gly Gly Arg Ala Thr Tyr Arg Gly Thr Ala Phe
610                 615                 620

Gly Ser Asp Asp Ala Gly Gly Lys Leu Thr Tyr Thr Ile Asp Phe Ala
625                 630                 635                 640

Ala Lys Gln Gly Asn Gly Lys Ile Glu His Leu Lys Ser Pro Glu Leu
                645                 650                 655

Asn Val Asp Leu Ala Ala Ala Asp Ile Lys Pro Asp Gly Lys Arg His
                660                 665                 670

Ala Val Ile Ser Gly Ser Val Leu Tyr Asn Gln Ala Glu Lys Gly Ser
            675                 680                 685

Tyr Ser Leu Gly Ile Phe Gly Gly Lys Ala Gln Glu Val Ala Gly Ser
690                 695                 700

Ala Glu Val Lys Thr Val Asn Gly Ile Arg His Ile Gly Leu Ala Ala
705                 710                 715                 720

Lys Gln

<210> SEQ ID NO 144
<211> LENGTH: 731
<212> TYPE: PRT
<213> ORGANISM: Artificial Sequence
<220> FEATURE:
<223> OTHER INFORMATION: Synthetic sequence

<400> SEQUENCE: 144

Met Ala Asn Lys Ala Val Asn Asp Phe Ile Leu Ala Met Asn Tyr Asp
1               5                  10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80
```

```
Thr Leu Leu Glu Asn Asn Pro Thr Leu Leu Ala Val Asp Arg Ala Pro
             85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Met Gln Tyr Glu Lys Ile Thr Ala His Ser Met Glu Gln Leu Lys
145                 150                 155                 160

Val Lys Phe Gly Ser Asp Phe Glu Lys Thr Gly Asn Ser Leu Asp Ile
                165                 170                 175

Asp Phe Asn Ser Val His Ser Gly Glu Lys Gln Ile Gln Ile Val Asn
            180                 185                 190

Phe Lys Gln Ile Tyr Tyr Thr Val Ser Val Asp Ala Val Lys Asn Pro
        195                 200                 205

Gly Asp Val Phe Gln Asp Thr Val Thr Val Glu Asp Leu Lys Gln Arg
    210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
                245                 250                 255

Val Glu Ala Ala Phe Glu Ala Leu Ile Lys Gly Val Lys Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp Ser Ser Gly Gly Gly Ser Gly Gly Gly Gly
465                 470                 475                 480

Val Ala Ala Asp Ile Gly Ala Gly Leu Ala Asp Ala Leu Thr Ala Pro
                485                 490                 495
```

```
Leu Asp His Lys Asp Lys Gly Leu Lys Ser Leu Thr Leu Glu Asp Ser
                500                 505                 510

Ile Ser Gln Asn Gly Thr Leu Thr Leu Ser Ala Gln Gly Ala Glu Arg
            515                 520                 525

Thr Phe Lys Ala Gly Asp Lys Asp Asn Ser Leu Asn Thr Gly Lys Leu
        530                 535                 540

Lys Asn Asp Lys Ile Ser Arg Phe Asp Phe Ile Arg Gln Ile Glu Val
545                 550                 555                 560

Asp Gly Gln Leu Ile Thr Leu Glu Ser Gly Glu Phe Gln Val Tyr Lys
                565                 570                 575

Gln Ser His Ser Ala Leu Thr Ala Leu Gln Thr Glu Gln Val Gln Asp
            580                 585                 590

Ser Glu His Ser Gly Lys Met Val Ala Lys Arg Gln Phe Arg Ile Gly
        595                 600                 605

Asp Ile Val Gly Glu His Thr Ser Phe Gly Lys Leu Pro Lys Asp Val
610                 615                 620

Met Ala Thr Tyr Arg Gly Thr Ala Phe Gly Ser Asp Asp Ala Gly Gly
625                 630                 635                 640

Lys Leu Thr Tyr Thr Ile Asp Phe Ala Ala Lys Gln Gly His Gly Lys
            645                 650                 655

Ile Glu His Leu Lys Ser Pro Glu Leu Asn Val Asp Leu Ala Ala Ala
        660                 665                 670

Asp Ile Lys Pro Asp Glu Lys His Ala Val Ile Ser Gly Ser Val
            675                 680                 685

Leu Tyr Asn Gln Ala Glu Lys Gly Ser Tyr Ser Leu Gly Ile Phe Gly
        690                 695                 700

Gly Gln Ala Gln Glu Val Ala Gly Ser Ala Glu Val Glu Thr Ala Asn
705                 710                 715                 720

Gly Ile Arg His Ile Gly Leu Ala Ala Lys Gln
                725                 730

<210> SEQ ID NO 145
<211> LENGTH: 730
<212> TYPE: PRT
<213> ORGANISM: Artificial Sequence
<220> FEATURE:
<223> OTHER INFORMATION: Synthetic sequence

<400> SEQUENCE: 145

Ala Asn Lys Ala Val Asn Asp Phe Ile Leu Ala Met Asn Tyr Asp Lys
1               5                   10                  15

Lys Lys Leu Leu Thr His Gln Gly Glu Ser Ile Glu Asn Arg Phe Ile
            20                  25                  30

Lys Glu Gly Asn Gln Leu Pro Asp Glu Phe Val Val Ile Glu Arg Lys
        35                  40                  45

Lys Arg Ser Leu Ser Thr Asn Thr Ser Asp Ile Ser Val Thr Ala Thr
    50                  55                  60

Asn Asp Ser Arg Leu Tyr Pro Gly Ala Leu Leu Val Val Asp Glu Thr
65                  70                  75                  80

Leu Leu Glu Asn Asn Pro Thr Leu Leu Ala Val Asp Arg Ala Pro Met
                85                  90                  95

Thr Tyr Ser Ile Asp Leu Pro Gly Leu Ala Ser Ser Asp Ser Phe Leu
            100                 105                 110

Gln Val Glu Asp Pro Ser Asn Ser Val Arg Gly Ala Val Asn Asp
        115                 120                 125
```

```
Leu Leu Ala Lys Trp His Gln Asp Tyr Gly Gln Val Asn Asn Val Pro
    130                 135                 140

Met Gln Tyr Glu Lys Ile Thr Ala His Ser Met Glu Gln Leu Lys Val
145                 150                 155                 160

Lys Phe Gly Ser Asp Phe Glu Lys Thr Gly Asn Ser Leu Asp Ile Asp
                165                 170                 175

Phe Asn Ser Val His Ser Gly Glu Lys Gln Ile Gln Ile Val Asn Phe
            180                 185                 190

Lys Gln Ile Tyr Tyr Thr Val Ser Val Asp Ala Val Lys Asn Pro Gly
        195                 200                 205

Asp Val Phe Gln Asp Thr Val Thr Val Glu Asp Leu Lys Gln Arg Gly
    210                 215                 220

Ile Ser Ala Glu Arg Pro Leu Val Tyr Ile Ser Ser Val Ala Tyr Gly
225                 230                 235                 240

Arg Gln Val Tyr Leu Lys Leu Glu Thr Thr Ser Lys Ser Asp Glu Val
                245                 250                 255

Glu Ala Ala Phe Glu Ala Leu Ile Lys Gly Val Lys Val Ala Pro Gln
            260                 265                 270

Thr Glu Trp Lys Gln Ile Leu Asp Asn Thr Glu Val Lys Ala Val Ile
        275                 280                 285

Leu Gly Gly Asp Pro Ser Ser Gly Ala Arg Val Val Thr Gly Lys Val
    290                 295                 300

Asp Met Val Glu Asp Leu Ile Gln Glu Gly Ser Arg Phe Thr Ala Asp
305                 310                 315                 320

His Pro Gly Leu Pro Ile Ser Tyr Thr Thr Ser Phe Leu Arg Asp Asn
                325                 330                 335

Val Val Ala Thr Phe Gln Asn Ser Thr Asp Tyr Val Glu Thr Lys Val
            340                 345                 350

Thr Ala Tyr Arg Asn Gly Asp Leu Leu Leu Asp His Ser Gly Ala Tyr
        355                 360                 365

Val Ala Gln Tyr Tyr Ile Thr Trp Asp Glu Leu Ser Tyr Asp His Gln
    370                 375                 380

Gly Lys Glu Val Leu Thr Pro Lys Ala Trp Asp Arg Asn Gly Gln Asp
385                 390                 395                 400

Leu Thr Ala His Phe Thr Thr Ser Ile Pro Leu Lys Gly Asn Val Arg
                405                 410                 415

Asn Leu Ser Val Lys Ile Arg Glu Cys Thr Gly Leu Ala Trp Glu Trp
            420                 425                 430

Trp Arg Thr Val Tyr Glu Lys Thr Asp Leu Pro Leu Val Arg Lys Arg
        435                 440                 445

Thr Ile Ser Ile Trp Gly Thr Thr Leu Tyr Pro Gln Val Glu Asp Lys
    450                 455                 460

Val Glu Asn Asp Ser Ser Gly Gly Gly Ser Gly Gly Gly Gly Val
465                 470                 475                 480

Ala Ala Asp Ile Gly Ala Gly Leu Ala Asp Ala Leu Thr Ala Pro Leu
                485                 490                 495

Asp His Lys Asp Lys Gly Leu Lys Ser Leu Thr Leu Glu Asp Ser Ile
            500                 505                 510

Ser Gln Asn Gly Thr Leu Thr Leu Ser Ala Gln Gly Ala Glu Arg Thr
        515                 520                 525

Phe Lys Ala Gly Asp Lys Asp Asn Ser Leu Asn Thr Gly Lys Leu Lys
    530                 535                 540

Asn Asp Lys Ile Ser Arg Phe Asp Phe Ile Arg Gln Ile Glu Val Asp
```

```
                545                 550                 555                 560
        Gly Gln Leu Ile Thr Leu Glu Ser Gly Glu Phe Gln Val Tyr Lys Gln
                            565                 570                 575

Ser His Ser Ala Leu Thr Ala Leu Gln Thr Glu Gln Val Gln Asp Ser
                        580                 585                 590

Glu His Ser Gly Lys Met Val Ala Lys Arg Gln Phe Arg Ile Gly Asp
                    595                 600                 605

Ile Val Gly Glu His Thr Ser Phe Gly Lys Leu Pro Lys Asp Val Met
                610                 615                 620

Ala Thr Tyr Arg Gly Thr Ala Phe Gly Ser Asp Asp Ala Gly Lys
        625                 630                 635                 640

Leu Thr Tyr Thr Ile Asp Phe Ala Ala Lys Gln Gly His Gly Lys Ile
                            645                 650                 655

Glu His Leu Lys Ser Pro Glu Leu Asn Val Asp Leu Ala Ala Ala Asp
                        660                 665                 670

Ile Lys Pro Asp Glu Lys His His Ala Val Ile Ser Gly Ser Val Leu
                    675                 680                 685

Tyr Asn Gln Ala Glu Lys Gly Ser Tyr Ser Leu Gly Ile Phe Gly Gly
                690                 695                 700

Gln Ala Gln Glu Val Ala Gly Ser Ala Glu Val Glu Thr Ala Asn Gly
        705                 710                 715                 720

Ile Arg His Ile Gly Leu Ala Ala Lys Gln
                            725                 730

<210> SEQ ID NO 146
<211> LENGTH: 180
<212> TYPE: PRT
<213> ORGANISM: Artificial Sequence
<220> FEATURE:
<223> OTHER INFORMATION: Synthetic sequence

<400> SEQUENCE: 146

Met Val Ser Ala Val Ile Gly Ser Ala Ala Val Gly Ala Lys Ser Ala
        1               5                   10                  15

Val Asp Arg Arg Thr Thr Gly Ala Gln Thr Asp Asp Asn Val Met Ala
                    20                  25                  30

Leu Arg Ile Glu Thr Thr Ala Arg Ser Tyr Leu Arg Gln Asn Asn Gln
                35                  40                  45

Thr Lys Gly Tyr Thr Pro Gln Ile Ser Val Val Gly Tyr Asn Arg His
            50                  55                  60

Leu Leu Leu Leu Gly Gln Val Ala Thr Glu Gly Glu Lys Gln Phe Val
        65                  70                  75                  80

Gly Gln Ile Ala Arg Ser Glu Gln Ala Ala Glu Gly Val Tyr Asn Tyr
                        85                  90                  95

Ile Thr Val Ala Ser Leu Pro Arg Thr Ala Gly Asp Ile Ala Gly Asp
                    100                 105                 110

Thr Trp Asn Thr Ser Lys Val Arg Ala Thr Leu Leu Gly Ile Ser Pro
                115                 120                 125

Ala Thr Gln Ala Arg Val Lys Ile Val Thr Tyr Gly Asn Val Thr Tyr
            130                 135                 140

Val Met Gly Ile Leu Thr Pro Glu Glu Gln Ala Gln Ile Thr Gln Lys
        145                 150                 155                 160

Val Ser Thr Thr Val Gly Val Gln Lys Val Ile Thr Leu Tyr Gln Asn
                        165                 170                 175

Tyr Val Gln Arg
```

<210> SEQ ID NO 147
<211> LENGTH: 179
<212> TYPE: PRT
<213> ORGANISM: Artificial Sequence
<220> FEATURE:
<223> OTHER INFORMATION: Synthetic sequence

<400> SEQUENCE: 147

```
Val Ser Ala Val Ile Gly Ser Ala Ala Val Gly Ala Lys Ser Ala Val
1               5                   10                  15
Asp Arg Arg Thr Thr Gly Ala Gln Thr Asp Asp Asn Val Met Ala Leu
            20                  25                  30
Arg Ile Glu Thr Thr Ala Arg Ser Tyr Leu Arg Gln Asn Asn Gln Thr
        35                  40                  45
Lys Gly Tyr Thr Pro Gln Ile Ser Val Val Gly Tyr Asn Arg His Leu
    50                  55                  60
Leu Leu Leu Gly Gln Val Ala Thr Glu Gly Glu Lys Gln Phe Val Gly
65                  70                  75                  80
Gln Ile Ala Arg Ser Glu Gln Ala Ala Glu Gly Val Tyr Asn Tyr Ile
                85                  90                  95
Thr Val Ala Ser Leu Pro Arg Thr Ala Gly Asp Ile Ala Gly Asp Thr
            100                 105                 110
Trp Asn Thr Ser Lys Val Arg Ala Thr Leu Leu Gly Ile Ser Pro Ala
        115                 120                 125
Thr Gln Ala Arg Val Lys Ile Val Thr Tyr Gly Asn Val Thr Tyr Val
    130                 135                 140
Met Gly Ile Leu Thr Pro Glu Glu Gln Ala Gln Ile Thr Gln Lys Val
145                 150                 155                 160
Ser Thr Thr Val Gly Val Gln Lys Val Ile Thr Leu Tyr Gln Asn Tyr
                165                 170                 175
Val Gln Arg
```

<210> SEQ ID NO 148
<211> LENGTH: 440
<212> TYPE: PRT
<213> ORGANISM: Artificial Sequence
<220> FEATURE:
<223> OTHER INFORMATION: Synthetic sequence

<400> SEQUENCE: 148

```
Met Val Ser Ala Val Ile Gly Ser Ala Ala Val Gly Ala Lys Ser Ala
1               5                   10                  15
Val Asp Arg Arg Thr Thr Gly Ala Gln Thr Asp Asp Asn Val Met Ala
            20                  25                  30
Leu Arg Ile Glu Thr Thr Ala Arg Ser Tyr Leu Arg Gln Asn Asn Gln
        35                  40                  45
Thr Lys Gly Tyr Thr Pro Gln Ile Ser Val Val Gly Tyr Asn Arg His
    50                  55                  60
Leu Leu Leu Leu Gly Gln Val Ala Thr Glu Gly Glu Lys Gln Phe Val
65                  70                  75                  80
Gly Gln Ile Ala Arg Ser Glu Gln Ala Ala Glu Gly Val Tyr Asn Tyr
                85                  90                  95
Ile Thr Val Ala Ser Leu Pro Arg Thr Ala Gly Asp Ile Ala Gly Asp
            100                 105                 110
Thr Trp Asn Thr Ser Lys Val Arg Ala Thr Leu Leu Gly Ile Ser Pro
```

```
            115                 120                 125
Ala Thr Gln Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Ser Ser Gly Ser Gly Gly Gly Gly Val Ala
            180                 185                 190

Ala Asp Ile Gly Thr Gly Leu Ala Asp Ala Leu Thr Ala Pro Leu Asp
            195                 200                 205

His Lys Asp Lys Gly Leu Lys Ser Leu Thr Leu Glu Asp Ser Ile Ser
            210                 215                 220

Gln Asn Gly Thr Leu Thr Leu Ser Ala Gln Gly Ala Glu Lys Thr Phe
225                 230                 235                 240

Lys Val Gly Asp Lys Asp Asn Ser Leu Asn Thr Gly Lys Leu Lys Asn
                245                 250                 255

Asp Lys Ile Ser Arg Phe Asp Phe Val Gln Lys Ile Glu Val Asp Gly
            260                 265                 270

Gln Thr Ile Thr Leu Ala Ser Gly Glu Phe Gln Ile Tyr Lys Gln Asp
            275                 280                 285

His Ser Ala Val Val Ala Leu Gln Ile Glu Lys Ile Asn Asn Pro Asp
            290                 295                 300

Lys Ile Asp Ser Leu Ile Asn Gln Arg Ser Phe Leu Val Ser Gly Leu
305                 310                 315                 320

Gly Gly Glu His Thr Ala Phe Asn Gln Leu Pro Ser Gly Lys Ala Glu
                325                 330                 335

Tyr His Gly Lys Ala Phe Ser Ser Asp Asp Ala Gly Gly Lys Leu Thr
            340                 345                 350

Tyr Thr Ile Asp Phe Ala Ala Lys Gln Gly His Gly Lys Ile Glu His
            355                 360                 365

Leu Lys Thr Pro Glu Gln Asn Val Glu Leu Ala Ser Ala Glu Leu Lys
            370                 375                 380

Ala Asp Glu Lys Ser His Ala Val Ile Leu Gly Asp Thr Arg Tyr Gly
385                 390                 395                 400

Ser Glu Glu Lys Gly Thr Tyr His Leu Ala Leu Phe Gly Asp Arg Ala
                405                 410                 415

Gln Glu Ile Ala Gly Ser Ala Thr Val Lys Ile Arg Glu Lys Val His
            420                 425                 430

Glu Ile Gly Ile Ala Gly Lys Gln
            435                 440

<210> SEQ ID NO 149
<211> LENGTH: 439
<212> TYPE: PRT
<213> ORGANISM: Artificial Sequence
<220> FEATURE:
<223> OTHER INFORMATION: Synthetic sequence

<400> SEQUENCE: 149

Val Ser Ala Val Ile Gly Ser Ala Val Gly Ala Lys Ser Ala Val
1               5                   10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
```

```
                35                  40                  45
Lys Gly Tyr Thr Pro Gln Ile Ser Val Val Gly Tyr Asn Arg His Leu
 50                  55                  60

Leu Leu Leu Gly Gln Val Ala Thr Glu Gly Glu Lys Gln Phe Val Gly
 65                  70                  75                  80

Gln Ile Ala Arg Ser Glu Gln Ala Ala Glu Gly Val Tyr Asn Tyr Ile
                 85                  90                  95

Thr Val Ala Ser Leu Pro Arg Thr Ala Gly Asp Ile Ala Gly Asp Thr
                100                 105                 110

Trp Asn Thr Ser Lys Val Arg Ala Thr Leu Leu Gly Ile Ser Pro Ala
                115                 120                 125

Thr Gln Ala Arg Val Lys Ile Val Thr Tyr Gly Asn Val Thr Tyr Val
                130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg Ser Ser Gly Ser Gly Gly Gly Val Ala Ala
                180                 185                 190

Asp Ile Gly Thr Gly Leu Ala Asp Ala Leu Thr Ala Pro Leu Asp His
                195                 200                 205

Lys Asp Lys Gly Leu Lys Ser Leu Thr Leu Asp Ser Ile Ser Gln
210                 215                 220

Asn Gly Thr Leu Thr Leu Ser Ala Gln Gly Ala Glu Lys Thr Phe Lys
225                 230                 235                 240

Val Gly Asp Lys Asp Asn Ser Leu Asn Thr Gly Lys Leu Lys Asn Asp
                245                 250                 255

Lys Ile Ser Arg Phe Asp Phe Val Gln Lys Ile Glu Val Asp Gly Gln
                260                 265                 270

Thr Ile Thr Leu Ala Ser Gly Glu Phe Gln Ile Tyr Lys Gln Asp His
                275                 280                 285

Ser Ala Val Val Ala Leu Gln Ile Glu Lys Ile Asn Asn Pro Asp Lys
290                 295                 300

Ile Asp Ser Leu Ile Asn Gln Arg Ser Phe Leu Val Ser Gly Leu Gly
305                 310                 315                 320

Gly Glu His Thr Ala Phe Asn Gln Leu Pro Ser Gly Lys Ala Glu Tyr
                325                 330                 335

His Gly Lys Ala Phe Ser Ser Asp Ala Gly Gly Lys Leu Thr Tyr
                340                 345                 350

Thr Ile Asp Phe Ala Ala Lys Gln Gly His Gly Lys Ile Glu His Leu
                355                 360                 365

Lys Thr Pro Glu Gln Asn Val Glu Leu Ala Ser Ala Glu Leu Lys Ala
                370                 375                 380

Asp Glu Lys Ser His Ala Val Ile Leu Gly Asp Thr Arg Tyr Gly Ser
385                 390                 395                 400

Glu Glu Lys Gly Thr Tyr His Leu Ala Leu Phe Gly Asp Arg Ala Gln
                405                 410                 415

Glu Ile Ala Gly Ser Ala Thr Val Lys Ile Arg Glu Lys Val His Glu
                420                 425                 430

Ile Gly Ile Ala Gly Lys Gln
                435

<210> SEQ ID NO 150
```

<211> LENGTH: 950
<212> TYPE: PRT
<213> ORGANISM: Artificial Sequence
<220> FEATURE:
<223> OTHER INFORMATION: Synthetic sequence

<400> SEQUENCE: 150

Met Ala Lys Thr Ala Asp Thr Pro Ala Thr Ser Lys Ala Thr Ile Arg
1               5                   10                  15

Asp Leu Asn Asp Pro Ser Gln Val Lys Thr Leu Gln Glu Lys Ala Gly
            20                  25                  30

Lys Gly Ala Gly Thr Val Val Ala Val Ile Ala Ala Gly Phe Asp Lys
        35                  40                  45

Asn His Glu Ala Trp Arg Leu Thr Asp Lys Ala Lys Ala Arg Tyr Gln
    50                  55                  60

Ser Lys Glu Asp Leu Glu Lys Ala Lys Lys His Gly Ile Thr Tyr
65                  70                  75                  80

Gly Glu Trp Val Asn Asp Lys Val Ala Tyr Tyr His Asp Tyr Ser Lys
                85                  90                  95

Asp Gly Lys Thr Ala Val Asp Gln Glu His Gly Thr His Val Ser Gly
            100                 105                 110

Ile Leu Ser Gly Asn Ala Pro Ser Glu Thr Lys Glu Pro Tyr Arg Leu
        115                 120                 125

Glu Gly Ala Met Pro Glu Ala Gln Leu Leu Met Arg Val Glu Ile
    130                 135                 140

Val Asn Gly Leu Ala Asp Tyr Ala Arg Asn Tyr Ala Gln Ala Ile Arg
145                 150                 155                 160

Asp Ala Ile Asn Leu Gly Ala Lys Val Ile Asn Met Ser Phe Gly Asn
                165                 170                 175

Ala Ala Leu Ala Tyr Ala Asn Leu Pro Asp Glu Thr Lys Lys Ala Phe
            180                 185                 190

Asp Tyr Ala Lys Ser Lys Gly Val Ser Ile Val Thr Ser Ala Gly Asn
        195                 200                 205

Asp Ser Ser Phe Gly Gly Lys Thr Arg Leu Pro Leu Ala Asp His Pro
    210                 215                 220

Asp Tyr Gly Val Val Gly Thr Pro Ala Ala Ala Asp Ser Thr Leu Thr
225                 230                 235                 240

Val Ala Ser Tyr Ser Pro Asp Lys Gln Leu Thr Glu Thr Val Thr Val
                245                 250                 255

Lys Thr Ala Asp Gln Gln Asp Lys Glu Met Pro Val Leu Ser Thr Asn
            260                 265                 270

Arg Phe Glu Pro Asn Lys Ala Tyr Asp Tyr Ala Tyr Ala Asn Arg Gly
        275                 280                 285

Thr Lys Glu Asp Asp Phe Lys Asp Val Lys Gly Lys Ile Ala Leu Ile
    290                 295                 300

Glu Arg Gly Asp Ile Asp Phe Lys Asp Lys Ile Ala Lys Ala Lys Lys
305                 310                 315                 320

Ala Gly Ala Val Gly Val Leu Ile Tyr Asp Asn Gln Asp Lys Gly Phe
                325                 330                 335

Pro Ile Glu Leu Pro Asn Val Asp Gln Met Pro Ala Ala Phe Ile Ser
            340                 345                 350

Arg Lys Asp Gly Leu Leu Leu Lys Asp Asn Pro Gln Lys Thr Ile Thr
        355                 360                 365

Phe Asn Ala Thr Pro Lys Val Leu Pro Thr Ala Ser Gly Thr Lys Leu
    370                 375                 380

```
Ser Arg Phe Ser Ser Trp Gly Leu Thr Ala Asp Gly Asn Ile Lys Pro
385                 390                 395                 400

Asp Ile Ala Ala Pro Gly Gln Asp Ile Leu Ser Ser Val Ala Asn Asn
            405                 410                 415

Lys Tyr Ala Lys Leu Ser Gly Thr Ala Met Ser Ala Pro Leu Val Ala
            420                 425                 430

Gly Ile Met Gly Leu Leu Gln Glu Gln Tyr Glu Thr Gln Tyr Pro Asp
            435                 440                 445

Met Thr Pro Ser Glu Arg Leu Asp Leu Ala Lys Lys Val Leu Met Ser
            450                 455                 460

Ser Ala Thr Ala Leu Tyr Asp Glu Asp Glu Lys Ala Tyr Phe Ser Pro
465                 470                 475                 480

Arg Gln Gln Gly Ala Gly Ala Val Asp Ala Lys Lys Ala Ser Ala Ala
                485                 490                 495

Thr Met Tyr Val Thr Asp Lys Asp Asn Thr Ser Ser Lys Val His Leu
            500                 505                 510

Asn Asn Val Ser Asp Lys Phe Glu Val Thr Val Thr Val His Asn Lys
            515                 520                 525

Ser Asp Lys Pro Gln Glu Leu Tyr Tyr Gln Ala Thr Val Gln Thr Asp
530                 535                 540

Lys Val Asp Gly Lys His Phe Ala Leu Ala Pro Lys Ala Leu Tyr Glu
545                 550                 555                 560

Thr Ser Trp Gln Lys Ile Thr Ile Pro Ala Asn Ser Ser Lys Gln Val
            565                 570                 575

Thr Val Pro Ile Asp Ala Ser Arg Phe Ser Lys Asp Leu Leu Ala Gln
            580                 585                 590

Met Lys Asn Gly Tyr Phe Leu Glu Gly Phe Val Arg Phe Lys Gln Asp
            595                 600                 605

Pro Lys Lys Glu Glu Leu Met Ser Ile Pro Tyr Ile Gly Phe Arg Gly
            610                 615                 620

Asp Phe Gly Asn Leu Ser Ala Leu Glu Lys Pro Ile Tyr Asp Ser Lys
625                 630                 635                 640

Asp Gly Ser Ser Tyr Tyr His Glu Ala Asn Ser Asp Ala Lys Asp Gln
                645                 650                 655

Leu Asp Gly Asp Gly Leu Gln Phe Tyr Ala Leu Lys Asn Asn Phe Thr
            660                 665                 670

Ala Leu Thr Thr Glu Ser Asn Pro Trp Thr Ile Ile Lys Ala Val Lys
            675                 680                 685

Glu Gly Val Glu Asn Ile Glu Asp Ile Glu Ser Ser Glu Ile Thr Glu
            690                 695                 700

Thr Ile Phe Ala Gly Thr Phe Lys Gln Asp Asp Ser His Tyr
705                 710                 715                 720

Tyr Ile His Arg His Ala Asn Gly Lys Pro Tyr Ala Ala Ile Ser Pro
            725                 730                 735

Asn Gly Asp Gly Asn Arg Asp Tyr Val Gln Phe Gln Gly Thr Phe Leu
            740                 745                 750

Arg Asn Ala Lys Asn Leu Val Ala Glu Val Leu Asp Lys Glu Gly Asn
            755                 760                 765

Val Val Trp Thr Ser Glu Val Thr Glu Gln Val Val Lys Asn Tyr Asn
            770                 775                 780

Asn Asp Leu Ala Ser Thr Leu Gly Ser Thr Arg Phe Glu Lys Thr Arg
785                 790                 795                 800
```

```
Trp Asp Gly Lys Asp Lys Asp Gly Lys Val Ala Asn Gly Thr Tyr
            805                 810                 815

Thr Tyr Arg Val Arg Tyr Thr Pro Ile Ser Ser Gly Ala Lys Glu Gln
        820                 825                 830

His Thr Asp Phe Asp Val Ile Val Asp Asn Thr Thr Pro Glu Val Ala
        835                 840                 845

Thr Ser Ala Thr Phe Ser Thr Glu Asp Arg Arg Leu Thr Leu Ala Ser
850                 855                 860

Lys Pro Lys Thr Ser Gln Pro Val Tyr Arg Glu Arg Ile Ala Tyr Thr
865                 870                 875                 880

Tyr Met Asp Glu Asp Leu Pro Thr Thr Glu Tyr Ile Ser Pro Asn Glu
                885                 890                 895

Asp Gly Thr Phe Thr Leu Pro Glu Glu Ala Glu Thr Met Glu Gly Ala
            900                 905                 910

Thr Val Pro Leu Lys Met Ser Asp Phe Thr Tyr Val Val Glu Asp Met
        915                 920                 925

Ala Gly Asn Ile Thr Tyr Thr Pro Val Thr Lys Leu Leu Glu Gly His
    930                 935                 940

Ser Asn Lys Pro Glu Gln
945                 950

<210> SEQ ID NO 151
<211> LENGTH: 949
<212> TYPE: PRT
<213> ORGANISM: Artificial Sequence
<220> FEATURE:
<223> OTHER INFORMATION: Synthetic sequence

<400> SEQUENCE: 151

Ala Lys Thr Ala Asp Thr Pro Ala Thr Ser Lys Ala Thr Ile Arg Asp
1               5                   10                  15

Leu Asn Asp Pro Ser Gln Val Lys Thr Leu Gln Glu Lys Ala Gly Lys
            20                  25                  30

Gly Ala Gly Thr Val Val Ala Val Ile Ala Ala Gly Phe Asp Lys Asn
        35                  40                  45

His Glu Ala Trp Arg Leu Thr Asp Lys Ala Lys Ala Arg Tyr Gln Ser
    50                  55                  60

Lys Glu Asp Leu Glu Lys Ala Lys Lys Glu His Gly Ile Thr Tyr Gly
65                  70                  75                  80

Glu Trp Val Asn Asp Lys Val Ala Tyr His Asp Tyr Ser Lys Asp
                85                  90                  95

Gly Lys Thr Ala Val Asp Gln Glu His Gly Thr His Val Ser Gly Ile
            100                 105                 110

Leu Ser Gly Asn Ala Pro Ser Glu Thr Lys Glu Pro Tyr Arg Leu Glu
        115                 120                 125

Gly Ala Met Pro Glu Ala Gln Leu Leu Leu Met Arg Val Glu Ile Val
    130                 135                 140

Asn Gly Leu Ala Asp Tyr Ala Arg Asn Tyr Ala Gln Ala Ile Arg Asp
145                 150                 155                 160

Ala Ile Asn Leu Gly Ala Lys Val Ile Asn Met Ser Phe Gly Asn Ala
                165                 170                 175

Ala Leu Ala Tyr Ala Asn Leu Pro Asp Glu Thr Lys Lys Ala Phe Asp
            180                 185                 190

Tyr Ala Lys Ser Lys Gly Val Ser Ile Val Thr Ser Ala Gly Asn Asp
        195                 200                 205
```

```
Ser Ser Phe Gly Gly Lys Thr Arg Leu Pro Leu Ala Asp His Pro Asp
    210                 215                 220
Tyr Gly Val Val Gly Thr Pro Ala Ala Ala Asp Ser Thr Leu Thr Val
225                 230                 235                 240
Ala Ser Tyr Ser Pro Asp Lys Gln Leu Thr Glu Thr Val Thr Val Lys
                245                 250                 255
Thr Ala Asp Gln Gln Asp Lys Glu Met Pro Val Leu Ser Thr Asn Arg
            260                 265                 270
Phe Glu Pro Asn Lys Ala Tyr Asp Tyr Ala Tyr Ala Asn Arg Gly Thr
        275                 280                 285
Lys Glu Asp Asp Phe Lys Asp Val Lys Gly Lys Ile Ala Leu Ile Glu
    290                 295                 300
Arg Gly Asp Ile Asp Phe Lys Asp Lys Ile Ala Lys Ala Lys Lys Ala
305                 310                 315                 320
Gly Ala Val Gly Val Leu Ile Tyr Asp Asn Gln Asp Lys Gly Phe Pro
                325                 330                 335
Ile Glu Leu Pro Asn Val Asp Gln Met Pro Ala Ala Phe Ile Ser Arg
            340                 345                 350
Lys Asp Gly Leu Leu Leu Lys Asp Asn Pro Gln Lys Thr Ile Thr Phe
        355                 360                 365
Asn Ala Thr Pro Lys Val Leu Pro Thr Ala Ser Gly Thr Lys Leu Ser
    370                 375                 380
Arg Phe Ser Ser Trp Gly Leu Thr Ala Asp Gly Asn Ile Lys Pro Asp
385                 390                 395                 400
Ile Ala Ala Pro Gly Gln Asp Ile Leu Ser Ser Val Ala Asn Asn Lys
                405                 410                 415
Tyr Ala Lys Leu Ser Gly Thr Ala Met Ser Ala Pro Leu Val Ala Gly
            420                 425                 430
Ile Met Gly Leu Leu Gln Glu Gln Tyr Glu Thr Gln Tyr Pro Asp Met
        435                 440                 445
Thr Pro Ser Glu Arg Leu Asp Leu Ala Lys Lys Val Leu Met Ser Ser
    450                 455                 460
Ala Thr Ala Leu Tyr Asp Glu Asp Glu Lys Ala Tyr Phe Ser Pro Arg
465                 470                 475                 480
Gln Gln Gly Ala Gly Ala Val Asp Ala Lys Lys Ala Ser Ala Ala Thr
                485                 490                 495
Met Tyr Val Thr Asp Lys Asp Asn Thr Ser Ser Lys Val His Leu Asn
            500                 505                 510
Asn Val Ser Asp Lys Phe Glu Val Thr Val Thr Val His Asn Lys Ser
        515                 520                 525
Asp Lys Pro Gln Glu Leu Tyr Tyr Gln Ala Thr Val Gln Thr Asp Lys
    530                 535                 540
Val Asp Gly Lys His Phe Ala Leu Ala Pro Lys Ala Leu Tyr Glu Thr
545                 550                 555                 560
Ser Trp Gln Lys Ile Thr Ile Pro Ala Asn Ser Ser Lys Gln Val Thr
                565                 570                 575
Val Pro Ile Asp Ala Ser Arg Phe Ser Lys Asp Leu Leu Ala Gln Met
            580                 585                 590
Lys Asn Gly Tyr Phe Leu Glu Gly Phe Val Arg Phe Lys Gln Asp Pro
        595                 600                 605
Lys Lys Glu Glu Leu Met Ser Ile Pro Tyr Ile Gly Phe Arg Gly Asp
    610                 615                 620
Phe Gly Asn Leu Ser Ala Leu Glu Lys Pro Ile Tyr Asp Ser Lys Asp
```

```
            625                 630                 635                 640
    Gly Ser Ser Tyr Tyr His Glu Ala Asn Ser Asp Ala Lys Asp Gln Leu
                    645                 650                 655

Asp Gly Asp Gly Leu Gln Phe Tyr Ala Leu Lys Asn Asn Phe Thr Ala
                660                 665                 670

Leu Thr Thr Glu Ser Asn Pro Trp Thr Ile Ile Lys Ala Val Lys Glu
                675                 680                 685

Gly Val Glu Asn Ile Glu Asp Ile Glu Ser Ser Glu Ile Thr Glu Thr
                690                 695                 700

Ile Phe Ala Gly Thr Phe Ala Lys Gln Asp Asp Ser His Tyr Tyr
    705                 710                 715                 720

Ile His Arg His Ala Asn Gly Lys Pro Tyr Ala Ala Ile Ser Pro Asn
                    725                 730                 735

Gly Asp Gly Asn Arg Asp Tyr Val Gln Phe Gln Gly Thr Phe Leu Arg
                740                 745                 750

Asn Ala Lys Asn Leu Val Ala Glu Val Leu Asp Lys Glu Gly Asn Val
                755                 760                 765

Val Trp Thr Ser Glu Val Thr Glu Gln Val Val Lys Asn Tyr Asn Asn
                770                 775                 780

Asp Leu Ala Ser Thr Leu Gly Ser Thr Arg Phe Glu Lys Thr Arg Trp
    785                 790                 795                 800

Asp Gly Lys Asp Lys Asp Gly Lys Val Val Ala Asn Gly Thr Tyr Thr
                805                 810                 815

Tyr Arg Val Arg Tyr Thr Pro Ile Ser Ser Gly Ala Lys Glu Gln His
                820                 825                 830

Thr Asp Phe Asp Val Ile Val Asp Asn Thr Thr Pro Glu Val Ala Thr
                835                 840                 845

Ser Ala Thr Phe Ser Thr Glu Asp Arg Arg Leu Thr Leu Ala Ser Lys
                850                 855                 860

Pro Lys Thr Ser Gln Pro Val Tyr Arg Glu Arg Ile Ala Tyr Thr Tyr
    865                 870                 875                 880

Met Asp Glu Asp Leu Pro Thr Thr Glu Tyr Ile Ser Pro Asn Glu Asp
                885                 890                 895

Gly Thr Phe Thr Leu Pro Glu Glu Ala Glu Thr Met Glu Gly Ala Thr
                900                 905                 910

Val Pro Leu Lys Met Ser Asp Phe Thr Tyr Val Val Glu Asp Met Ala
                915                 920                 925

Gly Asn Ile Thr Tyr Thr Pro Val Thr Lys Leu Leu Glu Gly His Ser
                930                 935                 940

Asn Lys Pro Glu Gln
    945

<210> SEQ ID NO 152
<211> LENGTH: 1210
<212> TYPE: PRT
<213> ORGANISM: Artificial Sequence
<220> FEATURE:
<223> OTHER INFORMATION: Synthetic sequence

<400> SEQUENCE: 152

Met Ala Lys Thr Ala Asp Thr Pro Ala Thr Ser Lys Ala Thr Ile Arg
1               5                   10                  15

Asp Leu Asn Asp Pro Ser Gln Val Lys Thr Leu Gln Glu Lys Ala Gly
                20                  25                  30

Lys Gly Ala Gly Thr Val Val Ala Val Ile Ala Ala Gly Phe Asp Lys
```

-continued

```
                35                  40                  45
Asn His Glu Ala Trp Arg Leu Thr Asp Lys Ala Lys Ala Arg Tyr Gln
 50                  55                  60

Ser Lys Glu Asp Leu Glu Lys Ala Lys Lys Glu His Gly Ile Thr Tyr
 65                  70                  75                  80

Gly Glu Trp Val Asn Asp Lys Val Ala Tyr Tyr His Asp Tyr Ser Lys
                     85                  90                  95

Asp Gly Lys Thr Ala Val Asp Gln Glu His Gly Thr His Val Ser Gly
                100                 105                 110

Ile Leu Ser Gly Asn Ala Pro Ser Glu Thr Lys Glu Pro Tyr Arg Leu
                115                 120                 125

Glu Gly Ala Met Pro Glu Ala Gln Leu Leu Met Arg Val Glu Ile
130                 135                 140

Val Asn Gly Leu Ala Asp Tyr Ala Arg Asn Tyr Ala Gln Ala Ile Arg
145                 150                 155                 160

Asp Ala Ile Asn Leu Gly Ala Lys Val Ile Asn Met Ser Phe Gly Asn
                165                 170                 175

Ala Ala Leu Ala Tyr Ala Asn Leu Pro Asp Glu Thr Lys Lys Ala Phe
                180                 185                 190

Asp Tyr Ala Lys Ser Lys Gly Val Ser Ile Val Thr Ser Ala Gly Asn
                195                 200                 205

Asp Ser Ser Phe Gly Gly Lys Thr Arg Leu Pro Leu Ala Asp His Pro
                210                 215                 220

Asp Tyr Gly Val Val Gly Thr Pro Ala Ala Asp Ser Thr Leu Thr
225                 230                 235                 240

Val Ala Ser Tyr Ser Pro Asp Lys Gln Leu Thr Glu Thr Val Thr Val
                245                 250                 255

Lys Thr Ala Asp Gln Gln Asp Lys Glu Met Pro Val Leu Ser Thr Asn
                260                 265                 270

Arg Phe Glu Pro Asn Lys Ala Tyr Asp Tyr Ala Tyr Ala Asn Arg Gly
                275                 280                 285

Thr Lys Glu Asp Asp Phe Lys Asp Val Lys Gly Lys Ile Ala Leu Ile
                290                 295                 300

Glu Arg Gly Asp Ile Asp Phe Lys Asp Lys Ile Ala Lys Ala Lys Lys
305                 310                 315                 320

Ala Gly Ala Val Gly Val Leu Ile Tyr Asp Asn Gln Asp Lys Gly Phe
                325                 330                 335

Pro Ile Glu Leu Pro Asn Val Asp Gln Met Pro Ala Ala Phe Ile Ser
                340                 345                 350

Arg Lys Asp Gly Leu Leu Leu Lys Asp Asn Pro Gln Lys Thr Ile Thr
                355                 360                 365

Phe Asn Ala Thr Pro Lys Val Leu Pro Thr Ala Ser Gly Thr Lys Leu
                370                 375                 380

Ser Arg Phe Ser Ser Trp Gly Leu Thr Ala Asp Gly Asn Ile Lys Pro
385                 390                 395                 400

Asp Ile Ala Ala Pro Gly Gln Asp Ile Leu Ser Ser Val Ala Asn Asn
                405                 410                 415

Lys Tyr Ala Lys Leu Ser Gly Thr Ala Met Ser Ala Pro Leu Val Ala
                420                 425                 430

Gly Ile Met Gly Leu Leu Gln Glu Gln Tyr Glu Thr Gln Tyr Pro Asp
                435                 440                 445

Met Thr Pro Ser Glu Arg Leu Asp Leu Ala Lys Lys Val Leu Met Ser
                450                 455                 460
```

```
Ser Ala Thr Ala Leu Tyr Asp Glu Asp Glu Lys Ala Tyr Phe Ser Pro
465                 470                 475                 480

Arg Gln Gln Gly Ala Gly Ala Val Asp Ala Lys Lys Ala Ser Ala Ala
            485                 490                 495

Thr Met Tyr Val Thr Asp Lys Asp Asn Thr Ser Ser Lys Val His Leu
                500                 505                 510

Asn Asn Val Ser Asp Lys Phe Glu Val Thr Val Thr Val His Asn Lys
                515                 520                 525

Ser Asp Lys Pro Gln Glu Leu Tyr Tyr Gln Ala Thr Val Gln Thr Asp
530                 535                 540

Lys Val Asp Gly Lys His Phe Ala Leu Ala Pro Lys Ala Leu Tyr Glu
545                 550                 555                 560

Thr Ser Trp Gln Lys Ile Thr Ile Pro Ala Asn Ser Ser Lys Gln Val
                565                 570                 575

Thr Val Pro Ile Asp Ala Ser Arg Phe Ser Lys Asp Leu Leu Ala Gln
                580                 585                 590

Met Lys Asn Gly Tyr Phe Leu Glu Gly Phe Val Arg Phe Lys Gln Asp
            595                 600                 605

Pro Lys Lys Glu Glu Leu Met Ser Ile Pro Tyr Ile Gly Phe Arg Gly
610                 615                 620

Asp Phe Gly Asn Leu Ser Ala Leu Glu Lys Pro Ile Tyr Asp Ser Lys
625                 630                 635                 640

Asp Gly Ser Ser Tyr Tyr His Glu Ala Asn Ser Asp Ala Lys Asp Gln
                645                 650                 655

Leu Asp Gly Asp Gly Leu Gln Phe Tyr Ala Leu Lys Asn Asn Phe Thr
                660                 665                 670

Ala Leu Thr Thr Glu Ser Asn Pro Trp Thr Ile Ile Lys Ala Val Lys
                675                 680                 685

Glu Gly Val Glu Asn Ile Glu Asp Ile Glu Ser Ser Glu Ile Thr Glu
690                 695                 700

Thr Ile Phe Ala Gly Thr Phe Ala Lys Gln Asp Asp Ser His Tyr
705                 710                 715                 720

Tyr Ile His Arg His Ala Asn Gly Lys Pro Tyr Ala Ala Ile Ser Pro
                725                 730                 735

Asn Gly Asp Gly Asn Arg Asp Tyr Val Gln Phe Gln Gly Thr Phe Leu
                740                 745                 750

Arg Asn Ala Lys Asn Leu Val Ala Glu Val Leu Asp Lys Glu Gly Asn
            755                 760                 765

Val Val Trp Thr Ser Glu Val Thr Glu Gln Val Val Lys Asn Tyr Asn
            770                 775                 780

Asn Asp Leu Ala Ser Thr Leu Gly Ser Thr Arg Phe Glu Lys Thr Arg
785                 790                 795                 800

Trp Asp Gly Lys Asp Lys Asp Gly Lys Val Val Ala Asn Gly Thr Tyr
                805                 810                 815

Thr Tyr Arg Val Arg Tyr Thr Pro Ile Ser Ser Gly Ala Lys Glu Gln
                820                 825                 830

His Thr Asp Phe Asp Val Ile Val Asp Asn Thr Thr Pro Glu Val Ala
                835                 840                 845

Thr Ser Ala Thr Phe Ser Thr Glu Asp Arg Arg Leu Thr Leu Ala Ser
            850                 855                 860

Lys Pro Lys Thr Ser Gln Pro Val Tyr Arg Glu Arg Ile Ala Tyr Thr
865                 870                 875                 880
```

Tyr Met Asp Glu Asp Leu Pro Thr Thr Glu Tyr Ile Ser Pro Asn Glu
            885                 890                 895

Asp Gly Thr Phe Thr Leu Pro Glu Glu Ala Glu Thr Met Glu Gly Ala
        900                 905                 910

Thr Val Pro Leu Lys Met Ser Asp Phe Thr Tyr Val Val Glu Asp Met
    915                 920                 925

Ala Gly Asn Ile Thr Tyr Thr Pro Val Thr Lys Leu Leu Glu Gly His
930                 935                 940

Ser Asn Lys Pro Glu Gln Ser Gly Ser Gly Ser Gly Gly Gly Gly Gly
945                 950                 955                 960

Val Ala Ala Asp Ile Gly Thr Gly Leu Ala Asp Ala Leu Thr Ala Pro
            965                 970                 975

Leu Asp His Lys Asp Lys Gly Leu Lys Ser Leu Thr Leu Glu Asp Ser
        980                 985                 990

Ile Ser Gln Asn Gly Thr Leu Thr Leu Ser Ala Gln Gly Ala Glu Lys
    995                 1000                1005

Thr Phe Lys Val Gly Asp Asp Asn Ser Leu Asn Thr Gly Lys
    1010                1015                1020

Leu Lys Asn Asp Lys Ile Ser Arg Phe Asp Phe Val Gln Lys Ile
    1025                1030                1035

Glu Val Asp Gly Gln Thr Ile Thr Leu Ala Ser Gly Glu Phe Gln
    1040                1045                1050

Ile Tyr Lys Gln Asp His Ser Ala Val Val Ala Leu Gln Ile Glu
    1055                1060                1065

Lys Ile Asn Asn Pro Asp Lys Ile Asp Ser Leu Ile Asn Gln Arg
    1070                1075                1080

Ser Phe Leu Val Ser Gly Leu Gly Gly Glu His Thr Ala Phe Asn
    1085                1090                1095

Gln Leu Pro Ser Gly Lys Ala Glu Tyr His Gly Lys Ala Phe Ser
    1100                1105                1110

Ser Asp Asp Ala Gly Gly Lys Leu Thr Tyr Thr Ile Asp Phe Ala
    1115                1120                1125

Ala Lys Gln Gly His Gly Lys Ile Glu His Leu Lys Thr Pro Glu
    1130                1135                1140

Gln Asn Val Glu Leu Ala Ser Ala Glu Leu Lys Ala Asp Glu Lys
    1145                1150                1155

Ser His Ala Val Ile Leu Gly Asp Thr Arg Tyr Gly Ser Glu Glu
    1160                1165                1170

Lys Gly Thr Tyr His Leu Ala Leu Phe Gly Asp Arg Ala Gln Glu
    1175                1180                1185

Ile Ala Gly Ser Ala Thr Val Lys Ile Arg Glu Lys Val His Glu
    1190                1195                1200

Ile Gly Ile Ala Gly Lys Gln
    1205                1210

<210> SEQ ID NO 153
<211> LENGTH: 1209
<212> TYPE: PRT
<213> ORGANISM: Artificial Sequence
<220> FEATURE:
<223> OTHER INFORMATION: Synthetic sequence

<400> SEQUENCE: 153

Ala Lys Thr Ala Asp Thr Pro Ala Thr Ser Lys Ala Thr Ile Arg Asp
1               5                   10                  15

```
Leu Asn Asp Pro Ser Gln Val Lys Thr Leu Gln Glu Lys Ala Gly Lys
             20                  25                  30

Gly Ala Gly Thr Val Val Ala Val Ile Ala Ala Gly Phe Asp Lys Asn
         35                  40                  45

His Glu Ala Trp Arg Leu Thr Asp Lys Ala Lys Ala Arg Tyr Gln Ser
 50                  55                  60

Lys Glu Asp Leu Glu Lys Ala Lys Lys Glu His Gly Ile Thr Tyr Gly
65                  70                  75                  80

Glu Trp Val Asn Asp Lys Val Ala Tyr Tyr His Asp Tyr Ser Lys Asp
                 85                  90                  95

Gly Lys Thr Ala Val Asp Gln Glu His Gly Thr His Val Ser Gly Ile
             100                 105                 110

Leu Ser Gly Asn Ala Pro Ser Glu Thr Lys Glu Pro Tyr Arg Leu Glu
         115                 120                 125

Gly Ala Met Pro Glu Ala Gln Leu Leu Leu Met Arg Val Glu Ile Val
130                 135                 140

Asn Gly Leu Ala Asp Tyr Ala Arg Asn Tyr Ala Gln Ala Ile Arg Asp
145                 150                 155                 160

Ala Ile Asn Leu Gly Ala Lys Val Ile Asn Met Ser Phe Gly Asn Ala
                 165                 170                 175

Ala Leu Ala Tyr Ala Asn Leu Pro Asp Glu Thr Lys Lys Ala Phe Asp
             180                 185                 190

Tyr Ala Lys Ser Lys Gly Val Ser Ile Val Thr Ser Ala Gly Asn Asp
         195                 200                 205

Ser Ser Phe Gly Gly Lys Thr Arg Leu Pro Leu Ala Asp His Pro Asp
210                 215                 220

Tyr Gly Val Val Gly Thr Pro Ala Ala Ala Asp Ser Thr Leu Thr Val
225                 230                 235                 240

Ala Ser Tyr Ser Pro Asp Lys Gln Leu Thr Glu Thr Val Thr Val Lys
                 245                 250                 255

Thr Ala Asp Gln Gln Asp Lys Glu Met Pro Val Leu Ser Thr Asn Arg
             260                 265                 270

Phe Glu Pro Asn Lys Ala Tyr Asp Tyr Ala Tyr Ala Asn Arg Gly Thr
         275                 280                 285

Lys Glu Asp Asp Phe Lys Asp Val Lys Gly Lys Ile Ala Leu Ile Glu
290                 295                 300

Arg Gly Asp Ile Asp Phe Lys Asp Lys Ile Lys Ala Lys Lys Ala
305                 310                 315                 320

Gly Ala Val Gly Val Leu Ile Tyr Asp Asn Gln Asp Lys Gly Phe Pro
                 325                 330                 335

Ile Glu Leu Pro Asn Val Asp Gln Met Pro Ala Ala Phe Ile Ser Arg
             340                 345                 350

Lys Asp Gly Leu Leu Leu Lys Asp Asn Pro Gln Lys Thr Ile Thr Phe
         355                 360                 365

Asn Ala Thr Pro Lys Val Leu Pro Thr Ala Ser Gly Thr Lys Leu Ser
370                 375                 380

Arg Phe Ser Ser Trp Gly Leu Thr Ala Asp Gly Asn Ile Lys Pro Asp
385                 390                 395                 400

Ile Ala Ala Pro Gly Gln Asp Ile Leu Ser Ser Val Ala Asn Asn Lys
                 405                 410                 415

Tyr Ala Lys Leu Ser Gly Thr Ala Met Ser Ala Pro Leu Val Ala Gly
             420                 425                 430

Ile Met Gly Leu Leu Gln Glu Gln Tyr Glu Thr Gln Tyr Pro Asp Met
```

-continued

```
                435                 440                 445
Thr Pro Ser Glu Arg Leu Asp Leu Ala Lys Lys Val Leu Met Ser Ser
450                 455                 460

Ala Thr Ala Leu Tyr Asp Glu Asp Lys Ala Tyr Phe Ser Pro Arg
465                 470                 475                 480

Gln Gln Gly Ala Gly Ala Val Asp Ala Lys Ala Ser Ala Ala Thr
                485                 490                 495

Met Tyr Val Thr Asp Lys Asp Asn Thr Ser Ser Lys Val His Leu Asn
                500                 505                 510

Asn Val Ser Asp Lys Phe Glu Val Thr Val Thr Val His Asn Lys Ser
        515                 520                 525

Asp Lys Pro Gln Glu Leu Tyr Tyr Gln Ala Thr Val Gln Thr Asp Lys
    530                 535                 540

Val Asp Gly Lys His Phe Ala Leu Ala Pro Lys Ala Leu Tyr Glu Thr
545                 550                 555                 560

Ser Trp Gln Lys Ile Thr Ile Pro Ala Asn Ser Ser Lys Gln Val Thr
                565                 570                 575

Val Pro Ile Asp Ala Ser Arg Phe Ser Lys Asp Leu Leu Ala Gln Met
            580                 585                 590

Lys Asn Gly Tyr Phe Leu Glu Gly Phe Val Arg Phe Lys Gln Asp Pro
        595                 600                 605

Lys Lys Glu Glu Leu Met Ser Ile Pro Tyr Ile Gly Phe Arg Gly Asp
610                 615                 620

Phe Gly Asn Leu Ser Ala Leu Glu Lys Pro Ile Tyr Asp Ser Lys Asp
625                 630                 635                 640

Gly Ser Ser Tyr Tyr His Glu Ala Asn Ser Asp Ala Lys Asp Gln Leu
                645                 650                 655

Asp Gly Asp Gly Leu Gln Phe Tyr Ala Leu Lys Asn Asn Phe Thr Ala
                660                 665                 670

Leu Thr Thr Glu Ser Asn Pro Trp Thr Ile Ile Lys Ala Val Lys Glu
        675                 680                 685

Gly Val Glu Asn Ile Glu Asp Ile Glu Ser Ser Glu Ile Thr Glu Thr
    690                 695                 700

Ile Phe Ala Gly Thr Phe Ala Lys Gln Asp Asp Ser His Tyr Tyr
705                 710                 715                 720

Ile His Arg His Ala Asn Gly Lys Pro Tyr Ala Ala Ile Ser Pro Asn
                725                 730                 735

Gly Asp Gly Asn Arg Asp Tyr Val Gln Phe Gln Gly Thr Phe Leu Arg
            740                 745                 750

Asn Ala Lys Asn Leu Val Ala Glu Val Leu Asp Lys Glu Gly Asn Val
        755                 760                 765

Val Trp Thr Ser Glu Val Thr Glu Gln Val Val Lys Asn Tyr Asn Asn
    770                 775                 780

Asp Leu Ala Ser Thr Leu Gly Ser Thr Arg Phe Glu Lys Thr Arg Trp
785                 790                 795                 800

Asp Gly Lys Asp Lys Asp Gly Lys Val Val Ala Asn Gly Thr Tyr Thr
                805                 810                 815

Tyr Arg Val Arg Tyr Thr Pro Ile Ser Ser Gly Ala Lys Glu Gln His
            820                 825                 830

Thr Asp Phe Asp Val Ile Val Asp Asn Thr Thr Pro Glu Val Ala Thr
        835                 840                 845

Ser Ala Thr Phe Ser Thr Glu Asp Arg Arg Leu Thr Leu Ala Ser Lys
    850                 855                 860
```

Pro Lys Thr Ser Gln Pro Val Tyr Arg Glu Arg Ile Ala Tyr Thr Tyr
865                 870                 875                 880

Met Asp Glu Asp Leu Pro Thr Thr Glu Tyr Ile Ser Pro Asn Glu Asp
            885                 890                 895

Gly Thr Phe Thr Leu Pro Glu Glu Ala Glu Thr Met Glu Gly Ala Thr
        900                 905                 910

Val Pro Leu Lys Met Ser Asp Phe Thr Tyr Val Val Glu Asp Met Ala
        915                 920                 925

Gly Asn Ile Thr Tyr Thr Pro Val Thr Lys Leu Leu Glu Gly His Ser
930                 935                 940

Asn Lys Pro Glu Gln Ser Ser Gly Ser Gly Ser Gly Gly Gly Gly Val
945                 950                 955                 960

Ala Ala Asp Ile Gly Thr Gly Leu Ala Asp Ala Leu Thr Ala Pro Leu
            965                 970                 975

Asp His Lys Asp Lys Gly Leu Lys Ser Leu Thr Leu Glu Asp Ser Ile
            980                 985                 990

Ser Gln Asn Gly Thr Leu Thr Leu Ser Ala Gln Gly Ala Glu Lys Thr
        995                 1000                1005

Phe Lys Val Gly Asp Lys Asp Asn Ser Leu Asn Thr Gly Lys Leu
    1010                1015                1020

Lys Asn Asp Lys Ile Ser Arg Phe Asp Phe Val Gln Lys Ile Glu
    1025                1030                1035

Val Asp Gly Gln Thr Ile Thr Leu Ala Ser Gly Glu Phe Gln Ile
    1040                1045                1050

Tyr Lys Gln Asp His Ser Ala Val Val Ala Leu Gln Ile Glu Lys
    1055                1060                1065

Ile Asn Asn Pro Asp Lys Ile Asp Ser Leu Ile Asn Gln Arg Ser
    1070                1075                1080

Phe Leu Val Ser Gly Leu Gly Gly Glu His Thr Ala Phe Asn Gln
    1085                1090                1095

Leu Pro Ser Gly Lys Ala Glu Tyr His Gly Lys Ala Phe Ser Ser
    1100                1105                1110

Asp Asp Ala Gly Gly Lys Leu Thr Tyr Thr Ile Asp Phe Ala Ala
    1115                1120                1125

Lys Gln Gly His Gly Lys Ile Glu His Leu Lys Thr Pro Glu Gln
    1130                1135                1140

Asn Val Glu Leu Ala Ser Ala Glu Leu Lys Ala Asp Glu Lys Ser
    1145                1150                1155

His Ala Val Ile Leu Gly Asp Thr Arg Tyr Gly Ser Glu Glu Lys
    1160                1165                1170

Gly Thr Tyr His Leu Ala Leu Phe Gly Asp Arg Ala Gln Glu Ile
    1175                1180                1185

Ala Gly Ser Ala Thr Val Lys Ile Arg Glu Lys Val His Glu Ile
    1190                1195                1200

Gly Ile Ala Gly Lys Gln
    1205

<210> SEQ ID NO 154
<211> LENGTH: 536
<212> TYPE: PRT
<213> ORGANISM: Artificial Sequence
<220> FEATURE:
<223> OTHER INFORMATION: Synthetic sequence

<400> SEQUENCE: 154

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Ala Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415
```

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
            435                 440                 445

Thr His Ile Ser Val Asn Gly Arg Lys Ile Arg Met Arg Cys Arg Ala
            450                 455                 460

Ile Asp Gly Asp Val Thr Phe Cys Arg Leu Lys Ser Pro Val Tyr Val
465                 470                 475                 480

Gly Asn Gly Val His Ala Asn Leu His Val Ala Phe His Arg Ser Ser
            485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Leu Val Asn Ser Lys Leu
            515                 520                 525

Ser Leu Phe Phe Glu Ile Lys Ser
            530                 535

<210> SEQ ID NO 155
<211> LENGTH: 535
<212> TYPE: PRT
<213> ORGANISM: Artificial Sequence
<220> FEATURE:
<223> OTHER INFORMATION: Synthetic sequence

<400> SEQUENCE: 155

Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
            50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
            85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
            130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
            210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Ala Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Leu Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 156
<211> LENGTH: 261
<212> TYPE: PRT
<213> ORGANISM: Artificial Sequence
<220> FEATURE:
<223> OTHER INFORMATION: Synthetic sequence

<400> SEQUENCE: 156

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

```
Asp Lys Asp Asn Ser Leu Asn Thr Gly Lys Leu Lys Asn Asp Lys Ile
 65                  70                  75                  80

Ser Arg Phe Asp Phe Val Gln Lys Ile Glu Val Asp Gly Gln Thr Ile
                 85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
                180                 185                 190

Pro Glu Gln Asn Val Glu Leu Ala Ser Glu Leu Lys Ala Asp Glu
                195                 200                 205

Lys Ser His Ala Val Ile Leu Gly Asp Thr Arg Tyr Gly Ser Glu Glu
210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 157
<211> LENGTH: 260
<212> TYPE: PRT
<213> ORGANISM: Artificial Sequence
<220> FEATURE:
<223> OTHER INFORMATION: Synthetic sequence

<400> SEQUENCE: 157

Ser Cys Gly Ser Gly Ser Gly Gly Gly Val Ala Ala Asp Ile Gly
 1               5                  10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Ser Gln Asn Gly Thr
        35                  40                  45

Leu Thr Leu Ser Ala Gln Gly Ala Glu Lys Thr Phe Lys Val Gly Asp
 50                  55                  60

Lys Asp Asn Ser Leu Asn Thr Gly Lys Leu Lys Asn Asp Lys Ile Ser
 65                  70                  75                  80

Arg Phe Asp Phe Val Gln Lys Ile Glu Val Asp Gly Gln Thr Ile Thr
                 85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Ser Gly Lys Ala Glu Tyr His Gly Lys
145                 150                 155                 160
```

Ala Phe Ser Ser Asp Asp Ala Gly Gly Lys Leu Thr Tyr Thr Ile Asp
            165                 170                 175

Phe Ala Ala Lys Gln Gly His Gly Lys Ile Glu His Leu Lys Thr Pro
        180                 185                 190

Glu Gln Asn Val Glu Leu Ala Ser Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
            245                 250                 255

Ala Gly Lys Gln
        260

<210> SEQ ID NO 158
<211> LENGTH: 260
<212> TYPE: PRT
<213> ORGANISM: Artificial Sequence
<220> FEATURE:
<223> OTHER INFORMATION: Synthetic sequence

<400> SEQUENCE: 158

Ser Ser Gly Ser Gly Cys Gly Gly Gly Val Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Ser Gln Asn Gly Thr
        35                  40                  45

Leu Thr Leu Ser Ala Gln Gly Ala Glu Lys Thr Phe Lys Val Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Ser Gly Lys Ala Glu Tyr His Gly Lys
145                 150                 155                 160

Ala Phe Ser Ser Asp Asp Ala Gly Gly Lys Leu Thr Tyr Thr Ile Asp
            165                 170                 175

Phe Ala Ala Lys Gln Gly His Gly Lys Ile Glu His Leu Lys Thr Pro
        180                 185                 190

Glu Gln Asn Val Glu Leu Ala Ser Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
            245                 250                 255

-continued

```
Ala Gly Lys Gln
            260
```

IMMUNOGENIC FUSION POLYPEPTIDES

CROSS REFERENCE TO RELATED APPLICATIONS

This application is a national phase application under 35 U.S.C. §371 of International Application No. PCT/IB2014/059462, filed on Mar. 5, 2014, which claims the benefit of U.S. provisional patent application Ser. No. 61/775,478, filed Mar. 8, 2013. All of the foregoing applications are hereby incorporated by reference in their entireties.

FIELD OF THE INVENTION

The present invention relates to *Neisseria meningitidis* compositions and methods thereof.

BACKGROUND OF THE INVENTION

*Neisseria meningitidis* is a Gram-negative encapsulated bacterium that can cause sepsis, meningitis and death. *N. meningitidis* can be classified into about 13 serogroups based on chemically and antigenically distinctive polysaccharide capsules. Five of the serogroups (A, B, C, Y, and W135) are responsible for the majority of disease. Meningococcal meningitis is a devastating disease that can kill children and young adults within hours despite the availability of antibiotics. There is a need for improved immunogenic compositions against meningococcal meningitis.

SUMMARY OF THE INVENTION

To meet these and other needs, the present invention relates to molecules, compositions, and methods that include *Neisseria meningitidis* polypeptides and carrier polypeptides.

In one aspect, the invention relates to an isolated polypeptide including the amino acid sequence of a carrier polypeptide and the amino acid sequence of an ORF2086 polypeptide. In one embodiment, the isolated polypeptide is a fusion polypeptide. In one embodiment, the ORF2086 polypeptide is a subfamily A polypeptide. In one embodiment, the ORF2086 polypeptide is a subfamily B polypeptide. In one embodiment, the ORF2086 polypeptide is lipidated. In one embodiment, the ORF2086 polypeptide is non-lipidated. In one embodiment, the ORF2086 polypeptide is A05. In one embodiment, the ORF2086 polypeptide is A12. In one embodiment, the ORF2086 polypeptide is A22. In one embodiment, the ORF2086 polypeptide is B01. In one embodiment, the ORF2086 polypeptide is B09. In one embodiment, the ORF2086 polypeptide is B15. In one embodiment, the ORF2086 polypeptide is B16. In one embodiment, the ORF2086 polypeptide is B22. In one embodiment, the ORF2086 polypeptide is B24. In one embodiment, the ORF2086 polypeptide is B44. In one embodiment, the ORF2086 polypeptide is A62. In one embodiment, the ORF2086 polypeptide is A04. In one embodiment, the ORF2086 polypeptide is A01. In one embodiment, the ORF2086 polypeptide is A06. In one embodiment, the ORF2086 polypeptide is A07. In one embodiment, the ORF2086 polypeptide is A15. In one embodiment, the ORF2086 polypeptide is A19. In one embodiment, the ORF2086 polypeptide is A20. In one embodiment, the ORF2086 polypeptide is A29. In one embodiment, the ORF2086 polypeptide is B02. In one embodiment, the ORF2086 polypeptide includes the amino acid sequence selected from the group consisting of SEQ ID NOs: 5, 19, and 22-65.

In one embodiment, the carrier polypeptide is a cytolysoid. In one embodiment, the cytolysoid is derived from a pneumolysin polypeptide from *Streptococcus pneumoniae*, a perfringolysin O polypeptide from *Clostridium perfringens*, a intermedilysin polypeptide from *Streptococcus intermedius*, a alveolysin polypeptide from *Bacillus alvei*, a anthrolysin polypeptide from *Bacillus anthracis*, a putative cereolysin polypeptide from *Bacillus cereus*, a ivanolysin O polypeptide from *Listeria ivanovii*, a pyolysin polypeptide from *Arcanobacterium pyogenes*, a seeligeriolysin O polypeptide from *Listeria seeligeri*, a streptolysin O polypeptide from *S. pyogenes*, a suilysin polypeptide from *Streptococcus suis*, a tetanolysin polypeptide from *Clostridium tetani*, a listeriolysin O polypeptide from *Listeria monocytogenes*, a streptolysin O polypeptide from *Streptococcus equisimilis*, a streptolysin O polypeptide from *S. canis*, a thuringiolysin O polypeptide from *Bacillus thuringiensis*, a latersporolysin O polypeptide from *B. laterosporus*, a botulinolysin polypeptide from *Clostridium botulinum*, a chauveolysin polypeptide from *C. chauvoei*, a bifermentolysin polypeptide from *C. bifermentans*, a sordellilysin polypeptide from *C. sordellii*, a histolyticolysin polypeptide from *Clostridium histiolyticum*, a novylysin polypeptide from *Clostridium novyi*, or a septicolysin O polypeptide from *Clostridium septicum*. In one embodiment, the cytolysoid is derived from a pneumolysin polypeptide from *Streptococcus pneumoniae*. In one embodiment, the cytolysoid includes a sequence having at least 90% sequence identity to SEQ ID NO: 1.

In one embodiment, the carrier polypeptide is detoxified as compared to the corresponding wild-type carrier polypeptide and is selected from the group consisting of tetanus toxin (TT), *Plasmodium falciparum* circumsporozite protein, hepatitis B surface antigen, hepatitis B nuclear core polypeptide, *H. influenzae* matrix polypeptide, *H. influenzae* haemagglutinin, diphtheria toxoid, diphtheria toxoid mutant $CRM_{197}$, group B *N. meningitidis* outer membrane polypeptide complex (OMPC), a cytolysoid, pneumococcal toxin pneumolysin, heat shock polypeptide from *Mycobacterium bovis*, heat shock polypeptide from *M. leprae*, cholera toxoid, *E. coli* LT, *E. coli* ST, exotoxin A from *Pseudomonas aeruginosa*, pneumococcal surface polypeptide A, pneumococcal adhesin polypeptide (PsaA), C5a peptidase from Group A or Group B *streptococcus*, *Haemophilus influenzae* polypeptide D, ovalbumin, keyhole limpet hemocyanin (KLH), bovine serum albumin (BSA), purified polypeptide derivative of tuberculin (PPD), PorB (from *N. meningitidis*), and derivatives, variants, or fragments thereof. In one embodiment, carrier polypeptide is not $CRM_{197}$.

In one embodiment, the polypeptide further includes a polypeptide sequence derived from pneumococcal bacteria. In one embodiment, isolated polypeptide does not include a polypeptide sequence derived from pneumococcal bacteria.

In one embodiment, the isolated polypeptide elicits a bactericidal antibody against a *N. meningitidis* serogroup B variant that is homologous with the ORF2086 polypeptide. In one embodiment, the isolated polypeptide elicits a bactericidal antibody against a *N. meningitidis* serogroup B variant that is heterologous to the ORF2086 polypeptide.

In one embodiment, the fusion polypeptide includes in the following order: the carrier polypeptide operably linked to the ORF2086 polypeptide. In one embodiment, the fusion polypeptide includes in the following order: an ORF2086 polypeptide operably linked to a carrier polypeptide. In one embodiment, the carrier polypeptide includes SEQ ID NO:

1 and the ORF2086 polypeptide includes SEQ ID NO: 5. In one embodiment, the isolated polypeptide includes SEQ ID NO: 2.

In a second aspect, the invention relates to an isolated polynucleotide that encodes a polypeptide according to any one of inventive polypeptides described herein.

In a third aspect, the invention relates to an immunogenic composition including a polypeptide according to any one of the inventive polypeptides described herein and a pharmaceutically acceptable excipient. In one embodiment, the immunogenic composition further includes at least one conjugate selected from: a) a conjugate of a capsular polysaccharide of *Neisseria meningitidis* serogroup A; b) a conjugate of a capsular polysaccharide of *Neisseria meningitidis* serogroup C; c) a conjugate of a capsular polysaccharide of *Neisseria meningitidis* serogroup W135; and d) a conjugate of a capsular polysaccharide of *Neisseria meningitidis* serogroup Y.

In a fourth aspect, the invention relates to a method for inducing an immune response against *Neisseria meningitidis* in a mammal. The method includes administering to the mammal an effective amount of the isolated polypeptide according to any of the embodiments described herein. In one embodiment, the immune response includes a bactericidal antibody. In one embodiment, the immune response is equal to an immune response of a mammal administered with a corresponding non-lipidated ORF2086 polypeptide in the absence of a carrier polypeptide, when assessed under identical conditions. In one embodiment, the immune response is greater than an immune response of a mammal administered with a corresponding non-lipidated ORF2086 polypeptide in the absence of a carrier polypeptide, when assessed under identical conditions. In one embodiment, the immune response is at most 10% less than an immune response of a mammal administered with a corresponding lipidated ORF2086 polypeptide in the absence of a carrier polypeptide, when assessed under identical conditions. In one embodiment, the immune response is at most 20% less than an immune response of a mammal administered with a corresponding lipidated ORF2086 polypeptide in the absence of a carrier polypeptide, when assessed under identical conditions.

In a fifth aspect, the invention relates to a method for inducing an immune response against *Neisseria meningitidis* in a mammal. The method includes administering to the mammal an effective amount of the immunogenic composition described herein. In one embodiment, the immune response includes a bactericidal antibody. In one embodiment, the immune response is equal to an immune response of a mammal administered with a corresponding lipidated ORF2086 polypeptide in the absence of a carrier polypeptide, when assessed under identical conditions. In one embodiment, the immune response is greater than an immune response of a mammal administered with a corresponding non-lipidated ORF2086 polypeptide in the absence of a carrier polypeptide, when assessed under identical conditions. In one embodiment, the immune response is at most 10% less than an immune response of a mammal administered with a corresponding lipidated ORF2086 polypeptide in the absence of a carrier polypeptide, when assessed under identical conditions. In one embodiment, the immune response is at most 20% less than an immune response of a mammal administered with a corresponding lipidated ORF2086 polypeptide in the absence of a carrier polypeptide, when assessed under identical conditions.

In a sixth aspect, the invention relates to an immunogenic composition including an ORF2086 polypeptide and a carrier polypeptide. In one embodiment, the composition is a conjugate. In one embodiment, the ORF2086 polypeptide is a subfamily A polypeptide. In one embodiment, the ORF2086 polypeptide is a subfamily B polypeptide. In one embodiment, the ORF2086 polypeptide is lipidated. In one embodiment, the ORF2086 polypeptide is non-lipidated. In one embodiment, the ORF2086 polypeptide is non-lipidated and non-pyruvylated. In one embodiment, the ORF2086 polypeptide is A05. In one embodiment, the ORF2086 polypeptide is A12. In one embodiment, the ORF2086 polypeptide is A22. In one embodiment, the ORF2086 polypeptide is B01. In one embodiment, the ORF2086 polypeptide is B09. In one embodiment, the ORF2086 polypeptide is B15. In one embodiment, the ORF2086 polypeptide is B16. In one embodiment, the ORF2086 polypeptide is B22. In one embodiment, the ORF2086 polypeptide is B24. In one embodiment, the ORF2086 polypeptide is B44. In one embodiment, the ORF2086 polypeptide is A62. In one embodiment, the ORF2086 polypeptide is A04. In one embodiment, the ORF2086 polypeptide is A01. In one embodiment, the ORF2086 polypeptide is A06. In one embodiment, the ORF2086 polypeptide is A07. In one embodiment, the ORF2086 polypeptide is A15. In one embodiment, the ORF2086 polypeptide is A19. In one embodiment, the ORF2086 polypeptide is A20. In one embodiment, the ORF2086 polypeptide is A29. In one embodiment, the ORF2086 polypeptide is B02. In one embodiment, the ORF2086 polypeptide includes the amino acid sequence selected from the group consisting of SEQ ID NOs: 5, 19, and 22-65.

In one embodiment, the carrier polypeptide is a cytolysoid. In one embodiment, the cytolysoid is derived from a pneumolysin polypeptide from *Streptococcus pneumoniae*, a perfringolysin O polypeptide from *Clostridium perfringens*, a intermedilysin polypeptide from *Streptococcus intermedius*, a alveolysin polypeptide from *Bacillus alvei*, a anthrolysin polypeptide from *Bacillus anthracis*, a putative cereolysin polypeptide from *Bacillus cereus*, a ivanolysin O polypeptide from *Listeria ivanovii*, a pyolysin polypeptide from *Arcanobacterium pyogenes*, a seeligeriolysin O polypeptide from *Listeria seeligeri*, a streptolysin O polypeptide from *S. pyogenes*, a suilysin polypeptide from *Streptococcus suis*, a tetanolysin polypeptide from *Clostridium tetani*, a listeriolysin O polypeptide from *Listeria monocytogenes*, a streptolysin O polypeptide from *Streptococcus equisimilis*, a streptolysin O polypeptide from *S. canis*, a thuringiolysin O polypeptide from *Bacillus thuringiensis*, a latersporolysin O polypeptide from *B. laterosporus*, a botulinolysin polypeptide from *Clostridium botulinum*, a chauveolysin polypeptide from *C. chauvoei*, a bifermentolysin polypeptide from *C. bifermentans*, a sordellilysin polypeptide from *C. sordellii*, a histolyticolysin polypeptide from *Clostridium histolyticum*, a novylysin polypeptide from *Clostridium novyi*, or a septicolysin O polypeptide from *Clostridium septicum*. In one embodiment, the cytolysoid is derived from a pneumolysin polypeptide from *Streptococcus pneumoniae*. In one embodiment, the cytolysoid includes a sequence having at least 90% sequence identity to SEQ ID NO: 1.

In one embodiment, the carrier polypeptide is detoxified as compared to the corresponding wild-type carrier polypeptide and is selected from the group consisting of tetanus toxin (TT), *Plasmodium falciparum* circumsporozite protein, hepatitis B surface antigen, hepatitis B nuclear core polypeptide, *H. influenzae* matrix polypeptide, *H. influenzae* haemagglutinin, diphtheria toxoid, diphtheria toxoid mutant CRM$_{197}$, group B *N. meningitidis* outer membrane polypeptide complex (OMPC), a cytolysoid, pneumococcal toxin pneumolysin, heat shock polypeptide from *Mycobacterium bovis*, heat shock polypeptide from *M. leprae*, cholera toxoid, *E. coli* LT, *E. coli* ST, exotoxin A from *Pseudomonas aeruginosa*, pneumococcal surface polypeptide A, pneumococcal adhesin polypeptide (PsaA), C5a peptidase from Group A or Group B *streptococcus*, *Haemophilus influenzae* polypeptide D, ovalbumin, keyhole limpet hemocyanin (KLH), bovine serum albumin (BSA), purified polypeptide derivative of tuberculin (PPD), PorB (from *N. meningitidis*), and derivatives, variants, or fragments thereof. In one embodiment, carrier polypeptide is CRM$_{197}$. In one embodiment, the carrier polypeptide is heterologous to the ORF2086 polypeptide.

In one embodiment, the composition further includes a polypeptide sequence derived from pneumococcal bacteria. In one embodiment, the composition does not include a polypeptide sequence derived from pneumococcal bacteria.

In one embodiment, the composition elicits a bactericidal antibody response against a *N. meningitidis* serogroup B strain expressing an ORF2086 variant that is homologous to the ORF2086 polypeptide. In one embodiment, the composition elicits a bactericidal antibody response against a *N. meningitidis* serogroup B strain expressing an ORF2086 variant that is heterologous to the ORF2086 polypeptide.

In one embodiment, the composition further includes at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135; and d) a conjugate of a capsular saccharide of *Neisseria meningitidis* serogroup Y. In one embodiment, the composition further includes a pharmaceutically acceptable excipient.

In a seventh aspect, the invention relates to a method for inducing an immune response against *Neisseria meningitidis* in a mammal. The method includes administering to the mammal an effective amount of the composition described herein. In one embodiment, the immune response includes a bactericidal antibody. In one embodiment, the immune response is equal to an immune response of a mammal administered with a corresponding lipidated ORF2086 polypeptide in the absence of a carrier polypeptide, when assessed under identical conditions. In one embodiment, the immune response is greater than an immune response of a mammal administered with a corresponding non-lipidated ORF2086 polypeptide in the absence of a carrier polypeptide, when assessed under identical conditions. In one embodiment, the immune response is at most 10% less than an immune response of a mammal administered with a corresponding lipidated ORF2086 polypeptide in the absence of a carrier polypeptide, when assessed under identical conditions. In one embodiment, the immune response is at most 20% less than an immune response of a mammal administered with a corresponding lipidated ORF2086 polypeptide in the absence of a carrier polypeptide, when assessed under identical conditions.

Figure 1:
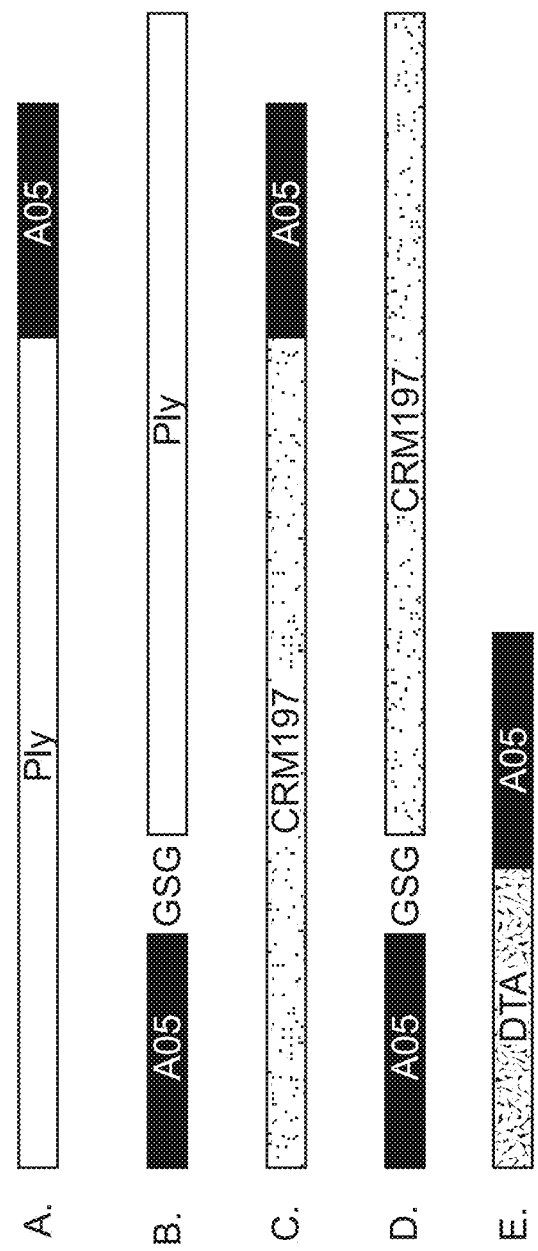
FIGS. 1A-E: Diagrammatic description of fusion polypeptides. A. Ply-A05 fusion; B A05-Ply fusion; C. CRM$_{197}$-A05 fusion; D. A05-CRM$_{197}$ fusion; E. DTA-A05 fusion.

SEQ ID NO: 23 sets forth the amino acid sequence for the *N. meningitidis*, serogroup B, 2086 variant A05, which includes an N-terminal Cys at amino acid position 1.

SEQ ID NO: 24 sets forth the amino acid sequence for the *N. meningitidis*, serogroup B, 2086 variant A04, which includes an N-terminal Cys at amino acid position 1.

SEQ ID NO: 25 sets forth the amino acid sequence for the *N. meningitidis*, serogroup B, 2086 variant A01, which includes an N-terminal Cys at amino acid position 1.

SEQ ID NO: 26 sets forth the amino acid sequence for the *N. meningitidis*, serogroup B, 2086 variant A06, which includes an N-terminal Cys at amino acid position 1.

SEQ ID NO: 27 sets forth the amino acid sequence for the *N. meningitidis*, serogroup B, 2086 variant A07, which includes an N-terminal Cys at amino acid position 1.

SEQ ID NO: 28 sets forth the amino acid sequence for the *N. meningitidis*, serogroup B, 2086 variant A12, which includes an N-terminal Cys at amino acid position 1.

SEQ ID NO: 29 sets forth the amino acid sequence for the *N. meningitidis*, serogroup B, 2086 variant A15, which includes an N-terminal Cys at amino acid position 1.

SEQ ID NO: 30 sets forth the amino acid sequence for the *N. meningitidis*, serogroup B, 2086 variant A19, which includes an N-terminal Cys at amino acid position 1.

SEQ ID NO: 31 sets forth the amino acid sequence for the *N. meningitidis*, serogroup B, 2086 variant A20, which includes an N-terminal Cys at amino acid position 1.

SEQ ID NO: 32 sets forth the amino acid sequence for the *N. meningitidis*, serogroup B, 2086 variant A29, which includes an N-terminal Cys at amino acid position 1.

SEQ ID NO: 33 sets forth the amino acid sequence for the *N. meningitidis*, serogroup B, 2086 variant B03, which includes an N-terminal Cys at amino acid position 1.

SEQ ID NO: 34 sets forth the amino acid sequence for the *N. meningitidis*, serogroup B, 2086 variant B02, which includes an N-terminal Cys at amino acid position 1.

SEQ ID NO: 35 sets forth the amino acid sequence for the *N. meningitidis*, serogroup B, 2086 variant B09, which includes an N-terminal Cys at amino acid position 1.

SEQ ID NO: 36 sets forth the amino acid sequence for the *N. meningitidis*, serogroup B, 2086 variant B15, which includes an N-terminal Cys at amino acid position 1.

SEQ ID NO: 37 sets forth the amino acid sequence for the *N. meningitidis*, serogroup B, 2086 variant B16, which includes an N-terminal Cys at amino acid position 1.

SEQ ID NO: 38 sets forth the amino acid sequence for the *N. meningitidis*, serogroup B, 2086 variant B22, which includes an N-terminal Cys at amino acid position 1.

SEQ ID NO: 39 sets forth the amino acid sequence for the *N. meningitidis*, serogroup B, 2086 variant B24, which includes an N-terminal Cys at amino acid position 1.

SEQ ID NO: 40 sets forth the amino acid sequence for the *N. meningitidis*, serogroup B, 2086 variant B44, which includes an N-terminal Cys at amino acid position 1.

SEQ ID NO: 41 sets forth the amino acid sequence for the *N. meningitidis*, serogroup B, 2086 variant A62, which includes an N-terminal Cys at amino acid position 1.

N-Terminal Cys is not Present

SEQ ID NO: 42 sets forth the amino acid sequence for the *N. meningitidis*, serogroup B, 2086 variant A01, which does not include an N-terminal Cys at amino acid position 1.

SEQ ID NO: 43 sets forth the amino acid sequence for the *N. meningitidis*, serogroup B, 2086 variant A04, which does not include an N-terminal Cys at amino acid position 1.

SEQ ID NO: 44 sets forth the amino acid sequence for the *N. meningitidis*, serogroup B, 2086 variant A05, which does not include an N-terminal Cys at amino acid position 1.

SEQ ID NO: 45 sets forth the amino acid sequence for the *N. meningitidis*, serogroup B, 2086 variant A06, which does not include an N-terminal Cys at amino acid position 1.

SEQ ID NO: 46 sets forth the amino acid sequence for the *N. meningitidis*, serogroup B, 2086 variant A07, which does not include an N-terminal Cys at amino acid position 1.

SEQ ID NO: 47 sets forth the amino acid sequence for the *N. meningitidis*, serogroup B, 2086 variant A12, which does not include an N-terminal Cys at amino acid position 1.

SEQ ID NO: 48 sets forth the amino acid sequence for the *N. meningitidis*, serogroup B, 2086 variant A15, which does not include an N-terminal Cys at amino acid position 1.

SEQ ID NO: 49 sets forth the amino acid sequence for the *N. meningitidis*, serogroup B, 2086 variant A19, which does not include an N-terminal Cys at amino acid position 1.

SEQ ID NO: 50 sets forth the amino acid sequence for the *N. meningitidis*, serogroup B, 2086 variant A20, which does not include an N-terminal Cys at amino acid position 1.

SEQ ID NO: 51 sets forth the amino acid sequence for the *N. meningitidis*, serogroup B, 2086 variant A22, which does not include an N-terminal Cys at amino acid position 1.

SEQ ID NO: 52 sets forth the amino acid sequence for the *N. meningitidis*, serogroup B, 2086 variant A29, which does not include an N-terminal Cys at amino acid position 1.

SEQ ID NO: 53 sets forth the amino acid sequence for the *N. meningitidis*, serogroup B, 2086 variant B01, which does not include an N-terminal Cys at amino acid position 1.

SEQ ID NO: 54 sets forth the amino acid sequence for the *N. meningitidis*, serogroup B, 2086 variant B02, which does not include an N-terminal Cys at amino acid position 1.

SEQ ID NO: 55 sets forth the amino acid sequence for the *N. meningitidis*, serogroup B, 2086 variant B09, which does not include an N-terminal Cys at amino acid position 1.

SEQ ID NO: 56 sets forth the amino acid sequence for the *N. meningitidis*, serogroup B, 2086 variant B15, which does not include an N-terminal Cys at amino acid position 1.

SEQ ID NO: 57 sets forth the amino acid sequence for the *N. meningitidis*, serogroup B, 2086 variant B16, which does not include an N-terminal Cys at amino acid position 1.

SEQ ID NO: 58 sets forth the amino acid sequence for the *N. meningitidis*, serogroup B, 2086 variant B22, which does not include an N-terminal Cys at amino acid position 1.

SEQ ID NO: 59 sets forth the amino acid sequence for the *N. meningitidis*, serogroup B, 2086 variant B24, which does not include an N-terminal Cys at amino acid position 1.

SEQ ID NO: 60 sets forth the amino acid sequence for the *N. meningitidis*, serogroup B, 2086 variant B44, which does not include an N-terminal Cys at amino acid position 1.

SEQ ID NO: 61 sets forth the amino acid sequence for the *N. meningitidis*, serogroup B, 2086 variant A62, which does not include an N-terminal Cys at amino acid position 1.

Modifications:

SEQ ID NO: 62 sets forth the amino acid sequence for the *N. meningitidis*, serogroup B, 2086 variant B09, wherein an N-terminal cysteine is not present and the sequence includes an additional Gly/Ser region, as compared to SEQ ID NO: 35.

SEQ ID NO: 63 sets forth the amino acid sequence for the *N. meningitidis*, serogroup B, 2086 variant B22, in which the N-terminal Cys at amino acid position 1 of SEQ ID NO: 38 is replaced with a Glycine.

SEQ ID NO: 64 sets forth the amino acid sequence for the *N. meningitidis*, serogroup B, 2086 variant A22, in which the N-terminal Cys at amino acid position 1 of SEQ ID NO: 22 is replaced with a Glycine.

SEQ ID NO: 65 sets forth a DNA sequence for a B22 gene, in which the codon for the N-terminal Cys at amino acid position 1 of SEQ ID NO: 38 is replaced with a codon for a Glycine.

Exemplary DNA Sequences Encoding ORF2086 Polypeptides

SEQ ID NO: 66 sets forth a DNA sequence for the *N. meningitidis*, serogroup B, 2086 variant A01 gene, which includes a codon encoding an N-terminal Cys.

SEQ ID NO: 67 sets forth a DNA sequence for the *N. meningitidis*, serogroup B, 2086 variant A29 gene, which includes a codon encoding an N-terminal Cys.

SEQ ID NO: 68 sets forth a DNA sequence for the *N. meningitidis*, serogroup B, 2086 variant A04 gene, which includes a codon encoding an N-terminal Cys.

SEQ ID NO: 69 sets forth a DNA sequence for the *N. meningitidis*, serogroup B, 2086 variant A05 gene, which includes a codon encoding an N-terminal Cys.

SEQ ID NO: 70 sets forth a DNA sequence for the *N. meningitidis*, serogroup B, 2086 variant A06 gene, which includes a codon encoding an N-terminal Cys.

SEQ ID NO: 71 sets forth a DNA sequence for the *N. meningitidis*, serogroup B, 2086 variant A07 gene, which includes a codon encoding an N-terminal Cys.

SEQ ID NO: 72 sets forth a DNA sequence for the *N. meningitidis*, serogroup B, 2086 variant A12 gene, which includes a codon encoding an N-terminal Cys.

SEQ ID NO: 73 sets forth a DNA sequence for the *N. meningitidis*, serogroup B, 2086 variant A15 gene, which includes a codon encoding an N-terminal Cys.

SEQ ID NO: 74 sets forth a DNA sequence for the *N. meningitidis*, serogroup B, 2086 variant A19 gene, which includes a codon encoding an N-terminal Cys.

SEQ ID NO: 75 sets forth a DNA sequence for the *N. meningitidis*, serogroup B, 2086 variant A20 gene, which includes a codon encoding an N-terminal Cys.

SEQ ID NO: 76 sets forth a DNA sequence for the *N. meningitidis*, serogroup B, 2086 variant A22 gene, which includes a codon encoding an N-terminal Cys.

SEQ ID NO: 77 sets forth a DNA sequence for the *N. meningitidis*, serogroup B, 2086 variant B01 gene, which includes a codon encoding an N-terminal Cys.

SEQ ID NO: 78 sets forth a DNA sequence for the *N. meningitidis*, serogroup B, 2086 variant B02 gene, which includes a codon encoding an N-terminal Cys.

SEQ ID NO: 79 sets forth a DNA sequence for the *N. meningitidis*, serogroup B, 2086 variant B44 gene, which includes a codon encoding an N-terminal Cys.

SEQ ID NO: 80 sets forth a DNA sequence for the *N. meningitidis*, serogroup B, 2086 variant B03 gene, which includes a codon encoding an N-terminal Cys.

SEQ ID NO: 81 sets forth a DNA sequence for the *N. meningitidis*, serogroup B, 2086 variant B09 gene, which includes a codon encoding an N-terminal Cys.

SEQ ID NO: 82 sets forth a DNA sequence for the *N. meningitidis*, serogroup B, 2086 variant B15 gene, which includes a codon encoding an N-terminal Cys.

SEQ ID NO: 83 sets forth a DNA sequence for the *N. meningitidis*, serogroup B, 2086 variant B16 gene, which includes a codon encoding an N-terminal Cys.

SEQ ID NO: 84 sets forth a DNA sequence for the *N. meningitidis*, serogroup B, 2086 variant B22 gene, which includes a codon encoding an N-terminal Cys.

SEQ ID NO: 85 sets forth a DNA sequence for the *N. meningitidis*, serogroup B, 2086 variant B24 gene, which includes a codon encoding an N-terminal Cys.

SEQ ID NO: 86 sets forth a DNA sequence for a *N. meningitidis*, serogroup B, 2086 variant A05 gene, wherein the codon encoding an N-terminal cysteine is deleted, as compared to SEQ ID NO: 69.

SEQ ID NO: 87 sets forth a DNA sequence for the *N. meningitidis*, serogroup B, 2086 variant A12-2 gene, which includes a codon encoding an N-terminal Cys.

Carrier Polypeptides

SEQ ID NO: 88 sets forth the amino acid sequence for a wild-type Pneumolysin from *Streptococcus pneumoniae*.

SEQ ID NO: 89 sets forth the amino acid sequence for a wild-type Perfringolysin O from *Clostridium perfringens*.

SEQ ID NO: 90 sets forth the amino acid sequence for a wild-type Intermedilysin from *Streptococcus intermedius*.

SEQ ID NO: 91 sets forth the amino acid sequence for a wild-type Alveolysin from *Bacillus alvei*.

SEQ ID NO: 92 sets forth the amino acid sequence for a wild-type Anthrolysin from *Bacillus anthracis*.

SEQ ID NO: 93 sets forth the amino acid sequence for a wild-type Putative Cereolysin from *Bacillus cereus*.

SEQ ID NO: 94 sets forth the amino acid sequence for a wild-type Ivanolysin O from *Listeria ivanovii*.

SEQ ID NO: 95 sets forth the amino acid sequence for a wild-type Pyolysin from *Arcanobacterium pyogenes*.

SEQ ID NO: 96 sets forth the amino acid sequence for a wild-type Seeligeriolysin O from *Listeria seeligeri*.

SEQ ID NO: 97 sets forth the amino acid sequence for a wild-type Streptolysin O from *Streptococcus pyogenes*.

SEQ ID NO: 98 sets forth the amino acid sequence for a wild-type Suilysin from *Streptococcus suis*.

SEQ ID NO: 99 sets forth the amino acid sequence for a wild-type Tetanolysin from *Clostridium tetani*.

SEQ ID NO: 100 sets forth the amino acid sequence for a wild-type Listeriolysin O from *Listeria monocytogenes*.

SEQ ID NO: 101 sets forth the amino acid sequence for a wild-type Thuringiolysin from *Bacillus thuringiensis* (previously annotated as perfringolysin).

SEQ ID NO: 102 sets forth the amino acid sequence for a region of the wild-type Pneumolysin from *Streptococcus pneumoniae* that includes a consensus sequence corresponding to residues 144 to 161 of wild-type pneumolysin.

SEQ ID NO: 103 sets forth the amino acid sequence for a region of the wild-type Perfringolysin O from *Clostridium perfringens* that includes a consensus sequence corresponding to residues 144 to 161 of wild-type pneumolysin.

SEQ ID NO: 104 sets forth the amino acid sequence for a region of the wild-type Intermedilysin from *Streptococcus intermedius* that includes a consensus sequence corresponding to residues 144 to 161 of wild-type pneumolysin.

SEQ ID NO: 105 sets forth the amino acid sequence for a region of the wild-type Alveolysin from *Bacillus alvei* that includes a consensus sequence corresponding to residues 144 to 161 of wild-type pneumolysin.

SEQ ID NO: 106 sets forth the amino acid sequence for a region of the wild-type Anthrolysin from *Bacillus anthracis* that includes a consensus sequence corresponding to residues 144 to 161 of wild-type pneumolysin.

SEQ ID NO: 107 sets forth the amino acid sequence for a region of the wild-type Putative Cereolysin from *Bacillus cereus* that includes a consensus sequence corresponding to residues 144 to 161 of wild-type pneumolysin.

SEQ ID NO: 108 sets forth the amino acid sequence for a region of the wild-type Ivanolysin O from *Listeria ivanovii* that includes a consensus sequence corresponding to residues 144 to 161 of wild-type pneumolysin.

SEQ ID NO: 109 sets forth the amino acid sequence for a region of the wild-type Perfringolysin O from *Clostridium perfringens* that includes a consensus sequence corresponding to residues 144 to 161 of wild-type pneumolysin.

SEQ ID NO: 110 sets forth the amino acid sequence for a region of the wild-type Seeligeriolysin O from *Listeria seeligeri* that includes a consensus sequence corresponding to residues 144 to 161 of wild-type pneumolysin.

SEQ ID NO: 111 sets forth the amino acid sequence for a region of the wild-type Streptolysin O from *Streptococcus pyogenes* that includes a consensus sequence corresponding to residues 144 to 161 of wild-type pneumolysin.

SEQ ID NO: 112 sets forth the amino acid sequence for a region of the wild-type suilysin from *Streptococcus suis* that includes a consensus sequence corresponding to residues 144 to 161 of wild-type pneumolysin.

SEQ ID NO: 113 sets forth the amino acid sequence for a region of the wild-type Tetanolysin from *Clostridium tetani* that includes a consensus sequence corresponding to residues 144 to 161 of wild-type pneumolysin.

SEQ ID NO: 114 sets forth the amino acid sequence for a region of the wild-type Listeriolysin O from *Listeria monocytogenes* that includes a consensus sequence corresponding to residues 144 to 161 of wild-type pneumolysin.

SEQ ID NO: 115 sets forth the amino acid sequence for a region of the wild-type Thuringiolysin from *Bacillus thuringiensis* (previously annotated as perfringolysin) that includes a consensus sequence corresponding to residues 144 to 161 of wild-type pneumolysin.

SEQ ID NO: 116 sets forth the amino acid sequence for a wild-type Perfringolysin O from *Clostridium perfringens*.

SEQ ID NO: 117 sets forth the amino acid sequence for a variant of the pneumolysoid that includes a mutation of the lysine at amino acid position 460 to an aspartic acid residue.

SEQ ID NO: 118 sets forth the amino acid sequence for a variant of a pneumolysoid. When compared to SEQ ID NO: 117, SEQ ID NO: 118 has an amino acid change from Lysine at position 208 to Arginine.

SEQ ID NO: 119 sets forth the amino acid sequence for an exemplary pneumolysoid that includes a substitution of asparagine in place of aspartic acid at amino acid position 385 and deletion of alanine 146 and arginine 147 of the wild-type pneumolysin sequence.

SEQ ID NO: 120 sets forth the amino acid sequence for an exemplary pneumolysoid that includes a substitution of phenylalanine in place of tryptophan at amino acid position 433 of the wild-type pneumolysin sequence.

Codon-Optimized Sequences

SEQ ID NO: 121 sets forth a codon-optimized DNA sequence for a B44 gene.

SEQ ID NO: 122 sets forth a codon-optimized DNA sequence for a B09 gene, wherein an N-terminal cysteine is not encoded, and wherein the sequence includes codons encoding an additional Gly/Ser region, as compared to SEQ ID NO: 81.

SEQ ID NO: 123 sets forth a codon-optimized DNA sequence for a B09 gene, wherein an N-terminal cysteine is not encoded.

SEQ ID NO: 124 sets forth a codon-optimized DNA sequence for a B09 gene, wherein an N-terminal cysteine is not encoded.

SEQ ID NO: 125 sets forth a codon-optimized DNA sequence encoding an A05 polypeptide.

SEQ ID NO: 126 sets forth a codon-optimized DNA sequence encoding an A05 polypeptide.

SEQ ID NO: 127 sets forth a codon-optimized DNA sequence encoding an A22 polypeptide.

SEQ ID NO: 128 sets forth a codon-optimized DNA sequence encoding an A62 polypeptide.

SEQ ID NO: 129 sets forth a codon-optimized DNA sequence encoding an A12 polypeptide.

Additional Sequences

SEQ ID NO: 130 sets forth the amino acid sequence for a B24 polypeptide. SEQ ID NO: 130 is identical to SEQ ID NO: 39 wherein the residues at positions 1-3 of SEQ ID NO: 39 are deleted.

SEQ ID NO: 131 sets forth a DNA sequence for an A22 polypeptide, in which the codon for the N-terminal Cys at amino acid position 1 of SEQ ID NO: 22 is replaced with a codon for a Glycine.

SEQ ID NO: 132 sets forth the amino acid sequence for an A22, in which the N-terminal Cys at amino acid position 1 of SEQ ID NO: 22 is replaced with a Glycine.

SEQ ID NO: 133 sets forth a DNA sequence for a B09 gene, wherein the codon encoding an N-terminal cysteine is not present.

SEQ ID NO: 134 sets forth a DNA sequence for a B44 gene, wherein the codon encoding an N-terminal cysteine is not present.

SEQ ID NO: 135 sets forth the amino acid sequence for a *N. meningitidis*, serogroup B, 2086 variant A05, wherein an N-terminal cysteine is not present.

SEQ ID NO: 136 sets forth the amino acid sequence for a pneumolysoid and non-lipidated A12 polypeptide (PLY-A12).

SEQ ID NO: 137 sets forth the amino acid sequence for a pneumolysoid and non-lipidated A12 polypeptide (PLY-A12), wherein the N-terminal methionine at position 1 of SEQ ID NO: 136 is removed.

SEQ ID NO: 138 sets forth the amino acid sequence for a pneumolysoid and non-lipidated B01 polypeptide (PLY-B01).

SEQ ID NO: 139 sets forth the amino acid sequence for a pneumolysoid and non-lipidated B01 polypeptide (PLY-B01), wherein the N-terminal methionine at position 1 of SEQ ID NO: 138 is removed.

SEQ ID NO: 140 sets forth the amino acid sequence for a pneumolysoid and non-lipidated B09 polypeptide (PLY-B09).

SEQ ID NO: 141 sets forth the amino acid sequence for a pneumolysoid and non-lipidated B09 polypeptide (PLY-B09), wherein the N-terminal methionine at position 1 of SEQ ID NO: 140 is removed.

SEQ ID NO: 142 sets forth the amino acid sequence for a pneumolysoid and non-lipidated B24 polypeptide (PLY-B24).

SEQ ID NO: 143 sets forth the amino acid sequence for a pneumolysoid and non-lipidated B24 polypeptide (PLY-B24), wherein the N-terminal methionine at position 1 of SEQ ID NO: 142 is removed.

SEQ ID NO: 144 sets forth the amino acid sequence for a pneumolysoid and non-lipidated B44 polypeptide (PLY-B44).

SEQ ID NO: 145 sets forth the amino acid sequence for a pneumolysoid and non-lipidated B44 polypeptide (PLY-B44), wherein the N-terminal methionine at position 1 of SEQ ID NO: 144 is removed.

SEQ ID NO: 146 sets forth the amino acid sequence for a GNA2091 polypeptide.

SEQ ID NO: 147 sets forth the amino acid sequence for a GNA2091 polypeptide, wherein the N-terminal methionine at position 1 of SEQ ID NO: 146 is removed.

SEQ ID NO: 148 sets forth the amino acid sequence for a GNA2091 and non-lipidated A05 polypeptide (GNA2091-A05).

SEQ ID NO: 149 sets forth the amino acid sequence for a GNA2091 and non-lipidated A05 polypeptide (GNA2091-A05), wherein the N-terminal methionine at position 1 of SEQ ID NO: 148 is removed.

SEQ ID NO: 150 sets forth the amino acid sequence for a streptococcal C5a peptidase (SCP) from *Streptococcus pyogenes*.

SEQ ID NO: 151 sets forth the amino acid sequence for an SCP, wherein the N-terminal methionine at position 1 of SEQ ID NO: 150 is removed.

SEQ ID NO: 152 sets forth the amino acid sequence for an SCP and non-lipidated A05 polypeptide (SCP-A05).

SEQ ID NO: 153 sets forth the amino acid sequence for an SCP and non-lipidated A05 polypeptide (SCP-A05), wherein the N-terminal methionine at position 1 of SEQ ID NO: 152 is removed.

SEQ ID NO: 154 sets forth the amino acid sequence for a $CRM_{197}$.

SEQ ID NO: 155 sets forth the amino acid sequence for a $CRM_{197}$, wherein the N-terminal methionine at position 1 of SEQ ID NO: 154 is removed.

SEQ ID NO: 156 sets forth the amino acid sequence for an A05 polypeptide as in SEQ ID NO: 5, wherein a cysteine is present at position 1.

SEQ ID NO: 157 sets forth the amino acid sequence for an A05 polypeptide as in SEQ ID NO: 5, wherein a cysteine is present at position 2.

SEQ ID NO: 158 sets forth the amino acid sequence for an A05 polypeptide as in SEQ ID NO: 5, wherein a cysteine is present at position 6.

DETAILED DESCRIPTION OF THE INVENTION

The inventors discovered, among other things, molecules and/or compositions including an ORF2086 polypeptide and a carrier polypeptide. The molecules and/or compositions may be made by genetic fusion or by conjugation or made synthetically.

The inventive polypeptides and conjugates of the invention surprisingly allow for effective induction of a broad immune response against *N. meningitidis*. In some embodiments, the fusion polypeptides and conjugates of the invention exhibit enhanced effectiveness in induction of an immune response against *N. meningitidis*, as compared to compositions including ORF2086 polypeptides in the absence of a carrier polypeptide. For example, the inventors discovered that the fusion polypeptides may provide broad coverage, e.g., eliciting bactericidal antibodies against multiple LP2086 variant strains even when the fusion polypeptide includes a ORF2086 polypeptide from one *N. meningitidis* strain. The enhanced effectiveness of the inventive compositions may allow for reduced doses or concentrations of ORF2086 polypeptides to be administered to a subject, as compared to compositions including ORF2086 polypeptides in the absence of a carrier polypeptide. The enhanced effectiveness of the inventive compositions also aids in minimizing cost of vaccine production, and allows for designs that provide efficacy to a broad range of serotypes.

A) Isolated Polypeptides and Fusion Polypeptides

In one aspect, the invention relates to an isolated polypeptide that includes the amino acid sequence of a carrier polypeptide and the amino acid sequence of an ORF2086 polypeptide. In one embodiment, the isolated polypeptide is a synthetically constructed polypeptide. In a preferred embodiment, the isolated polypeptide is a fusion polypeptide that includes operably linked polypeptides. At least one polypeptide component of a given isolated and/or fusion polypeptide includes a carrier polypeptide, or an active variant or fragment thereof, which is operably linked to an ORF2086 polypeptide or an active variant or fragment thereof.

As used herein, a "fusion polypeptide" or "fusion protein" refers to a polypeptide having an in-frame genetic linkage of at least two polypeptides. Upon transcription/translation, a single polypeptide is made. Accordingly, multiple polypeptides, or fragments thereof, may be incorporated into a single polypeptide. Multiple forms of fusion polypeptides are disclosed herein and discussed in detail below.

"Operably linked" refers to a functional linkage between two or more elements. For example, an operable linkage between two polypeptides may fuse both polypeptides together in-frame to produce a single fusion polypeptide. In one embodiment, the ORF2086 polypeptide and the carrier polypeptide are fused in-frame to each other.

1) ORF2086 Polypeptide.

The isolated polypeptide may include any ORF2086 polypeptide. In one embodiment, the ORF2086 polypeptide is a subfamily A polypeptide. In one embodiment, the ORF2086 polypeptide is a subfamily B polypeptide. In one embodiment, the ORF2086 polypeptide is lipidated. In one embodiment, the ORF2086 polypeptide is non-lipidated. In one embodiment, the ORF2086 polypeptide is non-lipidated and non-pyruvylated. In one embodiment, the ORF2086 polypeptide is A04. In one embodiment, the ORF2086 polypeptide is A05. In one embodiment, the ORF2086 polypeptide is A06. In one embodiment, the ORF2086 polypeptide is A07. In one embodiment, the ORF2086 polypeptide is A12. In one embodiment, the ORF2086 polypeptide is A15. In one embodiment, the ORF2086 polypeptide is A19. In one embodiment, the ORF2086 polypeptide is A20. In one embodiment, the ORF2086 polypeptide is A01. In one embodiment, the ORF2086 polypeptide is A22. In one embodiment, the ORF2086 polypeptide is A29. In one embodiment, the ORF2086 polypeptide is B01. In one embodiment, the ORF2086 polypeptide is B02. In one embodiment, the ORF2086 polypeptide is B09. In one embodiment, the ORF2086 polypeptide is B15. In one embodiment, the ORF2086 polypeptide is B16. In one embodiment, the ORF2086 polypeptide is B22. In one embodiment, the ORF2086 polypeptide is B24. In one embodiment, the ORF2086 polypeptide is B44. In one embodiment, the ORF2086 polypeptide is A62. Preferably, the ORF2086 polypeptide is A05. ORF2086 polypeptides are described in more detail below. ORF2086 polypeptides are described in WO2012032489 and US Patent Publication number US20120093852, each of which is incorporated herein by reference in its entirety. ORF2086 polypeptides are also described in WO2013132452 and US patent publication number US20130243807, each of which is incorporated herein by reference in its entirety.

2) Carrier Polypeptide.

The isolated polypeptide may include any carrier polypeptide. Preferably, the carrier polypeptide is detoxified or exhibits decreased toxicity as compared to the corresponding wild-type carrier polypeptide. In one embodiment, the carrier polypeptide is a cytolysoid. In a preferred embodiment, the cytolysoid is derived from a pneumolysin polypeptide from *Streptococcus pneumoniae*, a perfringolysin O polypeptide from *Clostridium perfringens*, a intermedilysin polypeptide from *Streptococcus intermedius*, a alveolysin polypeptide from *Bacillus alvei*, a anthrolysin polypeptide from *Bacillus anthracis*, a putative cereolysin polypeptide from *Bacillus cereus*, an ivanolysin O polypeptide from *Listeria ivanovii*, a pyolysin polypeptide from *Arcanobacterium pyogenes*, a seeligeriolysin O polypeptide from *Listeria seeligeri*, a streptolysin O polypeptide from *Streptococcus pyogenes*, a suilysin polypeptide from *Streptococcus suis*, a tetanolysin polypeptide from *Clostridium tetani*, a listeriolysin O polypeptide from *Listeria monocytogenes*, a streptolysin O polypeptide from *Streptococcus equisimilis*, a streptolysin O polypeptide from *S. canis*, a thuringiolysin O polypeptide from *Bacillus thuringiensis*, a latersporolysin O polypeptide from *B. laterosporus*, a botulinolysin polypeptide from *Clostridium botulinum*, a chauveolysin polypeptide from *Clostridium chauvoei*, a bifermentolysin polypeptide from *C. bifermentans*, a sordellilysin polypeptide from *Clostridium sordellii*, a histolyticolysin polypeptide from *Clostridium histiolyticum*, a novylysin polypeptide from *Clostridium novyi*, or a septicolysin O polypeptide from *Clostridium septicum*.

Additional examples of a carrier protein include streptococcal C5a peptidase (SCP) from *Streptococcus pyogenes*, GNA2091 (also known as accessory protein 936) from *Neisseria*, and $CRM_{197}$. Further examples and descriptions of carrier proteins are provided below in section C.

In a preferred embodiment, the cytolysoid is derived from a pneumolysin polypeptide from *Streptococcus pneumoniae*. In a more preferred embodiment, the cytolysoid includes a sequence having at least 50%, 60%, 70%, 80%, 90%, 91%, 92%, 93%, 94%, 95%, 96% 97%, 98%, 99%, or greater sequence identity to SEQ ID NO: 1. In a most preferred embodiment, the cytolysoid includes SEQ ID NO: 1.

In another embodiment, the carrier polypeptide is detoxified or exhibits decreased toxicity as compared to the corresponding wild-type carrier polypeptide, and is selected from the group consisting of tetanus toxin (TT), *Plasmodium falciparum* circumsporozite protein, hepatitis B surface antigen, hepatitis B nuclear core polypeptide, *H. influenzae* matrix polypeptide, *H. influenzae* haemagglutinin, diphtheria toxoid, diphtheria toxoid mutant $CRM_{197}$, group B *N. meningitidis* outer membrane polypeptide complex (OMPC), a cytolysoid, pneumococcal toxin pneumolysin, heat shock polypeptide from *Mycobacterium bovis*, heat shock polypeptide from *M. leprae*, cholera toxoid, *E. coli* LT, *E. coli* ST, exotoxin A from *Pseudomonas aeruginosa*, pneumococcal surface polypeptide A, pneumococcal adhesin polypeptide (PsaA), C5a peptidase from Group A or Group B *streptococcus, Haemophilus influenzae* polypeptide D, ovalbumin, keyhole limpet hemocyanin (KLH), bovine serum albumin (BSA), purified polypeptide derivative of tuberculin (PPD), PorB (from *N. meningitidis*), and derivatives, variants, or fragments thereof.

In one embodiment, the fusion polypeptide does not include $CRM_{197}$. Carrier polypeptides are described in more detail below.

3) Assembly:

The fusion polypeptide may be direct, i.e., in the absence of an empirical linker molecule, or the fusion may be through a linker molecule. For example, the fusion polypeptide may include polypeptide components such as a linker peptide between the polypeptides of the fusion polypeptide, or a peptide tag for affinity purification (for example at the N- or C-terminus). Exemplary linker peptides include a Gly-Ser-Gly (GSG) linker. A linker molecule may include one or more amino acid residues, typically from about 2 to about 30 amino acid residues, preferably 3 to 25 residues. In a preferred embodiment, the fusion polypeptide does not include a linker peptide. An exemplary fusion polypeptide that does not include a linker is a fusion polypeptide that includes in the following order a carrier polypeptide and an ORF2086 polypeptide, such as, for example, in SEQ ID NO: 2. Additional examples include PLY-A12 (SEQ ID NO: 127), PLY-B01 (SEQ ID NO: 139), PLY-B09 (SEQ ID NO: 141), PLY-B24 (SEQ ID NO: 143), PLY-B44 (SEQ ID NO: 145), GNA2091-A05 (SEQ ID NO: 149), and SCP-A05 (SEQ ID NO: 153).

The fusion polypeptide may be assembled in various combinations. The carrier polypeptide may be at either at the N-terminal or C-terminal end of the fusion polypeptide, or it may be flanked by immunogenic bacterial polypeptides, e.g., flanked by ORF2086 polypeptides. The ORF2086 polypeptide may be fused to the N-terminus or C-terminus of the carrier polypeptide. For example, in one embodiment, the fusion polypeptide includes in the following order: the carrier polypeptide operably linked to the ORF2086 polypeptide. In a preferred embodiment, the fusion polypeptide does not include a linker when the carrier polypeptide is operably linked to the ORF2086 polypeptide in said order. In such preferred embodiments, the native stalk region of the ORF2086 polypeptide may serve as a linker between the polypeptides. Stalk regions of an ORF2086 polypeptide are described in WO2012032489 and US Patent Publication No. US20120093852, each of which is incorporated herein by reference in its entirety.

In another embodiment, the fusion polypeptide includes in the following order: an ORF2086 polypeptide operably linked to a carrier polypeptide. In a preferred embodiment, the fusion polypeptide includes a linker when the carrier polypeptide is operably linked to the ORF2086 polypeptide in said order.

In one embodiment, the fusion polypeptide includes one ORF2086 polypeptide linked to one carrier polypeptide, but other conformations are within the scope of the invention. For example, in another embodiment, the fusion polypeptide includes at most 1, 2, 3, 4, or 5 immunogenic bacterial polypeptides. In another embodiment, the fusion polypeptide includes at most 1, 2, 3, 4, or 5 carrier polypeptides.

In some embodiments, the fusion polypeptide further comprises a third or additional polypeptides. The source of the third or additional polypeptides may include, but is not limited to, *N. meningitidis*. In one embodiment, a third polypeptide is fused in-frame to the ORF2086 polypeptide or to the carrier polypeptide. In another embodiment, when multiple carrier polypeptides or variants or fragments thereof are included in the fusion polypeptide, the third polypeptide may be located at the N-terminal or C-terminal end of the fusion polypeptide, or it may be located internally in the fusion polypeptide so that it is flanked by carrier protein polypeptides. In one embodiment, the fusion polypeptide includes a polypeptide sequence derived from pneumococcal bacteria. In another embodiment, the fusion polypeptide does not include a polypeptide sequence derived from pneumococcal bacteria.

Preferably, the fusion polypeptide includes polypeptides that are derived from bacterial species that are different from the bacterial species from which the carrier polypeptide is derived. Accordingly, in one embodiment, the carrier protein is heterologous to the ORF2086 polypeptide and to any additional polypeptides included in the fusion polypeptide. "Heterologous" in reference to a polypeptide is a polypeptide that originates from a different protein and/or from a different bacterial species.

4) Exemplary Isolated and/or Fusion Polypeptides—

In one aspect, the invention relates to an isolated polypeptide that includes the amino acid sequence for a pneumolysoid (such as, e.g., SEQ ID NO: 1) and a non-lipidated ORF2086 polypeptide (such as, e.g., any one polypeptide having the amino acid sequence selected from SEQ ID NO: 42-61, and any one polypeptide described in section D "ORF Polypeptides" below). For example, in one embodiment, the isolated polypeptide includes a pneumolysoid (SEQ ID NO: 1) and a non-lipidated A12 (SEQ ID NO: 47) to produce PLY-A12 (SEQ ID NO: 136). In another embodiment, the isolated polypeptide includes a pneumolysoid (SEQ ID NO: 1) and a non-lipidated B01 (SEQ ID NO: 53) to produce PLY-B01 (SEQ ID NO: 138). In another embodiment, the isolated polypeptide includes a pneumolysoid (SEQ ID NO: 1) and a non-lipidated B09 (SEQ ID NO: 55) to produce PLY-B09 (SEQ ID NO: 140). In another embodiment, the isolated polypeptide includes a pneumolysoid (SEQ ID NO: 1) and a non-lipidated B24 (SEQ ID NO: 59) to produce PLY-B24 (SEQ ID NO: 142). In another embodiment, the isolated polypeptide includes a pneumolysoid (SEQ ID NO: 1) and a non-lipidated B44 (SEQ ID NO: 60) to produce PLY-B44 SEQ ID NO: 144).

a) PLY and A05:

In one aspect, the invention relates to an isolated polypeptide that includes the amino acid sequence for a pneumolysoid and a non-lipidated A05 polypeptide. In one embodiment, the pneumolysoid includes the amino acid sequence set forth in SEQ ID NO: 1. Preferably, the pneumolysoid is encoded by a DNA sequence set forth in SEQ ID NO: 3. In one embodiment, the A05 polypeptide includes the amino acid sequence set forth in SEQ ID NO: 5. In one embodiment, the isolated polypeptide is a fusion polypeptide.

In one embodiment, the fusion polypeptide includes in the following order: the carrier polypeptide operably linked to the ORF2086 polypeptide. For example, in one embodiment, the fusion polypeptide includes the amino acid sequence set forth in SEQ ID NO: 2 (PLY-A05). In one embodiment, the fusion polypeptide is encoded by a DNA sequence set forth in SEQ ID NO: 4.

In another embodiment, the fusion polypeptide includes in the following order: the ORF2086 polypeptide operably linked to the carrier polypeptide. For example, in one embodiment, the fusion polypeptide includes the amino acid sequence set forth in SEQ ID NO: 8 (A05-PLY). In one embodiment, the fusion polypeptide is encoded by a DNA sequence set forth in SEQ ID NO: 7.

In another embodiment, the fusion polypeptide further includes a linker peptide. In one embodiment, the linker includes a Gly-Ser-Gly (GSG) peptide. The fusion polypeptide having the amino acid sequence set forth in SEQ ID NO: 8 includes a GSG linker.

b) $CRM_{197}$ and A05:

In one aspect, the invention relates to an isolated polypeptide that includes the amino acid sequence for $CRM_{197}$ (such as, e.g., SEQ ID NO: 155) and a non-lipidated ORF2086 polypeptide (such as, e.g., any one polypeptide having the amino acid sequence selected from SEQ ID NO: 42-61, and any one polypeptide described in section D "ORF Polypeptides" below).

In one aspect, the invention relates to an isolated polypeptide that includes the amino acid sequence for $CRM_{197}$ and a non-lipidated A05 polypeptide. In one embodiment, $CRM_{197}$ includes the amino acid sequence set forth in SEQ ID NO: 10. In another embodiment, $CRM_{197}$ includes the amino acid sequence set forth in SEQ ID NO: 155. Preferably, $CRM_{197}$ is encoded by a DNA sequence set forth in SEQ ID NO: 9. In one embodiment, the A05 polypeptide includes the amino acid sequence set forth in SEQ ID NO: 5. In one embodiment, the isolated polypeptide is a fusion polypeptide.

In one embodiment, the fusion polypeptide includes in the following order: the carrier polypeptide operably linked to the ORF2086 polypeptide. For example, in one embodiment, the fusion polypeptide includes the amino acid sequence set forth in SEQ ID NO: 14 ($CRM_{197}$-A05). In one embodiment, the fusion polypeptide is encoded by a DNA sequence set forth in SEQ ID NO: 13.

In another embodiment, the fusion polypeptide includes in the following order: the ORF2086 polypeptide operably linked to the carrier polypeptide. For example, in one embodiment, the fusion polypeptide includes the amino acid sequence set forth in SEQ ID NO: 16 (A05-$CRM_{197}$). In one embodiment, the fusion polypeptide is encoded by a DNA sequence set forth in SEQ ID NO: 15.

In a further embodiment, the fusion polypeptide further includes a linker peptide. In one embodiment, the linker includes a Gly-Ser-Gly (GSG) peptide. The fusion polypeptide having the amino acid sequence set forth in SEQ ID NO: 16 includes a GSG linker.

In one aspect, the invention relates to an isolated polypeptide that includes the amino acid sequence for a fragment of $CRM_{197}$ and a non-lipidated A05 polypeptide. In one embodiment, the fragment of $CRM_{197}$ (e.g., amino acid residues 1-193 of $CRM_{197}$ shown in SEQ ID NO: 10; DT-A region) includes the amino acid sequence set forth in SEQ ID NO: 12. Preferably, the fragment of $CRM_{197}$ is encoded by a DNA sequence set forth in SEQ ID NO: 11. In one embodiment, the A05 polypeptide includes the amino acid sequence set forth in SEQ ID NO: 5. In one embodiment, the isolated polypeptide is a fusion polypeptide.

In one embodiment, the fusion polypeptide includes in the following order: the fragment of $CRM_{197}$ operably linked to the ORF2086 polypeptide. For example, in one embodiment, the fusion polypeptide includes the amino acid sequence set forth in SEQ ID NO: 18 (DT-A-A05). In one embodiment, the fusion polypeptide is encoded by a DNA sequence set forth in SEQ ID NO: 17.

c) GNA2091 and A05:

In one aspect, the invention relates to an isolated polypeptide that includes the amino acid sequence for GNA2091 (such as, e.g., SEQ ID NO: 147) and a non-lipidated ORF2086 polypeptide (such as, e.g., any one polypeptide having the amino acid sequence selected from SEQ ID NO: 42-61, and any one polypeptide described in section D "ORF Polypeptides" below).

In one aspect, the invention relates to an isolated polypeptide that includes the amino acid sequence for GNA2091 and a non-lipidated A05 polypeptide. In one embodiment, GNA2091 includes the amino acid sequence set forth in SEQ ID NO: 147. In one embodiment, the A05 polypeptide includes the amino acid sequence set forth in SEQ ID NO: 5. In one embodiment, the isolated polypeptide is a fusion polypeptide.

In one embodiment, the fusion polypeptide includes in the following order: the GNA2091 operably linked to the ORF2086 polypeptide. For example, in one embodiment, the fusion polypeptide includes the amino acid sequence set forth in SEQ ID NO: 149 (GNA2091-A05).

d) SCP and A05:

In one aspect, the invention relates to an isolated polypeptide that includes the amino acid sequence for SCP (such as, e.g., SEQ ID NO: 151) and a non-lipidated ORF2086 polypeptide (such as, e.g., any one polypeptide having the amino acid sequence selected from SEQ ID NO: 42-61, and any one polypeptide described in section D "ORF Polypeptides" below).

In one aspect, the invention relates to an isolated polypeptide that includes the amino acid sequence for SCP and a non-lipidated A05 polypeptide. In one embodiment, SCP includes the amino acid sequence set forth in SEQ ID NO: 151. In one embodiment, the A05 polypeptide includes the amino acid sequence set forth in SEQ ID NO: 5. In one embodiment, the isolated polypeptide is a fusion polypeptide.

In one embodiment, the fusion polypeptide includes in the following order: the SCP operably linked to the ORF2086 polypeptide. For example, in one embodiment, the fusion polypeptide includes the amino acid sequence set forth in SEQ ID NO: 153 (SCP-A05).

5) Immunogenic Compositions Including a Fusion Polypeptide:

In one aspect, the invention relates to an immunogenic composition including an isolated and/or fusion polypeptide as described above. The immunogenic composition further includes a pharmaceutically acceptable excipient.

In one embodiment, the immunogenic composition further includes at least one conjugate selected from: a) a conjugate of a capsular saccharide of Neisseria meningitidis serogroup A; b) a conjugate of a capsular saccharide of Neisseria meningitidis serogroup C; c) a conjugate of a capsular saccharide of Neisseria meningitidis serogroup W135; and d) a conjugate of a capsular saccharide of Neisseria meningitidis serogroup Y. Such conjugates of a capsular saccharide of Neisseria meningitidis are known in the art. Descriptions of N. meningitidis capsular saccharide conjugates and polysaccharide conjugates are described below.

6) Immune Responses:

In one aspect, the fusion polypeptide induces an immune response against N. meningitidis in a mammal. In one embodiment, the fusion polypeptide induces a bactericidal antibody against a N. meningitidis serogroup B strain expressing an ORF2086 variant that is homologous to the ORF2086 polypeptide. For example, a fusion polypeptide including a carrier protein and an A05 polypeptide may induce a bactericidal antibody against an N. meningitidis serogroup B A05-expressing strain. In another embodiment, the fusion polypeptide induces a bactericidal antibody response against a N. meningitidis serogroup B strain expressing an ORF2086 variant that is heterologous to the ORF2086 polypeptide. For example, a fusion polypeptide including a carrier protein and an A05 polypeptide may induce a bactericidal antibody response against an N. meningitidis serogroup B A22-expressing strain.

Surprisingly, the inventors discovered that a fusion polypeptide that includes a non-lipidated ORF2086 polypeptide and a carrier polypeptide may induce an immune response in a mammal that is better than the immune response induced by a composition that includes a non-lipidated form of the same ORF2086 polypeptide in the absence of the carrier polypeptide, when assessed under identical conditions.

In one embodiment, the immune response induced by the fusion polypeptide is equal to the immune response in a mammal administered with a corresponding non-lipidated ORF2086 polypeptide in the absence of a carrier polypeptide, when assessed under identical conditions.

In another embodiment, the immune response induced by the fusion polypeptide is equal to the immune response in a mammal administered with a corresponding lipidated ORF2086 polypeptide in the absence of a carrier polypeptide, when assessed under identical conditions.

In one embodiment, the immune response induced by the fusion polypeptide is greater than the immune response in a mammal administered with a corresponding non-lipidated ORF2086 polypeptide in the absence of a carrier polypeptide, when assessed under identical conditions. For example, the immune response induced by the inventive polypeptide may be greater by at least 1%, 5%, 10%, 20%, 30%, 40%, 50%, or more.

In another embodiment, the immune response induced by the fusion polypeptide is greater than the immune response in a mammal administered with a corresponding lipidated ORF2086 polypeptide in the absence of a carrier polypeptide, when assessed under identical conditions. For example, the immune response induced by the inventive polypeptide may be greater by at least 1%, 5%, 10%, 20%, 30%, 40%, 50%, or more.

In another embodiment, the immune response to the fusion polypeptide is at most 30%, 25%, 20%, 15%, 10%, or 5% less than the immune response in a mammal administered with a corresponding lipidated ORF2086 polypeptide in the absence of a carrier polypeptide, when assessed under identical conditions.

In a further aspect, the invention relates to a method for inducing an immune response against Neisseria meningitidis in a mammal. The immune response may be against any one N. meningitidis serogroup or a combination of N. meningitidis serogroups (e.g., A, B, C, W135, X, and/or Y). The method includes administering to the mammal an effective amount of the isolated polypeptide as described. In one embodiment, the isolated polypeptide includes a fusion polypeptide as described above. In another embodiment, the method includes administering to the mammal an effective amount of an immunogenic composition that includes an isolated and/or fusion polypeptide as described. The immune response induced by the method may include a bactericidal antibody. Bactericidal antibody responses are described below.

B) Conjugates

In one aspect, the invention relates to an immunogenic composition including an ORF2086 polypeptide and a carrier polypeptide. In one embodiment, the immunogenic composition includes a conjugate of an ORF2086 polypeptide linked to a carrier polypeptide. The polypeptides may be linked via any bond such that the polypeptides are stable under physiological conditions. In one embodiment, the polypeptides are linked by covalent bonds. In another embodiment, the polypeptides are linked by non-covalent bonds. The conjugates may be prepared using methods known in the art.

1) ORF2086 Polypeptide.

The conjugate may include any ORF2086 polypeptide. In one embodiment, the ORF2086 polypeptide is a subfamily A polypeptide. In one embodiment, the ORF2086 polypeptide is a subfamily B polypeptide. In one embodiment, the ORF2086 polypeptide is lipidated. In one embodiment, the ORF2086 polypeptide is non-lipidated. In one embodiment, the ORF2086 polypeptide is non-lipidated and non-pyruvylated. In one embodiment, the ORF2086 polypeptide is A04. In one embodiment, the ORF2086 polypeptide is A05. In one embodiment, the ORF2086 polypeptide is A06. In one embodiment, the ORF2086 polypeptide is A07. In one embodiment, the ORF2086 polypeptide is A12. In one embodiment, the ORF2086 polypeptide is A15. In one embodiment, the ORF2086 polypeptide is A19. In one embodiment, the ORF2086 polypeptide is A20. In one embodiment, the ORF2086 polypeptide is A01. In one embodiment, the ORF2086 polypeptide is A22. In one embodiment, the ORF2086 polypeptide is A29. In one embodiment, the ORF2086 polypeptide is B01. In one embodiment, the ORF2086 polypeptide is B02. In one embodiment, the ORF2086 polypeptide is B09. In one embodiment, the ORF2086 polypeptide is B15. In one embodiment, the ORF2086 polypeptide is B16. In one embodiment, the ORF2086 polypeptide is B22. In one embodiment, the ORF2086 polypeptide is B24. In one embodiment, the ORF2086 polypeptide is B44. In one embodiment, the ORF2086 polypeptide is A62. Preferably, the ORF2086 polypeptide is A05. ORF2086 polypeptides are described in more detail below.

In a preferred embodiment, the ORF2086 polypeptide is a non-pyruvylated, non-lipidated ORF2086 polypeptide, as described in WO2013132452 and US patent publication number US20130243807, each of which is incorporated herein by reference in its entirety. The term "non-pyruvylated" refers to a polypeptide having no pyruvate content. Non-lipidated ORF2086 polypeptides having a pyruvate content typically exhibited a mass shift of +70 or +71, as compared to the corresponding wild-type polypeptide. In one embodiment, the inventive polypeptide does not exhibit a mass shift of +70 or +71 as compared to the corresponding wild-type non-lipidated polypeptide when measured by mass spectrometry. In another embodiment, the inventive polypeptide does not exhibit a mass shift of +70 or +71 as compared to the corresponding non-lipidated polypeptide that has an initial cysteine at position 1 of the N-terminus when measured by mass spectrometry.

2) Carrier Polypeptide.

The conjugate may include any carrier polypeptide. Preferably, the carrier polypeptide is detoxified or exhibits decreased toxicity as compared to the corresponding wild-type carrier polypeptide. In one embodiment, the carrier polypeptide is a cytolysoid. In a preferred embodiment, the cytolysoid is derived from a pneumolysin polypeptide from *Streptococcus pneumoniae*, a perfringolysin O polypeptide from *Clostridium perfringens*, an intermedilysin polypeptide from *Streptococcus intermedius*, a alveolysin polypeptide from *Bacillus alvei*, a anthrolysin polypeptide from *Bacillus anthracis*, a putative cereolysin polypeptide from *Bacillus cereus*, a ivanolysin O polypeptide from *Listeria ivanovii*, a pyolysin polypeptide from *Arcanobacterium pyogenes*, a seeligeriolysin O polypeptide from *Listeria seeligeri*, a streptolysin O polypeptide from *Streptococcus pyogenes*, a suilysin polypeptide from *Streptococcus suis*, a tetanolysin polypeptide from *Clostridium tetani*, a listeriolysin O polypeptide from *Listeria monocytogenes*, a streptolysin O polypeptide from *Streptococcus equisimilis*, a streptolysin O polypeptide from *Streptococcus canis*, a thuringiolysin O polypeptide from *Bacillus thuringiensis*, a latersporolysin O polypeptide from *Brevibacillus. laterosporus*, a botulinolysin polypeptide from *Clostridium botulinum*, a chauveolysin polypeptide from *C Clostridium chauvoei*, a bifermentolysin polypeptide from *Clostridium bifermentans*, a sordellilysin polypeptide from *Clostridium sordellii*, a histolyticolysin polypeptide from *Clostridium histiolyticum*, a novylysin polypeptide from *Clostridium novyi*, or a septicolysin O polypeptide from *Clostridium septicum*.

In a preferred embodiment, the cytolysoid is derived from a pneumolysin polypeptide from *Streptococcus pneumoniae*. In a more preferred embodiment, the cytolysoid includes a sequence having at least 90% sequence identity to SEQ ID NO: 1.

In another embodiment, the carrier polypeptide is detoxified or exhibits decreased toxicity as compared to the corresponding wild-type carrier polypeptide, and is selected from the group consisting of tetanus toxin (TT), *Plasmodium falciparum* circumsporozite protein, hepatitis B surface antigen, hepatitis B nuclear core polypeptide, *H. influenzae* matrix polypeptide, *H. influenzae* haemagglutinin, diphtheria toxoid, diphtheria toxoid mutant $CRM_{197}$, group B *N. meningitidis* outer membrane polypeptide complex (OMPC), a cytolysoid, pneumococcal toxin pneumolysin, heat shock polypeptide from *Mycobacterium bovis*, heat shock polypeptide from *M. leprae*, cholera toxoid, *E. coli* LT, *E. coli* ST, exotoxin A from *Pseudomonas aeruginosa*, pneumococcal surface polypeptide A, pneumococcal adhesin polypeptide (PsaA), C5a peptidase from Group A or Group B *Streptococcus* spp., *Haemophilus influenzae* polypeptide D, ovalbumin, keyhole limpet hemocyanin (KLH), bovine serum albumin (BSA), purified polypeptide derivative of tuberculin (PPD), PorB from *N. meningitidis*, and derivatives, variants, or fragments thereof. In a preferred embodiment, the conjugate includes $CRM_{197}$. Carrier polypeptides are described in more detail below.

Additional examples of a carrier protein include streptococcal C5a peptidase (SCP) from *Streptococcus pyogenes*, GNA2091 (also known as accessory protein 936) from *Neisseria*, and $CRM_{197}$. Further examples and descriptions of carrier proteins are provided below in section C.

3) Assembly:

In one embodiment, the conjugate includes an ORF2086 polypeptide directly linked to the carrier polypeptide. For example, the polypeptides of the conjugate are coupled in the absence of a linker molecule. In another embodiment, the conjugate includes an ORF2086 polypeptide indirectly linked to the carrier polypeptide. For example, the carrier polypeptide may be linked to an intermediate and that intermediate is linked to the ORF2086 polypeptide.

In one embodiment, the conjugate includes one ORF2086 polypeptide linked to one carrier polypeptide, but other conformations are within the scope of the invention. For example, in another embodiment, the conjugate includes at most 1, 2, 3, 4, or 5, 6, 7, 8, 9, or 10 immunogenic bacterial polypeptides. In one embodiment, the conjugate includes at most 1, 2, 3, 4, 5, 6, 7, 8, 9, or 10 ORF2086 polypeptides. In another embodiment, the conjugate includes at most 1, 2, 3, 4, or 5 carrier polypeptides.

In some embodiments, the conjugate further comprises a third or subsequent additional polypeptides. The source of the third or additional polypeptides may include, but is not limited to, *N. meningitidis*. In one embodiment, a third polypeptide is fused in-frame to the ORF2086 polypeptide or to the carrier polypeptide. In one embodiment, the conjugate includes a polypeptide sequence derived from pneumococcal bacteria. In another embodiment, the conjugate does not include a polypeptide sequence derived from pneumococcal bacteria.

Non-pyruvylated non-lipidated ORF2086 proteins are described in WO2013132452 and US patent publication number US20130243807, each of which is incorporated herein by reference in its entirety. Methods of removing or reducing the likelihood of pyruvylation modification following expression of non-lipidated ORF2086 proteins are also described therein.

An additional method for removing pyruvylation includes treatment of the protein with zinc sulfate.

Yet another method includes genetic modifications to the non-lipidated ORF2086 protein to delete the initial cysteine at position 1 of the N-terminus and replacing any amino acid residue at the N-terminus with a cysteine residue. For example, in one embodiment, the non-lipidated ORF2086 protein includes an amino acid sequence wherein a cysteine residue is not at position 1 of the N-terminus of the ORF2086 protein and wherein a serine residue is replaced with a cysteine residue, as compared to the corresponding wild-type non-lipidated ORF2086 protein.

Preferably, the amino acid residue to be replaced by a cysteine residue is at most 20, 19, 18, 17, 16, 15, 14, 13, 12, 11, 10, 9, 8, 7, 6, or 5 amino acids from the initial residue of the N-terminus.

For example, in one embodiment, the non-lipidated ORF2086 protein includes an amino acid sequence wherein a cysteine residue is not at position 1 of the N-terminus of the ORF2086 protein and wherein a residue at position 2 is replaced with a cysteine residue, as compared to the corresponding wild-type non-lipidated ORF2086 protein.

Preferably, the amino acid residue to be replaced by a cysteine residue is serine residue located at most 20, 19, 18, 17, 16, 15, 14, 13, 12, 11, 10, 9, 8, 7, 6, or 5 amino acids from the initial residue of the N-terminus. For example, the non-lipidated ORF2086 protein includes an amino acid sequence wherein a cysteine residue is not at position 1 of the N-terminus of the ORF2086 protein and wherein a serine residue at position 2 is replaced with a cysteine residue, as compared to the corresponding wild-type non-lipidated ORF2086 protein. Compare, for example, SEQ ID NO: 5, SEQ ID NO: 156, and SEQ ID NO: 157.

In another embodiment, the non-lipidated ORF2086 protein includes an amino acid sequence wherein a cysteine residue is not at position 1 of the N-terminus of the ORF2086 protein and wherein a serine residue at position 6 is replaced with a cysteine residue, as compared to the corresponding wild-type non-lipidated ORF2086 protein. Compare, for example, SEQ ID NO: 5, SEQ ID NO: 156, and SEQ ID NO: 158.

Preferably, the conjugate includes polypeptides that are derived from bacterial species that are different from the bacterial species from which the carrier polypeptide is derived. Accordingly, in one embodiment, the carrier protein is heterologous to the ORF2086 polypeptide and to any additional polypeptides included in the conjugate. "Heterologous" in reference to a polypeptide is a polypeptide that originates from a different protein and/or from a different bacteria species.

The conjugation between the carrier polypeptide and the ORF2086 polypeptide, optionally through a cross-linker, may be done according to methods known in the art. Preferably, a bond between a carrier polypeptide and the ORF2086 polypeptide is accomplished using an activated carrier polypeptide having at least one activated terminus suitable for reaction with a nucleophilic center (e.g., lysine or cysteine residue of a protein).

In one embodiment, the carrier protein is maleimide-activated through a non-specific NHS-ester reaction to lysine residues. The single N-terminal cysteine of the ORF2086 polypeptide is then conjugated to a maleimide of the carrier protein.

As is known in the art, maleimides react with sulfhydryl groups to form stable thioether bonds. N-ethyl maleimide (NEM) is one example of a thiol-reactive reagent. For example, a pneumolysin protein may be prepared for conjugation by derivatization of the protein with NEM followed by activation with SM(PEG)$_4$.

In another embodiment, the carrier polypeptide is activated with sulfosuccinimidyl-4-(N-maleimidomethyl)cyclohexane-1-carboxylate (Sulfo-SMCC). Sulfo-SMCC is a water-soluble amine-to-sulfhydryl crosslinker. It contains an amine-reactive N-hydroxysuccinimide (NHS ester) and a sulfhydryl-reactive maleimide group. In one example, an SCP protein may be activated with Sulfo-SMCC.

4) Immunogenic Compositions Including a Conjugate:

In one aspect, the invention relates to an immunogenic composition including a conjugate as described above. The immunogenic composition further includes a pharmaceutically acceptable excipient.

In one embodiment, the immunogenic composition includes at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135; and d) a conjugate of a capsular saccharide of *Neisseria meningitidis* serogroup Y. Such conjugates of a capsular saccharide of *Neisseria meningitidis* are known in the art. Descriptions of *N. meningitidis* capsular saccharide conjugates and polysaccharide conjugates are described below.

5) Immune Responses:

In one aspect, the conjugate induces an immune response against *N. meningitidis* in a mammal. In one embodiment, the conjugate induces a bactericidal antibody against a *N. meningitidis* serogroup B variant that is homologous to the ORF2086 polypeptide. For example, a conjugate including a carrier protein and an A05 polypeptide may induce a bactericidal antibody against an *N. meningitidis* serogroup B A05-expressing strain. In another embodiment, the conjugate induces a bactericidal antibody against a *N. meningitidis* serogroup B variant that is heterologous to the ORF2086 polypeptide. For example, a conjugate including a carrier protein and an A05 polypeptide may induce a bactericidal antibody against an *N. meningitidis* serogroup B A22-expressing strain.

In one embodiment, a conjugate that includes a non-lipidated ORF2086 polypeptide and a carrier polypeptide may induce an immune response in a mammal that is comparable to the immune response induced by a composition that includes a lipidated form of the same ORF2086 polypeptide in the absence of the carrier polypeptide, when assessed under identical conditions.

In one embodiment, the immune response induced by the conjugate is equal to the immune response of a mammal administered with a composition including a corresponding non-lipidated ORF2086 polypeptide in the absence of a carrier polypeptide, when assessed under identical conditions.

In another embodiment, the immune response induced by the conjugate is equal to the immune response of a mammal administered with a composition including a corresponding lipidated ORF2086 polypeptide in the absence of a carrier polypeptide, when assessed under identical conditions.

In another embodiment, the immune response induced by the conjugate is greater than the immune response of a mammal administered with a composition including a corresponding lipidated ORF2086 polypeptide in the absence of a carrier polypeptide, when assessed under identical conditions. For example, the immune response induced by the conjugate may be greater by at least 1%, 5%, 10%, 20%, 30%, 40%, 50%, or more.

In another embodiment, the immune response induced by the conjugate is greater than the immune response of a mammal administered with a composition including a corresponding non-lipidated ORF2086 polypeptide in the absence of a carrier polypeptide, when assessed under identical conditions. For example, the immune response induced by the conjugate may be greater by at least 1%, 5%, 10%, 20%, 30%, 40%, 50%, or more.

In a further embodiment, the immune response of the conjugate is at most 30%, 25%, 20%, 15%, 10%, or 5% less than an immune response of a mammal administered with a composition including the corresponding lipidated ORF2086 polypeptide in the absence of a carrier polypeptide, when assessed under identical conditions.

In another aspect, the invention relates to a method for inducing an immune response against *Neisseria meningitidis* in a mammal. The immune response may be against any one *N. meningitidis* serogroup or a combination of *N. meningitidis* serogroups (e.g., A, B, C, W135, X, and/or Y). The method includes administering to the mammal an effective amount of the isolated polypeptide as described. In one embodiment, the isolated polypeptide includes a conjugate as described above. In another embodiment, the method includes administering to the mammal an effective amount of an immunogenic composition that includes an isolated polypeptide and/or conjugate as described. The immune response induced by the method may include a bactericidal antibody. Bactericidal antibody responses are described below.

C) Carrier Polypeptide

A carrier protein or polypeptide is a polypeptide entity that induces an immune response directed against a molecule linked to the carrier polypeptide. By linking a carrier polypeptide to a molecule (e.g., to an ORF2086 polypeptide), it is possible to increase the immunogenicity of the antigenic polypeptide.

Exemplary carrier polypeptides include detoxified forms of the following: tetanus toxin (TT), *Plasmodium falciparum* circumsporozite protein, hepatitis B surface antigen, hepatitis B nuclear core protein, *H. influenzae* matrix protein, *H. influenzae* haemagglutinin, diphtheria toxoid, diphtheria toxoid mutant $CRM_{197}$, group B *N. meningitidis* outer membrane protein complex (OMPC), a cytolysoid, pneumococcal toxin pneumolysin, heat shock protein from *Mycobacterium bovis*, heat shock protein from *M. leprae*, cholera toxoid, *E. coli* LT, *E. coli* ST, exotoxin A from *Pseudomonas aeruginosa*, pneumococcal surface protein A, pneumococcal adhesin protein (PsaA), C5a peptidase from Group A or Group B *streptococcus, Haemophilus influenzae* protein D, ovalbumin, keyhole limpet hemocyanin (KLH), bovine serum albumin (BSA), purified protein derivative of tuberculin (PPD), PorB (from *N. meningitidis*), and derivatives, variants, or fragments thereof. The carrier polypeptide preferably exhibits less toxicity than the corresponding wild-type form of the carrier polypeptide.

Diphtheria Toxoids:

In a preferred embodiment, the carrier polypeptide is a diphtheria toxoid or a variant or fragment thereof, more preferably, $CRM_{197}$. $CRM_{197}$ is a non-toxic variant (i.e., toxoid) of diphtheria toxin. In one embodiment, $CRM_{197}$ is isolated from cultures of *Corynebacterium diphtheriae* strain C7 (6197) grown in casamino acids and yeast extract-based medium. In another embodiment, $CRM_{197}$ is prepared recombinantly in accordance with the methods described in U.S. Pat. No. 5,614,382. In some embodiments, $CRM_{197}$ is prepared in *Pseudomonas fluorescens*. Other diphtheria toxoids known in the art may be used, such as, for example, $CRM_{176}$, $CRM_{228}$, $CRM_{45}$, $CRM_9$, $CRM_{102}$, $CRM_{103}$ and $CRM_{107}$.

The diphtheria toxoid may include a full length diphtheria toxoid polypeptide, active variants or fragments thereof, or any immunogenic fragment of the diphtheria toxoid. Exemplary diphtheria toxoids include toxoids that have a deletion or mutation of Glu 148 to Asp, Gln or Ser and/or Ala 158 to Gly and other mutations, as compared to the corresponding wild-type diphtheria toxin, as disclosed in U.S. Pat. No. 4,709,017 or U.S. Pat. No. 4,950,740; mutation of at least one or more of the residues Lys 516, Lys 526, Phe 530 and/or Lys 534 and other mutations disclosed in U.S. Pat. No. 5,917,017 or U.S. Pat. No. 6,455,673; or fragments disclosed in U.S. Pat. No. 5,843,711.

An additional exemplary diphtheria toxoid includes a fragment of CRM that includes amino acids 1-193 of $CRM_{197}$, as shown in SEQ ID NO: 12), known as a "DT-A" region.

In one embodiment, a $CRM_{197}$ protein includes a sequence having at least 50%, 60%, 70%, 80%, 90%, 91%, 92%, 93%, 94%, 95%, 96% 97%, 98%, 99%, or greater sequence identity to SEQ ID NO: 10. In a most preferred embodiment, the carrier protein includes SEQ ID NO: 10.

In another preferred embodiment, the $CRM_{197}$ protein includes a sequence having at least 50%, 60%, 70%, 80%, 90%, 91%, 92%, 93%, 94%, 95%, 96% 97%, 98%, 99%, or greater sequence identity to SEQ ID NO: 155. In a most preferred embodiment, the $CRM_{197}$ protein includes SEQ ID NO: 155.

Cytolysoids: In another preferred embodiment, the carrier polypeptide is a cytolysoid or a variant or fragment thereof. In a more preferred embodiment, the carrier polypeptide is a pneumococcal toxin pneumolysin that is detoxified or exhibits less toxicity than the corresponding wild-type form of the pneumococcal toxin pneumolysin.

As used herein, "cytolysoid" refers to a modified cytolysin, wherein modification of the protein inactivates, detoxifies, or reduces the toxicity, oligomerization and/or hemolytic properties of the cytolysoid protein while retaining immunogenic activity.

Cytolysins are associated with a family of pore-forming toxins that are produced by various species from at least the genera *Clostridium, Streptococcus, Listeria, Bacillus,* and *Arcanobacterium*. Cytolysins may be known as hemolytic proteins. The amino acid sequences of exemplary wild-type cytolysins are shown in SEQ ID NOs: 88-101. Such cytolysins are cholesterol-binding cytolysins.

A reduction in the toxicity of the cytolysin protein (i.e., a reduction in toxicity, oligomerization, and/or hemolysis) includes at least a 1%, 5%, 10%, 20%, 30%, 40%, 50%, 60%, 70%, 80%, 90% or greater statistically significant decrease relative to an appropriate control, such as compared to the corresponding wild-type cytolysin protein. Methods to assay for cytolysin activity are known in the art.

Modifications that may inactivate or reduce the toxic activity (i.e., oligomerization and/or hemolysis) of cytolysins are known in the art. These modifications may be amino acid substitutions, deletions, and/or additions. Such modifications are known in the art. Some examples include, but are not limited to, those described in WO2005/108419 and WO2005/108580 which disclose cytolysoids having a mutation (e.g., a substitution or deletion) within the region corresponding to amino acid residues from 144 to 161 of the wild-type pneumolysin protein. This region of pneumolysin has a consensus sequence that is shared among the cytolysins. The mutant cytolysins have reduced oligomerization and/or hemolytic activity as compared to the wild-type cytolysin, and are therefore less toxic. The mutant may have a substitution or deletion of one or more of the amino acid residues within the regions corresponding to amino acids 144 to 161 of the wild-type pneumolysin sequence. Thus, the cytolysoid may have a mutation at one or more of the amino acids residues corresponding to amino acids 144, 145, 146, 147, 148, 149, 150, 151, 152, 153, 154, 155, 156, 157, 158, 159, 160 or 161 of wild-type pneumolysin.

The regions of the cytolysins described by SEQ ID NOS: 88-101 corresponding to residues 144 to 161 of wild-type pneumolysin are listed below.

cytolysoid includes a deletion of alanine 146 and arginine 147 as compared to the corresponding wild-type cytolysin.

The mutant may have a substitution at a residue corresponding to Y181 of perfringolysin. This residue corresponds to Y150 of pneumolysin. Such mutants may be

| Cytolysin | Consensus sequence to pneumolysin aa 144-161 | Amino acid position |
|---|---|---|
| Pneumolysin from *Streptococcus pneumoniae* (SEQ ID NO: 88) | VPARMQYEKITAHSMEQL (SEQ ID NO: 102) | V144-L161 |
| Perfringolysin O from *Clostridium perfringens* (SEQ ID NO: 89) | LPARTQYSESMVYSKSQI (SEQ ID NO: 103) | L175-I192 |
| Intermedilysin from *Streptococcus intermedius* (SEQ ID NO: 90) | VPARMQYESISAQSMSQL (SEQ ID NO: 104) | V202-L219 |
| Alveolysin from *Bacillus alvei* (SEQ ID NO: 91) | LPARLQYAESMVYSQNQI (SEQ ID NO: 105) | L177-I194 |
| Anthrolysin from *Bacillus anthracis* (SEQ ID NO: 92) | LPARTQYSESMVYSKSQL (SEQ ID NO: 106) | L188-L205 |
| Putative Cereolysin from *Bacillus cereus* (SEQ ID NO: 93) | LPARTQYSESMVYSKSQI (SEQ ID NO: 107) | L175-I192 |
| Ivanolysin O from *Listeria ivanovii* (SEQ ID NO: 94) | ISAKIDYDQEMAYSESQL (SEQ ID NO: 108) | I199-L216 |
| Perfringolysin O from *Clostridium perfringens* (SEQ ID NO: 116) | LPARTQYSESMVYSKSQI (SEQ ID NO: 109) | L174-I191 |
| Seeligeriolysin O from *Listeria seeligeri* (SEQ ID NO: 96) | INAKIDYSDEMAYSESQL (SEQ ID NO: 110) | I201-L218 |
| Streptolysin O from *S. pyogenes* (SEQ ID NO: 97) | LPARTQYTESMVYSKSQI (SEQ ID NO: 111) | L249-I266 |
| Suilysin from *Streptococcus suis* (SEQ ID NO: 98) | TQAELQYDETMAYSMSQL (SEQ ID NO: 112) | T172-L189 |
| Tetanolysin from *Clostridium tetani* (SEQ ID NO: 99) | IPTRMSYSDTMVYSQSQL (SEQ ID NO: 113) | I201-L218 |
| Listeriolysin O from *Listeria monocytogenes* (SEQ ID NO: 100) | VSAKIDYDDEMAYSESQL (SEQ ID NO: 114) | V200-L217 |
| Thuringiolysin from *Bacillus thuringiensis* (SEQ ID NO: 101) | LPARMQYTESMVYSKSQI (SEQ ID NO: 115) | L188-I205 |

Certain preferred mutant cytolysin proteins differ from the wild type protein by the substitution or deletion of two adjacent amino acids within the region corresponding to amino acid residues 144 to 151 of the wild type pneumolysin sequence. Examples of such double mutants are those which contain substitutions or deletions of amino acids corresponding to valine 144 and proline 145, alanine 146 and arginine 147, methionine 148 and glutamine 149, or tyrosine 150 and glutamic acid 151, i.e., the corresponding amino acids shown in the table above. In a preferred embodiment, the cytolysoid includes a deletion of alanine 146 and arginine 147 as compared to the corresponding wild-type cytolysin.

derived from perfringolysin, or from other cytolysin proteins.

Further mutants of cytolysins having reduced haemolytic activity are described in WO 90/06951, and contain at least one amino acid substitution or deletion in at least one of the regions corresponding to amino acids 257-297, 367-397 or 424-437 of the wild type pneumolysin sequence, and in particular at positions corresponding to amino acids 367, 384, 385, 428, 433 and 435 of the pneumolysin sequence.

Thus the cytolysin protein used in the methods and compositions described herein may include one or more such mutations in addition to, or instead of, the mutation in the region corresponding to amino acids 144-161 of the pneumolysin sequence.

The cytolysin proteins may include other mutations relative to the wild-type sequences. These mutations may themselves reduce one or more biological activities of the cytolysin protein, such as the haemolytic activity, the oligomerisation activity, or the ability to activate complement, or they may be phenotypically silent.

Deletions and substitutions are examples of mutations which may be used to provide the mutant proteins of the invention with reduced toxicity. Non-conservative substitutions may be particularly suitable for reducing toxicity of the mutant, as a mutant having a non-conservative mutation is less likely to retain wild-type levels of function relative to one having a conservative substitution. Additional, non-limiting, examples of cytolysoids in the art are disclosed in U.S. Patent Application Publication No. 2009/0285846A1 (WO2012/134975) and U.S. Patent Application Publication No. 2010/0166795 (WO2007/144647).

Active variants or fragments of the various cytolysoids may include at least 65%, 70%, 75%, 80%, 85%, 90%, 91%, 92%, 93%, 94%, 95%, 96%, 97%, 98%, 99% or more sequence identity to a cytolysoid polypeptide provided herein in that they maintain carrier polypeptide activity. Active variants of cytolysoids are known in the art. See, for example, SEQ ID NOs: 117-120 and SEQ ID NO: 1. See also, for example, U.S. Patent Application No. 2009/0285846A1 and U.S. Patent Application No. 2010/0166795.

Fragments of wild-type or mutant cytolysin proteins which retain carrier polypeptide activity may also be used. Such fragments may be, for example, at least 50 amino acids in length, at least 100 amino acids in length, at least 200 amino acids in length, at least 300 amino acids in length, or at least 400 amino acids in length, as long as they retain carrier polypeptide activity.

Pneumolysoids:

In a preferred embodiment, the carrier polypeptide includes a pneumolysoid polypeptide or a variant or fragment thereof. Pneumolysin is a pore forming toxin and is the major cytolysin produced by Streptococcus pneumoniae. The amino acid sequence of wild-type or native pneumolysin is set forth in SEQ ID NO: 21.

As used herein, "pneumolysoid" refers to a modified pneumolysin (a pneumolysin toxoid), wherein the modification of the protein inactivates or reduces the toxicity, oligomerization, hemolytic and/or complement activating properties of the pneumolysoid protein while still retaining carrier polypeptide activity, as compared to the corresponding wild-type pneumolysin.

Exemplary pneumolysoids that may be employed in the various compositions provided herein are described in, for example, WO2005/108419, WO2005/108580, WO 90/06951, U.S. Patent Application No. 2009/0285846A1 and U.S. Patent Application No. 2010/0166795. WO2005/108419 and WO2005/108580 disclose pneumolysoids having a mutation (e.g., a substitution or deletion) within the region of amino acids 144 to 161 of the wild-type pneumolysin protein. These mutants have reduced toxicity, oligomerization and/or hemolytic activity as compared to the wild-type pneumolysin, and are therefore less toxic.

The mutant may have a substitution or deletion of one or more amino acids 144 to 161 of the wild-type pneumolysin sequence. Thus, the pneumolysoid may have a mutation at one or more of the amino acid residues 144, 145, 146, 147, 148, 149, 150, 151, 152, 153, 154, 155, 156, 157, 158, 159, 160 or 161 of wild-type pneumolysin. In addition, pneumolysoids having reduced hemolytic activity and having at least one amino acid substitution or deletion in at least one of the regions corresponding to amino acids 257-297, 367-397 or 424-437 of the wild-type pneumolysin are described in WO 90/06951.

Further examples of a pneumolysoid includes SEQ ID NO: 1, or an active variant or fragment thereof. Another example includes a pneumolysoid having a mutation of the lysine at amino acid position 460 to an aspartic acid residue (SEQ ID NO: 117) as compared to the corresponding wild-type pneumolysin (SEQ ID NO: 21). Such a variant pneumolysoid is disclosed in U.S. Patent Application No. 2009/0285846A1. A variant of SEQ ID NO: 117 is provided herein and is set forth in SEQ ID NO: 118. The active variant includes an amino acid change from Lysine at position 208 to Arginine when compared to SEQ ID NO: 117.

The pneumolysoid set forth in SEQ ID NO: 119, or an active variant or fragment thereof, includes a substitution of asparagine in place of aspartic acid at amino acid position 385 and deletion of alanine 146 and arginine 147 of the wild-type pneumolysin sequence. This pneumolysoid set forth in SEQ ID NO: 119 may be deficient in both hemolysis and complement activation and is disclosed in U.S. Patent Application No. 2010/0166795.

The pneumolysoid set forth in SEQ ID NO: 120, or an active variant or fragment thereof, includes an amino acid substitution of phenylalanine in place of tryptophan at amino acid position 433 of the wild-type pneumolysin sequence. This pneumolysoid set forth in SEQ ID NO: 120 may be deficient in hemolysis and is disclosed in U.S. Pat. No. 6,716,432.

In a most preferred embodiment, the fusion polypeptide includes a pneumolysoid having SEQ ID NO: 1 or active variants or fragments thereof. The polypeptide of SEQ ID NO: 1 includes an A146R147 deletion, as compared to the wild-type pneumolysin.

Accordingly, active variants or fragments of pneumolysoids are provided herein. Such active variants may comprise at least 65%, 70%, 75%, 80%, 85%, 90%, 91%, 92%, 93%, 94%, 95%, 96%, 97%, 98%, 99% or more sequence identity to SEQ ID NOs: 88-120 or SEQ ID NO: 21. Active variants of pneumolysin are also described, for example, in US 2010/0166795 and US 2009/0285846A1, herein incorporated by reference. The art provides guidance regarding the preparation of such variants, as described elsewhere herein. Thus, in one embodiment, the fusion polypeptide includes the pneumolysoid set forth in any one of the amino acid sequence set forth in SEQ ID NOs: 88-101, SEQ ID NO: 21, or SEQ ID NO: 1, or an active variant thereof having at least 80%, 85%, 90%, 91%, 92%, 93%, 94%, 95%, 96%, 97%, 98%, 99% sequence identity to the amino acid sequence of SEQ ID NO: 21.

In one embodiment, the carrier protein is derived from streptococcal C5a peptidase (SCP) from Streptococcus pyogenes. In a preferred embodiment, the carrier protein includes a sequence having at least 50%, 60%, 70%, 80%, 90%, 91%, 92%, 93%, 94%, 95%, 96% 97%, 98%, 99%, or greater sequence identity to SEQ ID NO: 151. In a most preferred embodiment, the carrier protein includes SEQ ID NO: 151.

In one embodiment, the carrier protein is derived from GNA2091. In a preferred embodiment, the carrier protein includes a sequence having at least 50%, 60%, 70%, 80%, 90%, 91%, 92%, 93%, 94%, 95%, 96% 97%, 98%, 99%, or greater sequence identity to SEQ ID NO: 147. In a most preferred embodiment, the carrier protein includes SEQ ID NO: 147.

D) ORF2086 Polypeptides

The term "ORF2086" as used herein refers to Open Reading Frame 2086 from a *Neisseria* species bacterium. *Neisseria* ORF2086, the proteins encoded therefrom, fragments of those proteins, and immunogenic compositions comprising those proteins are known in the art and are described, e.g., in WO2003/063766, and in U.S. Patent Application Publication Nos. US 20060257413, US 20090202593, WO2012032489, and US 20120093852, each of which is hereby incorporated by reference in its entirety. ORF2086 polypeptides are also described in WO2013132452 and US patent publication number US20130243807, each of which is incorporated herein by reference in its entirety. Examples of an ORF2086 polypeptide include a polypeptide having any one of the sequences set forth in SEQ ID NOs: 22-87, such as any one of the amino acid sequences set forth in SEQ ID NOs: 5, 19, 22-65.

The term "P2086" generally refers to the protein encoded by ORF2086. The "P" before "2086" is an abbreviation for "protein." The P2086 proteins of the invention may be lipidated or non-lipidated. "LP2086" and "P2086" typically refer to lipidated and non-lipidated forms of a 2086 protein, respectively. The P2086 protein of the invention may be recombinant. "rLP2086" and "rP2086" typically refer to lipidated and non-lipidated forms of a recombinant 2086 protein, respectively. "2086" is also known as factor H-binding protein (fHBP).

The term "wild-type non-lipidated ORF2086 polypeptide" or "wild-type non-lipidated 2086 polypeptide" or "wild-type non-lipidated polypeptide" as used herein refers to an ORF2086 polypeptide having an amino acid sequence that is identical to the amino acid sequence of the corresponding mature lipidated ORF2086 polypeptide found in nature. The only difference between the non-lipidated and lipidated molecules is that the wild-type non-lipidated ORF2086 polypeptide is not lipidated with a tripalmitoyl lipid tail at the N-terminal cysteine.

The term "N-terminal cysteine" refers to a cysteine (Cys) residue at the N-terminus or N-terminal tail of a polypeptide. More specifically, the "N-terminal cysteine" as used herein refers to the N-terminal cysteine at which LP2086 lipoproteins are lipidated with a tripalmitoyl lipid tail, as is known in the art.

In one embodiment, the inventive polypeptides and compositions include an ORF2086 polypeptide, wherein the ORF2086 polypeptide does not include a cysteine residue at the N-terminus of the ORF2086 polypeptide. Examples of an ORF2086 polypeptide wherein an N-terminal cysteine is not present includes polypeptides described in SEQ ID NOs: 42-65 and SEQ ID NOs: 131-134.

In one embodiment, the isolated polypeptide includes an ORF2086 polypeptide, wherein a cysteine is not present at the N-terminus of the ORF2086 polypeptide.

In another embodiment, the fusion polypeptide includes an ORF2086 polypeptide, wherein a cysteine is not present at the N-terminus of the ORF2086 polypeptide.

In yet another embodiment, the ORF2086 polypeptide in a ORF2086 polypeptide-carrier polypeptide conjugate does not include a cysteine at the N-terminus of the ORF2086 polypeptide.

Figure 2:
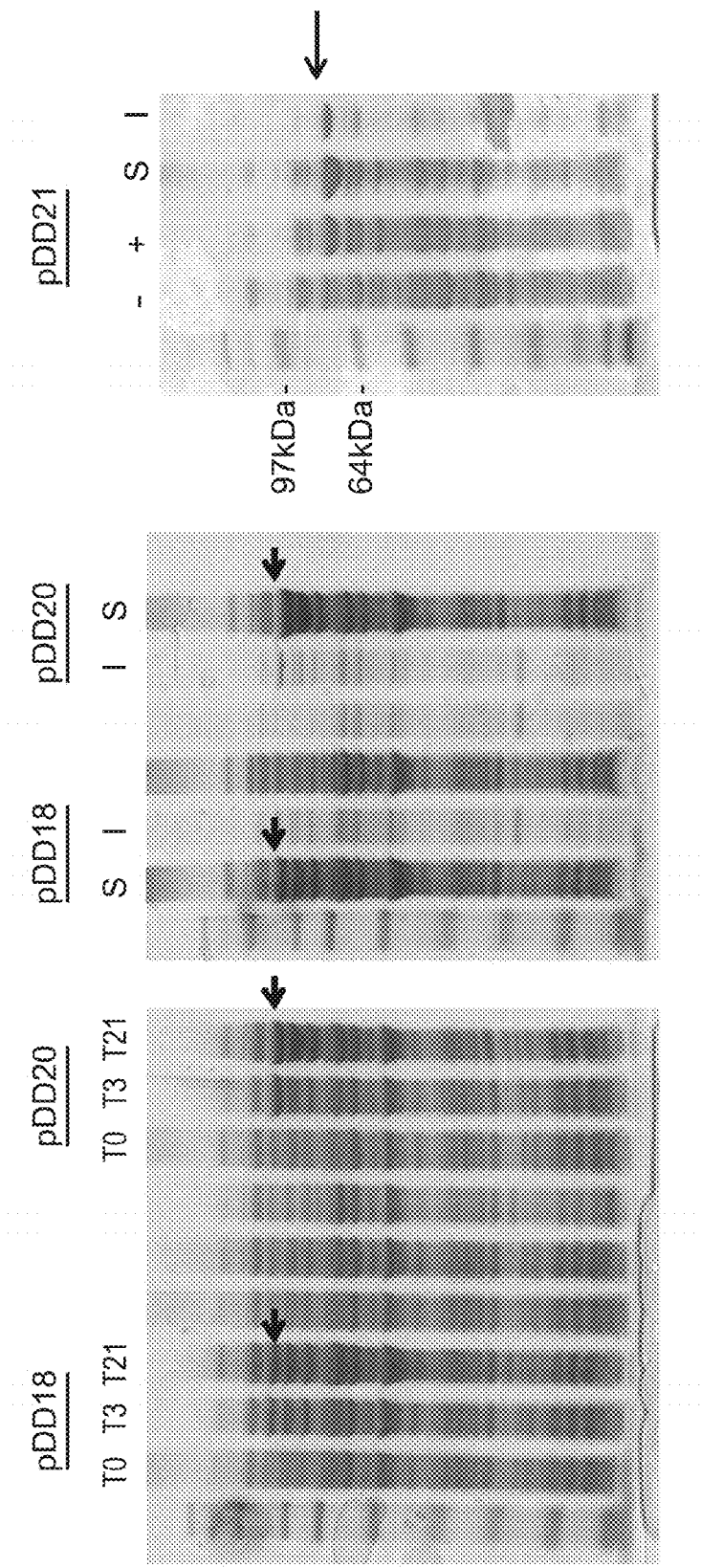
FIG. 2: Expression of Ply-A05 fusion proteins at 30° C. in small scale flask cultures. T0, preinduction sample; T3 3 h SEQ ID NO: 22 sets forth the amino acid sequence for the *N. meningitidis*, serogroup B, 2086 variant A22, which includes an N-terminal Cys at amino acid position 1.
Figure 3:
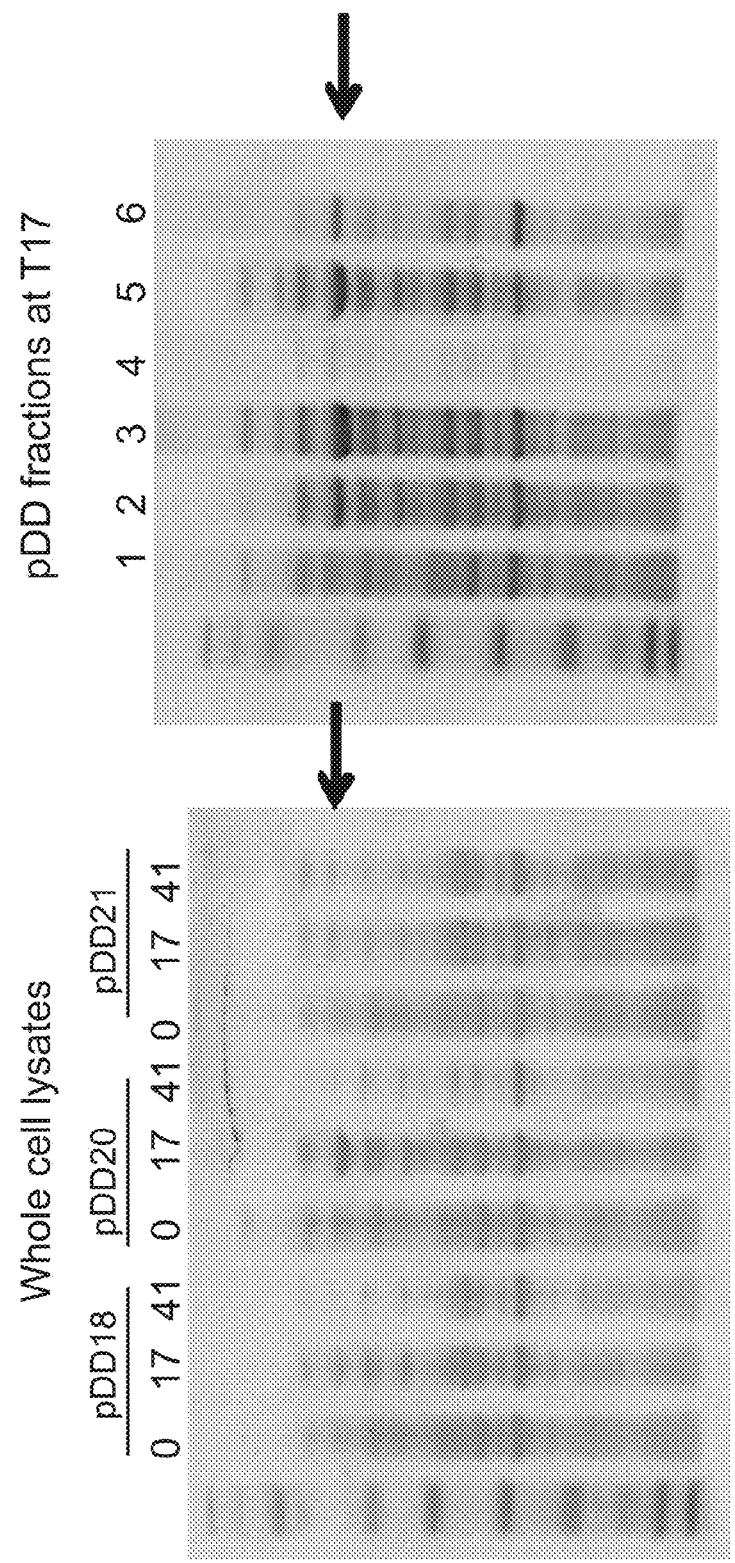
Figure 4:
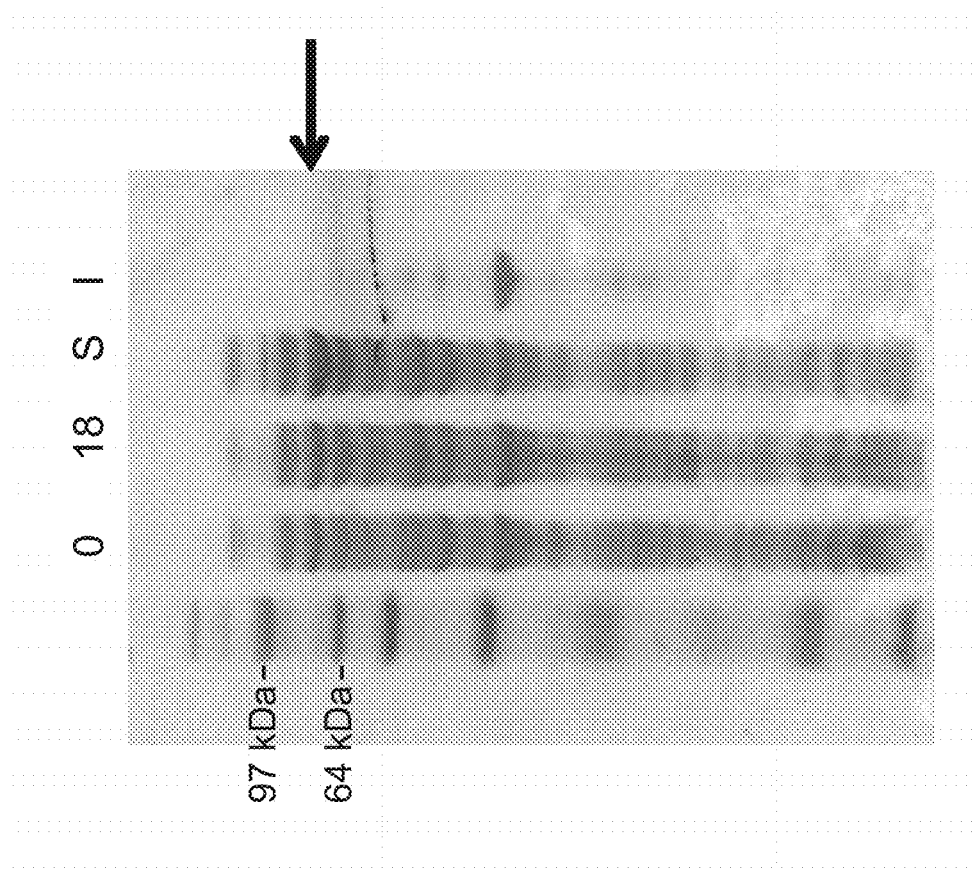

The term "Gly/Ser stalk" as used herein refers to consecutive Gly and Ser residues at the N-terminus of an ORF2086 polypeptide. There may be at least 2, 3, 4, 5, 6, 7, 8, 9, 10, 11, 12, 13, 14, or 15 Gly and Ser residues, preferably between 5 and 12 Gly and Ser residues, in the Gly/Ser stalk. In one embodiment, the ORF2086 polypeptide includes at least 2 and at most 15 consecutive Gly and/or Ser residues. The native Gly/Ser stalks of ORF2086 polypeptide variants are represented by the underlined sequences in FIG. 2A-2C of WO2012032489 and US Patent Publication No. US20120093852, each of which is incorporated herein by reference in its entirety.

In one embodiment, the Gly/Ser stalk of the ORF2086 polypeptide includes a modification as compared to the wild-type or native ORF2086 polypeptide. Examples of a modification to the native Gly/Ser stalk of an ORF2086 polypeptide includes a deletion of a Gly and/or Ser residue, a substitution of a Gly with a Ser residue or a substitution of a Ser residue with a Gly residue, an addition of a Gly and/or Ser residue, and any combination thereof. Examples of an ORF2086 polypeptide that includes a modification of the native Gly/Ser stalk region include, for example, polypeptides described by SEQ ID NOs: 62-65 and SEQ ID NOs: 131-134.

As is known in the art, the non-lipidated form of an ORF2086 polypeptide may lack the original leader sequence or may include a leader sequence that is replaced with a portion of a sequence that does not specify a site for fatty acid acylation in a host cell. See, for example, WO2003/063766, U.S. Pat. No. 8,101,194, WO2012032489, and US Patent Publication No. US20120093852, each of which is incorporated herein by reference in its entirety. Examples of a non-lipidated ORF2086 polypeptide include a polypeptide having any one of the sequences set forth in SEQ ID NOs: 22-65. In a preferred embodiment, the non-lipidated ORF2086 polypeptide includes a polypeptide having any one of the sequences set forth in SEQ ID NOs: 42-65.

In one embodiment, the ORF2086 polypeptide is encoded by any one of the polynucleotide sequences set forth in SEQ ID NOs: 66-87. In a preferred embodiment, the ORF2086 polypeptide is encoded by a sequence that does not encode a cysteine at the N-terminus or at amino acid residue position 1 of the ORF2086 polypeptide. Exemplary polynucleotide sequences include SEQ ID NOs: 131-134.

In another preferred embodiment, the ORF2086 polypeptide is encoded by a codon-optimized sequence of any one of the polynucleotide sequences set forth in SEQ ID NOs: 66-87. Codon-optimized sequences encoding an ORF2086 polypeptide are described in WO2012032489, US Patent Publication No. US20120093852, PCT/IB2013/051791, and U.S. patent application Ser. No. 13/787,594, each of which is incorporated herein by reference in its entirety. Exemplary codon-optimized sequences include the polynucleotide sequences set forth in SEQ ID NOs: 121-129.

The ORF2086 polypeptide may be derived from a *Neisseria* species, including strains of *Neisseria meningitidis* (serogroups A, B, C, D, W-135, X, Y, Z, and 29E), *Neisseria gonorrhoeae*, and *Neisseria lactamica*, as well as immunogenic portions and/or biological equivalents of said proteins.

The ORF2086 polypeptides include Subfamily A proteins and Subfamily B proteins, immunogenic portions thereof, and/or biological equivalents thereof. The ORF2086 polypeptides or equivalents thereof, etc. may be lipidated or non-lipidated. Preferably, the ORF2086 polypeptide is non-lipidated. Alternatively, the immunogenic compositions may include combinations of lipidated and non-lipidated ORF2086 polypeptides.

ORF2086 Subfamily A proteins and Subfamily B polypeptides are known in the art. See WO2003/063766 and U.S. Pat. No. 8,101,194, which disclose SEQ ID NOs: 260 to 278 therein as representing amino acid sequences associated with proteins of 2086 Subfamily A. In addition, SEQ ID NOS: 279 to 299 disclosed in WO2003/063766 and U.S. Pat. No. 8,101,194 represent amino acid sequences associated with proteins of 2086 Subfamily B. WO2003/063766 and U.S. Pat. No. 8,101,194 are each incorporated herein by reference in its entirety. ORF2086 subfamily A and Subfamily B polypeptides are also described in WO2012032489, US Patent Publication No. US20120093852, PCT/IB2013/051791, now WO2013132452, and U.S. patent application Ser. No. 13/787,594, now publication number US20130243807, each of which is incorporated herein by reference in its entirety.

In one embodiment, the non-lipidated polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to a sequence encoding the corresponding lipidated polypeptide.

In a one embodiment, the ORF2086 polypeptide includes at least 2, 3, 4, 5, 6, 7, 8, 9, 10, 11, 12, 13, 14, or 15 consecutive serine and/or glycine residues at the N-terminus of the ORF2086 polypeptide. Preferably, the ORF2086 polypeptide includes at least 3, 4, 5, 6, 7, 8, 9, or 10 and at most 15, 14, 13, 12, 11, or 10 consecutive serine and/or glycine residues at the N-terminus of the ORF2086 polypeptide. The presence of such residues may facilitate in construction of the fusion polypeptide.

In an exemplary embodiment, the ORF2086 polypeptide includes its respective native Gly/Ser stalk region. For example, the B44 polypeptide includes a stalk region as shown in underlining in FIG. 2C of WO2012032489 and US Patent Publication No. US20120093852, each of which is incorporated herein by reference in its entirety. See, for example, residues 2-12 of SEQ ID NO: 40 and residues 1-11 of SEQ ID NO: 60. As another example, the A12 polypeptide includes a stalk region as shown in underlining in FIG. 2A of WO2012032489 and US Patent Publication No. US20120093852, each of which is incorporated herein by reference in its entirety. See, for example, residues 2-7 of SEQ ID NO: 28 and residues 1-6 of SEQ ID NO: 47.

In one embodiment, the ORF2086 polypeptide includes at least about 200, 210, 220, 230, 240, 250, 255, or 260 consecutive amino acids, and at most about 270, 269, 268, 267, 266, 265, 264, 263, 260, 259, 258, 257, 256, or 255 consecutive amino acids. Any minimum value may be combined with any maximum value to define a range. More preferably, the polypeptide has at least 254 or 262 consecutive amino acids. In some embodiments, the polypeptide has at most 254 consecutive amino acids. In other embodiments, the polypeptide has at most 262 consecutive amino acids. In one embodiment, the ORF2086 polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to a sequence encoding the corresponding ORF2086 polypeptide. For example, in an exemplary embodiment, the A62 polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to SEQ ID NO: 41.

As used herein, the term "non-pyruvylated" refers to a polypeptide having no pyruvate content. Non-lipidated ORF2086 polypeptides having a pyruvate content typically exhibited a mass shift of +70, as compared to the corresponding wild-type polypeptide. In one embodiment, the inventive polypeptide does not exhibit a mass shift of +70 as compared to the corresponding wild-type non-lipidated polypeptide when measured by mass spectrometry. Non-pyruvylated ORF2086 polypeptides are also described in WO2012032489, US Patent Publication No. US20120093852, PCT/IB2013/051791, and U.S. patent application Ser. No. 13/787,594, each of which is incorporated herein by reference in its entirety.

E) Polynucleotides

In one aspect, the invention relates to an isolated polynucleotide that encodes any one of the isolated polypeptides described herein. In one aspect, the invention relates to an isolated polynucleotide that encodes any one of the fusion polypeptides described herein. In one embodiment, the isolated polynucleotide sequence is a codon-optimized sequence.

In one embodiment, the ORF2086 polypeptide is encoded by a codon-optimized polynucleotide sequence. Examples of a codon-optimized sequence encoding an ORF2086 polypeptide include sequences set forth in SEQ ID NOs: 121-129. In a preferred embodiment, the isolated polypeptide is encoded by a polynucleotide sequence that includes a codon-optimized polynucleotide sequence encoding a ORF2086 polypeptide. In a more preferred embodiment, the fusion polypeptide is encoded by a polynucleotide sequence that includes a codon-optimized polynucleotide sequence encoding an ORF2086 polypeptide. In another preferred embodiment, the ORF2086 polypeptide in a carrier-ORF2086 polypeptide conjugate is encoded by a codon-optimized polynucleotide sequence.

F) Fragments of the Polynucleotides and Polypeptides

Active variants and fragments of the disclosed polynucleotides and polypeptides are also described herein. "Variants" refer to substantially similar sequences. As used herein, a "variant polypeptide" refers to a polypeptide derived from the native protein by a modification of one or more amino acid residues at any position of the native protein. The modification may include a deletion (so-called truncation) of one or more amino acid residues at the N-terminal and/or C-terminal end of the native protein, deletion and/or addition of one or more amino acid residues at one or more internal sites in the native protein, or a substitution of one or more amino acid residues at one or more sites in the native protein. Variant polypeptides continue to possess the desired biological activity of the native polypeptide, that is, they are immunogenic. A variant of a polypeptide or polynucleotide sequence disclosed herein will typically have at least about 65%, 70%, 75%, 80%, 85%, 90%, 91%, 92%, 93%, 94%, 95%, 96%, 97%, 98%, 99% or more sequence identity with the reference sequence.

The term "fragment" refers to a portion of an amino acid or nucleotide sequence comprising a specified number of contiguous amino acid or nucleotide residues. In particular embodiments, a fragment of a polypeptide disclosed herein may retain the biological activity of the full-length polypeptide and hence be immunogenic. Fragments of a polynucleotide may encode protein fragments that retain the biological activity of the protein and hence be immunogenic. Alternatively, fragments of a polynucleotide that are useful as PCR primers generally do not encode protein fragments that retain biological activity. Thus, fragments of a nucleotide sequence disclosed herein may range from at least about 15, 20, 30, 40, 50, 60, 70, 80, 90, 100, 110, 120, 130, 140, 150, 175, 200, 225, 250, 300, 400, 500, 600, 700, 800, 900, 1000, 1100, 1200, 1300, 1400, or 1500 contiguous nucleotides or up to the full-length polynucleotide. Fragments of a polypeptide sequence disclosed herein may comprise at least 10, 15, 20, 25, 30, 50, 60, 70, 80, 90, 100, 110, 120, 130, 140, 150, 160, 170, 180, 190, 200, 225, 250, 275, 300, 325, 350, 375, 400, 425, 450, 475, or 500 contiguous amino acids, or up to the total number of amino acids present in the full-length polypeptide.

G) Meningococcal Conjugates

In one embodiment, the immunogenic composition further includes at least one conjugate selected from the group consisting of: a conjugate of a capsular saccharide of *Neisseria meningitidis* serogroup A; a conjugate of a capsular saccharide of *Neisseria meningitidis* serogroup C; a conjugate of a capsular saccharide of *Neisseria meningitidis* serogroup W135; and a conjugate of a capsular saccharide of *Neisseria meningitidis* serogroup Y.

In a preferred embodiment, the immunogenic composition includes a conjugate of a capsular polysaccharide of *Neisseria meningitidis* and a carrier protein. Preferably, the carrier protein in the saccharide conjugate is a bacterial toxin, such as a diphtheria or tetanus toxin, or toxoids or mutants thereof. Most preferably, the carrier protein is $CRM_{197}$. For example, in one embodiment, the composition includes at least one conjugate selected from (a) a conjugate of the capsular polysaccharide of serogroup A *N. meningitidis* and $CRM_{197}$; (b) a conjugate of the capsular polysaccharide of serogroup C *N. meningitidis* and $CRM_{197}$; (c) a conjugate of the capsular polysaccharide of serogroup W135 *N. meningitidis* and $CRM_{197}$; and (d) a conjugate of the capsular polysaccharide of serogroup Y *N. meningitidis* and $CRM_{197}$.

The capsular saccharides of serogroups A, C, W135, and Y are characterized and known in the art, and are described in WO2012032489 and US Patent Publication No. US20120093852, each of which is incorporated herein by reference in its entirety.

H) Bactericidal Immune Responses

In another aspect, the isolated polypeptides and compositions described herein elicit a bactericidal immune response in a mammal against an ORF2086 polypeptide from serogroup B *N. meningitidis*. The compositions have the ability to induce bactericidal anti-meningococcal antibodies after administration to a mammal, and in preferred embodiments may induce antibodies that are bactericidal against strains of *N. meningitidis* that express LP2086 variants from the respective subfamilies. Further information on bactericidal responses is given below.

In one embodiment, the isolated polypeptide and/or composition described herein elicits a bactericidal immune response against a *N. meningitidis* serogroup B strain expressing an ORF2086 variant that is homologous to the ORF2086 polypeptide. In a preferred embodiment, a composition including a subfamily A polypeptide elicits a bactericidal immune response against a strain of *N. meningitidis* serogroup B that expresses a homologous subfamily A LP2086 variant. In a another preferred embodiment, a composition including a subfamily A polypeptide elicits a bactericidal immune response against a strain of *N. meningitidis* serogroup B that expresses a heterologous subfamily A LP2086 variant.

In another preferred embodiment, the isolated polypeptide and/or composition described herein elicits a bactericidal immune response against a *N. meningitidis* serogroup B strain expressing an ORF2086 variant that is heterologous to the ORF2086 polypeptide.

In one embodiment, the compositions elicit a bactericidal immune response against a strain of *N. meningitidis* serogroup B that expresses a heterologous subfamily LP2086 variant. For example, a composition including a subfamily A polypeptide may elicit a bactericidal immune response against strains of *N. meningitidis* serogroup B that expresses either a subfamily A or a subfamily B LP2086 variant.

In a further aspect, the isolated polypeptides and compositions described herein elicit a bactericidal immune response against at least one of serogroup A, serogroup B, serogroup C, serogroup W135, serogroup X, and/or serogroup Y strains of *N. meningitidis*. In a preferred embodiment, the compositions elicit a bactericidal immune response at least against serogroup B, serogroup C, and serogroup Y of *N. meningitidis*.

Bactericidal antibodies are an indicator of protection in humans and preclinical studies serve as a surrogate. Any new immunogenic composition candidate described herein preferably elicits these functional antibodies.

In one embodiment, the immune response and/or induction of bactericidal antibodies is measured by a serum bactericidal assay (SBA). An exemplary SBA is described below.

In a preferred embodiment, the inventive polypeptide and/or composition induces an immune response in a mammal, wherein the response is at least a 1-fold rise, 2-fold rise, at least a 3-fold rise, or preferably at least a 4-fold rise or greater than the immune response in the mammal in the absence of the inventive polypeptide and/or composition. For example, in one embodiment, the inventive polypeptide and/or composition induces an immune response in a mammal, wherein the response is at least a 1-fold rise, 2-fold rise, a 3-fold rise, or preferably at least a 4-fold rise or greater than the immune response in the mammal prior to administration of the inventive polypeptide and/or composition. In an exemplary embodiment, an isolated polypeptide including SEQ ID NO: 2 induces an immune response in a mammal, wherein the response is at least 1-fold, 2-fold, 3-fold, or preferably at least 4-fold greater than the immune response in the mammal in the absence of the polypeptide.

General Descriptions

The term "mammals" as used herein refers to any mammal, such as, for example, humans, mice, rabbits, or non-human primates. In a preferred embodiment, the mammal is a human.

Example 1: Cloning and Expression of Fusion Polypeptides Including A05

The fHBP A05 gene used is shown in SEQ ID NO: 6 (expression construct pEB042).

Design of PLY Fusions

The version of pneumolysin (PLY) used in these studies was termed delta 6 (Δ6PLY). It contains a deletion of amino acid residues A146R147. The resultant gene is 1410 bp (SEQ ID NO: 3) and 470 amino acids (SEQ ID NO: 1). Two Δ6PLY fusions to A05 were designed. One had Δ6PLY at the N terminal end of the fusion polypeptide (SEQ ID NO: 4 DNA and SEQ ID NO: 2, protein; FIG. 1A). The stalk region of A05 served as a flexible linker between the proteins. In the second fusion, A05 was placed at the N-terminus followed by the Gly-Ser-Gly linker (GSG), followed by the PLY gene (SEQ ID NO: 7, DNA; SEQ ID NO: 8, protein, FIG. 1B).

Several additional pneumolysin fusion protein constructs have been made and verified for expression. These additional constructs use the stalk region of the respective fHBP variants as a flexible linker. These include PLY-A12 (SEQ ID NO: 136), PLY-B01 (SEQ ID NO: 138), PLY-B09 (SEQ ID NO: 140), PLY-B24 (SEQ ID NO: 142), PLY-B44 SEQ ID NO: 144), Design of CRM$_{197}$-A05 Fusions CRM$_{197}$ was used both as the full length protein (536 amino acids, SEQ ID NO: 9, DNA; SEQ ID NO: 10, protein) or the DT-A region (amino acids 1-193 of CRM$_{197}$; SEQ ID NO: 11, DNA; SEQ ID NO: 12, protein). Two A05 fusions were made using the full length $CRM_{197}$, (i) N-terminal $CRM_{197}$ fused to A05 (SEQ ID NO: 13, DNA; SEQ ID NO: 14, protein FIG. 1C), and (ii) N-terminal A05, followed by the GSG linker and then $CRM_{197}$ (SEQ ID NO: 15, DNA; SEQ ID NO: 16; protein, FIG. 1D). One version of the DT-A-A05 fusion was made: N-terminal DT-A fused to A05 at the C terminus (SEQ ID NO: 17, DNA; SEQ ID NO: 18, protein, FIG. 1E).

Design of A05 Fusion Protein Constructs that Use Alternative Protein Carriers

Additional constructs were designed to evaluate alternative protein carriers fused with the A05 fHBP variant. These protein carriers include, (i) GNA2091 from *N. meningitidis*, and (ii) streptococcal C5a peptidase (SCP) from *Streptococcus pyogenes*. The fusion protein in the former case is composed of 180 amino acids from GNA2091 (SEQ ID NO: 146) at the N-terminal end fused to A05 at the C-terminal end, using the stalk region of A05 as the flexible linker between the proteins (GNA2091-A05 SEQ ID NO: 148), The second example is composed of 950 amino acids from SCP (SEQ ID NO: 150) at the N-terminal end fused to A05 at the C-terminal end, using the stalk region of A05 as the flexible linker between the proteins (SCP-A05 SEQ ID NO: 152), Expression Vectors Used in these Studies Initial fusion proteins were cloned into pET30a at the NdeI-BamHI sites via the InFusion® (Clontech) reaction. Fusions were subsequently cloned into a panel of 6 vectors selected to evaluate different promoters in order to optimize protein expression (rhaT, lac, and the arabinose promoter). The vectors also varied in the strength of the Shine Delgarno sequences that promote translation initiation. The vectors are based on the pET30a backbone, substituting the T7 promoter and regulatory genes for these specific elements.

Cell Lines and Expression

All expression plasmids were transformed into *E. coli*. Expression strains were grown overnight in HySoy plus 0.5% glucose and 50 μg/ml kanamycin at 30° C. Overnight cultures were seeded in to fresh HySoy media plus 50 μg/ml kanamycin at a 1:50 dilution. Cells were grown at either 30° C. or 20° C. At an $OD_{600}$~1.0, cultures were induced with the appropriate inducer and incubated at the same temperatures overnight. Cells were harvested and samples assessed for solubility by either adding BUGBUSTER™ (EMD) reagent or by sonication followed by centrifugation. Whole cell lysates and soluble/insoluble fractions were run on Tris-Bis 4-12% gels and stained with Coomassie stain.

Results

Table 1 shows the results of $CRM_{197}$-A05 (SEQ ID NO: 14) fusion cloning. In general, $CRM_{197}$-A05 clones gave products with multiple mutations in the open reading frame. All fusion clones produced recombinant protein that was 100% insoluble. The DT-A-A05 (SEQ ID NO: 18) fusion construct also produced insoluble protein.

Table 2 shows the results of Ply-A05 fusion proteins. While expression of Ply-A05 or A05-Ply from pET30a at 30° C. produced insoluble fusion protein, the alternative vectors produced partially soluble protein. In particular, Ply-A05 fusion proteins expressed from pRHAM (pDD18), pRAME (pDD21) and pDK347 (pDD20) at 30° C. were largely soluble (FIG. 2). pDD18 was chosen for fermentation, however the conditions used (Apollon medium, 30° C. growth, 0.2% rhamnose induction) produced insoluble protein. Small scale shake flask cultures of pDD18, pDD20 and pDD21 were grown at 20° C. to determine if lower temperature might enhance the solubility of the fusion protein. Unlike pDD20, the pDD18 and pDD21 cultures did not express detectable amounts of Ply-A05 protein at 20° C. (FIG. 3). Therefore, six 1 liter flask cultures of pDD20 were produced for protein purification (FIG. 4). The fusion protein expressed from pDD20 has a single amino acid change (L32F) in the pneumolysin portion of the fusion protein.

TABLE 1

$CRM_{197}$-A05 fusion proteins produced.

| Construct | Insert | Plasmid | Strain | Expression Level | Solubility | Sequence |
|---|---|---|---|---|---|---|
| pDD23 | CRM-A05 | pRHAM (rhamnose) | BD686 | {+} | not tested | V543G |
| pDD24 | CRM-A05 | pRAME (rhaT w/enhancer) | BD686 | {++} | insoluble | L164F, S446N, V482I, V651I |
| pDD25 | CRM-A05 | pDK329 (ara) | BD686 | {+} | not tested | correct |
| pDD26 | CRM-A05 | pDK338 (lac) | BD686 | {−} | not tested | N373H |
| pDD27 | CRM-A05 | pDK347 (lac w/ enhancer) | BD686 | {+} | insoluble | correct |
| pDD28 | CRM-A05 | pDK363 (ara w/enhancer) | BD686 | {+++} | insoluble | correct |
| pDD14 | DTA-A05 | pET30a | BD686 | {+++++} | insoluble | R259K, T394S |
| pDD31 | DTA-A05 | pRAME (rhaT w/enhancer) | BD686 | {−} | not tested | R259K, T394S |
| pDD34 | DTA-A05 | pDK347 (lac w/ enhancer) | BD686 | {−} | not tested | R259K, T394S |
| pDD35 | DTA-A05 | pDK363 (ara w/enhancer) | BD686 | {++++} | insoluble | R259K, T394S |
| pLN15 | A05-CRM | pET30a | BD686 | {++++++} | insoluble | correct |

TABLE 2

Ply-A05 fusion proteins produced.

| construct | insert | plasmid | strain | expression level | solubility | sequence |
|---|---|---|---|---|---|---|
| pDD15 | Ply-A05 | pET30a | BD686 | {+++++} | insoluble | correct |
| pDD18 | Ply-A05 | pRHAM (rhamnose) | BD686 | {+++} | soluble | correct |
| pDD19 | Ply-A05 | pDK329 (ara) | BD686 | {+} | not tested | correct |
| pDD20 | Ply-A05 | pDK347 (lac w/ enhancer) | BD686 | {++++} | soluble | L32F |
| pDD21 | Ply-A05 | pRAME (rhaTw/ enhancer) | BD686 | {++++} | mostly soluble | correct |
| pDD22 | Ply-A05 | pDK338 (lac) | BD686 | {+} | not tested | correct |
| pDD29 | Ply-A05 | pDK363 (ara w/enhancer) | BD686 | {+++++} | mostly insoluble | correct |
| pLN116 | A05-Ply | pET30a | BD686 | {+++++} | insoluble | correct |

Example 2: Serum Bactericidal Assay

Functional antibody titers were determined by serum bactericidal assay (SBA) against *Neisseria meningitidis* strains expressing an LP2086 variant with sequence homologous or heterologous to those contained in the vaccine.

Bactericidal antibodies in serum from macaques or rabbits immunized with ORF2086 vaccine were detected using SBAs with human complement. Rabbit immune sera or macaque immune sera were heat-inactivated to remove intrinsic complement activity and subsequently serially diluted 1:2 in Dulbecco's PBS with Ca2+ and Mg2+ (D-PBS) in a 96-well microtiter plate to test for serum bactericidal activity against *N. meningitidis* strains. Bacteria used in the assay were grown in GC media supplemented with Kellogg's supplement (GCK) and 4.2% NaHCO$_3$ and monitored by optical density at 650 nm. Bacteria were harvested for use in the assay at a final OD$_{650}$ of 0.50-0.60, diluted in D-PBS and 1000-3000 CFU were added to the assay mixture with 20% human complement.

Human serum with no detectable bactericidal activity was used as the exogenous complement source. Complement sources were tested for suitability against each individual *N. meningitidis* test strain. A complement source was used only if the number of bacteria surviving in control reactions without added immune sera was >50% of the input.

After a 30 min incubation with agitation at 700 rpm on a shaker at 37° C. with 5% CO$_2$, D-PBS was added to the reaction mixture and aliquots transferred to microfilter plates filled with 50% GCK media. The microfilter plates were filtered, incubated overnight at 37° C. with 5% CO$_2$, and microcolonies were stained and quantified. The serum bactericidal titers were defined as the interpolated reciprocal serum dilution that yielded a 50% reduction in colony forming units (CFU) compared to the CFU in control wells without immune sera using these assay conditions. Enhanced susceptibility to killing with ORF2086 immune sera relative to pre-immune sera was noted if there was a 4-fold or greater rise in SBA titer. Sera that were negative against the assay strain at the starting dilution were assigned a titer of one half the limit of detection for the assay (i.e., 4).

Example 3: Immunogenicity of Fusion Polypeptide (SEQ ID NO: 2)

The bactericidal activity of serum samples from mice immunized with nonlipidated versions of fHBP protein alleles is generally lower than serum samples from mice immunized with the lipidated fHBP counterparts. Similarly, the SBA response against *N. meningitidis* strains that express two distinct subfamily A fHBP variants (A05 and A22) is greater following immunization of nonhuman primates (NHPs) with lipidated A05 (SEQ ID NO: 19) than nonlipidated A05 (SEQ ID NO: 44) (Table 3).

TABLE 3

The bactericidal titer against *N. meningitidis* strains that express A05 and A22 fHBP variants is greater in serum from NHPs vaccinated with lipidated A05 (SEQ ID NO: 19) compared with nonlipidated A05 (SEQ ID NO: 5).

| | | % Responders ≥4X rise PD3 SBA Titers | |
|---|---|---|---|
| A05 Vaccine | Dose (mcg) | A05 | A22 |
| Lipidated | 30 | 100 | 60 |
| | 10 | 70 | 80 |
| Non-Lipidated | 120 | 30 | 0 |
| | 60 | 50 | 20 |
| | 30 | 50 | 0 |
| | 10 | 40 | 10 |

Additional compositions have been evaluated to provide coverage using combinations of nonlipidated proteins. In this investigation we demonstrate that immunogenicity may be enhanced with recombinant proteins composed of nonlipidated variants of fHBP genetically fused to a carrier protein. The same findings could also be extended to fHBP variants that are conjugated to carrier proteins.

In the current example a recombinant fusion protein (SEQ ID NO: 2) composed of attenuated *Streptococcus pneumoniae* pneumolysin (Δ6PLY) genetically fused to the *N. meningitidis* fHBP A05 variant (SEQ ID NO: 5) is tested.

The attenuated Δ6PLY (SEQ ID NO: 1) is produced by site-directed mutagenesis. Specifically, the immunogenic Δ6 PLY variant (deletion of the A146R147 dipeptide) eliminates both the pore forming cytolytic activity and the pro-inflammatory phenotype that is characteristic of wild type PLY (SEQ ID NO: 21).

To explore whether the attenuated Δ6PLY could stabilize and therefore enhance the immunogenicity of the nonlipidated A05, a recombinant protein composed of *Str. pneumoniae* Δ6PLY genetically fused to *N. meningitidis* fHBP variant A05 was constructed (SEQ ID NO: 2) for testing. In the current example, non-human primates (NHPs) were immunized with the Δ6PLY-A05 fusion protein (SEQ ID NO: 2) or the lipidated bivalent A05 (SEQ ID NO: 19)/B01

(SEQ ID NO: 20) composition and boosted on weeks 4 and 8. Serum from animals taken at 10 wks (post-dose 3, PD3) was evaluated for bactericidal activity against an A05 expressing strain of N. meningitidis. SBA titers in PD3 samples from both treatment groups were elevated compared to prevaccination titers (Table 4). The immune response to Δ6PLY-A05 (SEQ ID NO: 2) was as strong as to the response to the lipidated A05 (SEQ ID NO: 19)/B01 (SEQ ID NO: 20) composition.

TABLE 4

Bactericidal activity against N. meningitidis serogroup B clinical isolates expressing either A05 (SEQ ID NO: 23) or A22 (SEQ ID NO: 22) fHBP protein variants using serum from NHPs vaccinated with Δ6PLY-A05 fusion protein (SEQ ID NO: 2) or the bivalent lipidated A05 (SEQ ID NO: 19)/B01 (SEQ ID NO: 20) composition.

| Antigenic Composition | Lipidated | Dose/0.5 mL | % Responders at PD3 with ≥4X rise SBA Titers | |
|---|---|---|---|---|
| | | | A05 | A22 |
| A05 (SEQ ID NO: 19) and B01 (SEQ ID NO: 20) | Yes | 10 mcg each | 80 | 60 |
| Δ6PLY-A05 (SEQ ID NO: 2) | No | 10 mcg | 100 | 100 |

The PD3 serum samples from Δ6PLY-A05 (SEQ ID NO: 2) vaccinated NHPs also had strong bactericidal activity against a strain of N. meningitidis expressing the fHBP A22 (SEQ ID NO: 22) variant (Table 4). The percent of animals that respond with a >4× rise in SBA titer using the A22 target strain of N. meningitidis was greater in the Δ6PLY-A05 treated NHPs than in the bivalent lipidated fHBP treatment group. In summary, the functional bactericidal activity against N. meningitidis strains that express two distinct subfamily A fHBP variants using serum from NHPs vaccinated with the non-lipidated Δ6PLY-A05 fusion protein is at least as strong as the activity from the lipidated bivalent rLP2086 treatment group.

To further explore the impact of Str. pneumoniae Δ6PLY relative to other carrier proteins on the immunogenicity of nonlipidated A05, a recombinant protein composed of GNA2091 from N. meningitidis fused with fHBP variant A05 was prepared for testing. In addition, a chemical conjugate of recombinant expressed streptococcal C5a peptidase (SCP) from Streptococcus pyogenes (zinc treated, see Example 4) coupled with fHBP variant A05 (SEQ ID NO: 5) was also prepared for immunogenicity assessment. In the current example, non-human primates (NHPs) were immunized with the respective A05 fusion proteins, the SCP-A05 chemical conjugate, the lipidated bivalent A05 (SEQ ID NO: 19)/B01 (SEQ ID NO: 20) composition, or the nonlipidated A05 (SEQ ID NO: 5) and boosted on weeks 4 and 8. The antigen dose was adjusted so that the equivalent of 10 mcg of A05 was administered with each vaccination. Serum from animals taken at 10 wks (post-dose 3, PD3) was evaluated for bactericidal activity against an A05 expressing strain of N. meningitidis. SBA titers in PD3 samples from the PLY-A05 (SEQ ID NO: 2) treatment group were, (i) elevated compared to prevaccination titers, (ii) comparable to the response to the lipidated bivalent A05/B01 composition, and (iii) superior to the immune response to both nonlipidated A05 and the GNA2091-A05 (SEQ ID NO: 149) fusion protein antigens (Table 5). While animals vaccinated with the SCP-A05 chemical conjugate did respond to the antigen, the magnitude of the immune response was not as robust as that detected in the PLY-A05 fusion protein treatment group.

TABLE 5

| Antigenic Composition | Lipidated | Amount of fHBP in antigen (mcg/0.5 mL) | PD3 GMT SBA Titers (A05) | % Responders >4X Rise SBA Titers (A05) |
|---|---|---|---|---|
| A05 (SEQ ID NO: 19) and B01 (SEQ ID NO: 20) | yes | 10 of each | 64 | 100 |
| A05 (SEQ ID NO: 5) | no | 10 | 19 | 80 |
| PLY-A05 (SEQ ID NO: 2) | no | 10 | 104 | 100 |
| GNA2091-A05 (SEQ ID NO: 149) | no | 10 | 16 | 60 |
| SCP-A05 (SEQ ID NO: 5) Conjugate | no | 10 | 43 | 80 |

Example 4: Post-Translational Modification Removal

When the cysteine in rP2086-A05-cys is located on the amino terminus (SEQ ID NO: 156), a significant amount of the protein is pyruvylated during fermentation. This pyruvylation modification was removed from the proteins by treatment with zinc sulfate. Mass spectra characterized the pyruvylated rP2086-A05-cys (SEQ ID NO: 156) as exhibiting a mass shift of +71 Da, as compared to the rP2086-A05-cys protein treated with zinc sulfate, which did not exhibit a mass shift of +71 as compared to the corresponding pyruvylated rP2086-A05-cys.

Moving the cysteine residue to other positions in the protein (e.g., moving the cysteine to positions 2 or 6, see SEQ ID NO: 157 and SEQ ID NO: 158, respectively) eliminated the pyruvylation issue. A description of these constructs is provided in Example 9.

In addition to standard chromatography techniques, to separate native rP2086-A05-cys from protein containing blocked thiols, a thiol reactive resin (Thioproply Sepharose 6B) was used. In this technique, the native rP2086-A05-cys binds to the column and the blocked rP2086-A05-cys is eluted in the flow through. The native rP2086-A05-cys is then eluted from the column using a reducing agent (preferably DTT).

As used in the following examples, the term "rP2086-A05-cys" refers to a non-pyruvylated, non-lipidated rP2085 A05 protein, regardless of how the pyruvylation modification is not present, e.g., naturally during fermentation, by zinc sulfate treatment, by genetic modifications to the protein to delete the initial cysteine at position 1 of the N-terminus and replacing a serine residue at positions 2 or 6 with a cysteine residue.

None of the processes described below have been optimized. Accordingly, other protein concentrations, protein ratios, reaction times and temperatures than those described could be used to produce rP2086-A05 conjugates.

Example 5: Conjugation of Pneumolysin to rP2086-A05-Cys Using an Amine-to-Sulfhydryl Crosslinker with Soluble Polyethylene Glycol (PEG) Spacer Arm Preparation of SM(PEG)$_4$-Activated Pneumolysin-NEM Intermediate:

Pneumolysin protein at approx 10 mg/ml in phosphate buffered saline is prepared for conjugation by derivatization of the protein with N-Ethyl Maleimide (NEM), followed by activation with SM(PEG)$_4$. A 10 fold molar excess NEM is incubated with pnemolysin at 20-25 deg C. and 1 mM EDTA for a time sufficient to completely block pneumolysin sulfhydryls. Typically 20 minutes is sufficient to prepare Pneumolysin-NEM intermediate. SM(PEG)$_4$ linker, obtained from a solution having a concentration of 100 mM and dissolved in dimethyl sulfoxide solvent, is incubated at a 10 fold molar excess over Pneumolysin-NEM intermediate for 30 minutes. The activation reaction is terminated by Size Exclusion Chromatography using a column packed with Sephadex G25 resin. The chromatographic fractions containing SM(PEG)$_4$-Activated Pneumolysin-NEM intermediate can be stored –80 C or immediately conjugated to Reduced MnB 2086 A05 Cysteine-stem mutant Protein intermediate.

The NEM modification is used to block the cysteine residue in pneumolysin so that it does not react with the SM(PEG) linker.

Example 6: Preparation of Reduced rP2086-A05-Cys rP2086-A05-cys at approx 1.3 mg/ml in phosphate buffered saline is incubated with a quantity of settled immobilized TCEP resin and 1 mM EDTA sufficient to completely reduce the sulfhydyls of MnB protein. Typically, a 30 minute incubation of rP2086-A05-cys with an equal volume of settled resin and 1 mM EDTA is sufficient to completely reduce the sulfhydryls. Reduced MnB protein intermediate is recovered by filtration through a 0.2 micron Polyethersulfone membrane and used immediately for conjugation.

Example 7: Conjugation of SM(PEG)$_4$-Activated Pneumolysin-NEM Intermediate to rP2086-A05-Cys The reduced rP2086-A05-cys intermediate is combined with SM(PEG)$_4$-Activated Pneumolysin-NEM intermediate to achieve a 4:1 molar ratio at protein concentrations of approximately 1.2 and 0.6 mg/mL respectively. The reaction proceeds for 2 hr at 20-25 deg C. and is terminated by the addition of Cysteamine-HCl pH 5.5, to the reaction solution to a 2 mM final concentration of cysteamine-HCl. The conjugation reaction product rP2086-A05-cys SM(PEG)$_4$ Pneumolysin-NEM conjugate reaction product is chromatographically purified from unconjugated SM(PEG)$_4$-Activated Pneumolysin-NEM intermediate by Immobilized Metal Affinity Chromatography (IMAC) using Nickel Sepharose 6 fast flow resin. The reaction product binds in a buffer composed of 20 mM Tris, 0.5M NaCl pH 7.7 and is eluted in 20 mM Tris, 0.5M NaCl pH 7.7 40 mM Imidazole. Further purification of the conjugate is achieved by removal of Reduced MnB 2086 A05 Cysteine-stem mutant Protein intermediate by Ion Exchange Chromatography using Q Sepharose HP resin. The reaction product binds in 20 mM Tris, pH 7.7 and is recovered in a salt gradient elution of 20 mM Tris, 0.5M NaCl pH 7.7. The Q fractions containing the conjugate are buffer exchanged by Size Exclusion Chromatography using a column packed with Sephadex G25 resin and sterile filtered.

Example 8: Conjugation of SCP to rP2086-A05-Cys Using an Amine-to-Sulfhydryl Crosslinker with a Cyclohexane Spacer Arm Preparation of SMCC-Activated SCP Intermediate:
SCP protein at approx 12.6 mg/ml in phosphate buffered saline is incubated at 25 deg C. with a 20 fold molar excess of Sulfosuccinimidyl-4-(N-maleimidomethyl)cyclohexane-1-carboxylate linker, (Sulfo-SMCC; obtained from a 20 mM stock prepared in 10 mM sodium phosphate pH 6.8) and 1 mM EDTA for 1 hour. The activation reaction is terminated by Size Exclusion Chromatography using a column packed with Sephadex G25 resin. The chromatographic fractions containing SMCC-Activated SCP intermediate can be stored –80° C. or immediately conjugated to reduced rP2086-A05-cys intermediate.

Preparation of Reduced rP2086-A05-Cys Intermediate:
rP2086-A05-cys at approx 3.8 mg/ml in phosphate buffered saline is incubated with 4 mM TCEP and 1 mM EDTA sufficient to completely reduce the sulfhydyls of MnB protein. Typically, a 1 hr incubation of MnB Protein with TCEP and 1 mM EDTA is sufficient to completely reduce the sulfhydryls. Reduced MnB protein is used immediately for conjugation.

Conjugation of SMCC-Activated SCP Intermediate to rP2086-A05-Cys:
The reduced rP2086-A05-cys is combined with SMCC-Activated SCP intermediate to achieve an equal weight ratio, (a 4:1 molar ratio), at protein concentrations of approximately 2.6 mg/ml and 2.6 mg/mL respectively. The reaction proceeds for 2.5 hr at 25 deg C. and is terminated by the addition of Cysteamine-HCl pH 5.5, to the reaction solution to a 2 mM final concentration of cysteamine-HCl. The conjugation reaction product MnB 2086 A05 Cysteine-mutant Protein SMCC-SCP conjugate reaction product is chromatographically purified from unconjugated SMCC-SCP Activated intermediate by Immobilized Metal Affinity Chromatography (IMAC) using Nickel Sepharose 6 fast flow resin. The reaction product binds in a buffer composed of 20 mM Tris, 0.5M NaCl pH 7.7 and is eluted in 20 mM Tris, 0.5M NaCl pH 7.7 40 mM Imidazole. Further purification of the conjugate is achieved by removal of Reduced MnB 2086 A05 Cysteine mutant Protein intermediate by Ion Exchange Chromatography using Q Sepharose HP resin. The reaction product binds in 20 mM Tris, pH 7.7 and is recovered in a salt gradient elution of 20 mM Tris, 0.5M NaCl pH 7.7. The Q fractions containing the conjugate are buffer exchanged by Size Exclusion Chromatography using a column packed with Sephadex G25 resin and sterile filtered.

Example 9: Generation of rP2086-A05-Cys Stalk Mutants

A Non-lipidated construct of A05 were designed to remove the lipidation signal and produce a recombinant protein with the cysteine at the N-terminus. The proteins were strongly expressed in *E. coli*. Purified proteins were analyzed using reverse-phase high performance liquid chromatography (RP-HPLC) interfaced with a quadruple time-of-flight mass spectrometer (QTOF-MS) to provide a means of monitoring formation of product related variants.

To assess whether moving the cysteine into the serine glycine stalk region of A05 would reduce the modifications on the cysteine while keeping it available for conjugation, two variants of A05 were constructed, one with the N-terminal cysteine moved to position 2 of the mature protein replacing the serine residue at this position (see SEQ ID NO: 157) and one with the cysteine moved to position 6 of the mature protein replacing the serine residue at this position (see SEQ ID NO: 158). This was accomplished by incorporating the codon changes in the 5' primer used for amplification of the gene. Both the 5' and 3' primers designed to amplify A05 had 15 base extensions with homology to pET30a cut with NdeI and BamHI. A05 and the vector were ligated using a Clontech InFusion® kit. After transformation, colonies were screened for inserts and those containing inserts were verified to contain the amino acid substitution by DNA sequencing.

The following clauses describe additional embodiments of the invention:

C1. An isolated polypeptide comprising the amino acid sequence of a carrier polypeptide and the amino acid sequence of an ORF2086 polypeptide.
C2. The polypeptide according to clause C1, wherein the isolated polypeptide is a fusion polypeptide.
C3. The polypeptide according to clause C1, wherein the ORF2086 polypeptide is a subfamily A polypeptide.
C4. The polypeptide according to clause C1, wherein the ORF2086 polypeptide is a subfamily B polypeptide.
C5. The polypeptide according to clause C1, wherein the ORF2086 polypeptide is lipidated.
C6. The polypeptide according to clause C1, wherein the ORF2086 polypeptide is non-lipidated.
C7. The polypeptide according to clause C1, wherein the ORF2086 polypeptide is A05.
C8. The polypeptide according to clause C1, wherein the ORF2086 polypeptide is A12.
C9. The polypeptide according to clause C1, wherein the ORF2086 polypeptide is A22.
C10. The polypeptide according to clause C1, wherein the ORF2086 polypeptide is B01.
C11. The polypeptide according to clause C1, wherein the ORF2086 polypeptide is B09.
C12. The polypeptide according to clause C1, wherein the ORF2086 polypeptide is B15.
C13. The polypeptide according to clause C1, wherein the ORF2086 polypeptide is B16.
C14. The polypeptide according to clause C1, wherein the ORF2086 polypeptide is B22.
C15. The polypeptide according to clause C1, wherein the ORF2086 polypeptide is B24.
C16. The polypeptide according to clause C1, wherein the ORF2086 polypeptide is B44.
C17. The polypeptide according to clause C1, wherein the ORF2086 polypeptide is A62.
C18. The polypeptide according to clause C1, wherein the ORF2086 polypeptide is A04.
C19. The polypeptide according to clause C1, wherein the ORF2086 polypeptide is A01.
C20. The polypeptide according to clause C1, wherein the ORF2086 polypeptide is A06.
C21. The polypeptide according to clause C1, wherein the ORF2086 polypeptide is A07.
C22. The polypeptide according to clause C1, wherein the ORF2086 polypeptide is A15.
C23. The polypeptide according to clause C1, wherein the ORF2086 polypeptide is A19.
C24. The polypeptide according to clause C1, wherein the ORF2086 polypeptide is A20.
C25. The polypeptide according to clause C1, wherein the ORF2086 polypeptide is A29.
C26. The polypeptide according to clause C1, wherein the ORF2086 polypeptide is B02.
C27. The polypeptide according to clause C1, wherein the ORF2086 polypeptide comprises the amino acid sequence selected from the group consisting of SEQ ID NOs: 5, 19, 22-65.
C28. The polypeptide according to clause C1, wherein the carrier polypeptide is a cytolysoid.
C29. The polypeptide according to clause C28, wherein the cytolysoid is derived from a pneumolysin polypeptide from *Streptococcus pneumoniae*, a perfringolysin O polypeptide from *Clostridium perfringens*, a intermedilysin polypeptide from *Streptococcus intermedius*, a alveolysin polypeptide from *Bacillus alvei*, a anthrolysin polypeptide from *Bacillus anthracis*, a putative cereolysin polypeptide from *Bacillus cereus*, a ivanolysin O polypeptide from *Listeria ivanovii*, a pyolysin polypeptide from *Arcanobacterium pyogenes*, a seeligeriolysin O polypeptide from *Listeria seeligeri*, a streptolysin O polypeptide from *S. pyogenes*, a suilysin polypeptide from *Streptococcus suis*, a tetanolysin polypeptide from *Clostridium tetani*, a listeriolysin O polypeptide from *Listeria monocytogenes*, a streptolysin O polypeptide from *Streptococcus equisimilis*, a streptolysin O polypeptide from *S. canis*, a thuringiolysin O polypeptide from *Bacillus thuringiensis*, a latersporolysin O polypeptide from *B. laterosporus*, a botulinolysin polypeptide from *Clostridium botulinum*, a chauveolysin polypeptide from *C. chauvoei*, a bifermentolysin polypeptide from *C. bifermentans*, a sordellilysin polypeptide from *C. sordellii*, a histolyticolysin polypeptide from *Clostridium histiolyticum*, a novylysin polypeptide from *Clostridium novyi*, or a septicolysin O polypeptide from *Clostridium septicum*.
C30. The polypeptide according to clause C29, wherein the cytolysoid is derived from a pneumolysin polypeptide from *Streptococcus pneumoniae*.
C31. The polypeptide according to clause C30, wherein the cytolysoid comprises a sequence having at least 90% sequence identity to SEQ ID NO: 1.
C32. The polypeptide according to clause C1, wherein the carrier polypeptide is detoxified as compared to the corresponding wild-type carrier polypeptide and is selected from the group consisting of tetanus toxin (TT), *Plasmodium falciparum* circumsporozite protein, hepatitis B surface antigen, hepatitis B nuclear core polypeptide, *H. influenzae* matrix polypeptide, *H. influenzae* haemagglutinin, diphtheria toxoid, diphtheria toxoid mutant $CRM_{197}$, group B *N. meningitidis* outer membrane polypeptide complex (OMPC), a cytolysoid, pneumococcal toxin pneumolysin, heat shock polypeptide from *Mycobacterium bovis*, heat shock polypeptide from *M. leprae*, cholera toxoid, *E. coli* LT, *E. coli* ST, exotoxin A from *Pseudomonas aeruginosa*, pneumococcal surface polypeptide A, pneumococcal adhesin polypeptide (PsaA), C5a peptidase from Group A or Group B *streptococcus, Haemophilus influenzae* polypeptide D, ovalbumin, keyhole limpet hemocyanin (KLH), bovine serum albumin (BSA), purified polypeptide derivative of tuberculin (PPD), PorB (from *N. meningitidis*), and derivatives, variants, or fragments thereof.

C33. The polypeptide according to clause C1, wherein the carrier polypeptide is $CRM_{197}$.

C34. The polypeptide according to clause C32, wherein the carrier polypeptide is not $CRM_{197}$.

C35. The polypeptide according to clause C1, wherein the carrier polypeptide is streptococcal C5a peptidase (SCP) from *Streptococcus pyogenes.*

C36. The polypeptide according to clause C1, wherein the carrier polypeptide is GNA2091.

C37. The polypeptide according to clause C1, further comprising a polypeptide sequence derived from pneumococcal bacteria.

C38. The polypeptide according to clause C1, wherein the isolated polypeptide does not comprise a polypeptide sequence derived from pneumococcal bacteria.

C39. The polypeptide according to clause C1, wherein the isolated polypeptide elicits a bactericidal antibody against a *N. meningitidis* serogroup B variant that is homologous with the ORF2086 polypeptide.

C40. The polypeptide according to clause C1, wherein the isolated polypeptide elicits a bactericidal antibody against a *N. meningitidis* serogroup B variant that is heterologous to the ORF2086 polypeptide.

C41. The polypeptide according to clause C2, wherein the fusion polypeptide comprises in the following order: the carrier polypeptide operably linked to the ORF2086 polypeptide.

C42. The polypeptide according to clause C2, wherein the fusion polypeptide comprises in the following order: an ORF2086 polypeptide operably linked to a carrier polypeptide.

C43. The polypeptide according to clause C2, wherein the carrier polypeptide comprises SEQ ID NO: 1 and the ORF2086 polypeptide comprises SEQ ID NO: 5.

C44. The polypeptide according to clause C43, wherein the isolated polypeptide comprises SEQ ID NO: 2.

C45. An isolated polynucleotide that encodes a polypeptide according to any one of clauses CC1-CC44.

C46. An immunogenic composition comprising a polypeptide according to any one of clauses CC1-CC44 and a pharmaceutically acceptable excipient.

C47. The composition according to clause C46, further comprising at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135; and d) a conjugate of a capsular saccharide of *Neisseria meningitidis* serogroup Y.

C48. A method for inducing an immune response against *Neisseria meningitidis* in a mammal comprising administering to the mammal an effective amount of the isolated polypeptide according to any one of clauses CC1-CC44.

C49. The method of clause C48, wherein the immune response comprises a bactericidal antibody.

C50. The method of clause C48, wherein the immune response is equal to an immune response of a mammal administered with a corresponding lipidated ORF2086 polypeptide in the absence of a carrier polypeptide, when assessed under identical conditions.

C51. The method of clause C48, wherein the immune response is greater than an immune response of a mammal administered with a corresponding non-lipidated ORF2086 polypeptide in the absence of a carrier polypeptide, when assessed under identical conditions.

C52. The method of clause C48, wherein the immune response is at most 10% less than an immune response of a mammal administered with a corresponding lipidated ORF2086 polypeptide in the absence of a carrier polypeptide, when assessed under identical conditions.

C53. The method of clause C48, wherein the immune response is at most 20% less than an immune response of a mammal administered with a corresponding lipidated ORF2086 polypeptide in the absence of a carrier polypeptide, when assessed under identical conditions.

C54. A method for inducing an immune response against *Neisseria meningitidis* in a mammal comprising administering to the mammal an effective amount of the immunogenic composition according to any one of clauses CC46-CC47.

C55. The method of clause C54, wherein the immune response comprises a bactericidal antibody.

C56. The method of clause C54, wherein the immune response is equal to an immune response of a mammal administered with a corresponding lipidated ORF2086 polypeptide in the absence of a carrier polypeptide, when assessed under identical conditions.

C57. The method of clause C54, wherein the immune response is greater than an immune response of a mammal administered with a corresponding non-lipidated ORF2086 polypeptide in the absence of a carrier polypeptide, when assessed under identical conditions.

C58. The method of clause C54, wherein the immune response is at most 10% less than an immune response of a mammal administered with a corresponding lipidated ORF2086 polypeptide in the absence of a carrier polypeptide, when assessed under identical conditions.

C59. The method of clause C54, wherein the immune response is at most 20% less than an immune response of a mammal administered with a corresponding lipidated ORF2086 polypeptide in the absence of a carrier polypeptide, when assessed under identical conditions.

C60. An immunogenic composition comprising an ORF2086 polypeptide and a carrier polypeptide.

C61. The composition according to clause C60, wherein the composition is a conjugate.

C62. The composition according to clause C60, wherein the ORF2086 polypeptide is a subfamily A polypeptide.

C63. The composition according to clause C60, wherein the ORF2086 polypeptide is a subfamily B polypeptide.

C64. The composition according to clause C60, wherein the ORF2086 polypeptide is lipidated.

C65. The composition according to clause C60, wherein the ORF2086 polypeptide is non-lipidated.

C66. The composition according to clause C60, wherein the ORF2086 polypeptide is non-lipidated and non-pyruvylated.

C67. The composition according to clause C60, wherein the ORF2086 polypeptide is A05.

C68. The composition according to clause C60, wherein the ORF2086 polypeptide is A12.
C69. The composition according to clause C60, wherein the ORF2086 polypeptide is A22.
C70. The composition according to clause C60, wherein the ORF2086 polypeptide is B01.
C71. The composition according to clause C60, wherein the ORF2086 polypeptide is B09.
C72. The composition according to clause C60, wherein the ORF2086 polypeptide is B15.
C73. The composition according to clause C60, wherein the ORF2086 polypeptide is B16.
C74. The composition according to clause C60, wherein the ORF2086 polypeptide is B22.
C75. The composition according to clause C60, wherein the ORF2086 polypeptide is B24.
C76. The composition according to clause C60, wherein the ORF2086 polypeptide is B44.
C77. The composition according to clause C60, wherein the ORF2086 polypeptide is A62.
C78. The polypeptide according to clause C60, wherein the ORF2086 polypeptide is A04.
C79. The polypeptide according to clause C60, wherein the ORF2086 polypeptide is A01.
C80. The polypeptide according to clause C60, wherein the ORF2086 polypeptide is A06.
C81. The polypeptide according to clause C60, wherein the ORF2086 polypeptide is A07.
C82. The polypeptide according to clause C60, wherein the ORF2086 polypeptide is A15.
C83. The polypeptide according to clause C60, wherein the ORF2086 polypeptide is A19.
C84. The polypeptide according to clause C60, wherein the ORF2086 polypeptide is A20.
C85. The polypeptide according to clause C60, wherein the ORF2086 polypeptide is A29.
C86. The polypeptide according to clause C60, wherein the ORF2086 polypeptide is B02.
C87. The composition according to clause C60, wherein the ORF2086 polypeptide comprises the amino acid sequence selected from the group consisting of SEQ ID NOs: 5, 19, 22-65.
C88. The composition according to clause C60, wherein the carrier polypeptide is a cytolysoid.
C89. The composition according to clause C88, wherein the cytolysoid is derived from a pneumolysin polypeptide from *Streptococcus pneumoniae*, a perfringolysin O polypeptide from *Clostridium perfringens*, a intermedilysin polypeptide from *Streptococcus intermedius*, a alveolysin polypeptide from *Bacillus alvei*, a anthrolysin polypeptide from *Bacillus anthracis*, a putative cereolysin polypeptide from *Bacillus cereus*, a ivanolysin O polypeptide from *Listeria ivanovii*, a pyolysin polypeptide from *Arcanobacterium pyogenes*, a seeligeriolysin O polypeptide from *Listeria seeligeri*, a streptolysin O polypeptide from *S. pyogenes*, a suilysin polypeptide from *Streptococcus suis*, a tetanolysin polypeptide from *Clostridium tetani*, a listeriolysin O polypeptide from *Listeria monocytogenes*, a streptolysin O polypeptide from *Streptococcus equisimilis*, a streptolysin O polypeptide from *S. canis*, a thuringiolysin O polypeptide from *Bacillus thuringiensis*, a latersporolysin O polypeptide from *B. laterosporus*, a botulinolysin polypeptide from *Clostridium botulinum*, a chauveolysin polypeptide from *C. chauvoei*, a bifermentolysin polypeptide from *C. bifermentans*, a sordellilysin polypeptide from *C. sordellii*, a histolyticolysin polypeptide from *Clostridium histiolyticum*, a novylysin polypeptide from *Clostridium novyi*, or a septicolysin O polypeptide from *Clostridium septicum*.
C90. The composition according to clause C89, wherein the cytolysoid is derived from a pneumolysin polypeptide from *Streptococcus pneumoniae*.
C91. The composition according to clause C90, wherein the cytolysoid comprises a sequence having at least 90% sequence identity to SEQ ID NO: 1.
C92. The composition according to clause C60, wherein the carrier polypeptide is detoxified as compared to the corresponding wild-type carrier polypeptide and is selected from the group consisting of tetanus toxin (TT), *Plasmodium falciparum* circumsporozite protein, hepatitis B surface antigen, hepatitis B nuclear core polypeptide, *H. influenzae* matrix polypeptide, *H. influenzae* haemagglutinin, diphtheria toxoid, diphtheria toxoid mutant CRM$_{197}$, group B *N. meningitidis* outer membrane polypeptide complex (OMPC), a cytolysoid, pneumococcal toxin pneumolysin, heat shock polypeptide from *Mycobacterium bovis*, heat shock polypeptide from *M. leprae*, cholera toxoid, *E. coli* LT, *E. coli* ST, exotoxin A from *Pseudomonas aeruginosa*, pneumococcal surface polypeptide A, pneumococcal adhesin polypeptide (PsaA), C5a peptidase from Group A or Group B *streptococcus*, *Haemophilus influenzae* polypeptide D, ovalbumin, keyhole limpet hemocyanin (KLH), bovine serum albumin (BSA), purified polypeptide derivative of tuberculin (PPD), PorB (from *N. meningitidis*), and derivatives, variants, or fragments thereof.
C93. The composition according to clause C60, wherein the carrier polypeptide is CRM$_{197}$.
C94. The composition according to clause C92, wherein the carrier polypeptide is CRM$_{197}$.
C95. The composition according to clause C60, wherein the carrier polypeptide is streptococcal C5a peptidase (SCP) from *Streptococcus pyogenes*.
C96. The composition according to clause C60, wherein the carrier polypeptide is GNA2091.
C97. The composition according to clause C60, wherein the carrier polypeptide is heterologous to the ORF2086 polypeptide.
C98. The composition according to clause C60, further comprising a polypeptide sequence derived from pneumococcal bacteria.
C99. The composition according to clause C60, wherein the composition does not comprise a polypeptide sequence derived from pneumococcal bacteria.
C100. The composition according to clause C60, wherein the composition elicits a bactericidal antibody response against a *N. meningitidis* serogroup B strain expressing an ORF2086 variant that is homologous to the ORF2086 polypeptide.
C101. The composition according to clause C60, wherein the composition elicits a bactericidal antibody response against a *N. meningitidis* serogroup B strain expressing an ORF2086 variant that is heterologous to the ORF2086 polypeptide.
C102. The composition according to clause C60, further comprising at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135; and d) a conjugate of a capsular saccharide of *Neisseria meningitidis* serogroup Y.

C103. The composition according to any one of clauses CC60-CC102, and a pharmaceutically acceptable excipient.
C104. A method for inducing an immune response against *Neisseria meningitidis* in a mammal comprising administering to the mammal an effective amount of the composition according to any one of clauses CC60-CC103.
C105. The method of clause C104, wherein the immune response comprises a bactericidal antibody.
C106. The method of clause C104, wherein the immune response is equal to an immune response of a mammal administered with a corresponding lipidated ORF2086 polypeptide in the absence of a carrier polypeptide, when assessed under identical conditions.
C107. The method of clause C104, wherein the immune response is greater than an immune response of a mammal administered with a corresponding non-lipidated ORF2086 polypeptide in the absence of a carrier polypeptide, when assessed under identical conditions.
C108. The method of clause C104, wherein the immune response is at most 10% less than an immune response of a mammal administered with a corresponding lipidated ORF2086 polypeptide in the absence of a carrier polypeptide, when assessed under identical conditions.
C109. The method of clause C104, wherein the immune response is at most 20% less than an immune response of a mammal administered with a corresponding lipidated ORF2086 polypeptide in the absence of a carrier polypeptide, when assessed under identical conditions.
C110. An isolated polypeptide comprising SEQ ID NO: 2.
C111. An isolated polypeptide comprising SEQ ID NO: 8.
C112. An isolated polypeptide comprising SEQ ID NO: 14.
C113. An isolated polypeptide comprising SEQ ID NO: 16.
C114. An isolated polypeptide comprising SEQ ID NO: 18.
C115. An isolated polypeptide comprising SEQ ID NO: 137.
C116. An isolated polypeptide comprising SEQ ID NO: 139.
C117. An isolated polypeptide comprising SEQ ID NO: 141.
C118. An isolated polypeptide comprising SEQ ID NO: 143.
C119. An isolated polypeptide comprising SEQ ID NO: 145.
C120. An isolated polypeptide comprising SEQ ID NO: 149.
C121. An isolated polypeptide comprising SEQ ID NO: 153.
C122. A fusion polypeptide comprising SEQ ID NO: 1 operably linked to any one sequence set forth in SEQ ID NO: 42 to SEQ ID NO: 61.
C123. A fusion polypeptide comprising SEQ ID NO: 147 operably linked to any one sequence set forth in SEQ ID NO: 42 to SEQ ID NO: 61.
C124. A fusion polypeptide comprising SEQ ID NO: 151 operably linked to any one sequence set forth in SEQ ID NO: 42 to SEQ ID NO: 61.
C125. A fusion polypeptide comprising SEQ ID NO: 10 operably linked to any one sequence set forth in SEQ ID NO: 42 to SEQ ID NO: 61.
C126. A fusion polypeptide comprising SEQ ID NO: 155 operably linked to any one sequence set forth in SEQ ID NO: 42 to SEQ ID NO: 61.
C127. A composition comprising a streptococcal C5a peptidase (SCP) from *Streptococcus pyogenes* conjugated to a polypeptide having the amino acid sequence of SEQ ID NO: 156.
C128. A composition comprising a streptococcal C5a peptidase (SCP) from *Streptococcus pyogenes* conjugated to a polypeptide having the amino acid sequence of SEQ ID NO: 157.
C129. A composition comprising a streptococcal C5a peptidase (SCP) from *Streptococcus pyogenes* conjugated to a polypeptide having the amino acid sequence of SEQ ID NO: 158.
C130. A composition comprising a pneumolysoid conjugated to a polypeptide having the amino acid sequence of SEQ ID NO: 156.
C131. A composition comprising a pneumolysoid conjugated to a polypeptide having the amino acid sequence of SEQ ID NO: 157.
C132. A composition comprising a pneumolysoid conjugated to a polypeptide having the amino acid sequence of SEQ ID NO: 158.
C133. A composition comprising a first fusion polypeptide comprising a pneumolysoid operably linked to a non-lipidated ORF2086 A05 and a second fusion polypeptide comprising a pneumolysoid operably linked to a non-lipidated ORF2086 B01.
C134. A composition comprising a first fusion polypeptide comprising the amino acid sequence of SEQ ID NO: 2 and a second fusion polypeptide comprising the amino acid sequence of SEQ ID NO: 139.
C135. A composition comprising a first fusion polypeptide comprising a pneumolysoid operably linked to a non-lipidated ORF2086 B01 and a second fusion polypeptide comprising a pneumolysoid operably linked to a non-lipidated ORF2086 B24.
C136. A composition comprising a first fusion polypeptide comprising a pneumolysoid operably linked to a non-lipidated ORF2086 B09 and a second fusion polypeptide comprising a pneumolysoid operably linked to a non-lipidated ORF2086 B44.

The invention claimed is:

1. An isolated polypeptide comprising the amino acid sequence set forth in SEQ ID NO: 2.

2. The isolated polypeptide according to claim 1, wherein the amino acid sequence is encoded by SEQ ID NO: 4.

3. An isolated polypeptide comprising the amino acid sequence set forth in SEQ ID NO: 8.

4. An isolated polypeptide comprising the amino acid sequence set forth in SEQ ID NO: 14.

5. An isolated polypeptide comprising the amino acid sequence set forth in SEQ ID NO: 16.

6. An isolated polypeptide comprising the amino acid sequence set forth in SEQ ID NO: 18.

* * * * *